United States Patent
Lavoie et al.

(10) Patent No.: US 12,180,491 B2
(45) Date of Patent: Dec. 31, 2024

(54) PLANT EXPRESSION ENHANCER

(71) Applicants: MEDICAGO INC., Quebec (CA); NATIONAL UNIVERSITY CORPORATION NARA INSTITUTE OF SCIENCE AND TECHNOLOGY, Nara (JP); MITSUBISHI TANABE PHARMA CORPORATION, Osaka (JP)

(72) Inventors: Pierre-Oliver Lavoie, Quebec (CA); Marc-Andre D'Aoust, Quebec (CA); Ko Kato, Nara (JP); Shotaro Yamasaki, Nara (JP)

(73) Assignee: ARAMIS BIOTECHNOLOGIES INC., Quebec (CA)

( * ) Notice: Subject to any disclaimer, the term of this patent is extended or adjusted under 35 U.S.C. 154(b) by 893 days.

(21) Appl. No.: 16/980,266

(22) PCT Filed: Mar. 14, 2019

(86) PCT No.: PCT/CA2019/050317
§ 371 (c)(1),
(2) Date: Sep. 11, 2020

(87) PCT Pub. No.: WO2019/173924
PCT Pub. Date: Sep. 19, 2019

(65) Prior Publication Data
US 2021/0246462 A1    Aug. 12, 2021

Related U.S. Application Data

(60) Provisional application No. 62/643,053, filed on Mar. 14, 2018.

(51) Int. Cl.
*C12N 15/82* (2006.01)
*C12N 15/86* (2006.01)

(52) U.S. Cl.
CPC ..... *C12N 15/8258* (2013.01); *C12N 15/8203* (2013.01); *C12N 15/8216* (2013.01); *C12N 15/86* (2013.01); *C12N 2760/16122* (2013.01); *C12N 2760/16222* (2013.01); *C12N 2770/16022* (2013.01); *C12N 2770/16023* (2013.01); *C12N 2770/18043* (2013.01)

(58) Field of Classification Search
CPC ................................................ C12N 15/8258
USPC ........................................................ 800/288
See application file for complete search history.

(56) References Cited

U.S. PATENT DOCUMENTS

2010/0287670 A1    11/2010    Sainsbury et al.

FOREIGN PATENT DOCUMENTS

| CA | 2984402 | 11/2016 |
|---|---|---|
| WO | 2009009876 | 1/2009 |
| WO | 2009076778 | 6/2009 |
| WO | 2010003225 | 1/2010 |
| WO | 2010148511 | 12/2010 |
| WO | 2012083445 | 6/2012 |
| WO | 2014153674 | 10/2014 |
| WO | 2015103704 A1 | 7/2015 |
| WO | 2016175132 | 11/2016 |
| WO | 2020168424 | 2/2020 |

OTHER PUBLICATIONS

Diamos et al. Frontiers in Plant Science 7:1-15 (Year: 2016).*
Oommenn et al The Plant Cell 6:1789-1803 (Year: 1994).*
Kim et al. Plant Molecular Biology 24: 105-117 (Year: 1994).*
Suzuki et al. Genbank Accession No. FS398156 (Year: 2009).*
Mardanova, Eugenia S., et al. Efficient Transient Expression of Recombinant Proteins in Plants by the Novel pEff Vector Based on the Genome of Potato Virus X., Feb. 28, 2017, Frontiers in Plant Science vol. 8, pp. 247-247.
GenBank Accession DR233261, created Feb. 24, 2006, last updated Feb. 15, 2011.
GenBank Access No. KA736759.1, TSA: Nicotiana benthamiana isotig00503.Nb_leaf mRNA sequence, submitted Aug. 14, 2012.
Diamos et.al "5' and 3' Untranslated Regions Strongly Enhance Perfrmance of Geminiviral Replicons in Nicotiana benthamiana leaves." (Frontiers in Plant Science, Feb. 24, 2016, vol. 7, pp. 1-15.
Yamasaski, Shotaro, et al. "*Arabidopsis thaliana* cold-regulated 47 gene 5'-untranslated region enables stable highlevel expression of transgenes." Journal of Bioscience and Bioengineering, vol. 125:1, pp. 124-130, 2018.
Accession EL172408 (EB3RODY01EHBFZ 8-day *Arabidopsis* seedlings, aerial tissues) Weber, A., et al. Sampling the *Arabidopsis* transcriptome with massively parallel pyrosequencing. Plant Physiol. 144:1, 32-44, 2007.
Accession EL131742 EB3RODY01CTWVV 8-day *Arabidopsis* seedlings, aerial tissues, Weber. A., et al. Sampling the *Arabidopsis* transcriptome with massively parallel pyrosequencing. Plant Physiol. 144:1, 32-44, 2007.
Davey MR et al., "Plant protoplasts: status and biotechnological perspectives", Biotechnology Advances, 2005, 23:131-171.
Dvir S. et al., "Deciphering the rules by which 5'-UTR sequences affectprotein expression in yeast", PNAS published online Jul. 15, 2013.

(Continued)

*Primary Examiner* — Li Zheng
(74) *Attorney, Agent, or Firm* — Ballard Spahr LLP

(57) ABSTRACT

An isolated expression enhancer active in a plant, portion of a plant or plant cell, the expression enhancer is provided. The isolated expression enhancer may be selected from the group consisting of nbMT78 (SEQ ID NO:1); nbATL75 (SEQ ID NO:2); nbDJ46 (SEQ ID NO:3); nbCHP79 (SEQ ID NO:4); nbEN42 (SEQ ID NO:5); atHSP69 (SEQ ID NO:6); atGRP62 (SEQ ID NO:7); atPK65 (SEQ ID NO:8); atRP46 (SEQ ID NO:9); nb30S72 (SEQ ID NO:10); nbGT61 (SEQ ID NO:11); nbPV55 (SEQ ID NO:12); nbPPI43 (SEQ ID NO:13); nbPM64 (SEQ ID NO:14); and nbH2A86 (SEQ ID NO:15). Methods for using the isolated expression enhancer are also provided.

19 Claims, 65 Drawing Sheets

Specification includes a Sequence Listing.

(56) References Cited

OTHER PUBLICATIONS

Leppek K et. al., "Functional 5' UTR mRNA structures in eukaryotic translation regulation and how to find them" Nature Reviews, Mar. 2018, Mol. Cell Biol. 19:158-174.
D'Aoust et al., The production of hemagglutinin-based virus-like particles in plants: a rapid, efficient and safe response to pandemic influenza, Plant Biotechnology Journal, 8, 1-13, 2010.
International Preliminary Report for PCT/CA2019/050317, Jun. 16, 2020.

* cited by examiner

PRIOR ART (Diamos et. al., 2016)

Figure 15A  nbMT78 (SEQ ID NO:1);

ACACAATTTGCTTTAGTGATTAAACTTTCTTTTACAACAAATTAAAGGTCTATTATCTCCCAACAACATAAGAAAACA

FIGURE 15B  nbATL75 (SEQ ID NO:2);

ATCTCCACCACCAAAAACCCTAATCGCCTCTCCGTTTCTTCATCAGATTCTCGGTTCTCTTCTTCTACAGCAACA

FIGURE 15C  nbDJ46 (SEQ ID NO:3);

ACTCACCAAGAAAATAAACAAATTAAAGAATTTTAAGAAAAACAAG

FIGURE 15D  nbCHP79 (SEQ ID NO:4);

ATTCTGCCCTCAGTTAACTAAATTATCTCTCTGATTAACAGTACTTTCTGATTTTCTGTGATTTCTACAAATCTGAGAC

FIGURE 15E  nbEN42 (SEQ ID NO:5);

ACTTTTGTATAGCTCCATTGAAATAGAGAAAAGAAAATAGCC

FIGURE 15F  atHSP69 (SEQ ID NO:6);

AAATTCAAAATTTAACACACAAACACAAACACACACACCAAAAAAAACACAGACCTTAAAAAAATAAAA

FIGURE 15G  atGRP62 (SEQ ID NO:7);

ATAACAAAACAAGATTTTGAAGTAAAACATAAAAGAAAATAAACCCTAAGAATATATCGAAA

FIGURE 15H  atPK65 (SEQ ID NO:8);

GCAAAAACAAAAATAAAAAAAACATCGCACAAGAAAATAAAAGATTTGTAGAATCAACTAAGAAA

FIGURE 15I  atRP46 (SEQ ID NO:9);

AGAAACAAAAGAATTAAAAAAAAAAAAAAAAAAAGAATAAAGAA

FIGURE 15J  nb30S72 (SEQ ID NO:10);

ATCTTTCCCTCAAAACCCTAGCCGCAGTCACTTCCGTAGGTGCTTACTTCGCTGTTAGTGCAATTCCAAA
CC

FIGURE 15K  nbGT61 (SEQ ID NO:11);

ATCCAGAAGTAGGAATTCTTCAGTATAATCTAGGGTTTTTTGAAAAGCAAATTGATCGAAA

FIGURE 15L  nbPV55 (SEQ ID NO:12);

AATTAAAGATCAATTCACTGTATCCCTCTTCTCCAAAAAAAACTCTGCTGTAGTC

FIGURE 15M  nbPPI43 (SEQ ID NO:13);

ACAAATCGTACACAGCGAAAACCTCACTGAAATATTTAGAGAG

FIGURE 15N  nbPM64 (SEQ ID NO:14);

AGAAAGATTTGTTTCCTCTGAAATAGTTTTACAGAGCCAGAAGAAGAAAAAGAAGAAGAGAGCA

FIGURE 15O  nbH2A86 (SEQ ID NO:15);

ACTCAACACTCAAATCGCAATCCAAAAGCTTCAATTTTTCCTAATACTTCTCTGTATTCAAGCTTCGTAA
ACTTTCATTCACATCA

FIGURE 15P  CPMV 160 (SEQ ID NO:16) PRIOR ART:

TATTAAAATCTTAATAGGTTTTGATAAAAGCGAACGTGGGGAAACCCGAACCAAACCTTCTTCTAAACTC
TCTCTCATCTCTCTTAAAGCAAACTTCTCTCTTGTCTTTCTTGCGTGAGCGATCTTCAACGTTGTCAGAT
CGTGCTTCGGCACCAGTACA

FIGURE 16A: Primers for Dasher constructs nbMT78_Dasher.c (SEQ ID NO:17)

TTAAAGGTCTATTATCTCCCAACAACATAAGAAAACAATGACTGCCCTGACCGAAGGTG

IF-Dasher(27-609).r (SEQ ID NO:18)

ACTAAAGAAAATAGGCCTTTACTGATAGGTATCGAGATCGACGGCCTTGACCACTT

IF-nbMT78.c (SEQ ID NO:19)

TTTCATTTGGAGAGGCACACAATTTGCTTTAGTGATTAAACTTTCTTTTACAACAAATTAAAGGTCTATT
ATCTCCCAACAACATAAGA

IF-(2X35S+C)_CPMV160.c (SEQ ID NO:23)

TTTCATTTGGAGAGGCTATTAAAATCTTAATAGGTTTTGATAAAAGCG nbGT61_Dasher.c (SEQ ID NO:24)

AGGGTTTTTTGAAAAGCAAATTGATCGAAAATGACTGCCCTGACCGAAGGTGCTAAGCT

IF-nbGT61.c (SEQ ID NO:25)

TTTCATTTGGAGAGGCATCCAGAAGTAGGAATTCTTCAGTATAATCTAGGGTTTTTTGAAAAGCAAATTG
ATCG nbATL75_Dasher.c (SEQ ID NO:26)

GATTCTCGGTTCTCTTCTTCTACAGCAACAATGACTGCCCTGACCGAAGGTGCTAAGCT

IF-nbATL75.c (SEQ ID NO:27)

TTTCATTTGGAGAGGCATCTCCACCACCAAAAACCCTAATCGCCTCTCCGTTTCTTCATCAGATTCTCGG
TTCTCTTCTTCTACAGC nbDJ46_Dasher.c (SEQ ID NO:28)

TAAACAAATTAAAGAATTTTAAGAAAAACAAGATGACTGCCCTGACCGAAGGTGCTAAG

IF-nbDJ46.c (SEQ ID NO:29)

TTTCATTTGGAGAGGCACTCACCAAGAAAATAAACAAATTAAAGAATTTTAAGAAAAAC nbCHP79_Dasher.c (SEQ ID NO:30)

TTCTGATTTTCTGTGATTTCTACAAATCTGAGACATGACTGCCCTGACCGAAGGTGCTA

IF-nbCHP79.c (SEQ ID NO:31)

TTTCATTTGGAGAGGCATTCTGCCCTCAGTTAACTAAATTATCTCTCTGATTAACAGTACTTTCTGATTT
CTGTGATTTCTACAA nbEN42_Dasher.c (SEQ ID NO:32)

CTCCATTGAAATAGAGAAAAGAAAATAGCCATGACTGCCCTGACCGAAGGTGCTAAGCT

IF-nbEN42.c (SEQ ID NO:33)

TTTCATTTGGAGAGGCACTTTTGTATAGCTCCATTGAAATAGAGAAAAGAAA

FIGURE 16A (continued-1)

nb30S72_Dasher.c (SEQ ID NO:34)

TGCTTACTTCGCTGTTAGTGCAATTCCAAACCATGACTGCCCTGACCGAAGGTGCTAAG

IF-nb30S72.c (SEQ ID NO:35)

TTTCATTTGGAGAGGCATCTTTCCCTCAAAACCCTAGCCGCAGTCACTTCCGTAGGTGCTTACTTCGCTGTTAGTGCAATTCCAA nbPV55_Dasher.c (SEQ ID NO:36)

CCCTCTTCTCCAAAAAAAACTCTGCTGTAGTCATGACTGCCCTGACCGAAGGTGCTAAG

IF-nbPV55.c (SEQ ID NO:37)

TTTCATTTGGAGAGGCAATTAAAGATCAATTCACTGTATCCCTCTTCTCCAAAAAAACTCTGCTGTAGT nbPPI43_Dasher.c (SEQ ID NO:38)

CAGCGAAAACCTCACTGAAATATTTAGAGAGATGACTGCCCTGACCGAAGGTGCTAAGC

IF-nbPPI43.c (SEQ ID NO:39)

TTTCATTTGGAGAGGCACAAATCGTACACAGCGAAAACCTCACTGAAATATTTAGAG nbPM64_Dasher.c (SEQ ID NO:40)

AGAGCCAGAAGAAGAAAAAGAAGAAGAGAGCAATGACTGCCCTGACCGAAGGTGCTAAG

IF-nbPM64.c (SEQ ID NO:41)

TTTCATTTGGAGAGGCAGAAAGATTTGTTTCCTCTGAAATAGTTTTACAGAGCCAGAAGAAGAAAAAGAAGAAGAGAGC nbH2A86_Dasher.c (SEQ ID NO:42)

GTATTCAAGCTTCGTAAACTTTCATTCACATCAATGACTGCCCTGACCGAAGGTGCTAA

IF-nbH2A86.c (SEQ ID NO:43)

TTTCATTTGGAGAGGCACTCAACACTCAAATCGCAATCCAAAAGCTTCAATTTTTCCTAATACTTCTCTGTATTCAAGCTTCGTAAACTTTCATTCACAT atHSP69_Dasher.c (SEQ ID NO:44)

CCAAAAAAAACACAGACCTTAAAAAAATAAAAATGACTGCCCTGACCGAAGGTGCTAAG

IF-atHSP69.c (SEQ ID NO:45)

TTTCATTTGGAGAGGCAAATTCAAAATTTAACACACAAACACAAACACACACCAAAAAAAACACAGACCTTAAAAAAATAAA atGRP62_Dasher.c (SEQ ID NO:46)

AAGAAAATAAACCCTAAGAATATATCGAAAATGACTGCCCTGACCGAAGGTGCTAAGCT

FIGURE 16A (continued -2)

IF-atGRP62.c (SEQ ID NO:47)

TTTCATTTGGAGAGGCATAACAAAACAAGATTTTGAAGTAAAACATAAAAGAAAATAAACCCTAAGAATA
TATCGAA atPK65_Dasher.c (SEQ ID NO:48)

AATAAAAGATTTGTAGAATCAACTAAGAAAATGACTGCCCTGACCGAAGGTGCTAAGCT

IF-atPK65.c (SEQ ID NO:49)

TTTCATTTGGAGAGGCGCAAAAACAAAAATAAAAAAAACATCGCACAAGAAAATAAAAGATTTGTAGAAT
CAACTAAGAA

IF-atRP46_Dasher.c (SEQ ID NO:50)

TTTCATTTGGAGAGGCAGAAACAAAAGAATTAAAAAAAAAAAAAAAAAAAAGAATAAAGAAATGACTGC
CCTGACCGAAGGTGCTAAG

FIGURE 16B: CPMV 160 5'UTR-Dasher nucleic acid sequence (SEQ ID NO:20)

TATTAAAATCTTAATAGGTTTTGATAAAAGCGAACGTGGGGAAACCCGAACCAAACCTTCTTCTAAACTC
TCTCTCATCTCTCTTAAAGCAAACTTCTCTCTTGTCTTTCTTGCGTGAGCGATCTTCAACGTTGTCAGAT
CGTGCTTCGGCACCAGTACAATGACTGCCCTGACCGAAGGTGCTAAGCTGTTTGAGAAGGAGATTCCGTA
CATCACCGAGCTGGAAGGGGACGTCGAAGGAATGAAGTTCATCATCAAGGGAGAAGGAACCGGGGACGCT
ACGACTGGAACCATTAAGGCCAAGTATATCTGTACCACTGGAGATCTGCCAGTGCCTTGGGCCACCCTTG
TGTCAACCCTCTCGTATGGAGTGCAGTGTTTTGCTAAGTACCCTAGCCACATTAAGGACTTCTTCAAATC
CGCCATGCCGGAAGGTTATACCCAAGAGCGCACCATTTCTTTTGAGGGAGATGGAGTGTACAAGACCCGC
GCGATGGTCACCTATGAGAGGGATCTATCTACAACCGGGTGACTCTGACTGGAGAAAACTTTAAGAAGG
ACGGGCATATTCTTCGGAAGAATGTCGCCTTCCAGTGCCCTCCCAGCATCCTTTACATTCTCCCCGACAC
TGTGAACAACGGAATCCGCGTGGAGTTCAATCAAGCCTACGACATCGAGGGGTGACGGAGAAGCTGGTG
ACCAAGTGTAGCCAGATGAATCGGCCACTGGCCGGTTCAGCGGCTGTCCACATTCCGCGCTACCATCATA
TCACTTATCACACTAAGCTCTCCAAAGACCGCGATGAGAGGAGAGATCACATGTGCCTGGTGGAAGTGGT
CAAGGCCGTCGATCTCGATACCTATCAGTAA

Figure 16C: Dasher nucleic acid sequence (SEQ ID NO:78)

ATGACTGCCCTGACCGAAGGTGCTAAGCTGTTTGAGAAGGAGATTCCGTACATCACCGAGCTGGAAGGGG
ACGTCGAAGGAATGAAGTTCATCATCAAGGGAGAAGGAACCGGGGACGCTACGACTGGAACCATTAAGGC
CAAGTATATCTGTACCACTGGAGATCTGCCAGTGCCTTGGGCCACCCTTGTGTCAACCCTCTCGTATGGA
GTGCAGTGTTTTGCTAAGTACCCTAGCCACATTAAGGACTTCTTCAAATCCGCCATGCCGGAAGGTTATA
CCCAAGAGCGCACCATTTCTTTTGAGGGAGATGGAGTGTACAAGACCCGCGCGATGGTCACCTATGAGAG
GGGATCTATCTACAACCGGGTGACTCTGACTGGAGAAAACTTTAAGAAGGACGGGCATATTCTTCGGAAG
AATGTCGCCTTCCAGTGCCCTCCCAGCATCCTTTACATTCTCCCCGACACTGTGAACAACGGAATCCGCG
TGGAGTTCAATCAAGCCTACGACATCGAGGGGGTGACGGAGAAGCTGGTGACCAAGTGTAGCCAGATGAA
TCGGCCACTGGCCGGTTCAGCGGCTGTCCACATTCCGCGCTACCATCATATCACTTATCACACTAAGCTC
TCCAAAGACCGCGATGAGAGGAGAGATCACATGTGCCTGGTGGAAGTGGTCAAGGCCGTCGATCTCGATA
CCTATCAGTAA

FIGURE 16D: Dasher amino acid sequence (SEQ ID NO:21)

MTALTEGAKLFEKEIPYITELEGDVEGMKFIIKGEGTGDATTGTIKAKYICTTGDLPVPWATLVSTLSYG
VQCFAKYPSHIKDFFKSAMPEGYTQERTISFEGDGVYKTRAMVTYERGSIYNRVTLTGENFKKDGHILRK
NVAFQCPPSILYILPDTVNNGIRVEFNQAYDIEGVTEKLVTKCSQMNRPLAGSAAVHIPRYHHITYHTKL
SKDRDERRDHMCLVEVVKAVDLDTYQ

FIGURE 16E: Construct 4467 (Dasher) from 2X35S promoter to NOS terminator (SEQ ID NO:75)

GTCAACATGGTGGAGCACGACACACTTGTCTACTCCAAAAATATCAAAGATACAGTCTCAGAAGACCAAA
GGGCAATTGAGACTTTTCAACAAAGGGTAATATCCGGAAACCTCCTCGGATTCCATTGCCCAGCTATCTG
TCACTTTATTGTGAAGATAGTGGAAAAGGAAGGTGGCTCCTACAAATGCCATCATTGCGATAAAGGAAAG
GCCATCGTTGAAGATGCCTCTGCCGACAGTGGTCCCAAAGATGGACCCCCACCCACGAGGAGCATCGTGG
AAAAAGAAGACGTTCCAACCACGTCTTCAAAGCAAGTGGATTGATGTGATAACATGGTGGAGCACGACAC
ACTTGTCTACTCCAAAAATATCAAAGATACAGTCTCAGAAGACCAAAGGGCAATTGAGACTTTTCAACAA
AGGGTAATATCCGGAAACCTCCTCGGATTCCATTGCCCAGCTATCTGTCACTTTATTGTGAAGATAGTGG
AAAAGGAAGGTGGCTCCTACAAATGCCATCATTGCGATAAAGGAAAGGCCATCGTTGAAGATGCCTCTGC
CGACAGTGGTCCCAAAGATGGACCCCCACCCACGAGGAGCATCGTGGAAAAAGAAGACGTTCCAACCACG
TCTTCAAAGCAAGTGGATTGATGTGATATCTCCACTGACGTAAGGGATGACGCACAATCCCACTATCCTT
CGCAAGACCCTTCCTCTATATAAGGAAGTTCATTTCATTTGGAGAGGCACACAATTTGCTTTAGTGATTA
AACTTTCTTTTACAACAAATTAAAGGTCTATTATCTCCCAACAACATAAGAAAACAATGACTGCCCTGAC
CGAAGGTGCTAAGCTGTTTGAGAAGGAGATTCCGTACATCACCGAGCTGGAAGGGACGTCGAAGGAATG
AAGTTCATCATCAAGGGAGAAGGAACCGGGGACGCTACGACTGGAACCATTAAGGCCAAGTATATCTGTA
CCACTGGAGATCTGCCAGTGCCTTGGGCCACCCTTGTGTCAACCCTCTCGTATGGAGTGCAGTGTTTTGC
TAAGTACCCTAGCCACATTAAGGACTTCTTCAAATCCGCCATGCCGGAAGGTTATACCCAAGAGCGCACC
ATTTCTTTTGAGGGAGATGGAGTGTACAAGACCCGCGCGATGGTCACCTATGAGAGGGGATCTATCTACA
ACCGGGTGACTCTGACTGGAGAAAACTTTAAGAAGGACGGGCATATTCTTCGGAAGAATGTCGCCTTCCA
GTGCCCTCCCAGCATCCTTTACATTCTCCCCGACACTGTGAACAACGGAATCCGCGTGGAGTTCAATCAA
GCCTACGACATCGAGGGGGTGACGGAGAAGCTGGTGACCAAGTGTAGCCAGATGAATCGGCCACTGGCCG
GTTCAGCGGCTGTCCACATTCCGCGCTACCATCATATCACTTATCACACTAAGCTCTCCAAAGACCGCGA
TGAGAGGAGAGATCACATGTGCCTGGTGGAAGTGGTCAAGGCCGTCGATCTCGATACCTATCAGTAAAGG
CCTATTTTCTTTAGTTTGAATTTACTGTTATTCGGTGTGCATTTCTATGTTTGGTGAGCGGTTTTCTGTG

FIGURE 16E (Continued)

CTCAGAGTGTGTTTATTTTATGTAATTTAATTTCTTTGTGAGCTCCTGTTTAGCAGGTCGTCCCTTCAGC
AAGGACACAAAAGATTTTAATTTTATTATCGTTCAAACATTTGGCAATAAAGTTTCTTAAGATTGAATC
CTGTTGCCGGTCTTGCGATGATTATCATATAATTTCTGTTGAATTACGTTAAGCATGTAATAATTAACAT
GTAATGCATGACGTTATTTATGAGATGGGTTTTTATGATTAGAGTCCCGCAATTATACATTTAATACGCG
ATAGAAAACAAAATATAGCGCGCAAACTAGGATAAATTATCGCGCGCGGTGTCATCTATGTTACTAGAT

FIGURE 16F: Cloning vector (for Dasher) 1666 from left to right T-DNA (SEQ ID NO: 22)

TGGCAGGATATATTGTGGTGTAAACAAATTGACGCTTAGACAACTTAATAACACATTGCGGACGTTTTTA
ATGTACTGAATTAACGCCGAATCCCGGGCTGGTATATTTATATGTTGTCAAATAACTCAAAAACCATAAA
AGTTTAAGTTAGCAAGTGTGTACATTTTTACTTGAACAAAAATATTCACCTACTACTGTTATAAATCATT
ATTAAACATTAGAGTAAAGAAATATGGATGATAAGAACAAGAGTAGTGATATTTTGACAACAATTTTGTT
GCAACATTTGAGAAAATTTTGTTGTTCTCTCTTTTCATTGGTCAAAAACAATAGAGAGAGAAAAAGGAAG
AGGGAGAATAAAAACATAATGTGAGTATGAGAGAGAAAGTTGTACAAAAGTTGTACCAAAATAGTTGTAC
AAATATCATTGAGGAATTTGACAAAAGCTACACAAATAAGGGTTAATTGCTGTAAATAAATAAGGATGAC
GCATTAGAGAGATGTACCATTAGAGAATTTTTGGCAAGTCATTAAAAAGAAAGAATAAATTATTTTTAAA
ATTAAAAGTTGAGTCATTTGATTAAACATGTGATTATTTAATGAATTGATGAAAGAGTTGGATTAAAGTT
GTATTAGTAATTAGAATTTGGTGTCAAATTTAATTTGACATTTGATCTTTTCCTATATATTGCCCCATAG
AGTCAGTTAACTCATTTTTATATTTCATAGATCAAATAAGAGAAATAACGGTATATTAATCCCTCCAAAA
AAAAAAAACGGTATATTTACTAAAAAATCTAAGCCACGTAGGAGGATAACAGGATCCCCGTAGGAGGATA
ACATCCAATCCAACCAATCACAACAATCCTGATGAGATAACCCACTTTAAGCCCACGCATCTGTGGCACA
TCTACATTATCTAAATCACACATTCTTCCACACATCTGAGCCACACAAAAACCAATCCACATCTTTATCA
CCCATTCTATAAAAAATCACACTTTGTGAGTCTACACTTTGATTCCCTTCAAACACATACAAAGAGAAGA
GACTAATTAATTAATTAATCATCTTGAGAGAAAATGGAACGAGCTATACAAGGAAACGACGCTAGGGAAC
AAGCTAACAGTGAACGTTGGGATGGAGGATCAGGAGGTACCACTTCTCCCTTCAAACTTCCTGACGAAAG
TCCGAGTTGGACTGAGTGGCGGCTACATAACGATGAGACGAATTCGAATCAAGATAATCCCCTTGGTTTC
AAGGAAAGCTGGGGTTTCGGGAAAGTTGTATTTAAGAGATATCTCAGATACGACAGGACGGAAGCTTCAC
TGCACAGAGTCCTTGGATCTTGGACGGGAGATTCGGTTAACTATGCAGCATCTCGATTTTTCGGTTTCGA
CCAGATCGGATGTACCTATAGTATTCGGTTTCGAGGAGTTAGTATCACCGTTTCTGGAGGGTCGCGAACT
CTTCAGCATCTCTGTGAGATGGCAATTCGGTCTAAGCAAGAACTGCTACAGCTTGCCCCAATCGAAGTGG
AAAGTAATGTATCAAGAGGATGCCCTGAAGGTACTCAAACCTTCGAAAAAGAAAGCGAGTAAGTTAAAAT
GCTTCTTCGTCTCCTATTTATAATATGGTTTGTTATTGTTAATTTTGTTCTTGTAGAAGAGCTTAATTAA
TCGTTGTTGTTATGAAATACTATTTGTATGAGATGAACTGGTGTAATGTAATTCATTTACATAAGTGGAG
TCAGAATCAGAATGTTTCCTCCATAACTAACTAGACATGAAGACCTGCCGCGTACAATTGTCTTATATTT
GAACAACTAAAATTGAACATCTTTTGCCACAACTTTATAAGTGGTTAATATAGCTCAAATATATGGTCAA
GTTCAATAGATTAATAATGGAAATATCAGTTATCGAAATTCATTAACAATCAACTTAACGTTATTAACTA
CTAATTTTATATCATCCCCTTTGATAAATGATAGTACACCAATTAGGAAGGAGCATGCTCGCCTAGGAGA
TTGTCGTTTCCCGCCTTCAGTTTGCAAGCTGCTCTAGCCGTGTAGCCAATACGCAAACCGCCTCTCCCCG
CGCGTTGGGAATTACTAGCGCGTGTCGACAAGCTTGCATGCCGGTCAACATGGTGGAGCACGACACACTT
GTCTACTCCAAAAATATCAAAGATACAGTCTCAGAAGACCAAAGGGCAATTGAGACTTTTCAACAAAGGG
TAATATCCGGAAACCTCCTCGGATTCCATTGCCCAGCTATCTGTCACTTTATTGTGAAGATAGTGGAAAA
GGAAGGTGGCTCCTACAAATGCCATCATTGCGATAAAGGAAAGGCCATCGTTGAAGATGCCTCTGCCGAC
AGTGGTCCCAAAGATGGACCCCCACCCACGAGGAGCATCGTGGAAAAAGAAGACGTTCCAACCACGTCTT
CAAAGCAAGTGGATTGATGTGATAACATGGTGGAGCACGACACACTTGTCTACTCCAAAAATATCAAAGA
TACAGTCTCAGAAGACCAAAGGGCAATTGAGACTTTTCAACAAAGGGTAATATCCGGAAACCTCCTCGGA

FIGURE 16F (continued-1)

```
TTCCATTGCCCAGCTATCTGTCACTTTATTGTGAAGATAGTGGAAAAGGAAGGTGGCTCCTACAAATGCC
ATCATTGCGATAAAGGAAAGGCCATCGTTGAAGATGCCTCTGCCGACAGTGGTCCCAAAGATGGACCCCC
ACCCACGAGGAGCATCGTGGAAAAAGAAGACGTTCCAACCACGTCTTCAAAGCAAGTGGATTGATGTGAT
ATCTCCACTGACGTAAGGGATGACGCACAATCCCACTATCCTTCGCAAGACCCTTCCTCTATATAAGGAA
GTTCATTTCATTTGGAGAGGACGTCACTCCTCAGCCAAAACGACACCCCATCTGTCTATCCACTGGCCC
CTGGATCTGCTGCCCAAACTAACTCCATGGTGACCCTGGGATGCCTGGTCAAGGGCTATTTCCCTGAGCC
AGTGACAGTGACCTGGAACTCTGGATCCCTGTCCAGCGGTGTGCACACCTTCCCAGCTGTCCTGCAGTCT
GACCTCTACACTCTGAGCAGCTCAGTGACTGTCCCCTCCAGCACCTGGCCCAGCGAGACCGTCACCTGCA
ACGTTGCCCACCCGGCCAGCAGCACCAAGGTGGACAAGAAATTGTGCCCAGGGATTGTGGTTGTAAGCC
TTGCATATGTACAGTCCCAGAAGTATCATCTGTCTTCATCTTCCCCCCAAAGCCCAAGGATGTGCTCACC
ATTACTCTGACTCCTAAGGTCACGTGTGTTGTGGTAGACATCAGCAAGGATGATCCCGAGGTCCAGTTCA
GCTGGTTTGTAGATGATGTGGAGGTGCACACAGCTCAGACGCAACCCCGGGAGGAGCAGTTCAACAGCAC
TTTCCGCTCAGTCAGTGAACTTCCCATCATGCACCAGGACTGGCTCAATGGCAAGGAGACGTCCAGATTT
TGGCGATCTATTCAACTGTCGCCAGTTCATTGGTACTGGTAGTCTCCCTGGGGCAATCAGTTTCTGGAT
GTGCTCTAATGGGTCTCTACAGTGTAGAATATGTATTTAAAGGCCTATTTTCTTTAGTTTGAATTTACTG
TTATTCGGTGTGCATTTCTATGTTTGGTGAGCGGTTTTCTGTGCTCAGAGTGTGTTTATTTTATGTAATT
TAATTTCTTTGTGAGCTCCTGTTTAGCAGGTCGTCCCTTCAGCAAGGACACAAAAAGATTTTAATTTTAT
TATCGTTCAAACATTTGGCAATAAAGTTTCTTAAGATTGAATCCTGTTGCCGGTCTTGCGATGATTATCA
TATAATTTCTGTTGAATTACGTTAAGCATGTAATAATTAACATGTAATGCATGACGTTATTTATGAGATG
GGTTTTTATGATTAGAGTCCCGCAATTATACATTTAATACGCGATAGAAAACAAAATATAGCGCGCAAAC
TAGGATAAATTATCGCGCGCGGTGTCATCTATGTTACTAGATCTCTAGAGTCTCAAGCTTGGCGCGCCCA
CGTGACTAGTGGCACTGGCCGTCGTTTTACAACGTCGTGACTGGGAAAACCCTGGCGTTACCCAACTTAA
TCGCCTTGCAGCACATCCCCCTTTCGCCAGCTGGCGTAATAGCGAAGAGGCCCGCACCGATCGCCCTTCC
CAACAGTTGCGCAGCCTGAATGGCGAATGCTAGAGCAGCTTGAGCTTGGATCAGATTGTCGTTTCCCGCC
TTCAGTTTAAACTATCAGTGTTTGACAGGATATATTGGCGGGTAAACCTAAGAGAAAAGAGCGTTTA
```

FIGURE 17A: Primers for H1 A Cal-7-09, H1 A-Mich-45-15, H3 HK-4801-14, HA B-Bris-60-08 and HA B-Phu-3073-13 constructs IF-H1cTMCT.s1-4r (SEQ ID NO:51)

ACTAAAGAAAATAGGCCTTTAAATACATATTCTACACTGTAGAGAC nbGT61_SpPDI.c (SEQ ID NO:52)

TAGGGTTTTTTGAAAAGCAAATTGATCGAAAATGGCGAAAAACGTTGCGATTTTCGGCT nbATL75_SpPDI.c (SEQ ID NO:53)

TTCTCGGTTCTCTTCTTCTACAGCAACAATGGCGAAAAACGTTGCGATTTTCGGCTTAT nbDJ46_SpPDI.c (SEQ ID NO:54)

AAACAAATTAAAGAATTTTAAGAAAACAAGATGGCGAAAAACGTTGCGATTTTCGGCT nbCHP79_SpPDI.c (SEQ ID NO:55)

CTTTCTGATTTTCTGTGATTTCTACAAATCTGAGACATGGCGAAAAACGTTGCGATTTT nbEN42_SpPDI.c (SEQ ID NO:56)

GCTCCATTGAAATAGAGAAAAGAAAATAGCCATGGCGAAAAACGTTGCGATTTTCGGCT nb30S72_SpPDI.c (SEQ ID NO:57)

AGGTGCTTACTTCGCTGTTAGTGCAATTCCAAACCATGGCGAAAAACGTTGCGATTTTC nbMT78_SpPDI.c (SEQ ID NO:58)

TATTATCTCCCAACAACATAAGAAAACAATGGCGAAAAACGTTGCGATTTTCGGCTTAT

FIGURE 17A (continued-1)

nbPV55_SpPDI.c (SEQ ID NO:59)

CCTCTTCTCCAAAAAAACTCTGCTGTAGTCATGGCGAAAAACGTTGCGATTTTCGGCT nbPPI43_SpPDI.c (SEQ ID NO:60)

CAGCGAAAACCTCACTGAAATATTTAGAGAGATGGCGAAAAACGTTGCGATTTTCGGCT nbPM64_SpPDI.c (SEQ ID NO:61)

CAGAAGAAGAAAAGAAGAAGAGAGCAATGGCGAAAAACGTTGCGATTTTCGGCTTATT nbH2A86_SpPDI.c (SEQ ID NO:62)

CAAGCTTCGTAAACTTTCATTCACATCAATGGCGAAAAACGTTGCGATTTTCGGCTTAT atHSP69_SpPDI.c (SEQ ID NO:63)

CAAAAAAAACACAGACCTTAAAAAAATAAAAATGGCGAAAAACGTTGCGATTTTCGGCT atGRP62_SpPDI.c (SEQ ID NO:64)

AAAGAAAATAAACCCTAAGAATATATCGAAAATGGCGAAAAACGTTGCGATTTTCGGCT atPK65_SpPDI.c (SEQ ID NO:65)

AAATAAAAGATTTGTAGAATCAACTAAGAAAATGGCGAAAAACGTTGCGATTTTCGGCT

IF-atRP46_SpPDI.c (SEQ ID NO:66)

TTTCATTTGGAGAGGCAGAAACAAAAGAATTAAAAAAAAAAAAAAAAAAAGAATAAAGAAATGGCGAA
AAACGTTGCGATTTTCGGC

IF-H3_Swi_13.r (SEQ ID NO:67)

ACTAAAGAAAATAGGCCTTCAAATGCAAATGTTGCACCTAATGTTGCCCTT

FIGURE17B: CPMV 160 5'UTR-PDI+H1 Cal nucleic acid sequence (SEQ ID NO:79)

TATTAAAATCTTAATAGGTTTTGATAAAAGCGAACGTGGGGAAACCCGAACCAAACCTTCTTCTAAACTC
TCTCTCATCTCTCTTAAAGCAAACTTCTCTCTTGTCTTTCTTGCGTGAGCGATCTTCAACGTTGTCAGAT
CGTGCTTCGGCACCAGTACAATGGCGAAAAACGTTGCGATTTTCGGCTTATTGTTTTCTCTTCTTGTGTT
GGTTCCTTCTCAGATCTTCGCGGACACATTATGTATAGGTTATCATGCGAACAATTCAACAGACACTGTA
GACACAGTACTAGAAAAGAATGTAACAGTAACACACTCTGTTAACCTTCTAGAAGACAAGCATAACGGGA
AACTATGCAAACTAAGAGGGGTAGCCCCATTGCATTTGGGTAAATGTAACATTGCTGGCTGGATCCTGGG
AAATCCAGAGTGTGAATCACTCTCCACAGCAAGCTCATGGTCCTACATTGTGGAAACACCTAGTTCAGAC
AATGGAACGTGTTACCCAGGAGATTTCATCGATTATGAGGAGCTAAGAGAGCAATTGAGCTCAGTGTCAT
CATTTGAAAGGTTTGAGATATTCCCCAAGACAAGTTCATGGCCCAATCATGACTCGAACAAAGGTGTAAC
GGCAGCATGTCCTCATGCTGGAGCAAAAAGCTTCTACAAAAATTTAATATGGCTAGTTAAAAAAGGAAAT
TCATACCCAAAGCTCAGCAAATCCTACATTAATGATAAAGGGAAAGAAGTCCTCGTGCTATGGGGCATTC
ACCATCCATCTACTAGTGCTGACCAACAAAGTCTCTATCAGAATGCAGATGCATATGTTTTTGTGGGGTC
ATCAAGATACAGCAAGAAGTTCAAGCCGGAAATAGCAATAAGACCCAAAGTGAGGGATCAAGAAGGGAGA
ATGAACTATTACTGGACACTAGTAGAGCCGGGAGACAAAATAACATTCGAAGCAACTGGAAATCTAGTGG
TACCGAGATATGCATTCGCAATGGAAAGAAATGCTGGATCTGGTATTATCATTTCAGATACACCAGTCCA
CGATTGCAATACAACTTGTCAAACACCCAAGGGTGCTATAAACACCAGCCTCCCATTTCAGAATATACAT
CCGATCACAATTGGAAAATGTCCAAAATATGTAAAAAGCACAAAATTGAGACTGGCCACAGGATTGAGGA
ATATCCCGTCTATTCAATCTAGAGGACTATTTGGGGCCATTGCCGGTTTCATTGAAGGGGGGTGGACAGG
GATGGTAGATGGATGGTACGGTTATCACCATCAAAATGAGCAGGGGTCAGGATATGCAGCCGACCTGAAG
AGCACACAGAATGCCATTGACGAGATTACTAACAAAGTAAATTCTGTTATTGAAAAGATGAATACACAGG
ACACAGCAGTAGGTAAAGAGTTCAACCACCTGGAAAAAAGAATAGAGAATTTAAATAAAAAAGTTGATGA
TGGTTTCCTGGACATTTGGACTTACAATGCCGAACTGTTGGTTCTATTGGAAAATGAAAGAACTTTGGAC
TACCACGATTCAAATGTGAAGAACTTATATGAAAAGGTAAGAAGCCAGCTAAAAAACAATGCCAAGGAAA
TTGGAAACGGCTGCTTTGAATTTTACCACAAATGCGATAACACGTGCATGGAAAGTGTCAAAAATGGGAC
TTATGACTACCCAAAATACTCAGAGGAAGCAAAATTAAACAGAGAAGAAATAGATGGGGTAAAGCTGGAA
TCAACAAGGATTTACCAGATTTTGGCGATCTATTCAACTGTCGCCAGTTCATTGGTACTGGTAGTCTCCC
TGGGGGCAATCAGTTTCTGGATGTGCTCTAATGGGTCTCTACAGTGTAGAATATGTATTTAA

FIGURE 17C: PDI+H1 Cal nucleic acid sequence (SEQ ID NO:80)

ATGGCGAAAAACGTTGCGATTTTCGGCTTATTGTTTTCTCTTCTTGTGTTGGTTCCTTCTCAGATCTTCG
CGGACACATTATGTATAGGTTATCATGCGAACAATTCAACAGACACTGTAGACACAGTACTAGAAAAGAA
TGTAACAGTAACACACTCTGTTAACCTTCTAGAAGACAAGCATAACGGGAAACTATGCAAACTAAGAGGG
GTAGCCCCATTGCATTTGGGTAAATGTAACATTGCTGGCTGGATCCTGGGAAATCCAGAGTGTGAATCAC
TCTCCACAGCAAGCTCATGGTCCTACATTGTGGAAACACCTAGTTCAGACAATGGAACGTGTTACCCAGG
AGATTTCATCGATTATGAGGAGCTAAGAGAGCAATTGAGCTCAGTGTCATCATTTGAAAGGTTTGAGATA
TTCCCCAAGACAAGTTCATGGCCCAATCATGACTCGAACAAAGGTGTAACGGCAGCATGTCCTCATGCTG
GAGCAAAAAGCTTCTACAAAAATTTAATATGGCTAGTTAAAAAAGGAAATTCATACCCAAAGCTCAGCAA
ATCCTACATTAATGATAAAGGGAAAGAAGTCCTCGTGCTATGGGGCATTCACCATCCATCTACTAGTGCT
GACCAACAAAGTCTCTATCAGAATGCAGATGCATATGTTTTTGTGGGGTCATCAAGATACAGCAAGAAGT
TCAAGCCGGAAATAGCAATAAGACCCAAAGTGAGGGATCAAGAAGGGAGAATGAACTATTACTGGACACT
AGTAGAGCCGGGAGACAAAATAACATTCGAAGCAACTGGAAATCTAGTGGTACCGAGATATGCATTCGCA
ATGGAAAGAAATGCTGGATCTGGTATTATCATTTCAGATACACCAGTCCACGATTGCAATACAACTTGTC
AAACACCCAAGGGTGCTATAAACACCAGCCTCCCATTTCAGAATATACATCCGATCACAATTGGAAAATG
TCCAAAATATGTAAAAAGCACAAAATTGAGACTGGCCACAGGATTGAGGAATATCCCGTCTATTCAATCT

FIGURE 17C (continued)

AGAGGACTATTTGGGGCCATTGCCGGTTTCATTGAAGGGGGGTGGACAGGGATGGTAGATGGATGGTACG
GTTATCACCATCAAAATGAGCAGGGGTCAGGATATGCAGCCGACCTGAAGAGCACACAGAATGCCATTGA
CGAGATTACTAACAAAGTAAATTCTGTTATTGAAAAGATGAATACACAGGACACAGCAGTAGGTAAAGAG
TTCAACCACCTGGAAAAAGAATAGAGAATTTAAATAAAAAAGTTGATGATGGTTTCCTGGACATTTGGA
CTTACAATGCCGAACTGTTGGTTCTATTGGAAAATGAAAGAACTTTGGACTACCACGATTCAAATGTGAA
GAACTTATATGAAAGGTAAGAAGCCAGCTAAAAAACAATGCCAAGGAAATTGGAAACGGCTGCTTTGAA
TTTTACCACAAATGCGATAACACGTGCATGGAAAGTGTCAAAAATGGGACTTATGACTACCCAAAATACT
CAGAGGAAGCAAAATTAAACAGAGAAGAAATAGATGGGGTAAAGCTGGAATCAACAAGGATTTACCAGAT
TTTGGCGATCTATTCAACTGTCGCCAGTTCATTGGTACTGGTAGTCTCCCTGGGGGCAATCAGTTTCTGG
ATGTGCTCTAATGGGTCTCTACAGTGTAGAATATGTATTTAA

FIGURE 17D: PDI+H1 Cal amino acid sequence (SEQ ID NO:81)

MAKNVAIFGLLFSLLVLVPSQIFADTLCIGYHANNSTDTVDTVLEKNVTVTHSVNLLEDKHNGKLCKLRG
VAPLHLGKCNIAGWILGNPECESLSTASSWSYIVETPSSDNGTCYPGDFIDYEELREQLSSVSSFERFEI
FPKTSSWPNHDSNKGVTAACPHAGAKSFYKNLIWLVKKGNSYPKLSKSYINDKGKEVLVLWGIHHPSTSA
DQQSLYQNADAYVFVGSSRYSKKFKPEIAIRPKVRDQEGRMNYYWTLVEPGDKITFEATGNLVVPRYAFA
MERNAGSGIIISDTPVHDCNTTCQTPKGAINTSLPFQNIHPITIGKCPKYVKSTKLRLATGLRNIPSIQS
RGLFGAIAGFIEGGWTGMVDGWYGYHHQNEQGSGYAADLKSTQNAIDEITNKVNSVIEKMNTQDTAVGKE
FNHLEKRIENLNKKVDDGFLDIWTYNAELLVLLENERTLDYHDSNVKNLYEKVRSQLKNNAKEIGNGCFE
FYHKCDNTCMESVKNGTYDYPKYSEEAKLNREEIDGVKLESTRIYQILAIYSTVASSLVLVVSLGAISFW
MCSNGSLQCRICI

FIGURE 17E: Cloning vector (for H3 and HA B) 4160 from left to right T-DNA (SEQ ID NO:76)

TGGCAGGATATATTGTGGTGTAAACAAATTGACGCTTAGACAACTTAATAACACATTGCGGACGTTTTA
ATGTACTGAATTAACGCCGAATCCCGGCTGGTATATTTATATGTTGTCAAATAACTCAAAAACCATAAA
AGTTTAAGTTAGCAAGTGTGTACATTTTTACTTGAACAAAAATATTCACCTACTACTGTTATAAATCATT
ATTAAACATTAGAGTAAAGAAATATGGATGATAAGAACAAGAGTAGTGATATTTTGACAACAATTTTGTT
GCAACATTTGAGAAAATTTTGTTGTTCTCTCTTTTCATTGGTCAAAAACAATAGAGAGAGAAAAAGGAAG
AGGGAGAATAAAAACATAATGTGAGTATGAGAGAGAAAGTTGTACAAAAGTTGTACCAAAATAGTTGTAC
AAATATCATTGAGGAATTTGACAAAAGCTACACAAATAAGGGTTAATTGCTGTAAATAAATAAGGATGAC
GCATTAGAGAGATGTACCATTAGAGAATTTTTGGCAAGTCATTAAAAAGAAAGAATAAATTATTTTTAAA
ATTAAAAGTTGAGTCATTTGATTAAACATGTGATTATTTAATGAATTGATGAAAGAGTTGGATTAAAGTT
GTATTAGTAATTAGAATTTGGTGTCAAATTTAATTTGACATTTGATCTTTTCCTATATATTGCCCCATAG
AGTCAGTTAACTCATTTTTATATTTCATAGATCAAATAAGAGAAATAACGGTATATTAATCCCTCCAAAA
AAAAAAAACGGTATATTTACTAAAAAATCTAAGCCACGTAGGAGGATAACAGGATCCCCGTAGGAGGATA
ACATCCAATCCAACCAATCACAACAATCCTGATGAGATAACCCACTTTAAGCCCACGCATCTGTGGCACA
TCTACATTATCTAAATCACACATTCTTCCACACATCTGAGCCACACAAAAACCAATCCACATCTTTATCA
CCCATTCTATAAAAAATCACACTTTGTGAGTCTACACTTTGATTCCCTTCAAACACATACAAAGAGAAGA
GACTAATTAATTAATTAATCATCTTGAGAGAAAATGGAACGAGCTATACAAGGAAACGACGCTAGGGAAC
AAGCTAACAGTGAACGTTGGGATGGAGGATCAGGAGGTACCACTTCTCCCTTCAAACTTCCTGACGAAAG

FIGURE 17E (Continued -1)

```
TCCGAGTTGGACTGAGTGGCGGCTACATAACGATGAGACGAATTCGAATCAAGATAATCCCCTTGGTTTC
AAGGAAAGCTGGGGTTTCGGGAAAGTTGTATTTAAGAGATATCTCAGATACGACAGGACGGAAGCTTCAC
TGCACAGAGTCCTTGGATCTTGGACGGGAGATTCGGTTAACTATGCAGCATCTCGATTTTTCGGTTTCGA
CCAGATCGGATGTACCTATAGTATTCGGTTTCGAGGAGTTAGTATCACCGTTTCTGGAGGGTCGCGAACT
CTTCAGCATCTCTGTGAGATGGCAATTCGGTCTAAGCAAGAACTGCTACAGCTTGCCCCAATCGAAGTGG
AAAGTAATGTATCAAGAGGATGCCCTGAAGGTACTCAAACCTTCGAAAAAGAAAGCGAGTAAGTTAAAAT
GCTTCTTCGTCTCCTATTTATAATATGGTTTGTTATTGTTAATTTTGTTCTTGTAGAAGAGCTTAATTAA
TCGTTGTTGTTATGAAATACTATTTGTATGAGATGAACTGGTGTAATGTAATTCATTTACATAAGTGGAG
TCAGAATCAGAATGTTTCCTCCATAACTAACTAGACATGAAGACCTGCCGCGTACAATTGTCTTATATTT
GAACAACTAAAATTGAACATCTTTTGCCACAACTTTATAAGTGGTTAATATAGCTCAAATATATGGTCAA
GTTCAATAGATTAATAATGGAAATATCAGTTATCGAAATTCATTAACAATCAACTTAACGTTATTAACTA
CTAATTTTATATCATCCCCTTTGATAAATGATAGTACACCAATTAGGAAGGAGCATGCTCGCCTAGGAGA
TTGTCGTTTCCCGCCTTCAGTTTGCAAGCTGCTCTAGCCGTGTAGCCAATACGCAAACCGCCTCTCCCCG
CGCGTTGGGAATTACTAGCGCGTGTCGACACGCGTGGCGCGCCCTGGTATATTTATATGTTGTCAAATAA
CTCAAAAACCATAAAAGTTTAAGTTAGCAAGTGTGTACATTTTTACTTGAACAAAAATATTCACCTACTA
CTGTTATAAATCATTATTAAACATTAGAGTAAAGAAATATGGATGATAAGAACAAGAGTAGTGATATTTT
GACAACAATTTTGTTGCAACATTTGAGAAAATTTTGTTGTTCTCTCTTTTCATTGGTCAAAAACAATAGA
GAGAGAAAAGGAAGAGGGAGAATAAAAACATAATGTGAGTATGAGAGAGAAAGTTGTACAAAAGTTGTA
CCAAAATAGTTGTACAAATATCATTGAGGAATTTGACAAAAGCTACACAAATAAGGGTTAATTGCTGTAA
ATAAATAAGGATGACGCATTAGAGAGATGTACCATTAGAGAATTTTTGGCAAGTCATTAAAAAGAAAGAA
TAAATTATTTTTAAAATTAAAAGTTGAGTCATTTGATTAAACATGTGATTATTTAATGAATTGATGAAAG
AGTTGGATTAAAGTTGTATTAGTAATTAGAATTTGGTGTCAAATTTAATTTGACATTTGATCTTTTCCTA
TATATTGCCCCATAGAGTCAGTTAACTCATTTTTATATTTCATAGATCAAATAAGAGAAATAACGGTATA
TTAATCCCTCCAAAAAAAAAAACGGTATATTTACTAAAAAATCTAAGCCACGTAGGAGGATAACAGGAT
CCCCGTAGGAGGATAACATCCAATCCAACCAATCACAACAATCCTGATGAGATAACCCACTTTAAGCCCA
CGCATCTGTGGCACATCTACATTATCTAAATCACACATTCTTCCACACATCTGAGCCACACAAAAACCAA
TCCACATCTTTATCACCCATTCTATAAAAAATCACACTTTGTGAGTCTACACTTTGATTCCCTTCAAACA
CATACAAAGAGAAGAGACTAATTAATTAATTAATCATCTTGAGAGAAAATGAGTCTTCTAACCGAGGTCG
AAACGCCTATCAGAAACGAATGGGGGTGCAGATGCAACGATTCAAGTGATCCTCTTGTTGTTGCCGCAAG
TATAATTGGGATTGTGCACCTGATATTGTGGATTATTGATCGCCTTTTTTCCAAAAGCATTTATCGTATC
TTTAAACACGGTTTAAAAAGAGGGCCTTCTACGGAAGGAGTACCAGAGTCTATGAGGGAAGAATATCGAG
AGGAACAGCAGAATGCTGTGGATGCTGACGATGGTCATTTTGTCAGCATAGAGCTGGAGTAAGAGCTCTA
AGTTAAAATGCTTCTTCGTCTCCTATTTATAATATGGTTTGTTATTGTTAATTTTGTTCTTGTAGAAGAG
CTTAATTAATCGTTGTTGTTATGAAATACTATTTGTATGAGATGAACTGGTGTAATGTAATTCATTTACA
TAAGTGGAGTCAGAATCAGAATGTTTCCTCCATAACTAACTAGACATGAAGACCTGCCGCGTACAATTGT
CTTATATTTGAACAACTAAAATTGAACATCTTTTGCCACAACTTTATAAGTGGTTAATATAGCTCAAATA
TATGGTCAAGTTCAATAGATTAATAATGGAAATATCAGTTATCGAAATTCATTAACAATCAACTTAACGT
TATTAACTACTAATTTTATATCATCCCCTTTGATAAATGATAGTACACCAATTAGGAAGGAACTAGGAGA
TTGTCGTTTCCCGCCTTCAGTTTGCAAGCTGCTCTAGCCGTGTAGCCAATACGCAAACCGCCTCTCCCCG
CGCGTTGGGAATTACTAGCGCGTGTCGACAAGCTTGCATGCCGGTCAACATGGTGGAGCACGACACACTT
GTCTACTCCAAAAATATCAAAGATACAGTCTCAGAAGACCAAAGGGCAATTGAGACTTTTCAACAAAGGG
TAATATCCGGAAACCTCCTCGGATTCCATTGCCCAGCTATCTGTCACTTTATTGTGAAGATAGTGGAAAA
GGAAGGTGGCTCCTACAAATGCCATCATTGCGATAAAGGAAGGCCATCGTTGAAGATGCCTCTGCCGAC
AGTGGTCCCAAAGATGGACCCCCACCCACGAGGAGCATCGTGGAAAAAGAAGACGTTCCAACCACGTCTT
CAAAGCAAGTGGATTGATGTGATAACATGGTGGAGCACGACACACTTGTCTACTCCAAAAATATCAAAGA
TACAGTCTCAGAAGACCAAAGGGCAATTGAGACTTTTCAACAAAGGGTAATATCCGGAAACCTCCTCGGA
```

FIGURE 17E (Continued-2)

TTCCATTGCCCAGCTATCTGTCACTTTATTGTGAAGATAGTGGAAAAGGAAGGTGGCTCCTACAAATGCC
ATCATTGCGATAAAGGAAAGGCCATCGTTGAAGATGCCTCTGCCGACAGTGGTCCCAAAGATGGACCCCC
ACCCACGAGGAGCATCGTGGAAAAAGAAGACGTTCCAACCACGTCTTCAAAGCAAGTGGATTGATGTGAT
ATCTCCACTGACGTAAGGGATGACGCACAATCCCACTATCCTTCGCAAGACCCTTCCTCTATATAAGGAA
GTTCATTTCATTTGGAGAGACGTCACTCCTCAGCCAAAACGACACCCCCATCTGTCTATCCACTGGCCCC
TGGATCTGCTGCCCAAACTAACTCCATGGTGACCCTGGGATGCCTGGTCAAGGGCTATTTCCCTGAGCCA
GTGACAGTGACCTGGAACTCTGGATCCCTGTCCAGCGGTGTGCACACCTTCCCAGCTGTCCTGCAGTCTG
ACCTCTACACTCTGAGCAGCTCAGTGACTGTCCCCTCCAGCACCTGGCCCAGCGAGACCGTCACCTGCAA
CGTTGCCCACCCGGCCAGCAGCACCAAGGTGGACAAGAAAATTGTGCCCAGGGATTGTGGTTGTAAGCCT
TGCATATGTACAGTCCCAGAAGTATCATCTGTCTTCATCTTCCCCCCAAAGCCCAAGGATGTGCTCACCA
TTACTCTGACTCCTAAGGTCACGTGTGTTGTGGTAGACATCAGCAAGGATGATCCCGAGGTCCAGTTCAG
CTGGTTTGTAGATGATGTGGAGGTGCACACAGCTCAGACGCAACCCCGGGAGGAGCAGTTCAACAGCACT
TTCCGCTCAGTCAGTGAACTTCCCATCATGCACCAGGACTGGCTCAATGGCAAGGAGACGTCCAGATTTT
GGCGATCTATTCAACTGTCGCCAGTTCATTGGTACTGGTAGTCTCCCTGGGGGCAATCAGTTTCTGGATG
TGCTCTAATGGGTCTCTACAGTGTAGAATATGTATTTAAAGGCCTATTTTCTTTAGTTTGAATTTACTGT
TATTCGGTGTGCATTTCTATGTTTGGTGAGCGGTTTTCTGTGCTCAGAGTGTGTTTATTTTATGTAATTT
AATTTCTTTGTGAGCTCCTGTTTAGCAGGTCGTCCCTTCAGCAAGGACACAAAAAGATTTTAATTTTATT
ATCGTTCAAACATTTGGCAATAAAGTTTCTTAAGATTGAATCCTGTTGCCGGTCTTGCGATGATTATCAT
ATAATTTCTGTTGAATTACGTTAAGCATGTAATAATTAACATGTAATGCATGACGTTATTTATGAGATGG
GTTTTTATGATTAGAGTCCCGCAATTATACATTTAATACGCGATAGAAAACAAAATATAGCGCGCAAACT
AGGATAAATTATCGCGCGCGGTGTCATCTATGTTACTAGATCTCTAGAGTCTCAAGCTTGGCGCGCCCAC
GTGACTAGTGGCACTGGCCGTCGTTTTACAACGTCGTGACTGGGAAAACCCTGGCGTTACCCAACTTAAT
CGCCTTGCAGCACATCCCCCTTTCGCCAGCTGGCGTAATAGCGAAGAGGCCCGCACCGATCGCCCTTCCC
AACAGTTGCGCAGCCTGAATGGCGAATGCTAGAGCAGCTTGAGCTTGGATCAGATTGTCGTTTCCCGCCT
TCAGTTTAAACTATCAGTGTTTGACAGGATATATTGGCGGGTAAACCTAAGAGAAAGAGCGTTTA

FIGURE 18A   CPMV 160 5'UTR-PDI+H1 Mich nucleic acid sequence   (SEQ ID NO:82)

TATTAAAATCTTAATAGGTTTTGATAAAAGCGAACGTGGGGAAACCCGAACCAAACCTTCTTCTAAACTC
TCTCTCATCTCTCTTAAAGCAAACTTCTCTCTTGTCTTTCTTGCGTGAGCGATCTTCAACGTTGTCAGAT
CGTGCTTCGGCACCAGTACAATGGCGAAAAACGTTGCGATTTTCGGCTTATTGTTTTCTCTTCTTGTGTT
GGTTCCTTCTCAGATCTTCGCGGACACATTATGTATAGGTTATCATGCGAACAATTCAACAGACACTGTA
GACACAGTACTAGAAAAGAATGTAACAGTAACACACTCTGTTAACCTTCTGGAAGACAAGCATAACGGAA
AACTATGCAAACTAAGAGGGGTAGCCCCATTGCATTTGGGTAAATGTAACATTGCTGGCTGGATCCTGGG
AAATCCAGAGTGTGAATCACTCTCCACAGCAAGTTCATGGTCCTACATTGTGGAAACATCTAATTCAGAC
AATGGAACGTGTTACCCAGGAGATTTCATCAATTATGAGGAGCTAAGAGAGCAATTGAGCTCAGTGTCAT
CATTTGAAAGGTTTGAGATATTCCCCAAGACAAGTTCATGGCCCAATCATGACTCGAACAAAGGTGTAAC
GGCAGCATGTCCTCACGCTGGAGCAAAAAGCTTCTACAAAAACTTGATATGGCTAGTTAAAAAAGGAAAT
TCATACCCAAAGCTTAACCAATCCTACATTAATGATAAAGGGAAAGAAGTCCTCGTGCTGTGGGGCATTC
ACCATCCATCTACTACTGCTGACCAACAAAGTCTCTATCAGAATGCAGATGCATATGTTTTTGTGGGGAC
ATCAAGATACAGCAAGAAGTTCAAGCCGGAAATAGCAACAAGACCCAAAGTGAGGGATCAAGAAGGGAGA
ATGAACTATTACTGGACACTAGTAGAGCCGGGAGACAAAATAACATTCGAAGCAACTGGAAATCTAGTGG
TACCGAGATATGCATTCACAATGGAAAGAAATGCTGGATCTGGTATTATCATTTCAGATACACCAGTCCA
CGATTGCAATACAACTTGTCAGACACCCGAGGGTGCTATAAACACCAGCCTCCCATTTCAGAATATACAT
CCGATCACAATTGGAAAATGTCCAAAGTATGTAAAAAGCACAAAATTGAGACTGGCCACAGGATTGAGGA

FIGURE 18A (Continued)

```
ATGTTCCGTCTATTCAATCTAGAGGCCTATTCGGGGCCATTGCCGGCTTCATTGAAGGGGGTGGACAGG
GATGGTAGATGGATGGTACGGTTATCACCATCAAAATGAGCAGGGGTCAGGATATGCAGCCGACCTGAAG
AGCACACAAAATGCCATTGACAAGATTACTAACAAAGTAAATTCTGTTATTGAAAAGATGAATACACAGG
ACACAGCAGTGGGTAAAGAGTTCAACCACCTGGAAAAAGAATAGAGAATCTAAATAAAAAGTTGATGA
TGGTTTCCTGGACATTTGGACTTACAATGCCGAACTGTTGGTTCTAATGGAAAATGAAAGAACTTTGGAC
TATCACGATTCAAATGTGAAGAACTTGTATGAAAAGTAAGAAACCAGTTAAAAAACAATGCCAAGGAAA
TTGGAAACGGCTGCTTTGAATTTTACCACAAATGCGATAACACGTGCATGGAAAGTGTCAAAAATGGGAC
TTATGACTACCCAAAATACTCAGAGGAAGCAAAATTAAACAGAGAAAAATAGATGGGGTAAAGCTGGAA
TCAACAAGGATTTACCAGATTTTGGCGATCTATTCAACTGTCGCCAGTTCATTGGTACTGGTAGTCTCCC
TGGGGGCAATCAGCTTCTGGATGTGCTCTAATGGGTCTCTACAGTGTAGAATATGTATTTAA
```

FIGURE 18B  PDI+H1 Mich nucleic acid sequence (SEQ ID NO:83)

```
ATGGCGAAAAACGTTGCGATTTTCGGCTTATTGTTTTCTCTTCTTGTGTTGGTTCCTTCTCAGATCTTCG
CGGACACATTATGTATAGGTTATCATGCGAACAATTCAACAGACACTGTAGACACAGTACTAGAAAAGAA
TGTAACAGTAACACACTCTGTTAACCTTCTGGAAGACAAGCATAACGGAAAACTATGCAAACTAAGAGGG
GTAGCCCCATTGCATTTGGGTAAATGTAACATTGCTGGCTGGATCCTGGGAAATCCAGAGTGTGAATCAC
TCTCCACAGCAAGTTCATGGTCCTACATTGTGGAAACATCTAATTCAGACAATGGAACGTGTTACCCAGG
AGATTTCATCAATTATGAGGAGCTAAGAGAGCAATTGAGCTCAGTGTCATCATTTGAAAGGTTTGAGATA
TTCCCCAAGACAAGTTCATGGCCCAATCATGACTCGAACAAAGGTGTAACGGCAGCATGTCCTCACGCTG
GAGCAAAAAGCTTCTACAAAAACTTGATATGGCTAGTTAAAAAAGGAAATTCATACCCAAAGCTTAACCA
ATCCTACATTAATGATAAAGGGAAAGAAGTCCTCGTGCTGTGGGCATTCACCATCCATCTACTACTGCT
GACCAACAAAGTCTCTATCAGAATGCAGATGCATATGTTTTTGTGGGGACATCAAGATACAGCAAGAAGT
TCAAGCCGGAAATAGCAACAAGACCCAAAGTGAGGGATCAAGAAGGGAGAATGAACTATTACTGGACACT
AGTAGAGCCGGGAGACAAAATAACATTCGAAGCAACTGGAAATCTAGTGGTACCGAGATATGCATTCACA
ATGGAAAGAAATGCTGGATCTGGTATTATCATTTCAGATACACCAGTCCACGATTGCAATACAACTTGTC
AGACACCCGAGGGTGCTATAAACACCAGCCTCCCATTTCAGAATATACATCCGATCACAATTGGAAAATG
TCCAAAGTATGTAAAAGCACAAAATTGAGACTGGCCACAGGATTGAGGAATGTTCCGTCTATTCAATCT
AGAGGCCTATTCGGGGCCATTGCCGGCTTCATTGAAGGGGGTGGACAGGGATGGTAGATGGATGGTACG
GTTATCACCATCAAAATGAGCAGGGGTCAGGATATGCAGCCGACCTGAAGAGCACACAAAATGCCATTGA
CAAGATTACTAACAAAGTAAATTCTGTTATTGAAAAGATGAATACACAGGACACAGCAGTGGGTAAAGAG
TTCAACCACCTGGAAAAAGAATAGAGAATCTAAATAAAAAGTTGATGATGGTTTCCTGGACATTTGGA
CTTACAATGCCGAACTGTTGGTTCTAATGGAAAATGAAAGAACTTTGGACTATCACGATTCAAATGTGAA
GAACTTGTATGAAAAGTAAGAAACCAGTTAAAAAACAATGCCAAGGAAATTGGAAACGGCTGCTTTGAA
TTTTACCACAAATGCGATAACACGTGCATGGAAAGTGTCAAAAATGGGACTTATGACTACCCAAAATACT
CAGAGGAAGCAAAATTAAACAGAGAAAAATAGATGGGGTAAAGCTGGAATCAACAAGGATTTACCAGAT
TTTGGCGATCTATTCAACTGTCGCCAGTTCATTGGTACTGGTAGTCTCCCTGGGGGCAATCAGCTTCTGG
ATGTGCTCTAATGGGTCTCTACAGTGTAGAATATGTATTTAA
```

FIGURE 18C: PDI+H1 Mich amino acid sequence (SEQ ID NO:84)

MAKNVAIFGLLFSLLVLVPSQIFADTLCIGYHANNSTDTVDTVLEKNVTVTHSVNLLEDKHNGKLCKLRG
VAPLHLGKCNIAGWILGNPECESLSTASSWSYIVETSNSDNGTCYPGDFINYEELREQLSSVSSFERFEI
FPKTSSWPNHDSNKGVTAACPHAGAKSFYKNLIWLVKKGNSYPKLNQSYINDKGKEVLVLWGIHHPSTTA
DQQSLYQNADAYVFVGTSRYSKKFKPEIATRPKVRDQEGRMNYYWTLVEPGDKITFEATGNLVVPRYAFT
MERNAGSGIIISDTPVHDCNTTCQTPEGAINTSLPFQNIHPITIGKCPKYVKSTKLRLATGLRNVPSIQS
RGLFGAIAGFIEGGWTGMVDGWYGYHHQNEQGSGYAADLKSTQNAIDKITNKVNSVIEKMNTQDTAVGKE
FNHLEKRIENLNKKVDDGFLDIWTYNAELLVLMENERTLDYHDSNVKNLYEKVRNQLKNNAKEIGNGCFE
FYHKCDNTCMESVKNGTYDYPKYSEEAKLNREKIDGVKLESTRIYQILAIYSTVASSLVLVVSLGAISFW
MCSNGSLQCRICI

FIGURE 18D: Cloning vector (for Norovirus VP1) 4170 from left to right T-DNA (SEQ ID NO:77)

TGGCAGGATATATTGTGGTGTAAACAAATTGACGCTTAGACAACTTAATAACACATTGCGGACGTTTTTA
ATGTACTGAATTAACGCCGAATCCCGGGCTGGTATATTTATATGTTGTCAAATAACTCAAAAACCATAAA
AGTTTAAGTTAGCAAGTGTGTACATTTTTACTTGAACAAAAATATTCACCTACTACTGTTATAAATCATT
ATTAAACATTAGAGTAAAGAAATATGGATGATAAGAACAAGAGTAGTGATATTTTGACAACAATTTTGTT
GCAACATTTGAGAAAATTTTGTTGTTCTCTCTTTTCATTGGTCAAAAACAATAGAGAGAGAAAAAGGAAG
AGGGAGAATAAAAACATAATGTGAGTATGAGAGAGAAAGTTGTACAAAAGTTGTACCAAAATAGTTGTAC
AAATATCATTGAGGAATTTGACAAAAGCTACACAAATAAGGGTTAATTGCTGTAAATAAATAAGGATGAC
GCATTAGAGAGATGTACCATTAGAGAATTTTTGGCAAGTCATTAAAAAGAAAGAATAAATTATTTTTAAA
ATTAAAAGTTGAGTCATTTGATTAAACATGTGATTATTTAATGAATTGATGAAAGAGTTGGATTAAAGTT
GTATTAGTAATTAGAATTTGGTGTCAAATTTAATTTGACATTTGATCTTTTCCTATATATTGCCCCATAG
AGTCAGTTAACTCATTTTTATATTTCATAGATCAAATAAGAGAAATAACGGTATATTAATCCCTCCAAAA
AAAAAAAACGGTATATTTACTAAAAAATCTAAGCCACGTAGGAGGATAACAGGATCCCCGTAGGAGGATA
ACATCCAATCCAACCAATCACAACAATCCTGATGAGATAACCCACTTTAAGCCCACGCATCTGTGGCACA
TCTACATTATCTAAATCACACATTCTTCCACACATCTGAGCCACACAAAAACCAATCCACATCTTTATCA
CCCATTCTATAAAAAATCACACTTTGTGAGTCTACACTTTGATTCCCTTCAAACACATACAAAGAGAAGA
GACTAATTAATTAATTAATCATCTTGAGAGAAAATGGAACGAGCTATACAAGGAAACGACGCTAGGGAAC
AAGCTAACAGTGAACGTTGGGATGGAGGATCAGGAGGTACCACTTCTCCCTTCAAACTTCCTGACGAAAG
TCCGAGTTGGACTGAGTGGCGGCTACATAACGATGAGACGAATTCGAATCAAGATAATCCCCTTGGTTTC
AAGGAAAGCTGGGGTTTCGGGAAAGTTGTATTTAAGAGATATCTCAGATACGACAGGACGGAAGCTTCAC
TGCACAGAGTCCTTGGATCTTGGACGGGAGATTCGGTTAACTATGCAGCATCTCGATTTTTCGGTTTCGA
CCAGATCGGATGTACCTATAGTATTCGGTTTCGAGGAGTTAGTATCACCGTTTCTGGAGGGTCGCGAACT
CTTCAGCATCTCTGTGAGATGGCAATTCGGTCTAAGCAAGAACTGCTACAGCTTGCCCCAATCGAAGTGG
AAAGTAATGTATCAAGAGGATGCCCTGAAGGTACTCAAACCTTCGAAAAAGAAAGCGAGTAAGTTAAAAT
GCTTCTTCGTCTCCTATTTATAATATGGTTTGTTATTGTTAATTTTGTTCTTGTAGAAGAGCTTAATTAA
TCGTTGTTGTTATGAAATACTATTTGTATGAGATGAACTGGTGTAATGTAATTCATTTACATAAGTGGAG
TCAGAATCAGAATGTTTCCTCCATAACTAACTAGACATGAAGACCTGCCGCGTACAATTGTCTTATATTT
GAACAACTAAAATTGAACATCTTTTGCCACAACTTTATAAGTGGTTAATATAGCTCAAATATATGGTCAA
GTTCAATAGATTAATAATGGAAATATCAGTTATCGAAATTCATTAACAATCAACTTAACGTTATTAACTA
CTAATTTTATATCATCCCCTTTGATAAATGATAGTACACCAATTAGGAAGGAGCATGCTCGCCTAGGAGA
TTGTCGTTTCCCGCCTTCAGTTTGCAAGCTGCTCTAGCCGTGTAGCCAATACGCAAACCGCCTCTCCCCG
CGCGTTGGGAATTACTAGCGCGTGTCGACAAGCTTGCATGCCGGTCAACATGGTGGAGCACGACACACTT
GTCTACTCCAAAAATATCAAAGATACAGTCTCAGAAGACCAAAGGGCAATTGAGACTTTTCAACAAAGGG
TAATATCCGGAAACCTCCTCGGATTCCATTGCCCAGCTATCTGTCACTTTATTGTGAAGATAGTGGAAAA

FIGURE 18D (Continued)

```
GGAAGGTGGCTCCTACAAATGCCATCATTGCGATAAAGGAAAGGCCATCGTTGAAGATGCCTCTGCCGAC
AGTGGTCCCAAAGATGGACCCCCACCCACGAGGAGCATCGTGGAAAAAGAAGACGTTCCAACCACGTCTT
CAAAGCAAGTGGATTGATGTGATAACATGGTGGAGCACGACACACTTGTCTACTCCAAAAATATCAAAGA
TACAGTCTCAGAAGACCAAAGGGCAATTGAGACTTTTCAACAAAGGGTAATATCCGGAAACCTCCTCGGA
TTCCATTGCCCAGCTATCTGTCACTTTATTGTGAAGATAGTGGAAAAGGAAGGTGGCTCCTACAAATGCC
ATCATTGCGATAAAGGAAAGGCCATCGTTGAAGATGCCTCTGCCGACAGTGGTCCCAAAGATGGACCCCC
ACCCACGAGGAGCATCGTGGAAAAAGAAGACGTTCCAACCACGTCTTCAAAGCAAGTGGATTGATGTGAT
ATCTCCACTGACGTAAGGGATGACGCACAATCCCACTATCCTTCGCAAGACCCTTCCTCTATATAAGGAA
GTTCATTTCATTTGGAGAGACGTCACTCCTCAGCCAAAACGACACCCCCATCTGTCTATCCACTGGCCCC
TGGATCTGCTGCCCAAACTAACTCCATGGTGACCCTGGGATGCCTGGTCAAGGGCTATTTCCCTGAGCCA
GTGACAGTGACCTGGAACTCTGGATCCCTGTCCAGCGGTGTGCACACCTTCCCAGCTGTCCTGCAGTCTG
ACCTCTACACTCTGAGCAGCTCAGTGACTGTCCCCTCCAGCACCTGGCCCAGCGAGACCGTCACCTGCAA
CGTTGCCCACCCGGCCAGCAGCACCAAGGTGGACAAGAAAATTGTGCCCAGGGATTGTGGTTGTAAGCCT
TGCATATGTACAGTCCCAGAAGTATCATCTGTCTTCATCTTCCCCCCAAAGCCCAAGGATGTGCTCACCA
TTACTCTGACTCCTAAGGTCACGTGTGTTGTGGTAGACATCAGCAAGGATGATCCCGAGGTCCAGTTCAG
CTGGTTTGTAGATGATGTGGAGGTGCACACAGCTCAGACGCAACCCCGGGAGGAGCAGTTCAACAGCACT
TTCCGCTCAGTCAGTGAACTTCCCATCATGCACCAGGACTGGCTCAATGGCAAGGAGACGTCCAGATTTT
GGCGATCTATTCAACTGTCGCCAGTTCATTGGTACTGGTAGTCTCCCTGGGGCAATCAGTTTCTGGATG
TGCTCTAATGGGTCTCTACAGTGTAGAATATGTATTTAAAGGCCTATTTTCTTTAGTTTGAATTTACTGT
TATTCGGTGTGCATTTCTATGTTTGGTGAGCGGTTTTCTGTGCTCAGAGTGTGTTTATTTTATGTAATTT
AATTTCTTTGTGAGCTCCTGTTTAGCAGGTCGTCCCTTCAGCAAGGACACAAAAAGATTTTAATTTTATT
ATCGTTCAAACATTTGGCAATAAAGTTTCTTAAGATTGAATCCTGTTGCCGGTCTTGCGATGATTATCAT
ATAATTTCTGTTGAATTACGTTAAGCATGTAATAATTAACATGTAATGCATGACGTTATTTATGAGATGG
GTTTTTATGATTAGAGTCCCGCAATTATACATTTAATACGCGATAGAAAACAAAATATAGCGCGCAAACT
AGGATAAATTATCGCGCGCGGTGTCATCTATGTTACTAGATCTCTAGGTAAAAATCCCAATTATATTTGG
TCTAATTTAGTTTGGTATTGAGTAAAACAAATTCGAACCAAACCAAAATATAAATATATAGTTTTTATAT
ATATGCCTTTAAGACTTTTTATAGAATTTTCTTTAAAAAATATCAAGAAATATTTGCGACTCTTCTGGCA
TGTAATATTTCGTTAAATATGAAGTGCTCCATTTTTATTAACTTTAAATAATTGGTTGTACGATCACTTT
CTTATCAAGTGTTACTAAAATGCGTCAATCTCTTTGTTCTTCCATATTCATATGTCAAAATCTATCAAAA
TTCTTATATATCTTTTTCGAATTTGAAGTGAAATTTCGATAATTTAAAATTAAATAGAACATATCATTAT
TTAGGTATCATATTGATTTTTATACTTAATTACTAAATTTGGTTAACTTTGAAAGTGTACATCAACGAAA
AATTAGTCAAACGACTAAAATAAATAAATATCATGTGTTATTAAGAAAATTCTCCTATAAGAATATTTTA
ATAGATCATATGTTTGTAAAAAAAATTAATTTTTACTAACACATATATTTACTTATCAAAAATTTGACAA
AGTAAGATTAAAATAATATTCATCTAACAAAAAAAAACCAGAAATGCTGAAAACCCGGCAAAACCGAA
CCAATCCAAACCGATATAGTTGGTTTGGTTTGATTTTGATATAAACCGAACCAACTCGGTCCATTTGCAC
CCCTAATCATAATAGCTTTAATATTTCAAGATATTATTAAGTTAACGTTGTCAATATCCTGGAAATTTTG
CAAAATGAATCAAGCCTATATGGCTGTAATATGAATTTAAAAGCAGCTCGATGTGGTGGTAATATGTAAT
TTACTTGATTCTAAAAAAATATCCCAAGTATTAATAATTTCTGCTAGGAAGAAGGTTAGCTACGATTTAC
AGCAAAGCCAGAATACAAAGAACCATAAAGTGATTGAAGCTCGAAATATACGAAGGAACAAATATTTTA
AAAAAATACGCAATGACTTGGAACAAAAGAAAGTGATATATTTTTGTTCTTAAACAAGCATCCCCTCTA
AAGAATGGCAGTTTTCCTTTGCATGTAACTATTATGCTCCCTTCGTTACAAAAATTTTGGACTACTATTG
GGAACTTCTTCTGAAAATTCTAGAGTCTCAAGCTTGGCGCGCCCACGTGACTAGTGGCACTGGCCGTCGT
TTTACAACGTCGTGACTGGGAAAACCCTGGCGTTACCCAACTTAATCGCCTTGCAGCACATCCCCCTTTC
GCCAGCTGGCGTAATAGCGAAGAGGCCCGCACCGATCGCCCTTCCCAACAGTTGCGCAGCCTGAATGGCG
AATGCTAGAGCAGCTTGAGCTTGGATCAGATTGTCGTTTCCCGCCTTCAGTTTAAACTATCAGTGTTTGA
CAGGATATATTGGCGGGTAAACCTAAGAGAAAAGAGCGTTTA
```

FIGURE 19A: CPMV 160 5'UTR-PDI+H3 HK nucleic acid sequence (SEQ ID NO:85)

TATTAAAATCTTAATAGGTTTTGATAAAAGCGAACGTGGGGAAACCCGAACCAAACCTTCTTCTAAACTC
TCTCTCATCTCTCTTAAAGCAAACTTCTCTCTTGTCTTTCTTGCGTGAGCGATCTTCAACGTTGTCAGAT
CGTGCTTCGGCACCAGTACAATGGCGAAAAACGTTGCGATTTTCGGCTTATTGTTTTCTCTTCTTGTGTT
GGTTCCTTCTCAGATCTTCGCGCAAAAAATTCCTGGAAATGACAATAGCACGGCAACGCTGTGCCTTGGG
CATCATGCAGTACCAAACGGAACGATAGTGAAAACAATCACGAATGACCGAATTGAAGTTACTAATGCTA
CTGAGCTGGTTCAGAATTCCTCAATAGGTGAAATATGCGACAGTCCTCATCAGATCCTTGATGGAGAAAA
CTGCACACTAATAGATGCTCTATTGGGAGACCCTCAGTGTGATGGCTTTCAAAATAAGAAATGGGACCTT
TTTGTTGAACGAAGCAAAGCCTACAGCAACTGTTACCCTTATGATGTGCCGGATTATGCCTCCCTTAGGT
CACTAGTTGCCTCATCCGGCACACTGGAGTTTAACAATGAAAGCTTCAATTGGACTGGAGTCACTCAAAA
CGGAACAAGTTCTGCTTGCATAAGGAGATCTAGTAGTAGTTTCTTTAGTAGATTAAATTGGTTGACCCAC
TTAAACTACACATACCCAGCATTGAACGTGACTATGCCAAACAATGAACAATTTGACAAATTGTACATTT
GGGGGGTTCACCACCCGGGTACGGACAAGGACCAAATCTTCCTGTATGCTCAATCATCAGGAAGAATCAC
AGTATCTACCAAAAGAAGCCAACAAGCTGTAATCCCAAATATCGGATCTAGACCCAGAATAAGGGATATC
CCTAGCAGAATAAGCATCTATTGGACAATAGTAAAACCGGGAGACATACTTTTGATTAACAGCACAGGGA
ATCTAATTGCTCCTAGGGGTTACTTCAAAATACGAAGTGGGAAAAGCTCAATAATGAGATCAGATGCACC
CATTGGCAAATGCAAGTCTGAATGCATCACTCCAAATGGAAGCATTCCCAATGACAAACCATTCCAAAAT
GTAAACAGGATCACATACGGGGCCTGTCCCAGATATGTTAAGCATAGCACTCTGAAATTGGCAACAGGAA
TGCGAAATGTACCAGAGAAACAAACTAGAGGCATATTTGGTGCAATAGCGGGTTTCATAGAAAATGGTTG
GGAGGGAATGGTGGATGGTTGGTACGGTTTCAGGCATCAAAATTCTGAGGGAAGAGGACAAGCAGCAGAT
CTCAAAAGCACTCAAGCAGCAATCGATCAAATCAATGGGAAGCTGGCTCGAGTGATCGGGAAAACCAACG
AGAAATTCCATCAGATTGAAAAAGAATTCTCAGAAGTAGAAGGAAGAATTCAGGACCTTGAGAAATATGT
TGAGGACACTAAAATAGATCTCTGGTCATACAACGCGGAGCTTCTTGTTGCCCTGGAGAACCAACATACA
ATTGATCTAACTGACTCAGAAATGAACAAACTGTTTGAAAAAACAAAGAAGCAACTGAGGGAAAATGCTG
AGGATATGGGCAATGGTTGTTTCAAAATATACCACAAATGTGACAATGCCTGCATAGGATCAATAAGAAA
TGGAACTTATGACCACAATGTGTACAGGGATGAAGCATTAAACAACCGGTTCCAGATCAAGGGAGTTGAG
CTGAAGTCAGGGTACAAAGATTGGATCCTATGGATTTCCTTTGCCATATCATCCCTTGTACTGTTAGTTG
CTTTGTTGGGGTTCATCATGTGGGCCTGCCAAAAGGGCAACATTAGGTGCAACATTTGCATTTGA

FIGURE 19B: PDI+H3 HK nucleic acid sequence (SEQ ID NO:86)

ATGGCGAAAAACGTTGCGATTTTCGGCTTATTGTTTTCTCTTCTTGTGTTGGTTCCTTCTCAGATCTTCG
CGCAAAAAATTCCTGGAAATGACAATAGCACGGCAACGCTGTGCCTTGGGCATCATGCAGTACCAAACGG
AACGATAGTGAAAACAATCACGAATGACCGAATTGAAGTTACTAATGCTACTGAGCTGGTTCAGAATTCC
TCAATAGGTGAAATATGCGACAGTCCTCATCAGATCCTTGATGGAGAAAACTGCACACTAATAGATGCTC
TATTGGGAGACCCTCAGTGTGATGGCTTTCAAAATAAGAAATGGGACCTTTTTGTTGAACGAAGCAAAGC
CTACAGCAACTGTTACCCTTATGATGTGCCGGATTATGCCTCCCTTAGGTCACTAGTTGCCTCATCCGGC
ACACTGGAGTTTAACAATGAAAGCTTCAATTGGACTGGAGTCACTCAAAACGGAACAAGTTCTGCTTGCA
TAAGGAGATCTAGTAGTAGTTTCTTTAGTAGATTAAATTGGTTGACCCACTTAAACTACACATACCCAGC
ATTGAACGTGACTATGCCAAACAATGAACAATTTGACAAATTGTACATTTGGGGGGTTCACCACCCGGGT
ACGGACAAGGACCAAATCTTCCTGTATGCTCAATCATCAGGAAGAATCACAGTATCTACCAAAAGAAGCC
AACAAGCTGTAATCCCAAATATCGGATCTAGACCCAGAATAAGGGATATCCCTAGCAGAATAAGCATCTA
TTGGACAATAGTAAAACCGGGAGACATACTTTTGATTAACAGCACAGGGAATCTAATTGCTCCTAGGGGT
TACTTCAAAATACGAAGTGGGAAAAGCTCAATAATGAGATCAGATGCACCCATTGGCAAATGCAAGTCTG
AATGCATCACTCCAAATGGAAGCATTCCCAATGACAAACCATTCCAAAATGTAAACAGGATCACATACGG
GGCCTGTCCCAGATATGTTAAGCATAGCACTCTGAAATTGGCAACAGGAATGCGAAATGTACCAGAGAAA

FIGURE 19B (Continued)

```
CAAACTAGAGGCATATTTGGTGCAATAGCGGGTTTCATAGAAAATGGTTGGGAGGGAATGGTGGATGGTT
GGTACGGTTTCAGGCATCAAAATTCTGAGGGAAGAGGACAAGCAGCAGATCTCAAAAGCACTCAAGCAGC
AATCGATCAAATCAATGGGAAGCTGGCTCGAGTGATCGGGAAAACCAACGAGAAATTCCATCAGATTGAA
AAAGAATTCTCAGAAGTAGAAGGAAGAATTCAGGACCTTGAGAAATATGTTGAGGACACTAAAATAGATC
TCTGGTCATACAACGCGGAGCTTCTTGTTGCCCTGGAGAACCAACATACAATTGATCTAACTGACTCAGA
AATGAACAAACTGTTTGAAAAAACAAAGAAGCAACTGAGGGAAAATGCTGAGGATATGGGCAATGGTTGT
TTCAAAATATACCACAAATGTGACAATGCCTGCATAGGATCAATAAGAAATGGAACTTATGACCACAATG
TGTACAGGGATGAAGCATTAAACAACCGGTTCCAGATCAAGGGAGTTGAGCTGAAGTCAGGGTACAAAGA
TTGGATCCTATGGATTTCCTTTGCCATATCATCCCTTGTACTGTTAGTTGCTTTGTTGGGGTTCATCATG
TGGGCCTGCCAAAAGGGCAACATTAGGTGCAACATTTGCATTTGA
```

FIGURE 19C: PDI+H3 HK amino acid sequence (SEQ ID NO:87)

```
MAKNVAIFGLLFSLLVLVPSQIFAQKIPGNDNSTATLCLGHHAVPNGTIVKTITNDRIEVTNATELVQNS
SIGEICDSPHQILDGENCTLIDALLGDPQCDGFQNKKWDLFVERSKAYSNCYPYDVPDYASLRSLVASSG
TLEFNNESFNWTGVTQNGTSSACIRRSSSSFFSRLNWLTHLNYTYPALNVTMPNNEQFDKLYIWGVHHPG
TDKDQIFLYAQSSGRITVSTKRSQQAVIPNIGSRPRIRDIPSRISIYWTIVKPGDILLINSTGNLIAPRG
YFKIRSGKSSIMRSDAPIGKCKSECITPNGSIPNDKPFQNVNRITYGACPRYVKHSTLKLATGMRNVPEK
QTRGIFGAIAGFIENGWEGMVDGWYGFRHQNSEGRGQAADLKSTQAAIDQINGKLARVIGKTNEKFHQIE
KEFSEVEGRIQDLEKYVEDTKIDLWSYNAELLVALENQHTIDLTDSEMNKLFEKTKKQLRENAEDMGNGC
FKIYHKCDNACIGSIRNGTYDHNVYRDEALNNRFQIKGVELKSGYKDWILWISFAISSLVLLVALLGFIM
WACQKGNIRCNICI
```

FIGURE 20A: CPMV 160 5'UTR-PDI+HA B Bri nucleic acid sequence (SEQ ID NO:88)

```
TATTAAAATCTTAATAGGTTTTGATAAAAGCGAACGTGGGGAAACCCGAACCAAACCTTCTTCTAAACTC
TCTCTCATCTCTCTTAAAGCAAACTTCTCTCTTGTCTTTCTTGCGTGAGCGATCTTCAACGTTGTCAGAT
CGTGCTTCGGCACCAGTACAATGGCGAAAAACGTTGCGATTTTCGGCTTATTGTTTTCTCTTCTTGTGTT
GGTTCCTTCTCAGATCTTCGCGGATCGAATCTGCACTGGAATAACATCGTCAAACTCACCACATGTCGTC
AAAACTGCTACTCAAGGGGAGGTCAATGTGACTGGTGTAATACCACTGACAACAACACCCACCAAATCTC
ATTTTGCAAATCTCAAAGGAACAGAAACCAGGGGGAAACTATGCCCAAAATGCCTCAACTGCACAGATCT
GGACGTAGCCTTGGGCAGACCAAAATGCACGGGGAAAATACCCTCGGCAAGAGTTTCAATACTCCATGAA
GTCAGACCTGTTACATCTGGGTGCTTTCCTATAATGCACGACAGAACAAAAATTAGACAGCTGCCTAACC
TTCTCCGAGGATACGAACATATCAGGTTATCAACCCATAACGTTATCAATGCAGAAAATGCACCAGGAGG
ACCCTACAAAATTGGAACCTCAGGGTCTTGCCCTAACATTACCAATGGAAACGGATTTTTCGCAACAATG
GCTTGGGCCGTCCCAAAAAACGACAAAAACAAAACAGCAACAAATCCATTAACAATAGAAGTACCATACA
TTTGTACAGAAGGAGAAGACCAAATTACCGTTTGGGGGTTCCACTCTGACAACGAGACCCAAATGGCAAA
GCTCTATGGGGACTCAAAGCCCCAGAAGTTCACCTCATCTGCCAACGGAGTGACCACACATTACGTTTCA
CAGATTGGTGGCTTCCCAAATCAAACAGAAGACGGAGGACTACCACAAAGTGGTAGAATTGTTGTTGATT
ACATGGTGCAAAAATCTGGGAAAACAGGAACAATTACCTATCAAAGGGGTATTTTATTGCCTCAAAAGGT
GTGGTGCGCAAGTGGCAGGAGCAAGGTAATAAAAGGATCCTTGCCTTTAATTGGAGAAGCAGATTGCCTC
CACGAAAAATACGGTGGATTAAACAAAAGCAAGCCTTACTACACAGGGGAACATGCAAAGGCCATAGGAA
ATTGCCCAATATGGGTGAAAACACCCTTGAAGCTGGCCAATGGAACCAAATATAGACCTCCTGGTGGAGG
ATGGGAAGGAATGATTGCAGGTTGGCACGGATACACATCCCATGGGGCACATGGAGTAGCGGTGGCAGCA
GACCTTAAGAGCACTCAAGAGGCCATAAACAAGATAACAAAAAATCTCAACTCTTTGAGTGAGCTGGAAG
TAAAGAATCTTCAAAGACTAAGCGGTGCCATGGATGAACTCCACAACGAAATACTAGAACTAGATGAGAA
AGTGGATGATCTCAGAGCTGATACAATAAGCTCACAAATAGAACTCGCAGTCCTGCTTTCCAATGAAGGA

FIGURE 20A (Continued)

ATAATAAACAGTGAAGATGAACATCTCTTGGCGCTTGAAAGAAAGCTGAAGAAAATGCTGGGCCCCTCTG
CTGTAGAGATAGGGAATGGATGCTTTGAAACCAAACACAAGTGCAACCAGACCTGTCTCGACAGAATAGC
TGCTGGTACCTTTGATGCAGGAGAATTTTCTCTCCCCACCTTTGATTCACTGAATATTACTGCTGCATCT
TTAAATGACGATGGATTGGATAATTACCAGATTTTGGCGATCTATTCAACTGTCGCCAGTTCATTGGTAC
TGGTAGTCTCCCTGGGGGCAATCAGTTTCTGGATGTGCTCTAATGGGTCTCTACAGTGTAGAATATGTAT
TTAA

FIGURE 20B: PDI+HA B Bri nucleic acid sequence (SEQ ID NO:89)

ATGGCGAAAAACGTTGCGATTTTCGGCTTATTGTTTTCTCTTCTTGTGTTGGTTCCTTCTCAGATCTTCG
CGGATCGAATCTGCACTGGAATAACATCGTCAAACTCACCACATGTCGTCAAAACTGCTACTCAAGGGGA
GGTCAATGTGACTGGTGTAATACCACTGACAACAACACCCACCAAATCTCATTTTGCAAATCTCAAAGGA
ACAGAAACCAGGGGGAAACTATGCCCAAAATGCCTCAACTGCACAGATCTGGACGTAGCCTTGGGCAGAC
CAAAATGCACGGGGAAAATACCCTCGGCAAGAGTTTCAATACTCCATGAAGTCAGACCTGTTACATCTGG
GTGCTTTCCTATAATGCACGACGAACAAAAATTAGACAGCTGCCTAACCTTCTCCGAGGATACGAACAT
ATCAGGTTATCAACCCATAACGTTATCAATGCAGAAAATGCACCAGGAGGACCCTACAAATTGGAACCT
CAGGGTCTTGCCCTAACATTACCAATGGAAACGGATTTTTCGCAACAATGGCTTGGGCCGTCCCAAAAA
CGACAAAAACAAAACAGCAACAAATCCATTAACAATAGAAGTACCATACATTTGTACAGAAGGAGAAGAC
CAAATTACCGTTTGGGGGTTCCACTCTGACAACGAGACCCAAATGGCAAAGCTCTATGGGGACTCAAAGC
CCCAGAAGTTCACCTCATCTGCCAACGGAGTGACCACACATTACGTTTCACAGATTGGTGGCTTCCCAAA
TCAAACAGAAGACGGAGGACTACCACAAAGTGGTAGAATTGTTGTTGATTACATGGTGCAAAAATCTGGG
AAAACAGGAACAATTACCTATCAAAGGGGTATTTTATTGCCTCAAAAGGTGTGGTGCGCAAGTGGCAGGA
GCAAGGTAATAAAAGGATCCTTGCCTTTAATTGGAGAAGCAGATTGCCTCCACGAAAAATACGGTGGATT
AAACAAAAGCAAGCCTTACTACACAGGGGAACATGCAAAGGCCATAGGAAATTGCCCAATATGGGTGAAA
ACACCCTTGAAGCTGGCCAATGGAACCAAATATAGACCTCCTGGTGGAGGATGGGAAGGAATGATTGCAG
GTTGGCACGGATACACATCCCATGGGGCACATGGAGTAGCGGTGGCAGCAGACCTTAAGAGCACTCAAGA
GGCCATAAACAAGATAACAAAAAATCTCAACTCTTTGAGTGAGCTGGAAGTAAAGAATCTTCAAAGACTA
AGCGGTGCCATGGATGAACTCCACAACGAAATACTAGAACTAGATGAGAAAGTGGATGATCTCAGAGCTG
ATACAATAAGCTCACAAATAGAACTCGCAGTCCTGCTTTCCAATGAAGGAATAATAAACAGTGAAGATGA
ACATCTCTTGGCGCTTGAAAGAAAGCTGAAGAAAATGCTGGGCCCCTCTGCTGTAGAGATAGGGAATGGA
TGCTTTGAAACCAAACACAAGTGCAACCAGACCTGTCTCGACAGAATAGCTGCTGGTACCTTTGATGCAG
GAGAATTTTCTCTCCCCACCTTTGATTCACTGAATATTACTGCTGCATCTTTAAATGACGATGGATTGGA
TAATTACCAGATTTTGGCGATCTATTCAACTGTCGCCAGTTCATTGGTACTGGTAGTCTCCCTGGGGGCA
ATCAGTTTCTGGATGTGCTCTAATGGGTCTCTACAGTGTAGAATATGTATTTAA

FIGURE 20C: PDI+HA B Bri amino acid sequence (SEQ ID NO:90)

MAKNVAIFGLLFSLLVLVPSQIFADRICTGITSSNSPHVVKTATQGEVNVTGVIPLTTTPTKSHFANLKG
TETRGKLCPKCLNCTDLDVALGRPKCTGKIPSARVSILHEVRPVTSGCFPIMHDRTKIRQLPNLLRGYEH
IRLSTHNVINAENAPGGPYKIGTSGSCPNITNGNGFFATMAWAVPKNDKNKTATNPLTIEVPYICTEGED
QITVWGFHSDNETQMAKLYGDSKPQKFTSSANGVTTHYVSQIGGFPNQTEDGGLPQSGRIVVDYMVQKSG
KTGTITYQRGILLPQKVWCASGRSKVIKGSLPLIGEADCLHEKYGGLNKSKPYYTGEHAKAIGNCPIWVK
TPLKLANGTKYRPPGGGWEGMIAGWHGYTSHGAHGVAVAADLKSTQEAINKITKNLNSLSELEVKNLQRL
SGAMDELHNEILELDEKVDDLRADTISSQIELAVLLSNEGIINSEDEHLLALERKLKKMLGPSAVEIGNG
CFETKHKCNQTCLDRIAAGTFDAGEFSLPTFDSLNITAASLNDDGLDNYQILAIYSTVASSLVLVVSLGA
ISFWMCSNGSLQCRICI

Figure 21A: CPMV 160 5'UTR-PDI+HA B Phu nucleic acid sequence (SEQ ID NO:91)

TATTAAAATCTTAATAGGTTTTGATAAAAGCGAACGTGGGGAAACCCGAACCAAACCTTCTTCTAAACTC
TCTCTCATCTCTCTTAAAGCAAACTTCTCTCTTGTCTTTCTTGCGTGAGCGATCTTCAACGTTGTCAGAT
CGTGCTTCGGCACCAGTACAATGGCGAAAAACGTTGCGATTTTCGGCTTATTGTTTTCTCTTCTTGTGTT
GGTTCCTTCTCAGATCTTCGCGGATCGAATCTGCACTGGGATAACATCTTCAAACTCACCTCATGTGGTC
AAAACAGCTACTCAAGGGGAGGTCAATGTGACTGGCGTGATACCACTGACAACAACACCAACAAAATCTT
ATTTTGCAAATCTCAAAGGAACAAGGACCAGAGGGAAACTATGCCCGGACTGTCTCAACTGTACAGATCT
GGATGTGGCCTTGGGCAGGCCAATGTGTGTGGGGACCACACCTTCTGCTAAAGCTTCAATACTCCATGAG
GTCAGACCTGTTACATCCGGGTGCTTTCCTATAATGCACGACAGAACAAAAATCAGGCAACTACCCAATC
TTCTCAGAGGATATGAAAAGATCAGGTTATCAACCCAAAACGTTATCGATGCAGAAAAAGCACCAGGAGG
ACCCTACAGACTTGGAACCTCAGGATCTTGCCCTAACGCTACCAGTAAAATCGGATTTTTTGCAACAATG
GCTTGGGCTGTCCCAAAGGACAACTACAAAAATGCAACGAACCCACTAACAGTGGAAGTACCATACATTT
GTACAGAAGGGGAAGACCAAATTACTGTTTGGGGGTTCCATTCGGATAACAAAACCCAAATGAAGAGCCT
CTATGGAGACTCAAATCCTCAAAAGTTCACCTCATCTGCTAATGGAGTAACCACGCATTATGTTTCTCAG
ATTGGCGACTTCCCAGATCAAACAGAAGACGGAGGACTACCACAAAGCGGCAGAATTGTTGTTGATTACA
TGATGCAAAAACCTGGGAAAACAGGAACAATTGTCTATCAAAGGGGTGTTTTGTTGCCTCAAAAGGTGTG
GTGCGCGAGTGGCAGGAGCAAAGTAATAAAAGGGTCATTGCCTTTAATTGGTGAAGCAGATTGCCTTCAT
GAAGAATACGGTGGATTAAACAAAAGCAAGCCTTACTACACAGGAAAACATGCAAAAGCCATAGGAAATT
GCCCAATATGGGTAAAAACACCTTTGAAGCTTGCCAATGGAACCAAATATAGACCTCCTGGTGGAGGATG
GGAAGGAATGATTGCAGGTTGGCACGGATACACATCTCACGGAGCACATGGAGTGGCAGTGGCGGCAGAC
CTTAAGAGTACACAAGAAGCTATAAATAAGATAACAAAAAATCTCAATTCTTTGAGTGAACTAGAAGTAA
AGAACCTTCAAAGACTAAGTGGTGCCATGGATGAACTCCACAACGAAATACTCGAGCTGGATGAAAAAGT
GGATGATCTCAGAGCTGACACTATAAGCTCACAAATAGAACTTGCAGTCTTGCTTTCCAACGAAGGAATA
ATAAACAGTGAAGACGAGCATCTATTGGCACTTGAGAGAAAACTAAAGAAAATGCTGGGTCCCTCTGCTG
TAGACATAGGAAACGGATGCTTCGAAACCAAACACAAATGCAACCAGACCTGCTTAGACAGGATAGCTGC
TGGCACCTTTAATGCAGGAGAATTTTCTCTCCCCACTTTTGATTCATTGAACATTACTGCTGCATCTTTA
AATGATGATGGATTGGATAACTACCAGATTTTGGCGATCTATTCAACTGTCGCCAGTTCATTGGTACTGG
TAGTCTCCCTGGGGGCAATCAGTTTCTGGATGTGCTCTAATGGGTCTCTACAGTGTAGAATATGTATTTA
A

FIGURE 21B: PDI+HA B Phu nucleic acid sequence (SEQ ID NO:92)

ATGGCGAAAAACGTTGCGATTTTCGGCTTATTGTTTTCTCTTCTTGTGTTGGTTCCTTCTCAGATCTTCG
CGGATCGAATCTGCACTGGGATAACATCTTCAAACTCACCTCATGTGGTCAAAACAGCTACTCAAGGGGA
GGTCAATGTGACTGGCGTGATACCACTGACAACAACACCAACAAAATCTTATTTTGCAAATCTCAAAGGA
ACAAGGACCAGAGGGAAACTATGCCCGGACTGTCTCAACTGTACAGATCTGGATGTGGCCTTGGGCAGGC
CAATGTGTGTGGGGACCACACCTTCTGCTAAAGCTTCAATACTCCATGAGGTCAGACCTGTTACATCCGG
GTGCTTTCCTATAATGCACGACAGAACAAAAATCAGGCAACTACCCAATCTTCTCAGAGGATATGAAAAG
ATCAGGTTATCAACCCAAAACGTTATCGATGCAGAAAAAGCACCAGGAGGACCCTACAGACTTGGAACCT
CAGGATCTTGCCCTAACGCTACCAGTAAAATCGGATTTTTTGCAACAATGGCTTGGGCTGTCCCAAAGGA
CAACTACAAAAATGCAACGAACCCACTAACAGTGGAAGTACCATACATTTGTACAGAAGGGGAAGACCAA
ATTACTGTTTGGGGGTTCCATTCGGATAACAAAACCCAAATGAAGAGCCTCTATGGAGACTCAAATCCTC
AAAAGTTCACCTCATCTGCTAATGGAGTAACCACGCATTATGTTTCTCAGATTGGCGACTTCCCAGATCA
AACAGAAGACGGAGGACTACCACAAAGCGGCAGAATTGTTGTTGATTACATGATGCAAAAACCTGGGAAA
ACAGGAACAATTGTCTATCAAAGGGGTGTTTTGTTGCCTCAAAAGGTGTGGTGCGCGAGTGGCAGGAGCA
AAGTAATAAAAGGGTCATTGCCTTTAATTGGTGAAGCAGATTGCCTTCATGAAGAATACGGTGGATTAAA

FIGURE 21B (Continued)

```
CAAAAGCAAGCCTTACTACACAGGAAAACATGCAAAAGCCATAGGAAATTGCCCAATATGGGTAAAAACA
CCTTTGAAGCTTGCCAATGGAACCAAATATAGACCTCCTGGTGGAGGATGGGAAGGAATGATTGCAGGTT
GGCACGGATACACATCTCACGGAGCACATGGAGTGGCAGTGGCGGCAGACCTTAAGAGTACACAAGAAGC
TATAAATAAGATAACAAAAAATCTCAATTCTTTGAGTGAACTAGAAGTAAAGAACCTTCAAAGACTAAGT
GGTGCCATGGATGAACTCCACAACGAAATACTCGAGCTGGATGAAAAGTGGATGATCTCAGAGCTGACA
CTATAAGCTCACAAATAGAACTTGCAGTCTTGCTTTCCAACGAAGGAATAATAAACAGTGAAGACGAGCA
TCTATTGGCACTTGAGAGAAAACTAAAGAAAATGCTGGGTCCCTCTGCTGTAGACATAGGAAACGGATGC
TTCGAAACCAAACACAAATGCAACCAGACCTGCTTAGACAGGATAGCTGCTGGCACCTTTAATGCAGGAG
AATTTTCTCTCCCCACTTTTGATTCATTGAACATTACTGCTGCATCTTTAAATGATGATGGATTGGATAA
CTACCAGATTTTGGCGATCTATTCAACTGTCGCCAGTTCATTGGTACTGGTAGTCTCCCTGGGGGCAATC
AGTTTCTGGATGTGCTCTAATGGGTCTCTACAGTGTAGAATATGTATTTAA
```

FIGURE 21C: PDI+HA B Phu amino acid sequence (SEQ ID NO:93)

```
MAKNVAIFGLLFSLLVLVPSQIFADRICTGITSSNSPHVVKTATQGEVNVTGVIPLTTTPTKSYFANLKG
TRTRGKLCPDCLNCTDLDVALGRPMCVGTTPSAKASILHEVRPVTSGCFPIMHDRTKIRQLPNLLRGYEK
IRLSTQNVIDAEKAPGGPYRLGTSGSCPNATSKIGFFATMAWAVPKDNYKNATNPLTVEVPYICTEGEDQ
ITVWGFHSDNKTQMKSLYGDSNPQKFTSSANGVTTHYVSQIGDFPDQTEDGGLPQSGRIVVDYMMQKPGK
TGTIVYQRGVLLPQKVWCASGRSKVIKGSLPLIGEADCLHEEYGGLNKSKPYYTGKHAKAIGNCPIWVKT
PLKLANGTKYRPPGGGWEGMIAGWHGYTSHGAHGVAVAADLKSTQEAINKITKNLNSLSELEVKNLQRLS
GAMDELHNEILELDEKVDDLRADTISSQIELAVLLSNEGIINSEDEHLLALERKLKKMLGPSAVDIGNGC
FETKHKCNQTCLDRIAAGTFNAGEFSLPTFDSLNITAASLNDDGLDNYQILAIYSTVASSLVLVVSLGAI
SFWMCSNGSLQCRICI
```

FIGURE 22A: Primers for GII.4 VP1 constructs

IF-GII4Syd12VP1.r (SEQ ID NO:68)

```
ACTAAAGAAAATAGGCCTTCAGACAGCCCTGCGTCTGCCAGTCCCATT
``` nbATL75+GII4Syd12.c (SEQ ID NO:69)

```
TTCTCGGTTCTCTTCTTCTACAGCAACAATGAAAATGGCCTCGAGTGACGCTAACCCTA
``` nbCHP79+GII4Syd12.c (SEQ ID NO:70)

```
TTCTGATTTTCTGTGATTTCTACAAATCTGAGACATGAAAATGGCCTCGAGTGACGCTA
``` nbMT78+GII4Syd12.c (SEQ ID NO:71)

```
TCTATTATCTCCCAACAACATAAGAAAACAATGAAAATGGCCTCGAGTGACGCTAACCC
``` atHSP69+GII4Syd12.c (SEQ ID NO:72)

```
AAACACAGACCTTAAAAAAATAAAAATGAAAATGGCCTCGAGTGACGCTAACCCTAGTG
```

Figure 22B: CPMV 160 5'UTR-VP1 (GII.4) nucleic acid sequence (SEQ ID NO:94)

TATTAAAATCTTAATAGGTTTTGATAAAAGCGAACGTGGGGAAACCCGAACCAAACCTTCTTCTAAACTC
TCTCTCATCTCTCTTAAAGCAAACTTCTCTCTTGTCTTTCTTGCGTGAGCGATCTTCAACGTTGTCAGAT
CGTGCTTCGGCACCAGTACAATGAAAATGGCCTCGAGTGACGCTAACCCTAGTGACGGCAGCGCCGCCAA
TCTTGTGCCTGAGGTTAATAATGAGGTGATGGCCCTGGAGCCTGTGGTGGGCGCAGCCATAGCAGCGCCC
GTGGCCGGTCAGCAGAATGTGATTGACCCGTGGATACGCAACAATTTTGTCCAAGCCCCTGGTGGGGAGT
TCACCGTTAGCCCGAGAAATGCGCCAGGAGAAATCCTGTGGTCGGCCAGCTTGGGACCCGATCTGAACCC
CTATTTGTCACATCTCGCTCGGATGTACAACGGGTATGCCGGCGGATTTGAAGTGCAGGTGATTCTGGCT
GGGAACGCGTTCACTGCTGGCAAAGTGATCTTTGCAGCGGTGCCTCCCAACTTCCCCACTGAAGGACTGT
CTCCAAGCCAGGTCACAATGTTTCCACACATCGTGGTGGACGTACGGCAGCTAGAGCCTGTCCTGATTCC
CCTCCCTGATGTACGCAATAATTTCTACCACTACAATCAATCCAATGATCCGACCATTAAACTCATCGCG
ATGTTGTACACCCCTCTGCGCGCTAACAATGCTGGAGACGACGTATTCACCGTGTCATGCAGAGTGCTCA
CCAGACCTTCACCAGACTTTGACTTTATCTTCTTAGTGCCCCCCACTGTTGAGAGCCGAACCAAGCCCTT
TAGTGTCCCCGTACTCACAGTCGAGGAGATGACAAATAGCCGCTTTCCAATCCCCCTTGAGAAACTGTTC
ACAGGACCTTCCTCGGCATTCGTGGTTCAGCCACAGAACGGACGCTGCACAACTGACGGCGTGCTGCTCG
GAACCACCCAGCTTAGCCCTGTTAATATCTGTACGTTTAGAGGCGACGTAACTCACATAACTGGCTCACG
GAACTATACCATGAATCTGGCATCACAGAATTGGAATGACTACGACCCAACCGAAGAGATTCCCGCACCT
CTTGGAACCCCCGACTTTGTGGGAAAAATACAGGGCGTCCTGACACAAACCACCAGAACCGATGGCTCCA
CACGGGGACACAAGGCAACCGTCTACACTGGCTCTGCCGATTTTGCCCCGAAACTGGGTAGAGTGCAGTT
TGAGACCGACACTGACCGGGACTTTGAAGCCAATCAGAATACTAAGTTCACACCTGTAGGAGTGATTCAG
GACGGGGGCACCACTCACCGGAACGAGCCGCAACAATGGGTCCTGCCCTCTTATAGCGGGAGGAATACTC
ATAATGTGCATTTGGCTCCTGCAGTGGCTCCCACGTTTCCCGGGGAACAACTGCTCTTTTTTCGTTCAAC
CATGCCTGGATGCTCCGGATATCCCAATATGGATCTCGATTGCCTGCTCCCACAGGAATGGGTGCAGTAT
TTTTATCAAGAGGCCGCACCAGCCCAATCCGACGTCGCACTTCTGCGGTTCGTGAATCCAGACACAGGCC
GCGTGTTGTTTGAGTGCAAATTGCACAAATCAGGATACGTTACAGTGGCTCATACTGGACAGCATGACCT
GGTGATCCCACCCAACGGATATTTTAGGTTCGACTCCTGGGTGAATCAGTTTTATACATTAGCCCCCATG
GGGAATGGGACTGGCAGACGCAGGGCTGTCTGA

FIGURE 22C: VP1 (GII.4) nucleic acid sequence (SEQ ID NO:95)

ATGAAAATGGCCTCGAGTGACGCTAACCCTAGTGACGGCAGCGCCGCCAATCTTGTGCCTGAGGTTAATA
ATGAGGTGATGGCCCTGGAGCCTGTGGTGGGCGCAGCCATAGCAGCGCCCGTGGCCGGTCAGCAGAATGT
GATTGACCCGTGGATACGCAACAATTTTGTCCAAGCCCCTGGTGGGGAGTTCACCGTTAGCCCGAGAAAT
GCGCCAGGAGAAATCCTGTGGTCGGCCAGCTTGGGACCCGATCTGAACCCCTATTTGTCACATCTCGCTC
GGATGTACAACGGGTATGCCGGCGGATTTGAAGTGCAGGTGATTCTGGCTGGGAACGCGTTCACTGCTGG
CAAAGTGATCTTTGCAGCGGTGCCTCCCAACTTCCCCACTGAAGGACTGTCTCCAAGCCAGGTCACAATG
TTTCCACACATCGTGGTGGACGTACGGCAGCTAGAGCCTGTCCTGATTCCCCTCCCTGATGTACGCAATA
ATTTCTACCACTACAATCAATCCAATGATCCGACCATTAAACTCATCGCGATGTTGTACACCCCTCTGCG
CGCTAACAATGCTGGAGACGACGTATTCACCGTGTCATGCAGAGTGCTCACCAGACCTTCACCAGACTTT
GACTTTATCTTCTTAGTGCCCCCCACTGTTGAGAGCCGAACCAAGCCCTTTAGTGTCCCCGTACTCACAG
TCGAGGAGATGACAAATAGCCGCTTTCCAATCCCCCTTGAGAAACTGTTCACAGGACCTTCCTCGGCATT
CGTGGTTCAGCCACAGAACGGACGCTGCACAACTGACGGCGTGCTGCTCGGAACCACCCAGCTTAGCCCT
GTTAATATCTGTACGTTTAGAGGCGACGTAACTCACATAACTGGCTCACGGAACTATACCATGAATCTGG
CATCACAGAATTGGAATGACTACGACCCAACCGAAGAGATTCCCGCACCTCTTGGAACCCCCGACTTTGT
GGGAAAAATACAGGGCGTCCTGACACAAACCACCAGAACCGATGGCTCCACACGGGGACACAAGGCAACC
GTCTACACTGGCTCTGCCGATTTTGCCCCGAAACTGGGTAGAGTGCAGTTTGAGACCGACACTGACCGGG
ACTTTGAAGCCAATCAGAATACTAAGTTCACACCTGTAGGAGTGATTCAGGACGGGGGCACCACTCACCG
GAACGAGCCGCAACAATGGGTCCTGCCCTCTTATAGCGGGAGGAATACTCATAATGTGCATTTGGCTCCT

FIGURE 22C (Continued)

GCAGTGGCTCCCACGTTTCCCGGGGAACAACTGCTCTTTTTTCGTTCAACCATGCCTGGATGCTCCGGAT
ATCCCAATATGGATCTCGATTGCCTGCTCCCACAGGAATGGGTGCAGTATTTTTATCAAGAGGCCGCACC
AGCCCAATCCGACGTCGCACTTCTGCGGTTCGTGAATCCAGACACAGGCCGCGTGTTGTTTGAGTGCAAA
TTGCACAAATCAGGATACGTTACAGTGGCTCATACTGGACAGCATGACCTGGTGATCCCACCCAACGGAT
ATTTTAGGTTCGACTCCTGGGTGAATCAGTTTTATACATTAGCCCCCATGGGGAATGGGACTGGCAGACG
CAGGGCTGTCTGA

FIGURE 22D: VP1 (GII.4) amino acid sequence (SEQ ID NO:96)

MKMASSDANPSDGSAANLVPEVNNEVMALEPVVGAAIAAPVAGQQNVIDPWIRNNFVQAPGGEFTVSPRN
APGEILWSASLGPDLNPYLSHLARMYNGYAGGFEVQVILAGNAFTAGKVIFAAVPPNFPTEGLSPSQVTM
FPHIVVDVRQLEPVLIPLPDVRNNFYHYNQSNDPTIKLIAMLYTPLRANNAGDDVFTVSCRVLTRPSPDF
DFIFLVPPTVESRTKPFSVPVLTVEEMTNSRFPIPLEKLFTGPSSAFVVQPQNGRCTTDGVLLGTTQLSP
VNICTFRGDVTHITGSRNYTMNLASQNWNDYDPTEEIPAPLGTPDFVGKIQGVLTQTTRTDGSTRGHKAT
VYTGSADFAPKLGRVQFETDTDRDFEANQNTKFTPVGVIQDGGTTHRNEPQQWVLPSYSGRNTHNVHLAP
AVAPTFPGEQLLFFRSTMPGCSGYPNMDLDCLLPQEWVQYFYQEAAPAQSDVALLRFVNPDTGRVLFECK
LHKSGYVTVAHTGQHDLVIPPNGYFRFDSWVNQFYTLAPMGNGTGRRRAV

FIGURE 23A: Primers for Rituximab constructs

IF**-HC(Ritux).s1-6r (SEQ ID NO:73)

ACTAAAGAAAATAGGCCTTCACTTTCCAGGAGAAAGAGAAAGGGACTTTTG

IF**-LC(Ritux).s1-6r (SEQ ID NO:74)

ACTAAAGAAAATAGGCCTTCAACACTCTCCCCTGTTGAAGCTCTTTGTGAC

FIGURE 23B: CPMV 160 5'UTR-PDI+Rituximab HC nucleic acid sequence (SEQ ID NO:97)

TATTAAAATCTTAATAGGTTTTGATAAAAGCGAACGTGGGGAAACCCGAACCAAACCTTCTTCTAAACTC
TCTCTCATCTCTCTTAAAGCAAACTTCTCTCTTGTCTTTCTTGCGTGAGCGATCTTCAACGTTGTCAGAT
CGTGCTTCGGCACCAGTACAATGGCGAAAAACGTTGCGATTTTCGGCTTATTGTTTTCTCTTCTTGTGTT
GGTTCCTTCTCAGATCTTCGCGCAGGTACAACTGCAGCAGCCTGGGGCTGAGCTGGTGAAGCCTGGGGCC
TCAGTGAAGATGTCCTGCAAGGCTTCTGGCTACACATTTACCAGTTACAATATGCACTGGGTAAAACAGA
CACCTGGTCGGGGCCTGGAATGGATTGGAGCTATTTATCCCGGAAATGGTGATACTTCCTACAATCAGAA
GTTCAAAGGCAAGGCCACATTGACTGCAGACAAATCCTCCAGCACAGCCTACATGCAGCTCAGCAGCCTG
ACATCTGAGGACTCTGCGGTCTATTACTGTGCAAGATCGACTTACTACGGCGGTGACTGGTACTTCAATG
TCTGGGGCGCAGGGACCACGGTCACCGTCTCTGCAGCTAGCACCAAGGGCCCATCGGTCTTCCCCCTGGC
ACCCTCCTCCAAGAGCACCTCTGGGGGCACAGCGGCCCTGGGCTGCCTGGTCAAGGACTACTTCCCCGAA
CCGGTGACGGTGTCGTGGAACTCAGGCGCCCTGACCAGCGGCGTGCACACCTTCCCGGCTGTCCTACAGT
CCTCAGGACTCTACTCCCTCAGCAGCGTGGTGACCGTGCCCTCCAGCAGCTTGGGCACCCAGACCTACAT
CTGCAACGTGAATCACAAGCCCAGCAACACCAAGGTGGACAAGAAAGTTGAGCCCAAATCTTGTGACAAA
ACTCACACATGCCCACCGTGCCCAGCACCTGAACTCCTGGGGGGACCGTCAGTCTTCCTCTTCCCCCCAA

FIGURE 23B (Continued)

AACCCAAGGACACCCTCATGATCTCCCGGACCCCTGAGGTCACATGCGTGGTGGTGGACGTGAGCCACGA
AGACCCTGAGGTCAAGTTCAACTGGTACGTGGACGGCGTGGAGGTGCATAATGCCAAGACAAAGCCGCGG
GAGGAGCAGTACAACAGCACGTACCGTGTGGTCAGCGTCCTCACCGTCCTGCACCAGGACTGGCTGAATG
GCAAGGAGTACAAGTGCAAGGTCTCCAACAAAGCCCTCCCAGCCCCCATCGAGAAAACCATCTCCAAAGC
CAAAGGGCAGCCTAGGGAACCACAAGTGTACACTCTTCCACCATCTAGGGATGAGCTTACTAAGAACCAA
GTTTCTCTTACTTGTCTTGTGAAGGGATTTTATCCATCTGACATCGCCGTGGAATGGGAATCCAACGGAC
AACCAGAGAACAATTACAAGACTACTCCACCAGTTCTTGATTCTGATGGATCCTTCTTTCTTTATTCCAA
GCTTACTGTTGATAAGTCCAGATGGCAGCAAGGAAATGTGTTCTCTTGTTCTGTTATGCACGAAGCTCTT
CATAATCATTATACTCAAAAGTCCCTTTCTCTTTCTCCTGGAAAGTGA

FIGURE 23C: PDI+Rituximab HC nucleic acid sequence (SEQ ID NO:98)

ATGGCGAAAAACGTTGCGATTTTCGGCTTATTGTTTTCTCTTCTTGTGTTGGTTCCTTCTCAGATCTTCG
CGCAGGTACAACTGCAGCAGCCTGGGGCTGAGCTGGTGAAGCCTGGGGCCTCAGTGAAGATGTCCTGCAA
GGCTTCTGGCTACACATTTACCAGTTACAATATGCACTGGGTAAAACAGACACCTGGTCGGGGCCTGGAA
TGGATTGGAGCTATTTATCCCGGAAATGGTGATACTTCCTACAATCAGAAGTTCAAAGGCAAGGCCACAT
TGACTGCAGACAAATCCTCCAGCACAGCCTACATGCAGCTCAGCAGCCTGACATCTGAGGACTCTGCGGT
CTATTACTGTGCAAGATCGACTTACTACGGCGGTGACTGGTACTTCAATGTCTGGGGCGCAGGGACCACG
GTCACCGTCTCTGCAGCTAGCACCAAGGGCCCATCGGTCTTCCCCCTGGCACCCTCCTCCAAGAGCACCT
CTGGGGGCACAGCGGCCCTGGGCTGCCTGGTCAAGGACTACTTCCCCGAACCGGTGACGGTGTCGTGGAA
CTCAGGCGCCCTGACCAGCGGCGTGCACACCTTCCCGGCTGTCCTACAGTCCTCAGGACTCTACTCCCTC
AGCAGCGTGGTGACCGTGCCCTCCAGCAGCTTGGGCACCCAGACCTACATCTGCAACGTGAATCACAAGC
CCAGCAACACCAAGGTGGACAAGAAAGTTGAGCCCAAATCTTGTGACAAAACTCACACATGCCCACCGTG
CCCAGCACCTGAACTCCTGGGGGGACCGTCAGTCTTCCTCTTCCCCCCAAAACCCAAGGACACCCTCATG
ATCTCCCGGACCCCTGAGGTCACATGCGTGGTGGTGGACGTGAGCCACGAAGACCCTGAGGTCAAGTTCA
ACTGGTACGTGGACGGCGTGGAGGTGCATAATGCCAAGACAAAGCCGCGGGAGGAGCAGTACAACAGCAC
GTACCGTGTGGTCAGCGTCCTCACCGTCCTGCACCAGGACTGGCTGAATGGCAAGGAGTACAAGTGCAAG
GTCTCCAACAAAGCCCTCCCAGCCCCCATCGAGAAAACCATCTCCAAAGCCAAAGGGCAGCCTAGGGAAC
CACAAGTGTACACTCTTCCACCATCTAGGGATGAGCTTACTAAGAACCAAGTTTCTCTTACTTGTCTTGT
GAAGGGATTTTATCCATCTGACATCGCCGTGGAATGGGAATCCAACGGACAACCAGAGAACAATTACAAG
ACTACTCCACCAGTTCTTGATTCTGATGGATCCTTCTTTCTTTATTCCAAGCTTACTGTTGATAAGTCCA
GATGGCAGCAAGGAAATGTGTTCTCTTGTTCTGTTATGCACGAAGCTCTTCATAATCATTATACTCAAAA
GTCCCTTTCTCTTTCTCCTGGAAAGTGA

Figure 23D: PDI+Rituximab HC amino acid sequence (SEQ ID NO:99)

MAKNVAIFGLLFSLLVLVPSQIFAQVQLQQPGAELVKPGASVKMSCKASGYTFTSYNMHWVKQTPGRGLE
WIGAIYPGNGDTSYNQKFKGKATLTADKSSSTAYMQLSSLTSEDSAVYYCARSTYYGGDWYFNVWGAGTT
VTVSAASTKGPSVFPLAPSSKSTSGGTAALGCLVKDYFPEPVTVSWNSGALTSGVHTFPAVLQSSGLYSL
SSVVTVPSSSLGTQTYICNVNHKPSNTKVDKKVEPKSCDKTHTCPPCPAPELLGGPSVFLFPPKPKDTLM
ISRTPEVTCVVVDVSHEDPEVKFNWYVDGVEVHNAKTKPREEQYNSTYRVVSVLTVLHQDWLNGKEYKCK
VSNKALPAPIEKTISKAKGQPREPQVYTLPPSRDELTKNQVSLTCLVKGFYPSDIAVEWESNGQPENNYK
TTPPVLDSDGSFFLYSKLTVDKSRWQQGNVFSCSVMHEALHNHYTQKSLSLSPGK

FIGURE 23E: CPMV 160 5'UTR-PDI+Rituximab LC nucleic acid sequence (SEQ ID NO:100)

TATTAAAATCTTAATAGGTTTTGATAAAAGCGAACGTGGGGAAACCCGAACCAAACCTTCTTCTAAACTC
TCTCTCATCTCTCTTAAAGCAAACTTCTCTCTTGTCTTTCTTGCGTGAGCGATCTTCAACGTTGTCAGAT
CGTGCTTCGGCACCAGTACAATGGCGAAAAACGTTGCGATTTTCGGCTTATTGTTTTCTCTTCTTGTGTT
GGTTCCTTCTCAGATCTTCGCGCAAATTGTTCTCTCCCAGTCTCCAGCAATCCTGTCTGCATCTCCAGGG
GAGAAGGTCACAATGACTTGCAGGGCCAGCTCAAGTGTAAGTTACATCCACTGGTTCCAGCAGAAGCCAG
GATCCTCCCCAAACCCTGGATTTATGCCACATCCAACCTGGCTTCTGGAGTCCCTGTTCGCTTCAGTGG
CAGTGGGTCTGGGACTTCTTACTCTCTCACAATCAGCAGAGTGGAGGCTGAAGATGCTGCCACTTATTAC
TGCCAGCAGTGGACTAGTAACCCACCCACGTTCGGAGGGGGGACCAAGCTGGAAATCAAACGTACGGTGG
CTGCACCATCTGTCTTCATCTTCCCGCCATCTGATGAGCAGTTGAAATCTGGAACTGCCTCTGTTGTGTG
CCTGCTGAATAACTTCTATCCCAGAGAGGCCAAAGTACAGTGGAAGGTGGATAACGCCCTCCAATCGGGT
AACTCCCAGGAGAGTGTCACAGAGCAGGACAGCAAGGACAGCACCTACAGCCTCAGCAGCACCCTGACGC
TGAGCAAAGCAGACTACGAGAAACACAAAGTCTACGCCTGCGAAGTCACCCATCAGGGCCTGAGCTCGCC
CGTCACAAAGAGCTTCAACAGGGGAGAGTGTTGA

FIGURE 23F: PDI+Rituximab LC nucleic acid sequence (SEQ ID NO:101)

ATGGCGAAAAACGTTGCGATTTTCGGCTTATTGTTTTCTCTTCTTGTGTTGGTTCCTTCTCAGATCTTCG
CGCAAATTGTTCTCTCCCAGTCTCCAGCAATCCTGTCTGCATCTCCAGGGGAGAAGGTCACAATGACTTG
CAGGGCCAGCTCAAGTGTAAGTTACATCCACTGGTTCCAGCAGAAGCCAGGATCCTCCCCAAACCCTGG
ATTTATGCCACATCCAACCTGGCTTCTGGAGTCCCTGTTCGCTTCAGTGGCAGTGGGTCTGGGACTTCTT
ACTCTCTCACAATCAGCAGAGTGGAGGCTGAAGATGCTGCCACTTATTACTGCCAGCAGTGGACTAGTAA
CCCACCCACGTTCGGAGGGGGGACCAAGCTGGAAATCAAACGTACGGTGGCTGCACCATCTGTCTTCATC
TTCCCGCCATCTGATGAGCAGTTGAAATCTGGAACTGCCTCTGTTGTGTGCCTGCTGAATAACTTCTATC
CCAGAGAGGCCAAAGTACAGTGGAAGGTGGATAACGCCCTCCAATCGGGTAACTCCCAGGAGAGTGTCAC
AGAGCAGGACAGCAAGGACAGCACCTACAGCCTCAGCAGCACCCTGACGCTGAGCAAAGCAGACTACGAG
AAACACAAAGTCTACGCCTGCGAAGTCACCCATCAGGGCCTGAGCTCGCCCGTCACAAAGAGCTTCAACA
GGGGAGAGTGTTGA

FIGURE 23G: PDI+Rituximab LC amino acid sequence (SEQ ID NO:102)

MAKNVAIFGLLFSLLVLVPSQIFAQIVLSQSPAILSASPGEKVTMTCRASSSVSYIHWFQQKPGSSPKPW
IYATSNLASGVPVRFSGSGSGTSYSLTISRVEAEDAATYYCQQWTSNPPTFGGGTKLEIKRTVAAPSVFI
FPPSDEQLKSGTASVVCLLNNFYPREAKVQWKVDNALQSGNSQESVTEQDSKDSTYSLSSTLTLSKADYE
KHKVYACEVTHQGLSSPVTKSFNRGEC

PLANT EXPRESSION ENHANCER

CROSS REFERENCE TO RELATED APPLICATIONS

The present application is a National Stage application filed under 35 U.S.C. § 371 of International Application No. PCT/CA2019/050317, filed on Mar. 14, 2019, which claims priority to U.S. Provisional Patent Application No. 62/643,053, filed Mar. 14, 2018, the entire contents of each of which are hereby incorporated by reference in their entireties.

FIELD OF INVENTION

The present invention relates to expression enhancers that are active in plants. The present invention also relates to the expression of proteins of interest in plants, and provides methods and compositions for the production of proteins of interest in plants.

SUBMISSION OF SEQUENCE LISTING

The Sequence Listing associated with this application is filed in electronic format via EFS-Web and hereby incorporated by reference into the specification in its entirety. The name of the text file containing the Sequence Listing is 18636_0015u1_SL. The size of the text file is 115 KB and the text file was created on Sep. 11, 2020.

BACKGROUND OF THE INVENTION

Plants offer great potential as production systems for recombinant proteins. One approach to producing foreign proteins in plants is to generate stable transgenic plant lines. However this is a time consuming and labor intensive process. An alternative to transgenic plants is the use of plant virus-based expression vectors. Plant virus-based vectors allow for the rapid, high level, transient expression of proteins in plants.

High level transient expression of foreign proteins in plants has been obtained using of vectors based on RNA plant viruses, including comoviruses, such as Cowpea mosaic virus (CPMV; see, for example, WO2007/135480; WO2009/087391; US 2010/0287670, Sainsbury F. et al., 2008, Plant Physiology; 148: 121-1218; Sainsbury F. et al., 2008, Plant Biotechnology Journal; 6: 82-92; Sainsbury F. et al., 2009, Plant Biotechnology Journal; 7: 682-693; Sainsbury F. et al. 2009, Methods in Molecular Biology, Recombinant Proteins From Plants, vol. 483: 25-39).

Modifications of the 5'UTR of the RNA-2 of the comovirus cowpea mosaic virus (CPMV) have resulted in additional expression enhancer activity (as determined level of expression of a nucleic acid of interest or a protein of interest), when compared to the wild type CPMV 5'UTR. For example, mutation of the start codon at position 161 in a CPMV RNA-2 vector (U162C; HT) increases the levels of expression of a protein encoded by a sequence inserted after the start codon at position 512. This permits the production of high levels of foreign proteins without the need for viral replication and was termed the CPMV-HT system (WO2009/087391; Sainsbury and Lomonossoff, 2008, Plant Physiol. 148, 1212-1218). In PEAQ expression plasmids (Sainsbury et al., 2009, Plant Biotechnology Journal, 7, pp 682-693; US 2010/0287670), the sequence to be expressed is positioned between the 5'UTR and the 3' UTR. The 5'UTR in the pEAQ series carries the U162C (HT) mutation.

Additional modification of the CPMV 5' UTR region, have been described that further increase expression of a nucleic acid of interest within a plant. For example, "CMPV HT+" (comprising nucleotides 1-160 of the CPMV 5' UTR with modified ATGs at position 115-117, and at position 161-163; WO2015/143567; which is incorporated herein by reference), and "CPMVX" (where X=160, 155, 150, or 114 nucleic acids in length; WO 2015/103704; which is incorporated herein by reference). An example of CMPVX is the expression enhancer "CPMV 160". Expression of a nucleic acid sequence operatively linked to CPMV HT+" resulted in a significant increase in production of a protein of interest that was encoded by the nucleic acid sequence, when compared to the production of the same protein of interest using the same nucleic acid sequence operatively linked to the "CPMV HT" expression enhancer (see FIGS. 2 and 3 of WO2015/143567). Furthermore, expression of a nucleic acid sequence operatively linked to the "CPMV 160" expression enhancer resulted in a significant increase in production of a protein of interest encoded by the nucleic acid sequence, when compared to the production of the same protein of interest using the same nucleic acid sequence operatively linked to the "CPMV HT+" expression enhancer (see FIGS. 2 and 3 of WO2015/143567).

Diamos et. al (Frontiers in Plant Science. 2016, vol7 pp. 1-15; which is incorporated herein by reference) describe several expression enhancers that may be used to increase production of proteins in plants (see Table 2 of Diamos et. al.), including the expression enhancer NbPsaK2 3'. As shown in FIG. 4 of Diamos et. al. (2016), production of protein of interst encoded by a nuclei acid that was operatively linked to NbPsaK2 3' resulted in enhanced protein production when compared to the production of the same protein encoded by the same nucleic acid sequence operatively linked to other truncated psaK expression enhancers.

SUMMARY OF THE INVENTION

The present invention relates to expression enhancers that are active in plants. The present invention also relates to the expression of proteins of interest in plants, and provides methods and compositions for the production of proteins of interest in plants.

It is an object of the invention to provide an improved expression enhancer active in a plant.

According to the present invention there is provided an isolated expression enhancer active in a plant, the expression enhancer selected from the group consisting of:
  nbMT78 (SEQ ID NO:1);
  nbATL75 (SEQ ID NO:2);
  nbDJ46 (SEQ ID NO:3);
  nbCHP79 (SEQ ID NO:4);
  nbEN42 (SEQ ID NO:5);
  atHSP69 (SEQ ID NO:6);
  atGRP62 (SEQ ID NO:7);
  atPK65 (SEQ ID NO:8);
  atRP46 (SEQ ID NO:9);
  nb30S72 (SEQ ID NO:10);
  nbGT61 (SEQ ID NO:11);
  nbPV55 (SEQ ID NO:12);
  nbPPI43 (SEQ ID NO:13);
  nbPM64 (SEQ ID NO:14);
  nbH2A86 (SEQ ID NO:15), and
a nucleic acid having from 90-100% sequence identity to the nucleotide sequence set forth in any one of SEQ ID NO's: 1-15. Wherein, the expression enhancer, when operatively linked to a nucleic acid of interest, for example a heterologous nucleic acid of interest, results in expression of the nucleic acid of interest. Additionally, the expression enhancer, when operatively linked to a nucleic acid of interest, for example a heterologous nucleic acid of interest, may increase the level of expression of the nucleic acid of interest, or the heterologous nucleic acid of interest, when compared to the level of expression of the same nucleic acid or heterologous nucleic acid of interest that is not operatively linked to the expression enhancer, or for example, when operatively linked to the prior art expression enhancer CPMV 160 (SEQ ID NO:16).

The present disclosure also provides for a nucleic acid sequence comprising one of the isolated expression enhancers as described above, the expression enhancer operatively linked with a heterologous nucleotide sequence encoding a protein of interest. The heterologous nucleotide sequence may encode a viral protein or an antibody, for example which is not to be considered limiting, the viral protein may be an influenza protein or a norovirus protein. If the protein of interest is an influenza protein then it may include M2, a hemagglutinin protein selected from the group of H1, H2, H3, H4, H5, H6, H7, H8, H9, H10, H11, H12, H13, H14, H15, H16, an influenza type B hemagglutinin, or a combination thereof. If the protein of interest is a norovirus protein, then it may include a VP1 protein, a VP2 protein, or a combination thereof, selected from the group of GI. 1, GI.2, GI.3, GI.5, GI.7, GII. 1, GII.2, GII.3, GII.4, GII.5, GII.6, GII.7, GII. 12, GII. 13, GII. 14, GII. 17 and GII.21.

The present invention also provides a plant expression system comprising one or more than one of the nucleic acid sequence described above. The plant expression system may further comprise a comovirus 3' UTR.

The present invention also provides a plant expression system comprising one or more than one of the isolated nucleic acid sequence operatively linked with a heterologous nucleic acid, or nucleotide sequence, as described above. The plant expression system may further comprise a comovirus 3' UTR.

Also disclosed herein is a method of producing a protein of interest in a plant or in a portion of a plant comprising, introducing into the plant or in the portion of a plant the plant expression system as described above, comprising the one or more than one of nucleic acid sequence, and incubating the plant, the portion of a plant, or plant cell, under conditions that permit expression of each of the heterologous nucleotide sequence encoding the protein of interest. For example, the protein of interest may be a viral protein, such as an influenza protein or a norovirus protein. If the protein of interest is an influenza protein then it may include M2, a hemagglutinin protein selected from the group of H1, H2, H3, H4, H5, H6, H7, H8, H9, H10, H11, H12, H13, H14, H15, H16, an influenza type B hemagglutinin, and a combination thereof. If the protein of interest is a norovirus protein, then it may include a VP1 protein, a VP2 protein, or a combination thereof, selected from the group of GI.1, GI.2, GI.3, GI.5, GII. 1, GII.2, GII.3, GII.4, GII.5, GII.6, GII.7, GII. 12, GII. 13, GII. 14, GII. 17 and GII.21.

A method of producing a multimeric protein of interest, is also described herein. The method involves co-expressing two or more than two of the nucleic acid sequence as described above, in a plant, the portion of a plant, or plant cell, in a stable or transient manner, wherein each of the two or more than two of the nucleic acid sequence encodes a component of the multimeric protein, and incubating the plant, the portion of a plant, or plant cell, under conditions that permit expression of each of the heterologous nucleotide sequence encoding the multimeric protein of interest.

Also provided herein is a plant, a portion of a plant, or plant cell that is transiently transformed, or stably transformed, with plant expression system as described above.

A plant-based expression system comprising an expression enhancer as described herein results in expression of the nucleic acid of interest. Furthermore, the plant-based expression system comprising an expression enhancer as described herein result in increasing or enhancing expression of a nucleotide sequence encoding a heterologous open reading frame that is operatively linked to the expression enhancer, either an expression enhancer obtained from a nucleic acid encoding a secreted protein (SPEE), or an expression enhancer obtained from a nucleic acid encoding a cytosolic protein (CPEE), as described herein. The increase in expression may be determined by comparing the level of expression obtained using the expression enhancer as described herein with the level of expression of the same nucleotide sequence encoding the heterologous open reading frame but not operatively linked to an expression enhancer, or for example, when operatively linked to the prior art expression enhancer CPMV 160 (SEQ ID NO:16).

The plant based expression systems, vectors, constructs and nucleic acids comprising one or more than one expression enhancer as described herein may also have a number of properties such as, for example, containing convenient cloning sites for genes or nucleotide sequences of interest, they may be used to easily transform plants in a cost-effective manner, they may cause efficient local or systemic transformation of inoculated plants. In addition, the transformation of a plant should provide a good yield of useful protein material.

This summary of the invention does not necessarily describe all features of the invention.

BRIEF DESCRIPTION OF THE DRAWINGS

These and other features of the invention will become more apparent from the following description in which reference is made to the appended drawings wherein.

Figure 3A:
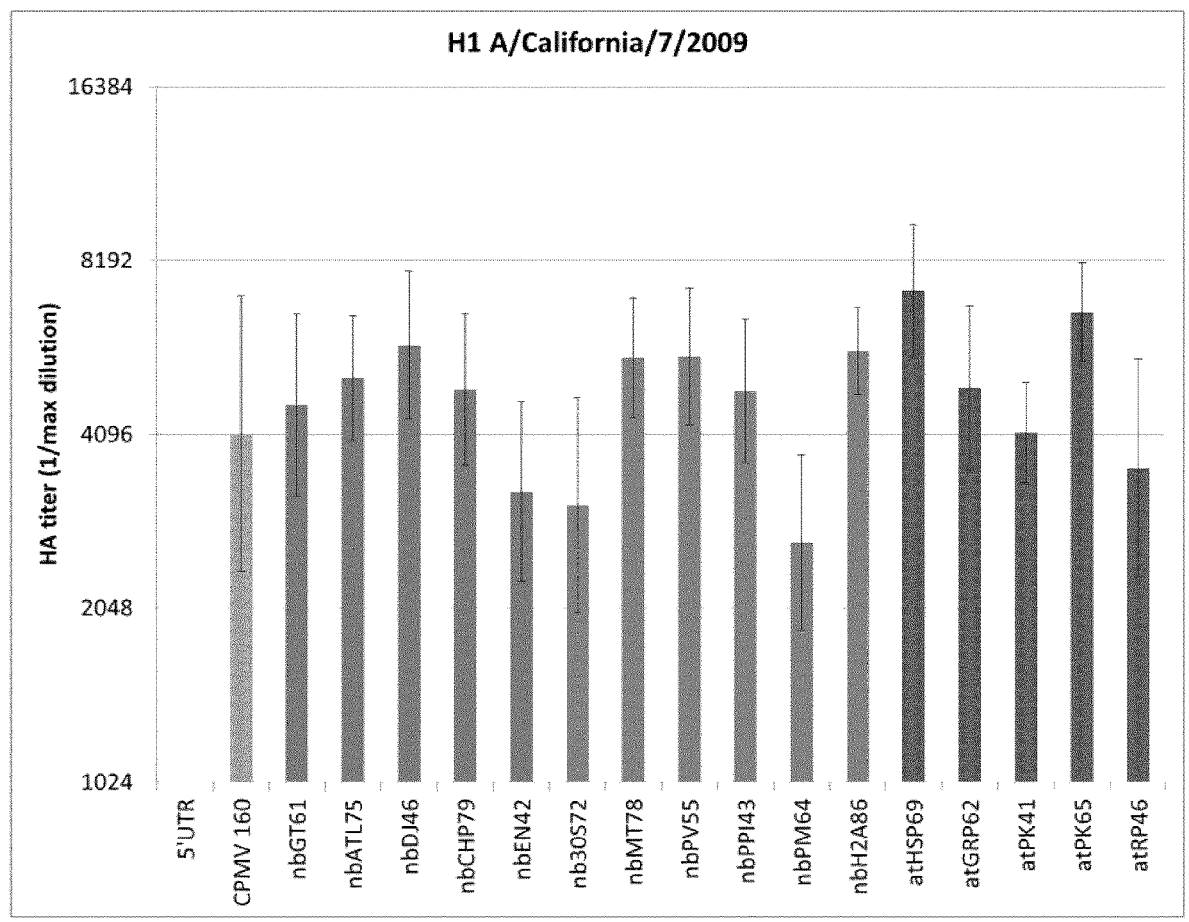

FIG. 3A shows HA titer of the H1 California/7/09 influenza virus produced in plants by expressing a nucleic acid encoding the H1 California protein wherein the nucleic acid encoding this protein is operatively linked to prior art expression enhancers CPMV 160 (described in WO 2015/103704) or atPK41 (described in Diamos et. al., Frontiers in Plant Science. 2016, vol7 pp. 1-15), or expression enhancers of the present invention: nbMT78 (SEQ ID NO:1); nbATL75 (SEQ ID NO:2); nbDJ46 (SEQ ID NO:3); nbCHP79 (SEQ ID NO:4); nbEN42 (SEQ ID NO:5) atHSP69 (SEQ ID NO:6) atGRP62 (SEQ ID NO:7); atPK65 (SEQ ID NO:8); atRP46 (SEQ ID NO:9) nb30S72 (SEQ ID NO:10); nbGT61 (SEQ ID NO:11); nbPV55 (SEQ ID NO:12); nbPPI43 (SEQ ID NO:13); nbPM64 (SEQ ID NO:14); and nbH2A86 (SEQ ID NO:15). FIG. 3B shows HA titer of H1 Mich/45/15, H3 HK/4801/14, HA B Bris/60/08, and HA B Phu/3073/13 produced in plants by expressing a nucleic acid encoding the indicated HA protein, wherein each of the nucleic acids encoding the indicated proteins is operatively linked to the prior art expression enhancer CPMV 160 (described in WO 2015/103704), or the expression enhancers of the present invention: nbMT78 (SEQ ID NO:1), nbATL75 (SEQ ID NO:2), nbCHP79 (SEQ ID NO:4), and atHSP69 (SEQ ID NO:6).

FIG. 4 shows relative yield of norovirus GII.4/Sydney 2012 VP1 VLPs, following gradient centrifugation, the VLP produced in plants by expressing a nucleic acid encoding the VP1 protein, wherein each of the nucleic acids encoding the VP1 protein is operatively linked to: prior art expression enhancer CPMV 160 (described in WO 2015/103704), prior art expression enhancer NbPsaK2 3' (termed nbPK74 herein; Diamos et al.), or the expression enhancers of the present invention: nbMT78 (SEQ ID NO:1). nbATL75 (SEQ ID NO:2), nbCHP79 (SEQ ID NO:4), and atHSP69 (SEQ ID NO:6).

FIG. 5 shows relative yield of the multimeric protein Rituximab produced in plants by co-expressing a first nucleic acid encoding the light chain (LC) of the Rituximab antibody, and second nucleic acid encoding the heavy chain (HC) of Rituximab antibody operatively linked to various combinations of expression enhancers. With reference to the HC nucleic acid: (160: the first and second nucleic acids encoding the multimeric protein are both operatively linked to prior art expression enhancers CPMV 160 (described in WO 2015/103704); nbATL75: the second nucleic acid encoding the HC multimeric protein is operatively linked to the nbATL75 expression enhancer, and the first nucleic acid encoding the LC is operatively linked to one of nbMT78 (SEQ ID NO:1), nbATL75 (SEQ ID NO:2), nbCHP79 (SEQ ID NO:4) and atHSP69 (SEQ ID NO:6) expression enhancer; nb('HP79: the second nucleic acid encoding the HC multimeric protein is operatively linked to the nbCHP79 expression enhancer, and the first nucleic acid encoding the LC is operatively linked to one of nbMT78 (SEQ ID NO:1), nbATL75 (SEQ ID NO:2), nbCHP79 (SEQ ID NO:4) and atHSP69 (SEQ ID NO:6) expression enhancer; nbMT78: the second nucleic acid encoding the HC multimeric protein is operatively linked to the nbMT78 expression enhancer, and the first nucleic acid encoding the LC is operatively linked to one of nbMT78 (SEQ ID NO:1), nbATL75 (SEQ ID NO:2), nbCHP79 (SEQ ID NO:4) and atHSP69 (SEQ ID NO:6) expression enhancer; atHSP69: the second nucleic acid encoding the HC multimeric protein is operatively linked to the atHSP69 expression enhancer, and the first nucleic acid encoding the LC is operatively linked to one of nbMT78 (SEQ ID NO:1), nbATL75 (SEQ ID NO:2), nbCHP79 (SEQ ID NO:4) and atHSP69 (SEQ ID NO:6) expression enhancer.

FIG. 6 shows constructs encoding Dasher; FIG. 6A shows construct 1666 (2X35S promoter—CPMV 3'UTR/NOS-based expression cassette that incorporates a sequence encoding co-expression of TBSV P19 suppressor of silencing under the alfalfa Plastocyanin gene promoter and terminator); FIG. 6B shows construct 4467 (2X35S-5'UTR nbMT78-Dasher (FPB-27-609)-CPMV 3'UTR/NOS); FIG. 6C shows construct 4160 (includes an influenza M2 ion channel gene under the control of Alfalfa Plastocyanin promoter and terminator, in addition to 2X35S promoter-CPMV 3'UTR/NOS-based expression cassette); FIG. 6D shows construct 4170 (includes a matrix attachment region (MAR) regulatory element from the tobacco RB7 gene after the NOS terminator, in addition to 2X35S promoter—CPMV 3'UTR/NOS-based expression cassette); FIG. 6E shows construct 4460 (2X35S-5' UTR CPMV 160-Dasher (FPB-27-609) CPMV 3'UTR/NOS); FIG. 6F shows construct 4461 (2X35S-5' UTR nbGT61-Dasher (FPB-27-609) CPMV 3'UTR/NOS); FIG. 6G shows construct 4462 (2X35S-5'UTR nbATL75-Dasher (FPB-27-609)-CPMV 3'UTR/NOS); FIG. 6H shows construct 4463 (2X35S-5'UTR nbDJ46-Dasher (FPB-27-609)-CPMV 3'UTR/NOS); FIG. 6I shows construct 4464 (2X35S-5'UTR nbCHP79-Dasher (FPB-27-609)-CPMV 3'UTR/NOS); FIG. 6J shows construct 4465 (2X35S-5'UTR nbEN42-Dasher (FPB-27-609)-CPMV 3'UTR/NOS); FIG. 6K shows construct 4466 (2X35S-5'UTR nb30S72-Dasher (FPB-27-609)-CPMV 3'UTR/NOS); FIG. 6L shows construct 4468 (2X35S-5'UTR nbPV55-Dasher (FPB-27-609)-CPMV 3'UTR/NOS); FIG. 6M shows construct 4469 (2X35S-5'UTR nbPPI43-Dasher (FPB-27-609)-CPMV 3'UTR/NOS); FIG. 6N shows construct 4470 (2X35S-5'UTR nbPM64-Dasher (FPB-27-609)-CPMV 3'UTR/NOS); FIG. 6O shows construct 4471 (2X35S-5'UTR nbH2A86-Dasher (FPB-27-609)-CPMV 3'UTR/NOS); FIG. 6P shows construct 4472 (2X35S-5'UTR atHSP69-Dasher (FPB-27-609)-CPMV 3'UTR/NOS); FIG. 6Q shows construct 4473 (2X35S-5'UTR atGRP62-Dasher (FPB-27-609)-CPMV 3'UTR/NOS); FIG. 6R shows construct 4474 (2X35S-5'UTR atPK65-Dasher (FPB-27-609)-CPMV 3'UTR/NOS); FIG. 6S shows construct 4475 (2X35S-5'UTR atRP46-Dasher (FPB-27-609)-CPMV 3'UTR/NOS);

FIG. 7 shows constructs encoding H1-A/California/7/09; FIG. 7A shows construct 4021 (2X35S-5'UTR CPMV 160-SpPDI-HA0 H1 A-Cal-7-09-CPMV 3'UTR/NOS); FIG. 7B shows construct 4061 (2X35S-5'UTR nbGT61-SpPDI-HA0 H1 A-Cal-7-09-CPMV 3'UTR/NOS); FIG. 7C shows construct 4062 (2X35S-5'UTR nbATL75-SpPDI-HA0 H1 A-Cal-7-09-CPMV 3'UTR/NOS); FIG. 7D shows construct 4063 (2X35S-5'UTR nbDJ46-SpPDI-HA0 H1 A-Cal-7-09-CPMV 3'UTR/NOS); FIG. 7E shows construct 4064 (2X35S-5'UTR nbCHP79-SpPDI-HA0 H1 A-Cal-7-09-CPMV 3'UTR/NOS); FIG. 7F shows construct 4065 (2X35S-5'UTR nbEN42-SpPDI-HA0 H1 A-Cal-7-09-CPMV 3'UTR/NOS); FIG. 7G shows construct 4066 (2X35S-5'UTR nb30S72-SpPDI-HA0 H1 A-Cal-7-09-CPMV 3'UTR/NOS); FIG. 7H shows construct 4067

Figure 7A:
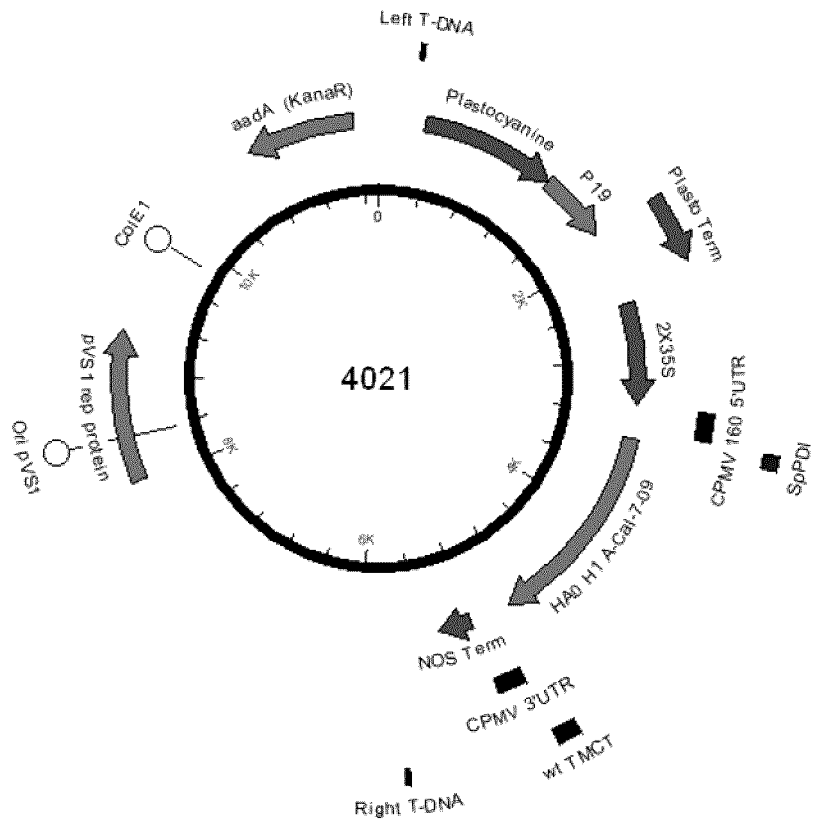
Figure 7B:
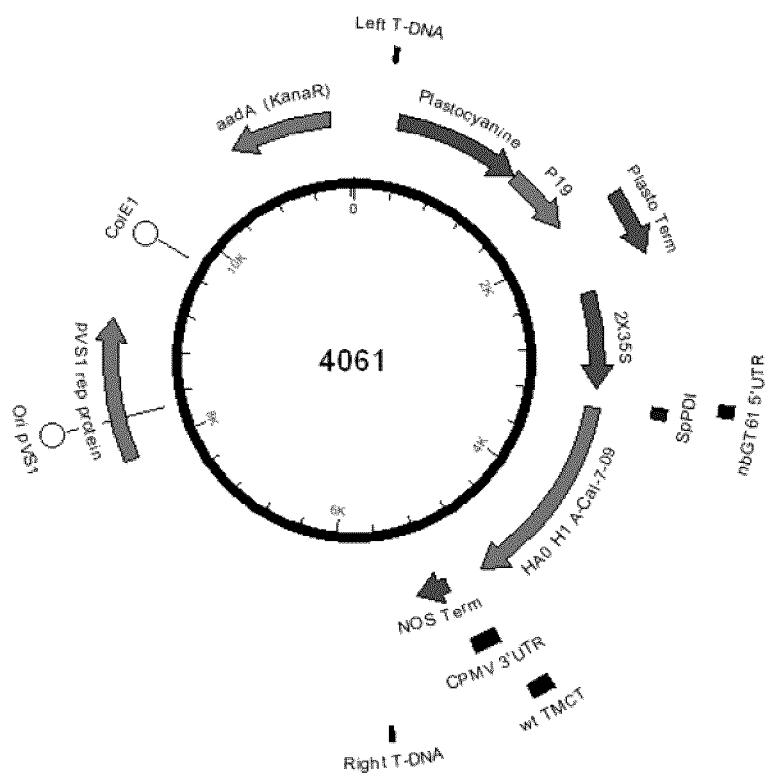
Figure 7C:
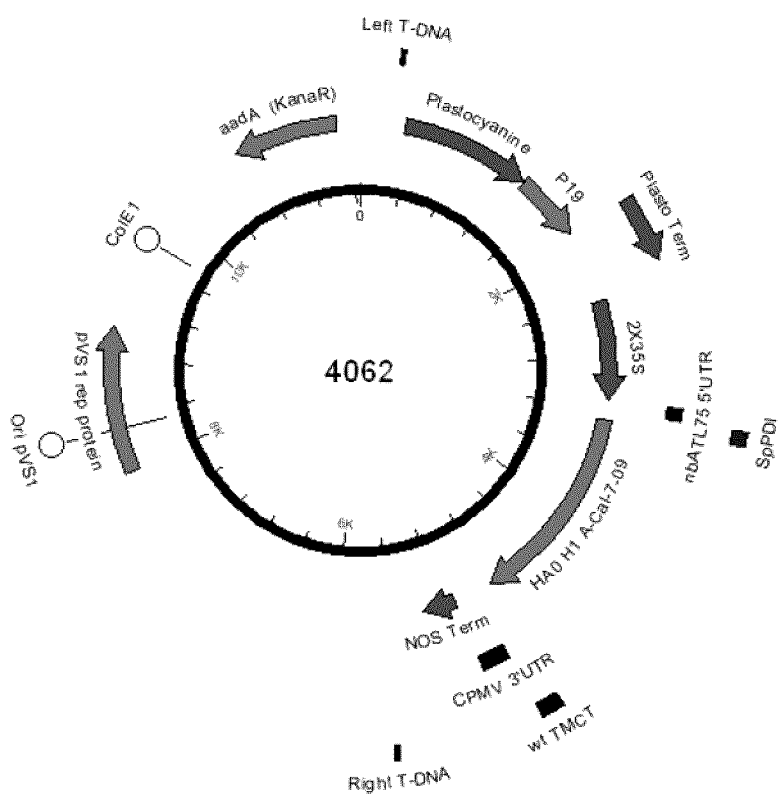
Figure 7D:
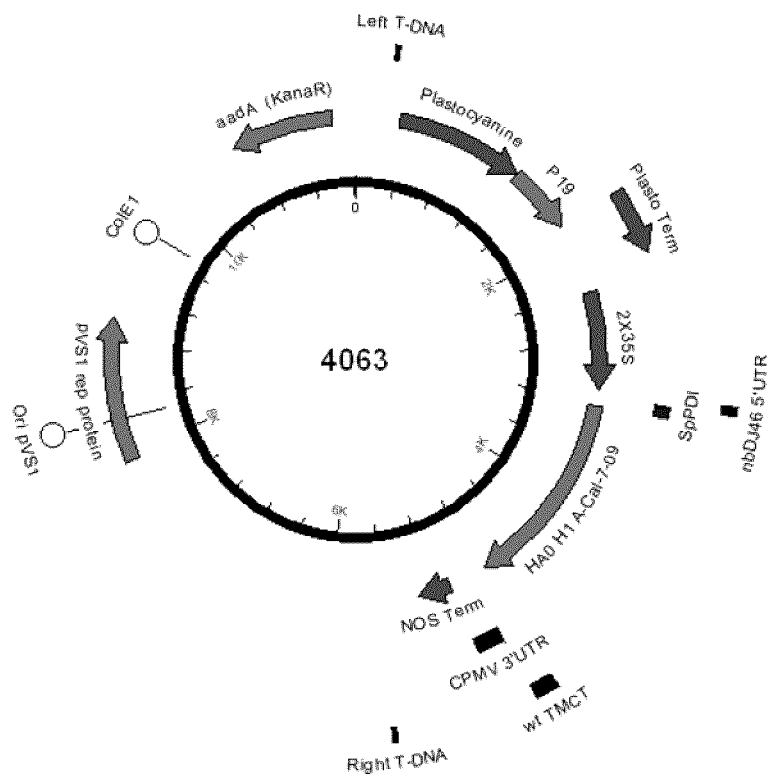
Figure 7E:
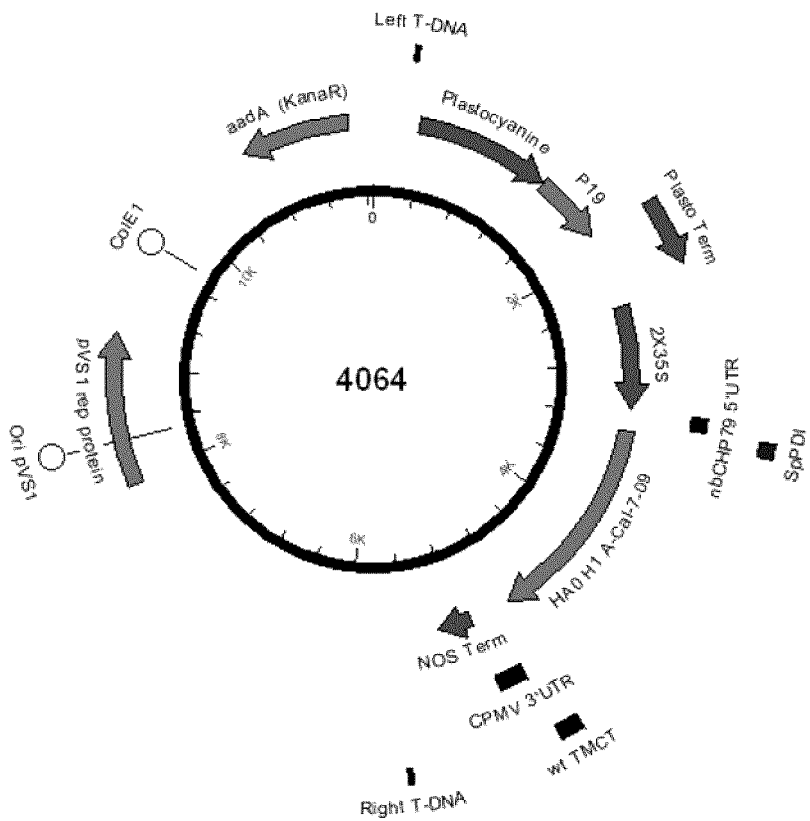
Figure 7F:
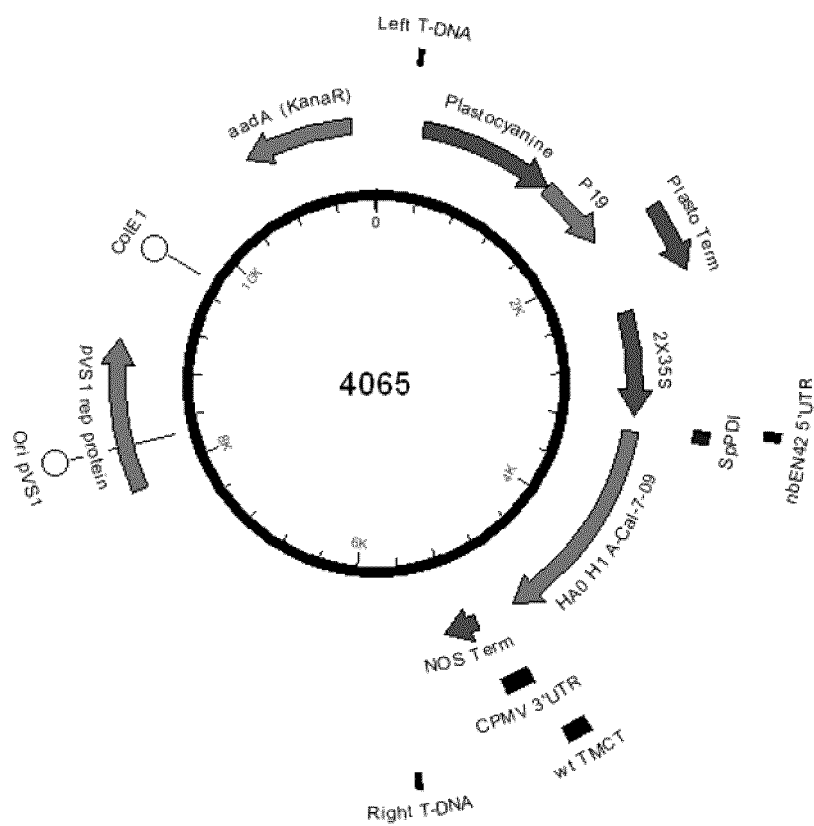
Figure 7G:
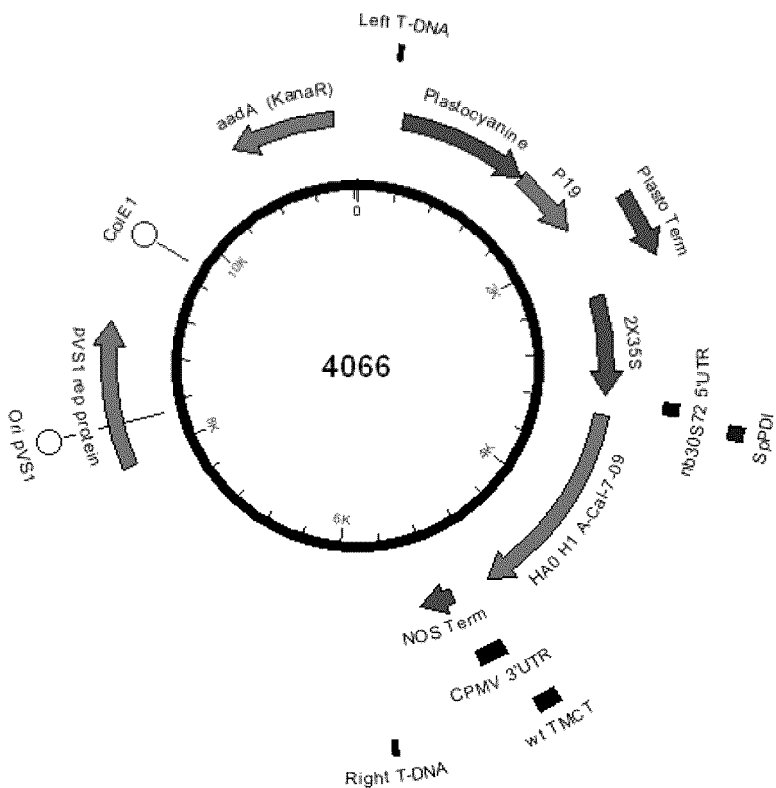
Figure 7H:
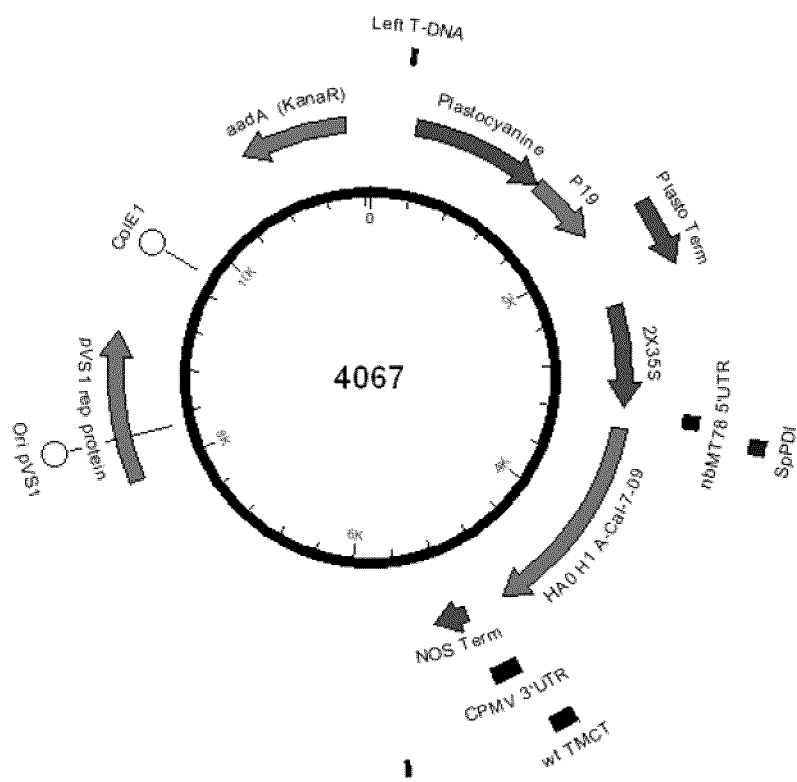
Figure 7I:
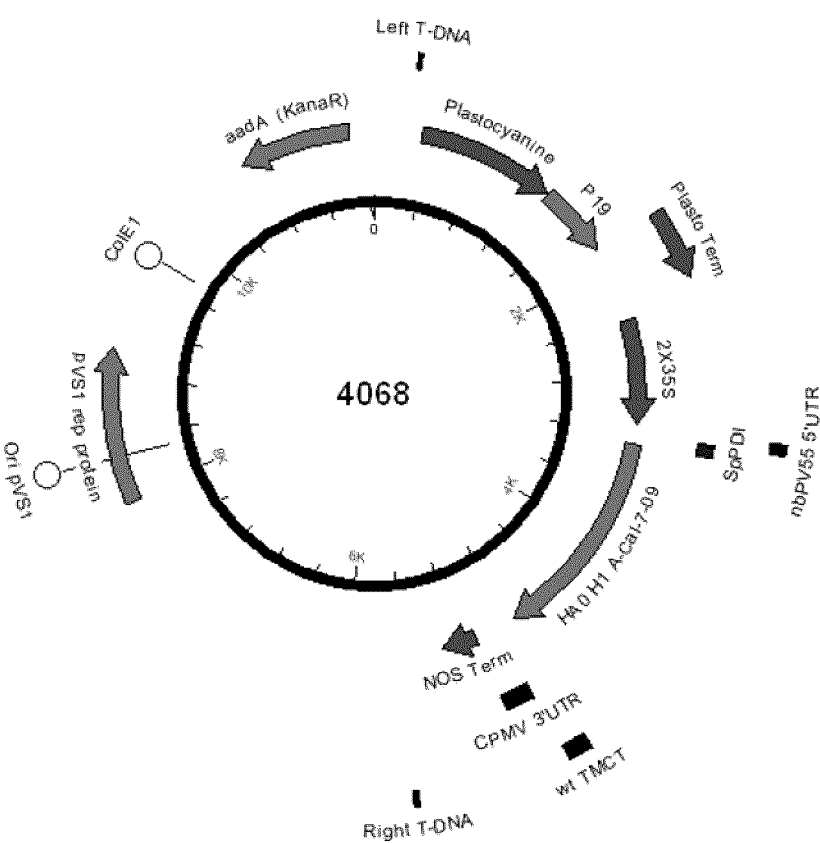
Figure 7J:
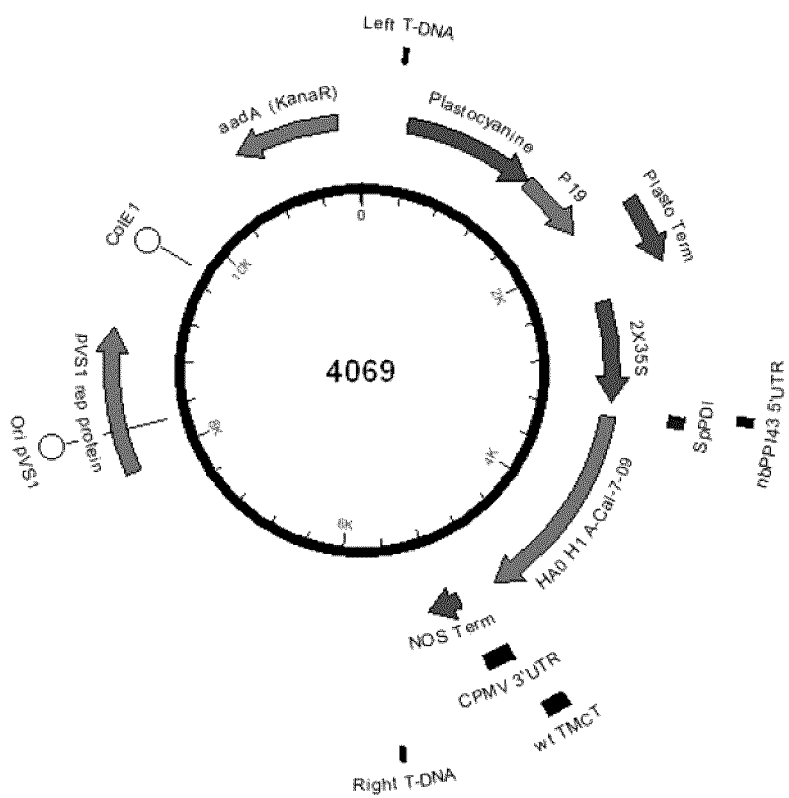
Figure 7K:
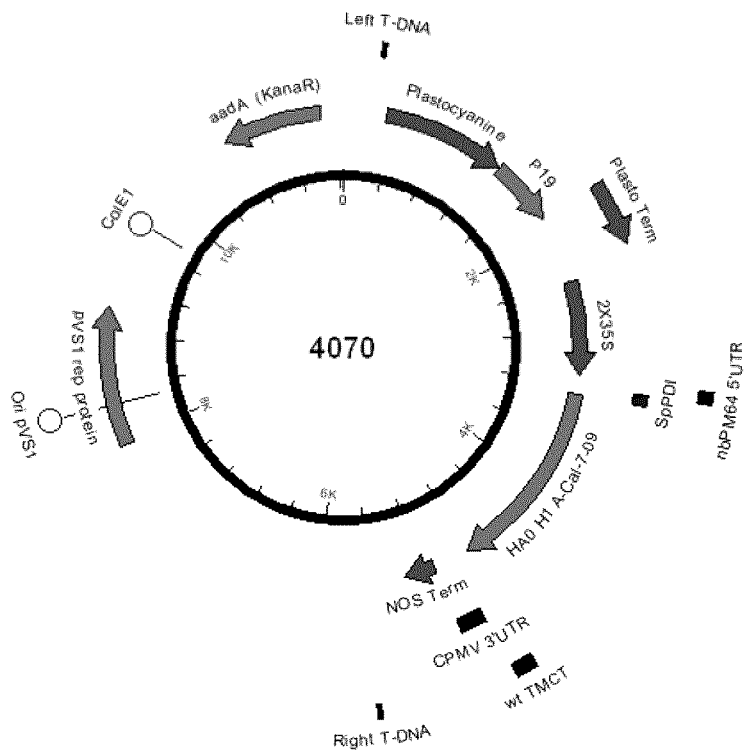
Figure 7L:
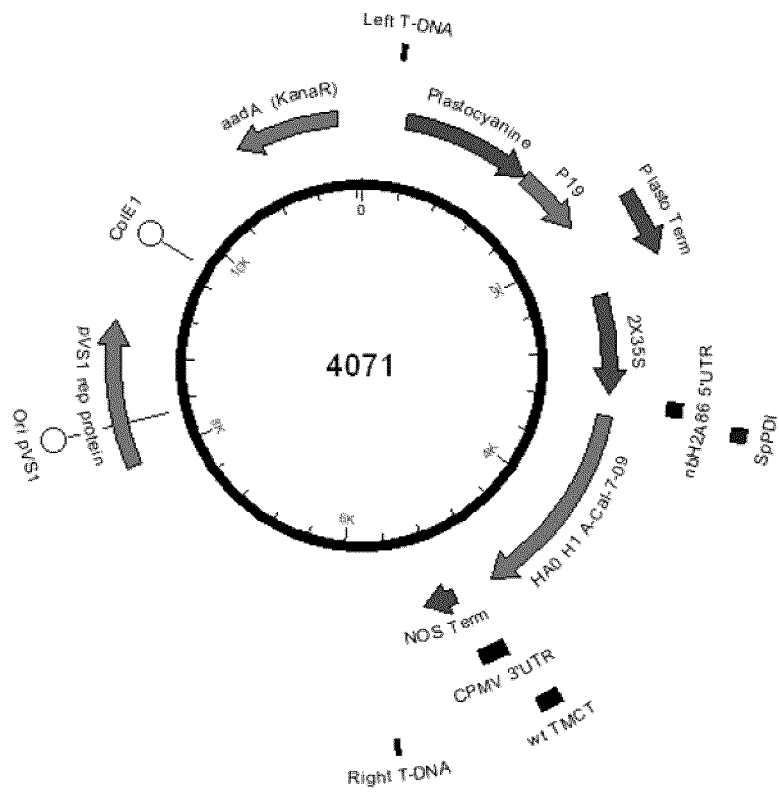
Figure 7M:
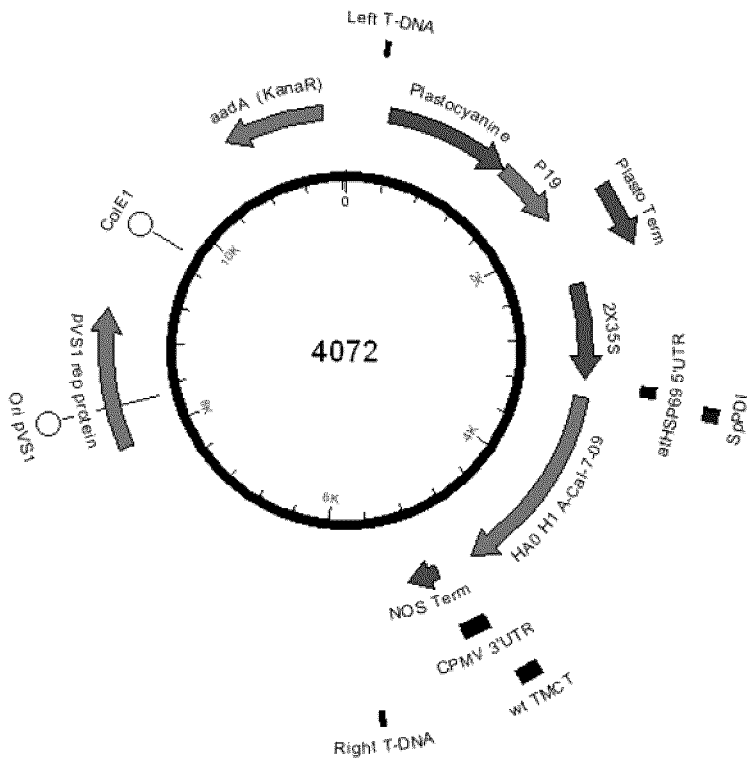
Figure 7N:
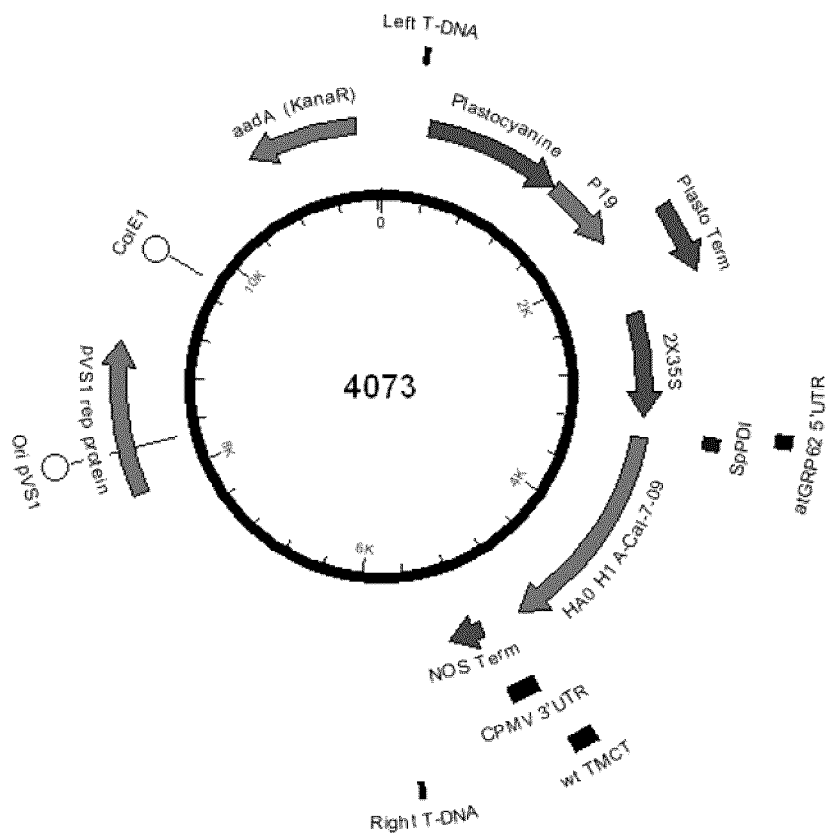
Figure 7O:
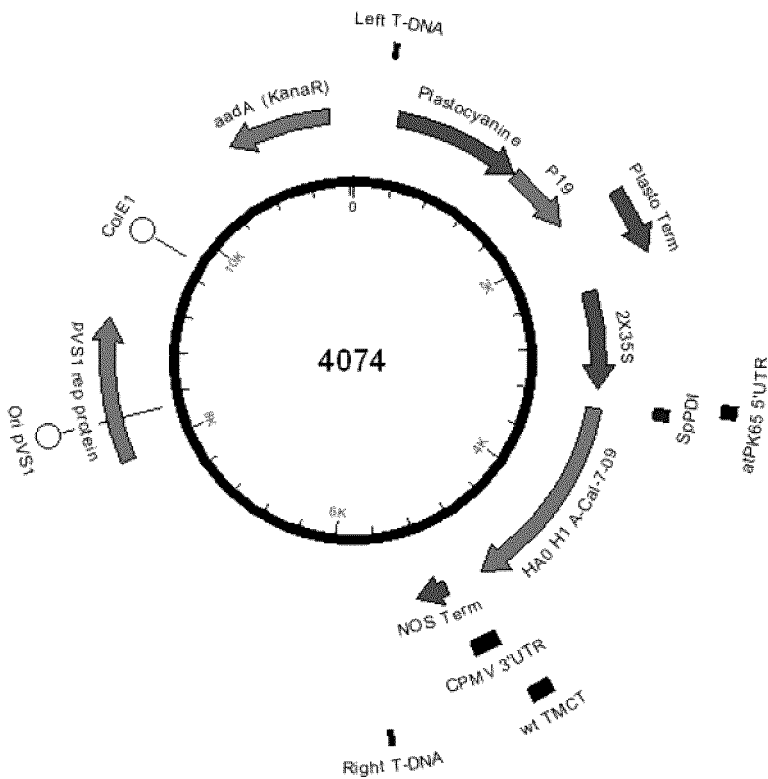
Figure 7P:
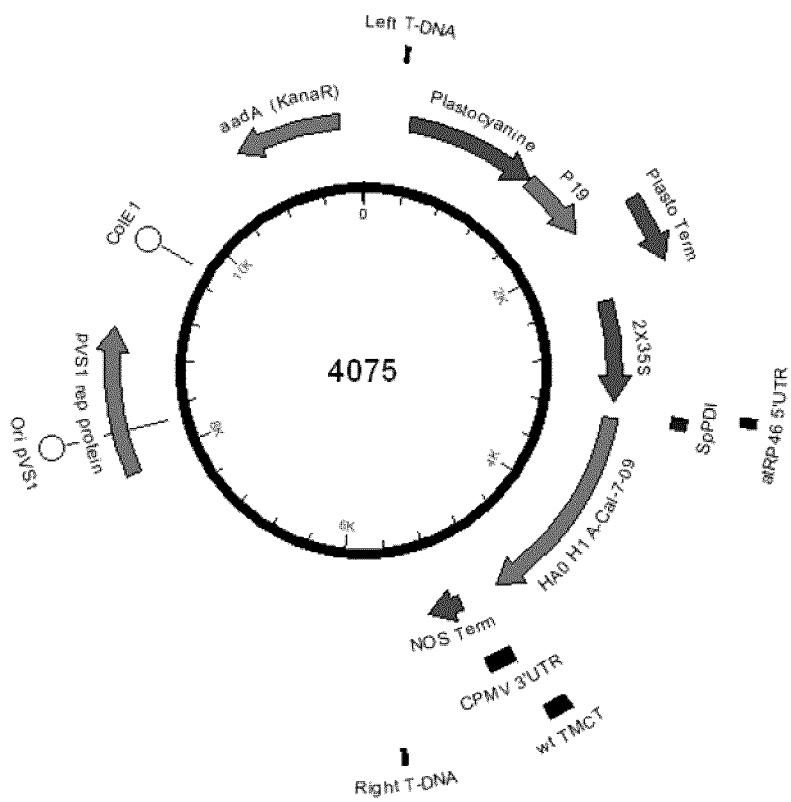
Figure 8A:
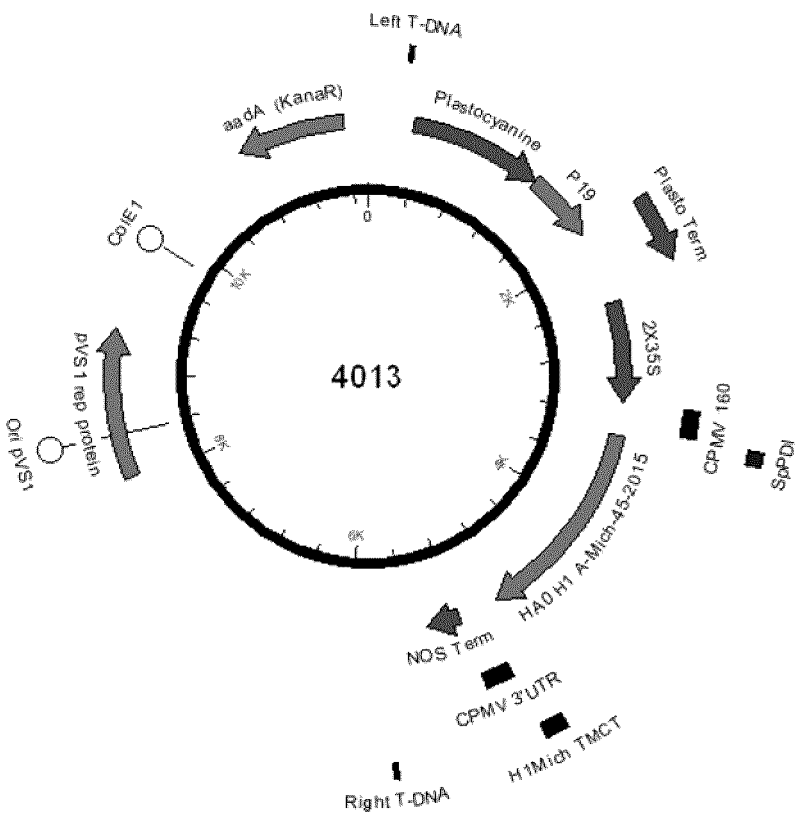
Figure 8B:
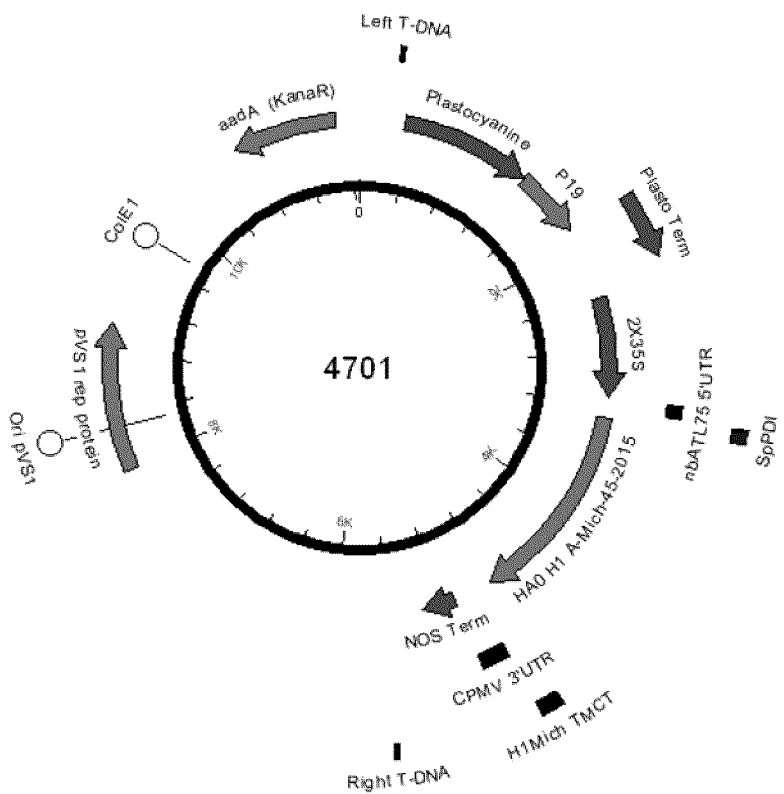
Figure 8C:
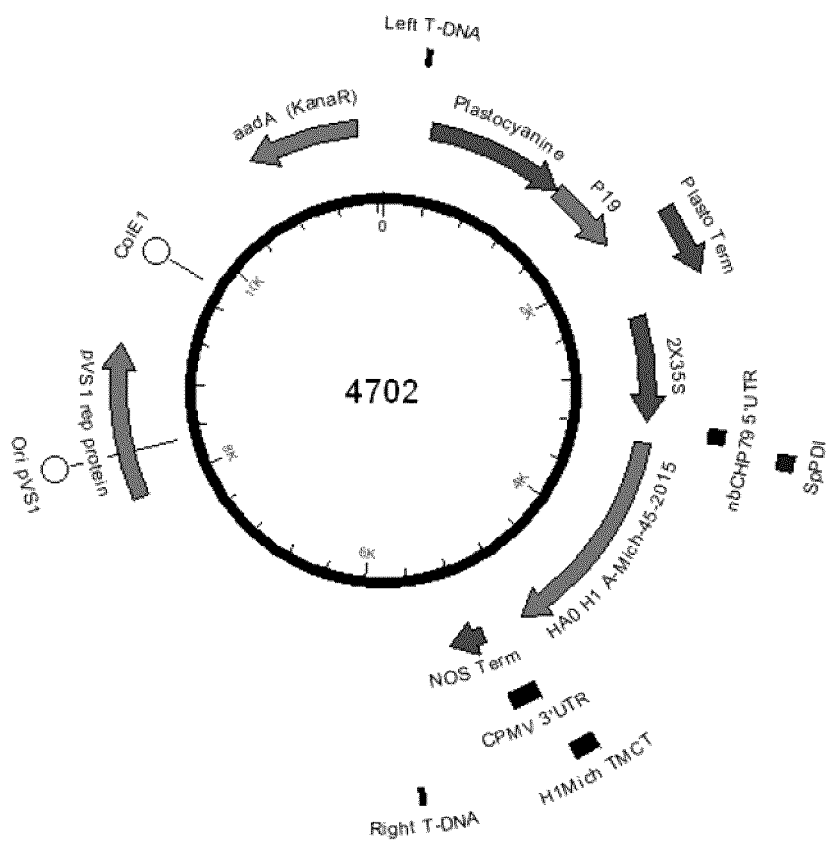
Figure 8D:
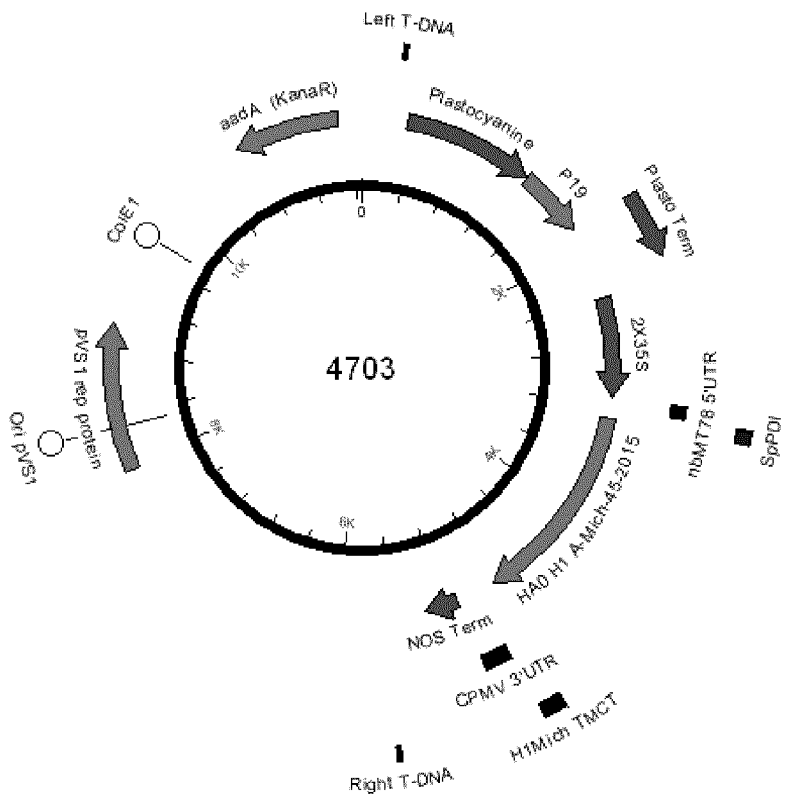
Figure 8E:
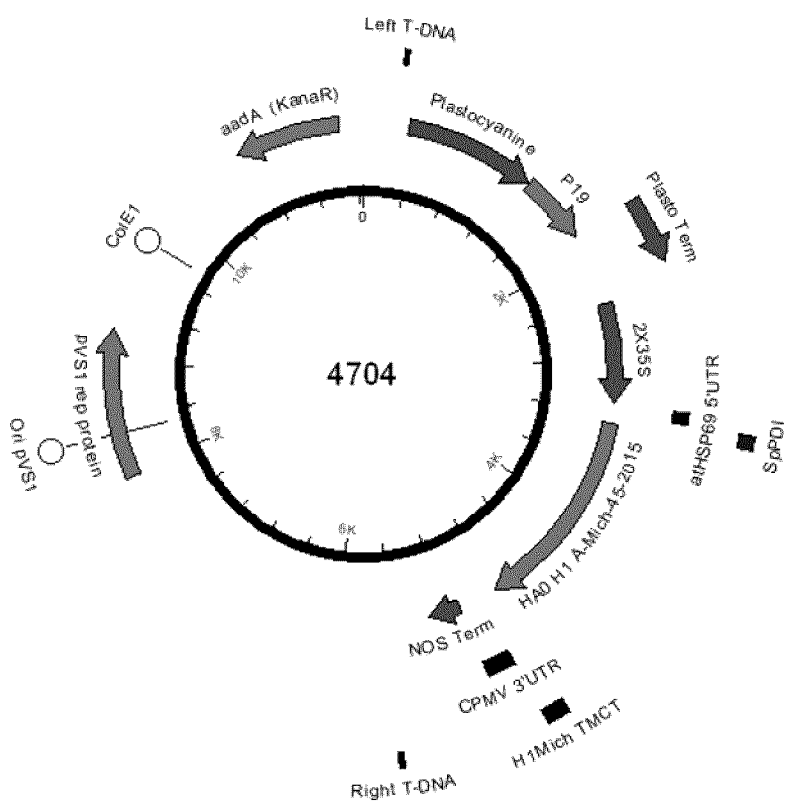
Figure 9A:
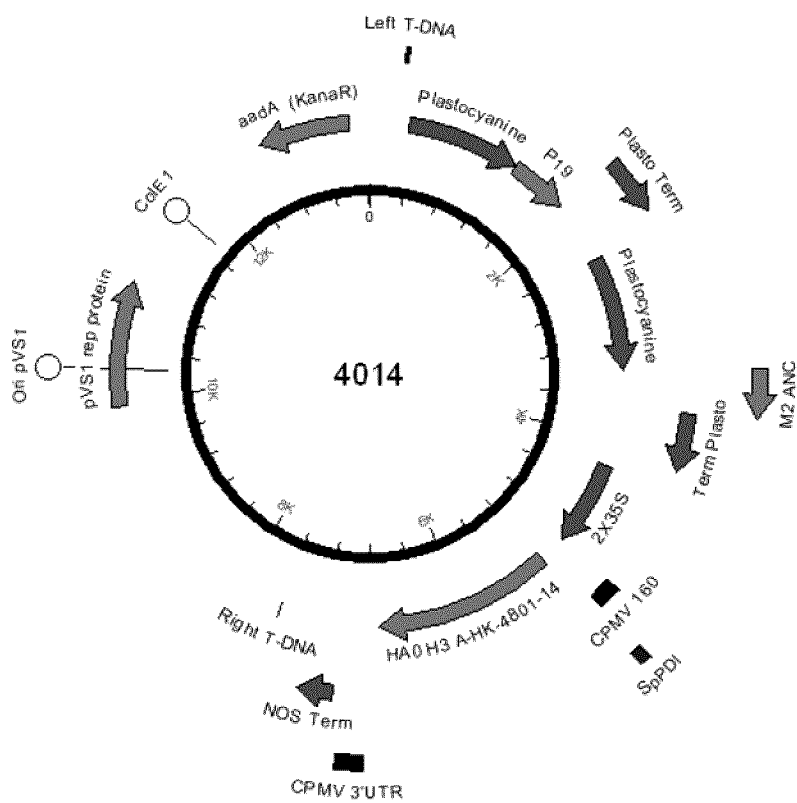
Figure 9B:
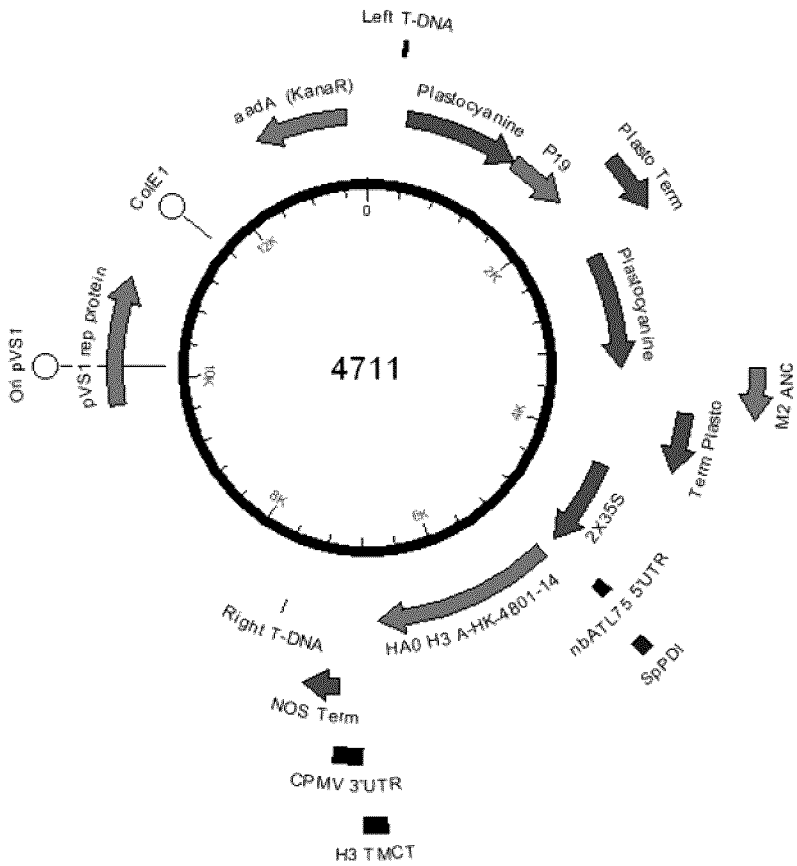
Figure 9C:
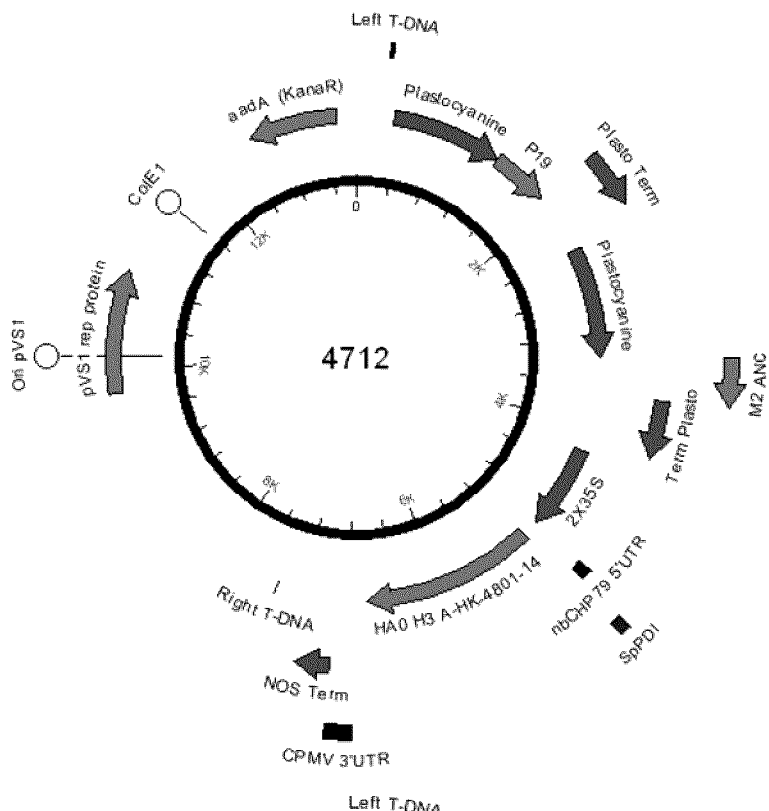
Figure 9D:
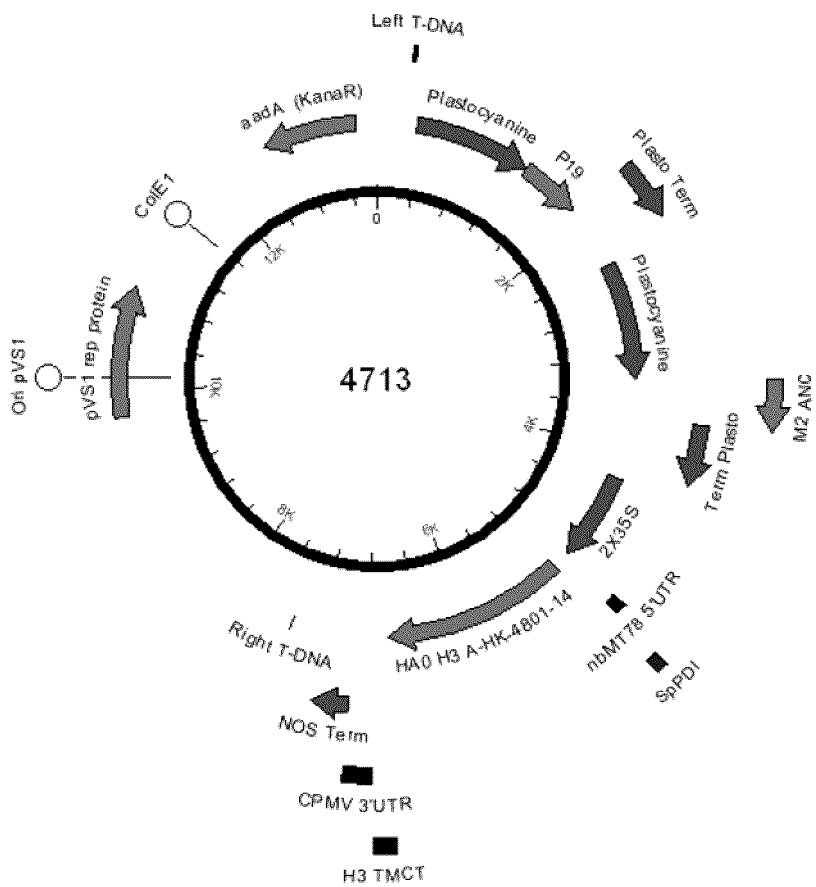
Figure 9E:
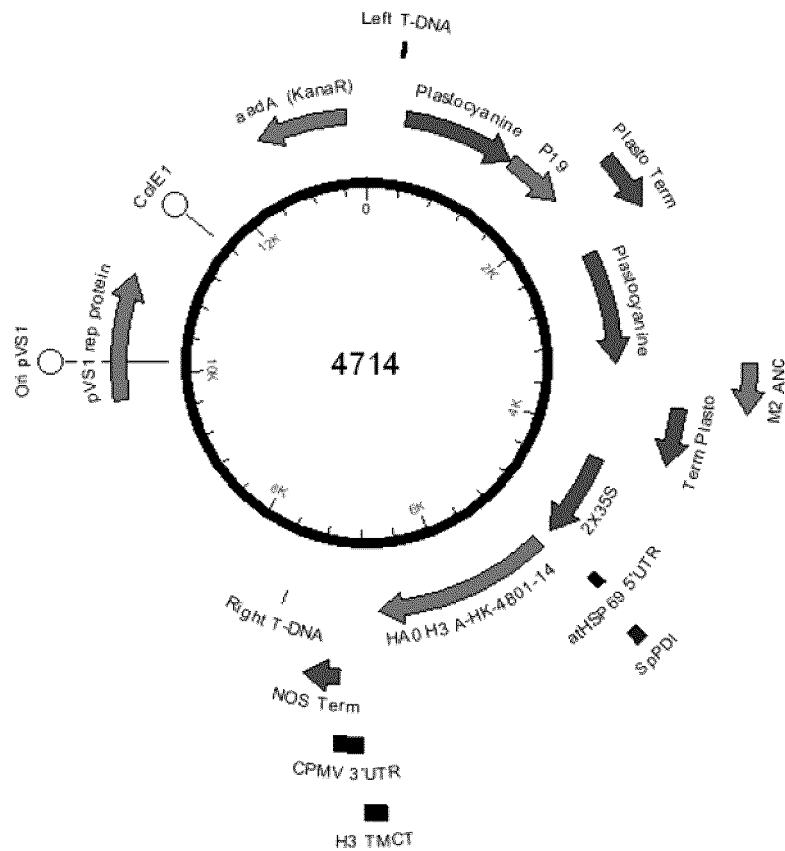
Figure 10A:
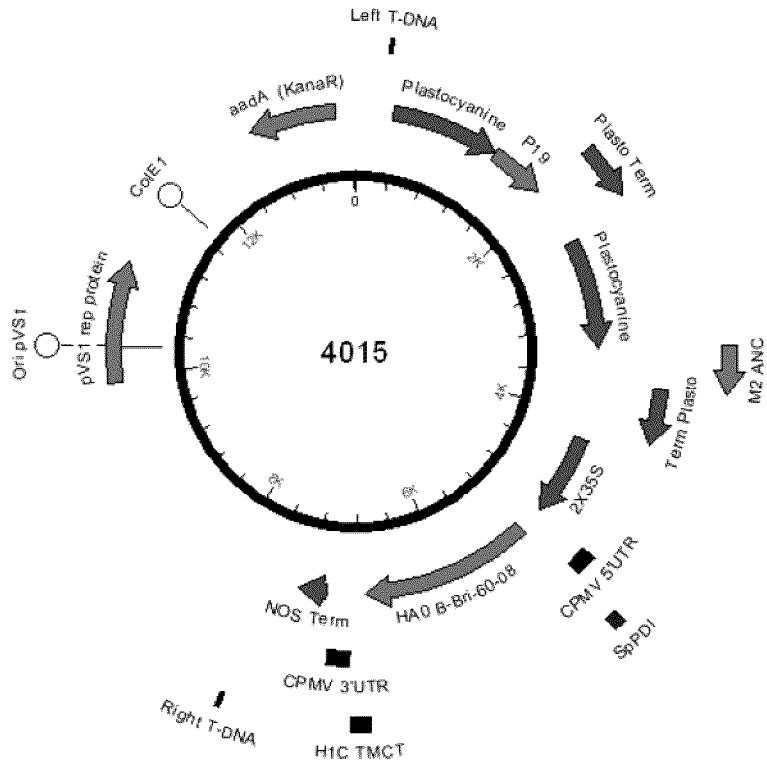
Figure 10B:
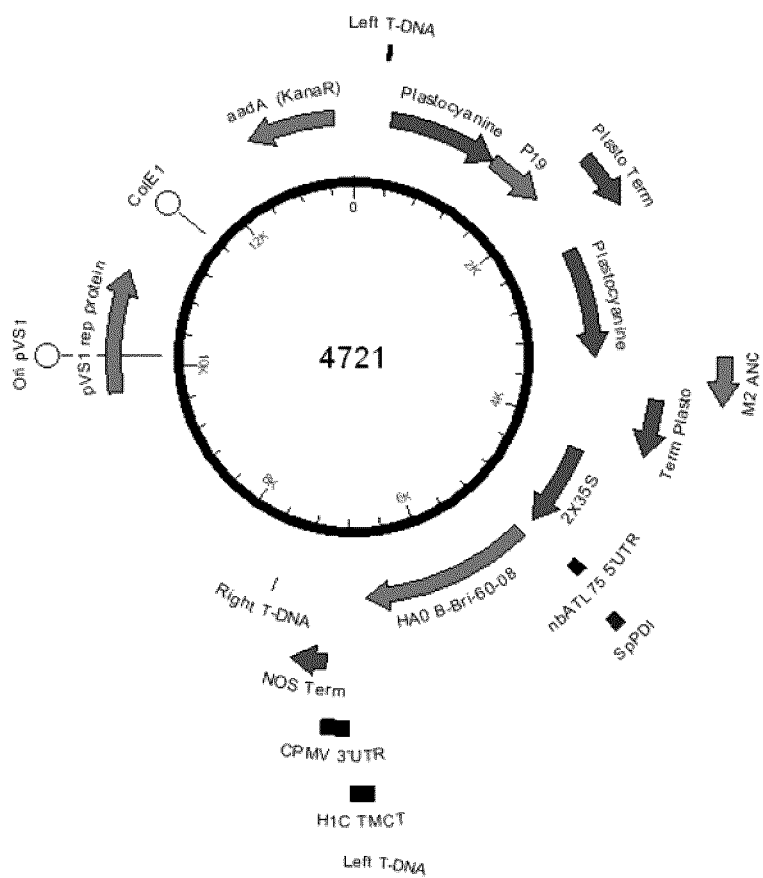
Figure 10C:
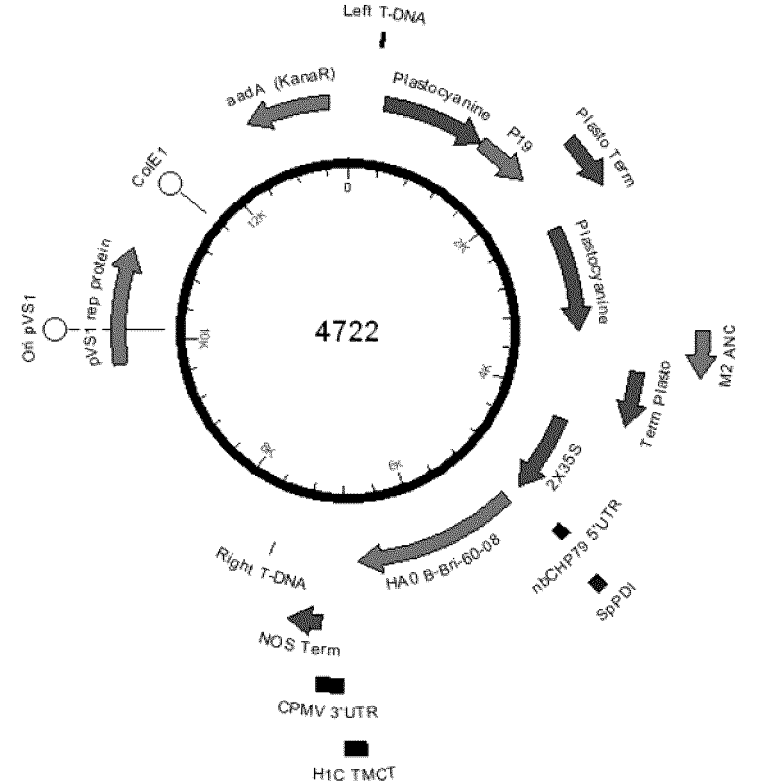
Figure 10D:
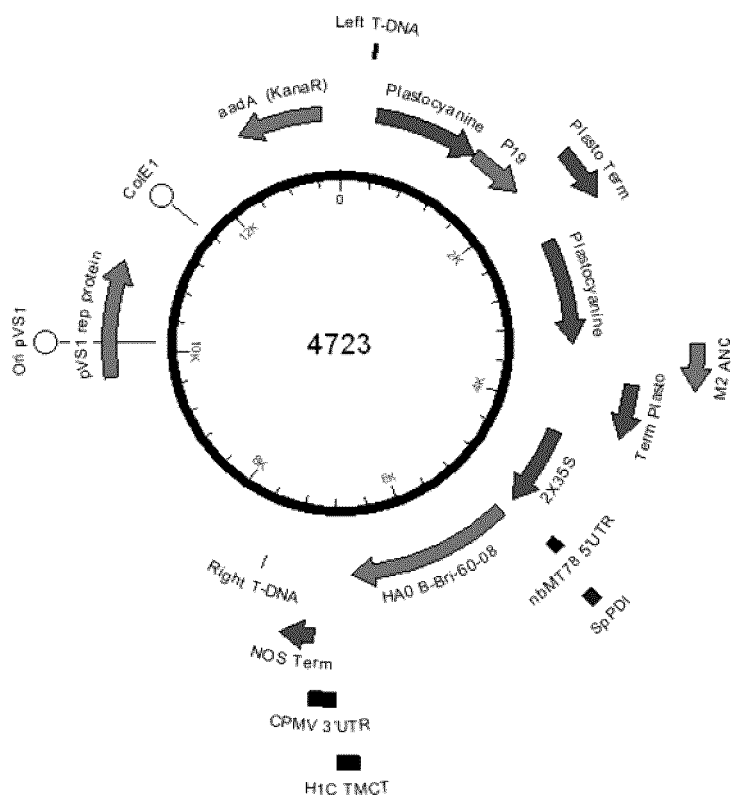
Figure 10E:
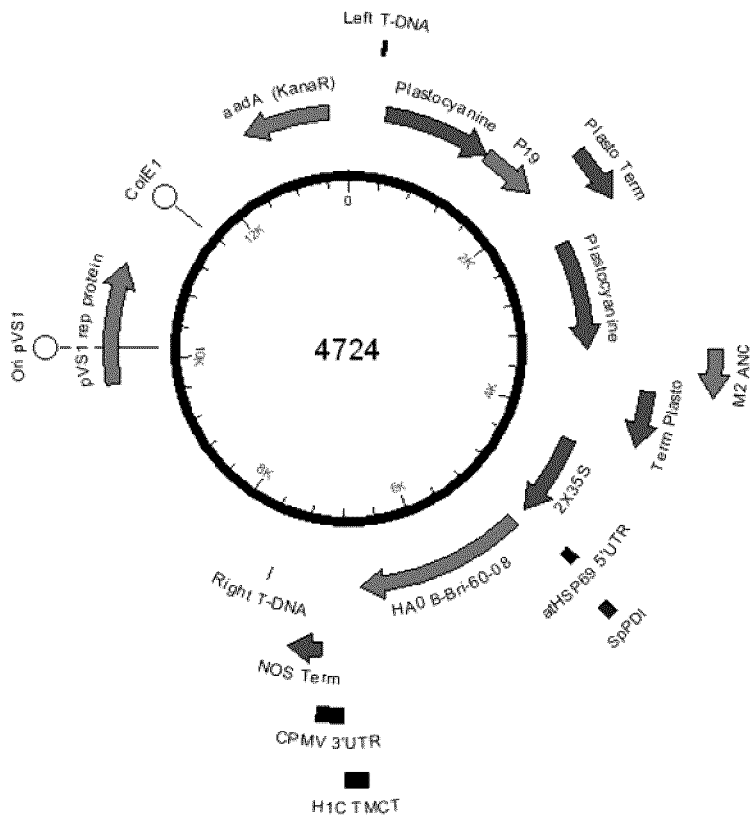
Figure 11A:
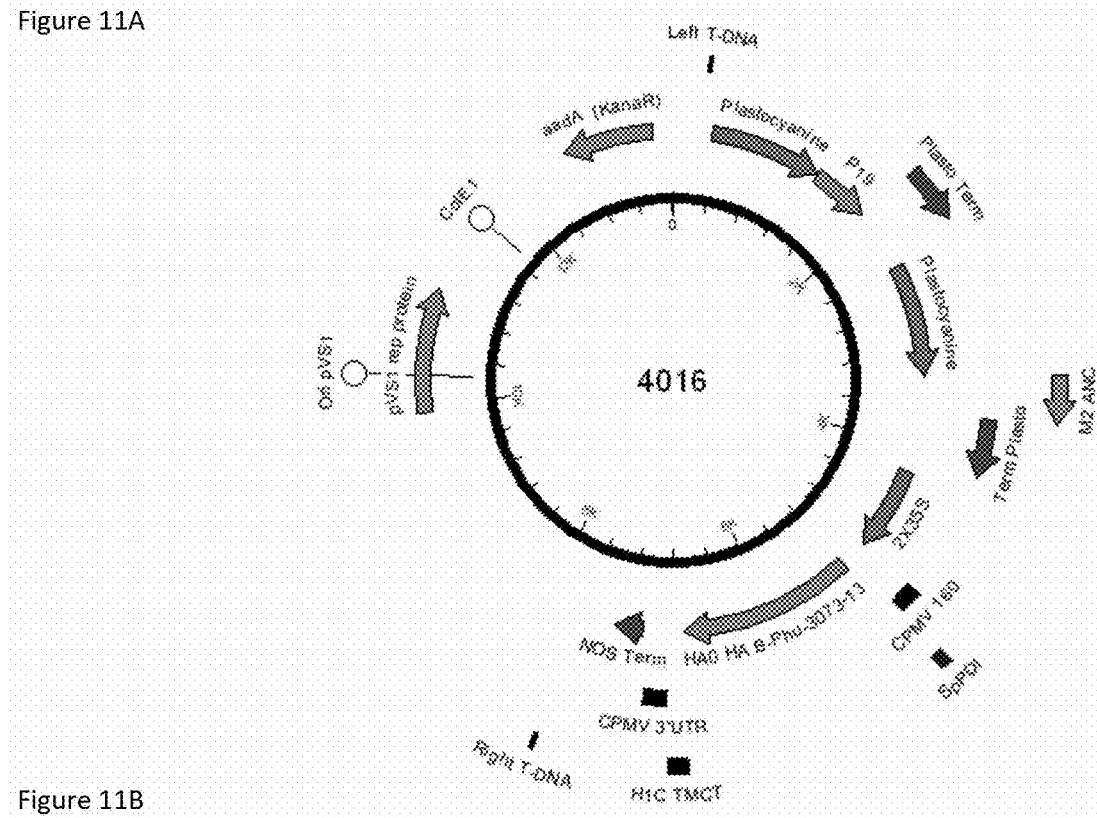
Figure 11B:
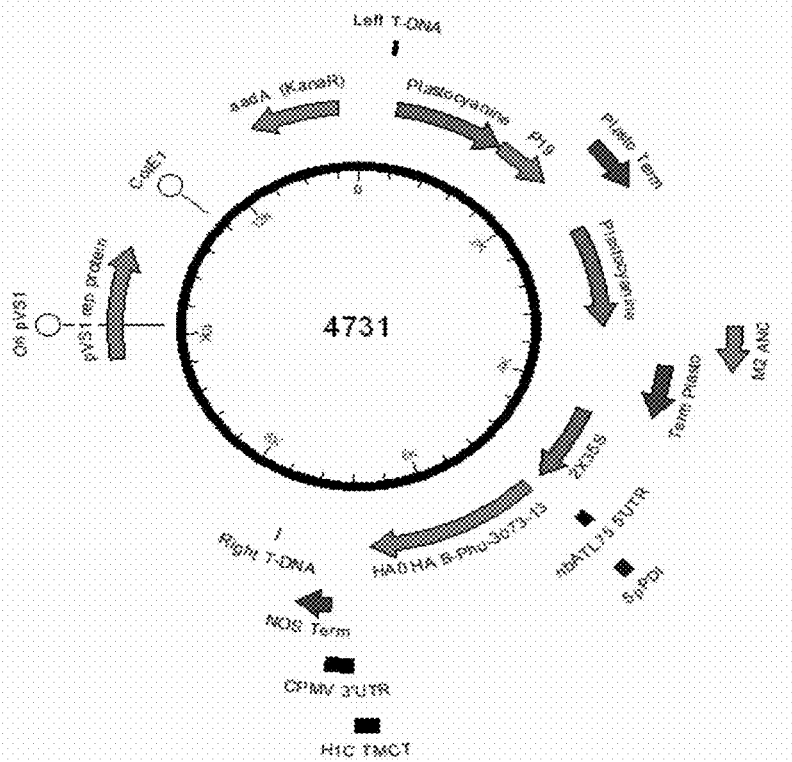
Figure 11C:
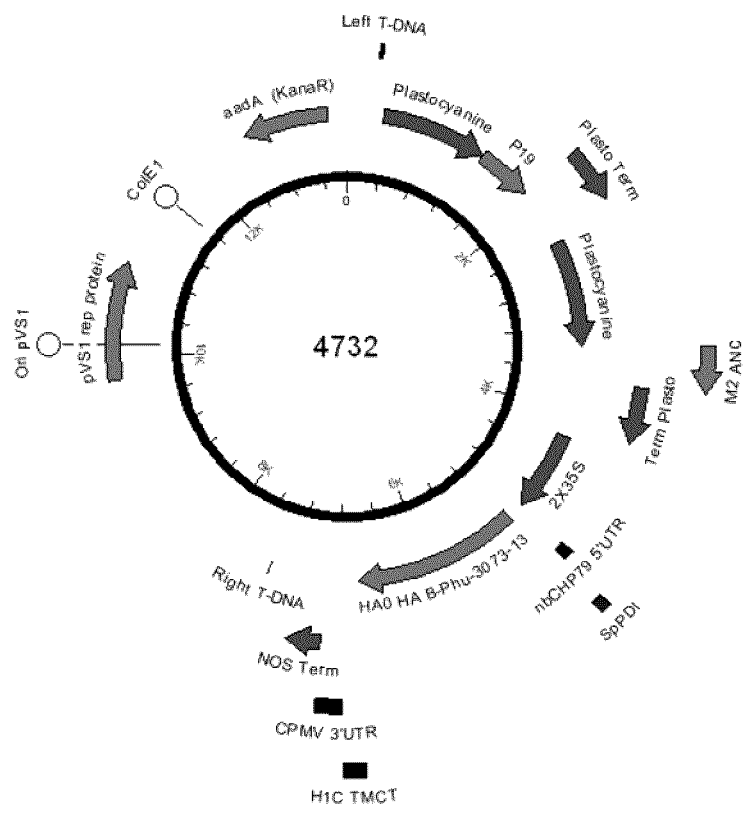
Figure 11D:
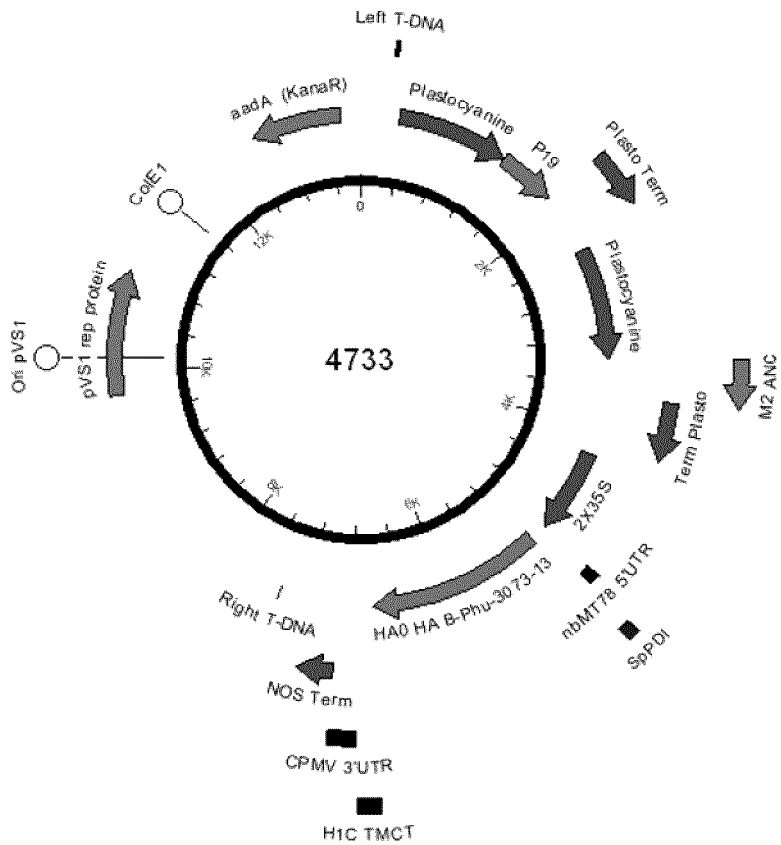
Figure 11E:
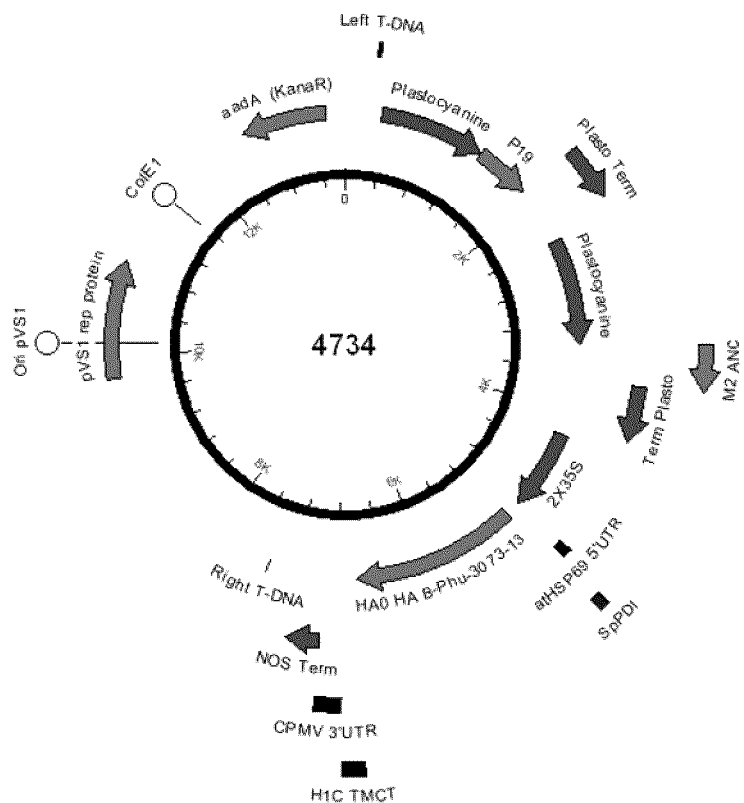
Figure 12A:
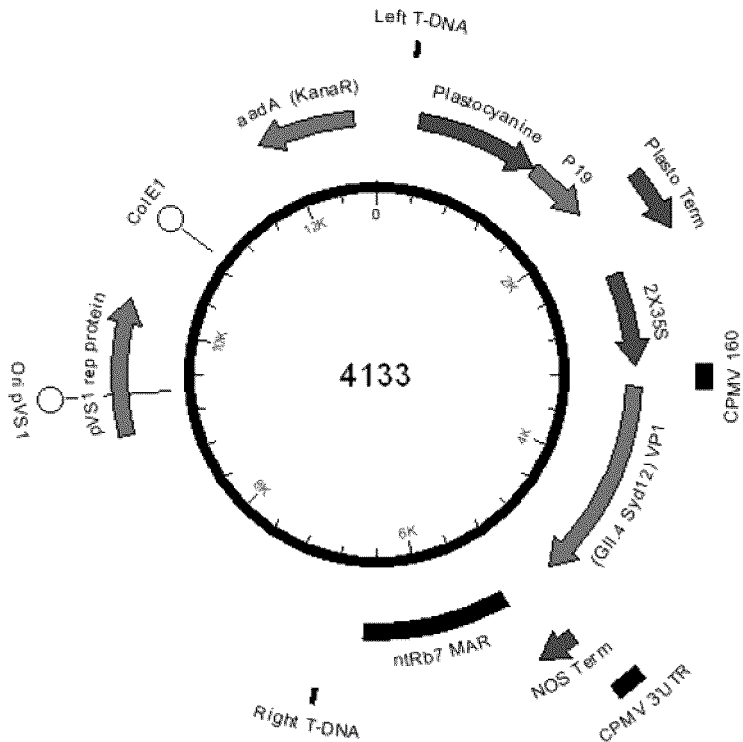
Figure 12B:
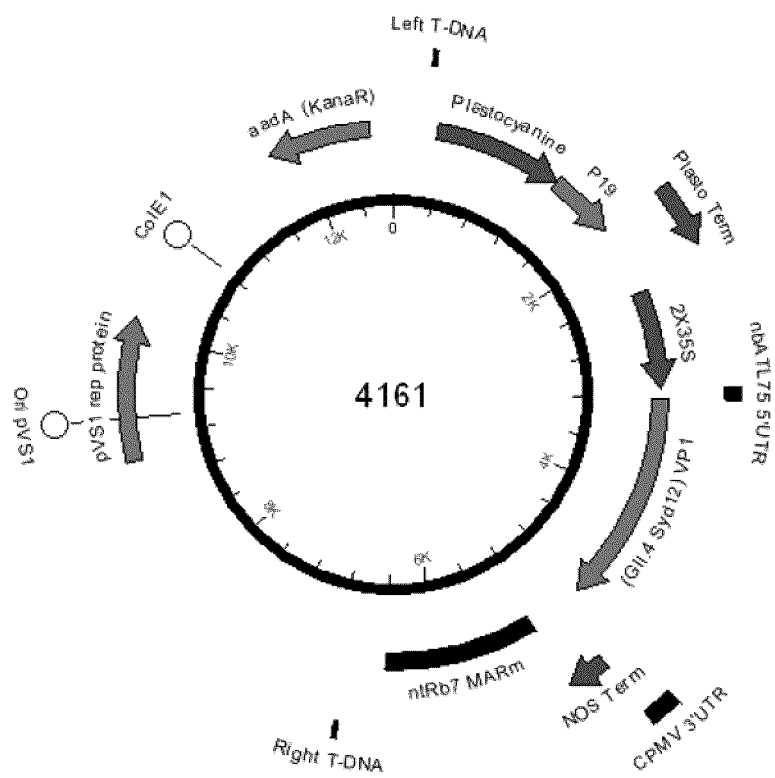
Figure 12C:
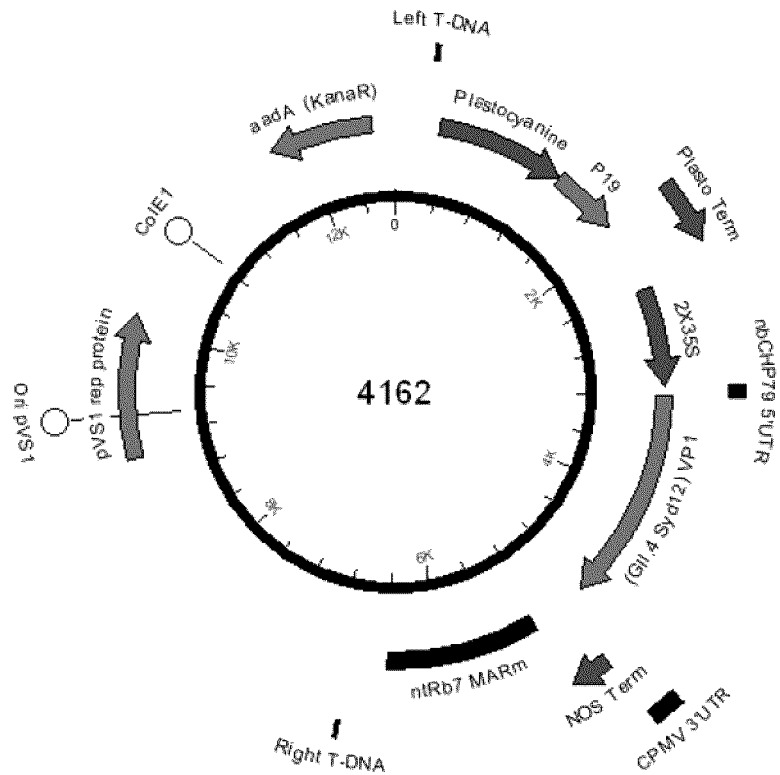
Figure 12D:
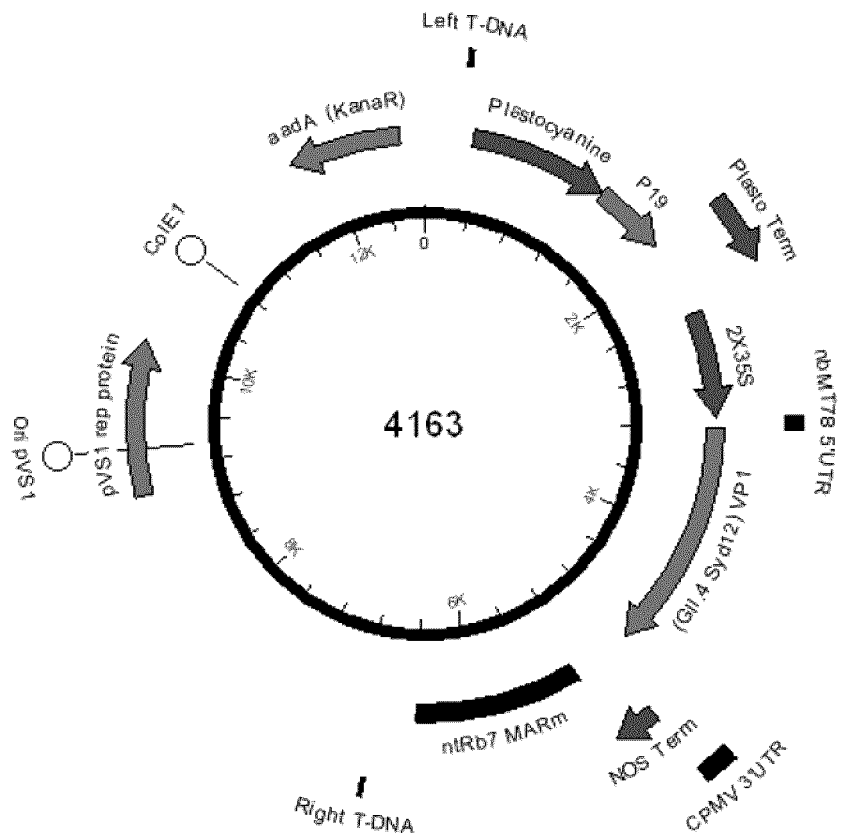
Figure 12E:
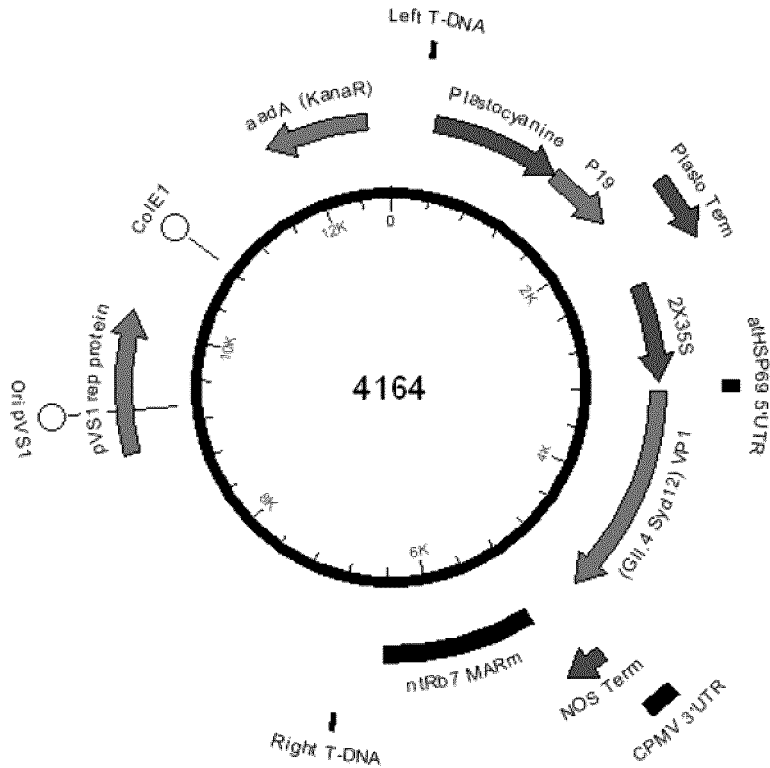
Figure 13A:
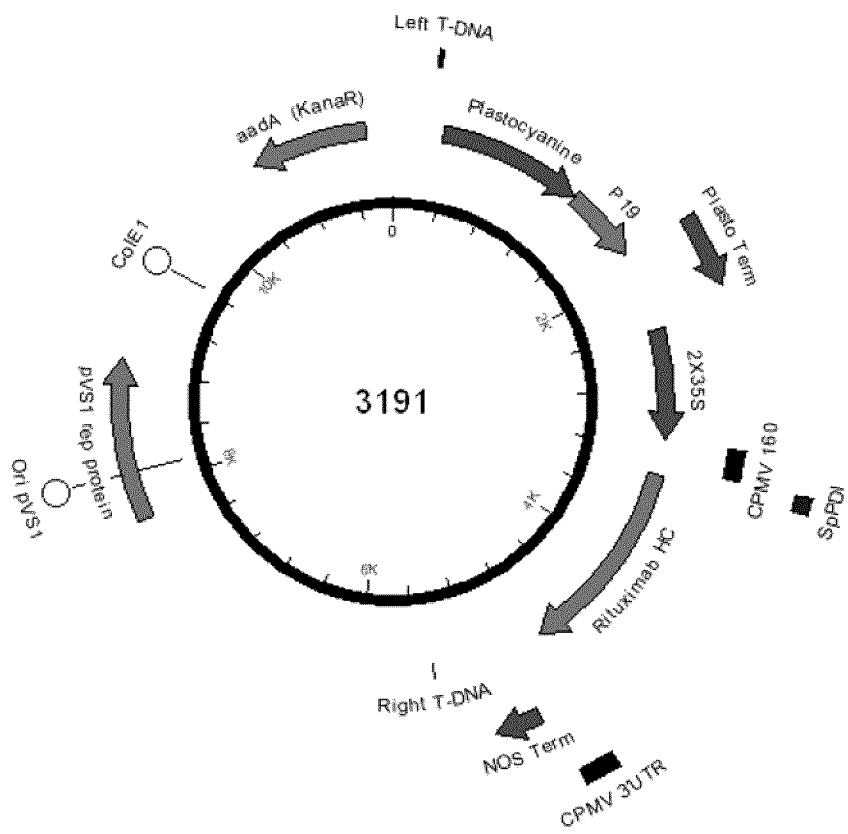
Figure 13B:
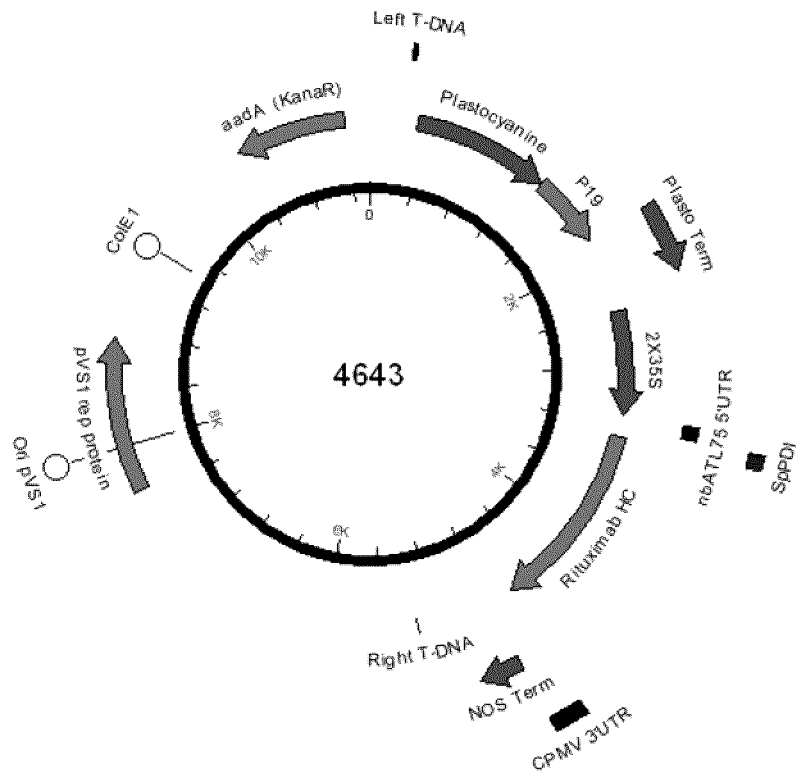
Figure 13C:
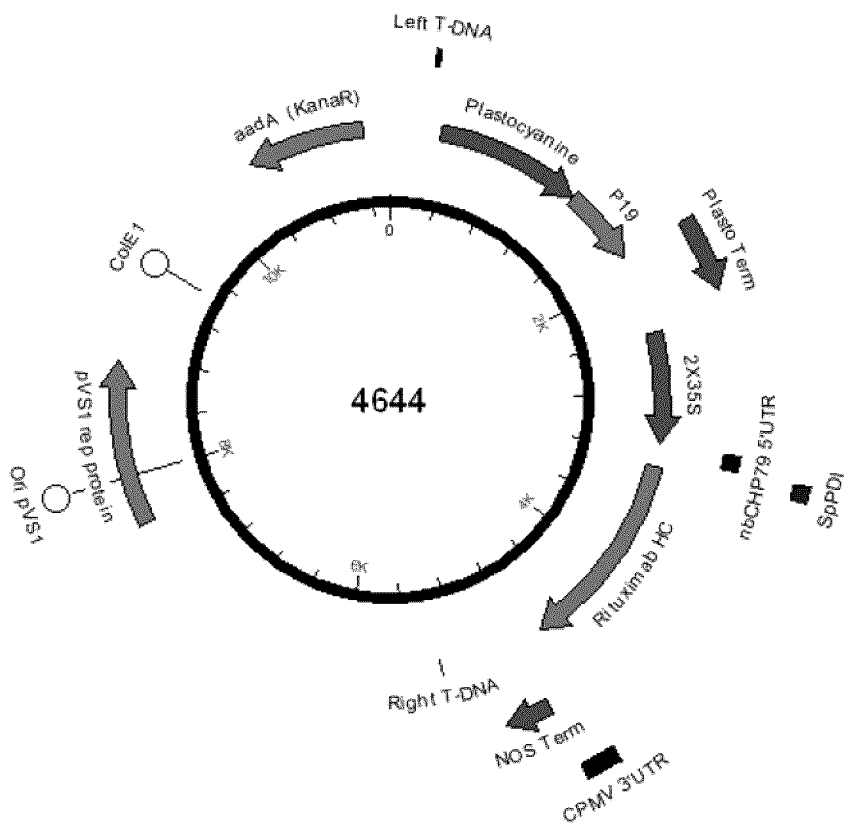
Figure 13D:
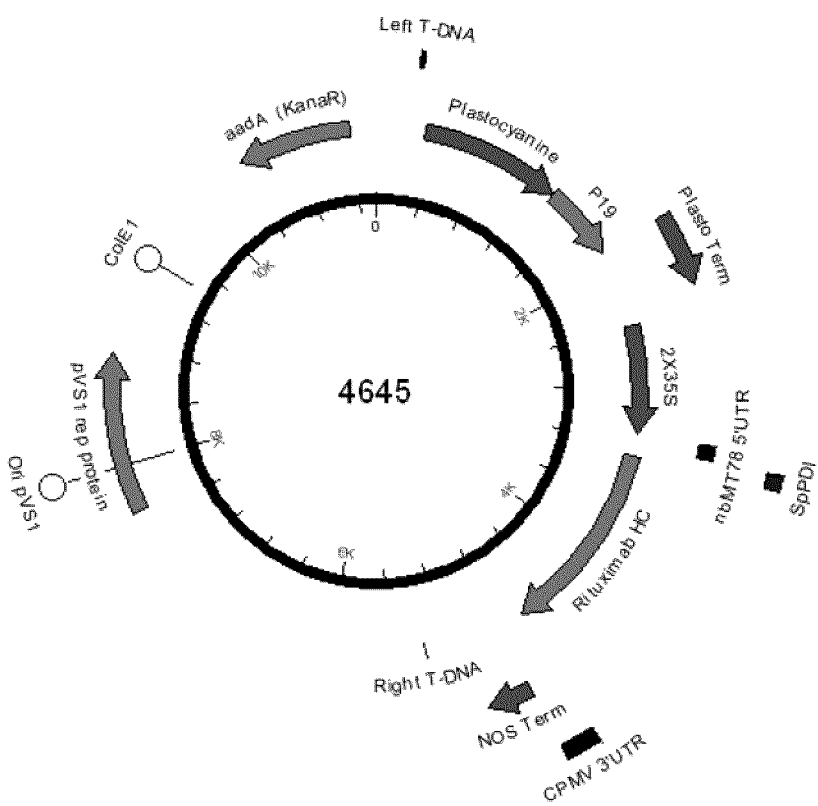
Figure 13E:
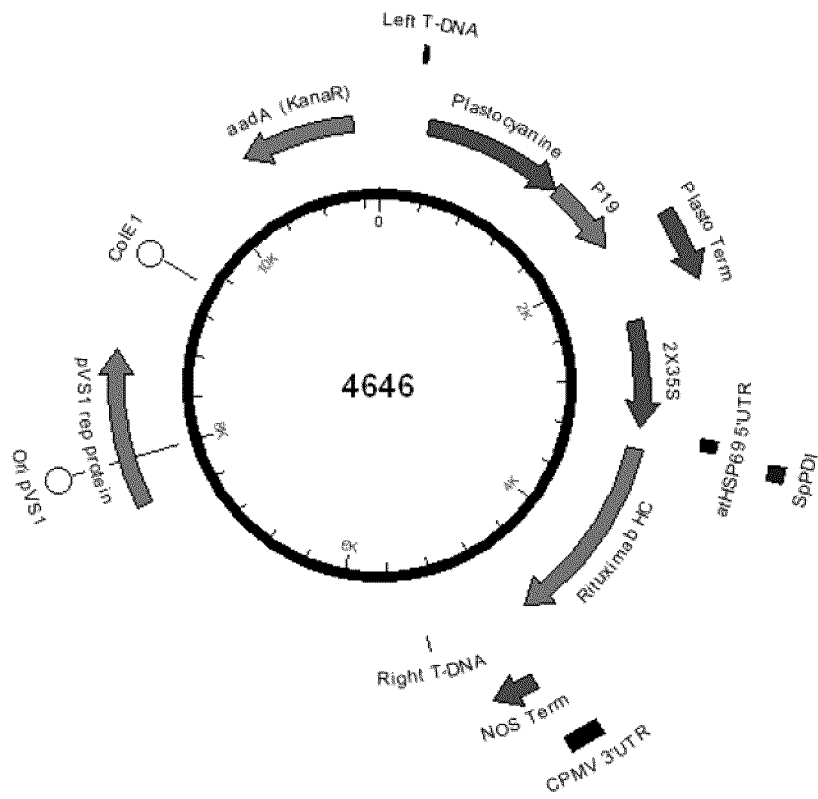
Figure 14A:
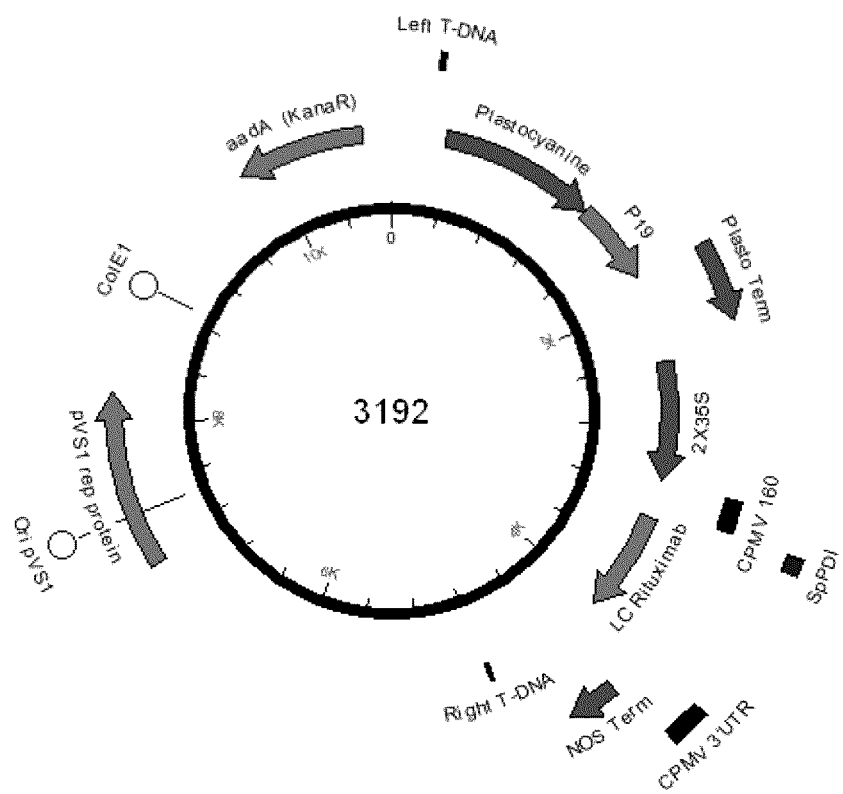
Figure 14B:
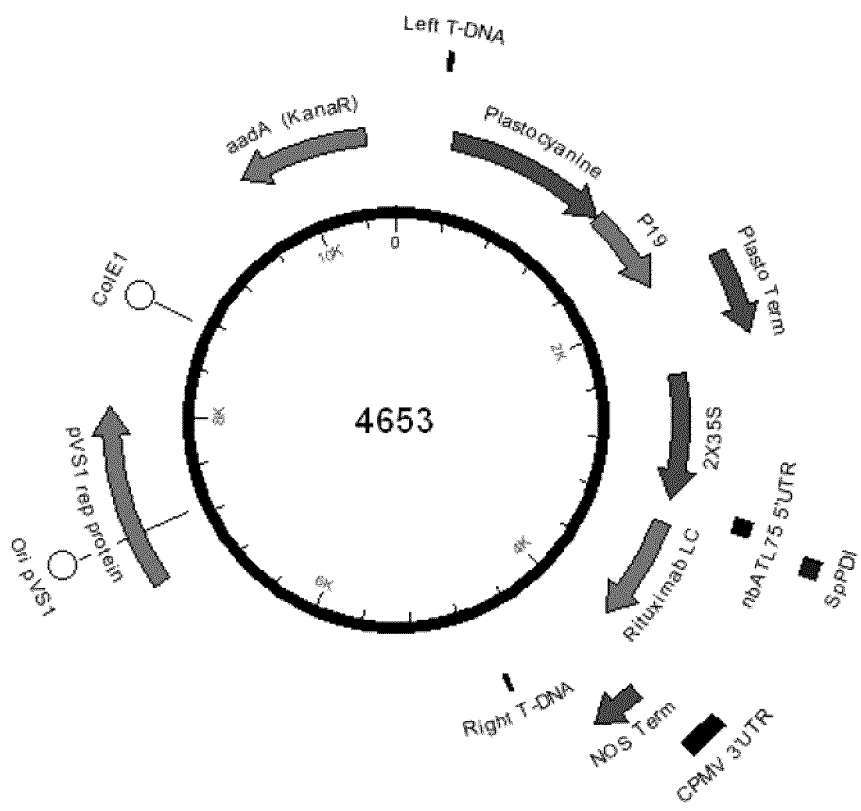
Figure 14C:
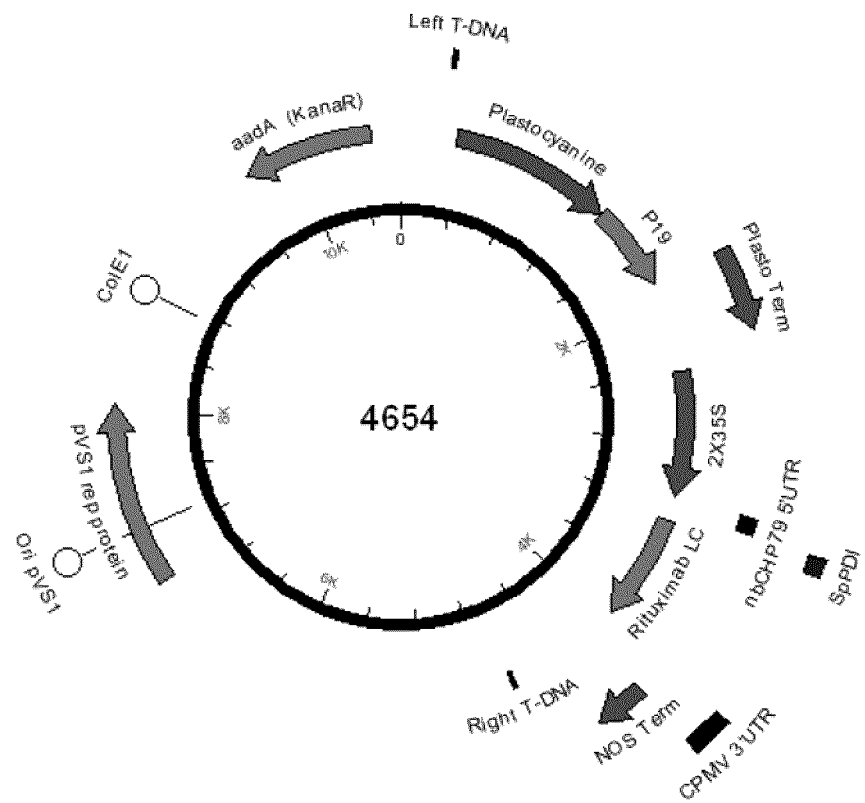
Figure 14D:
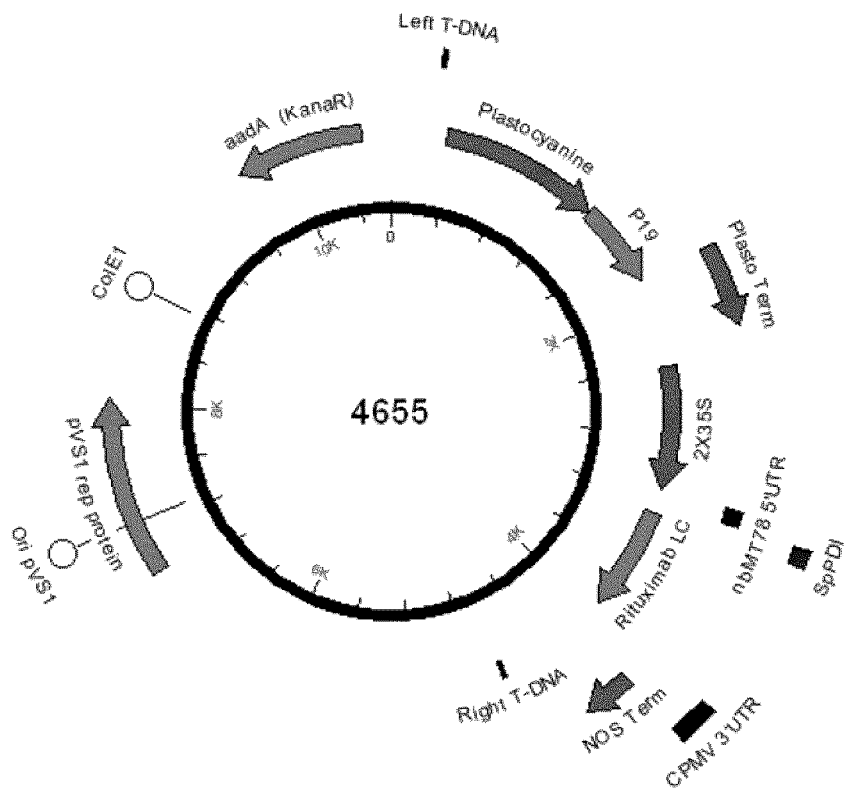
Figure 14E:
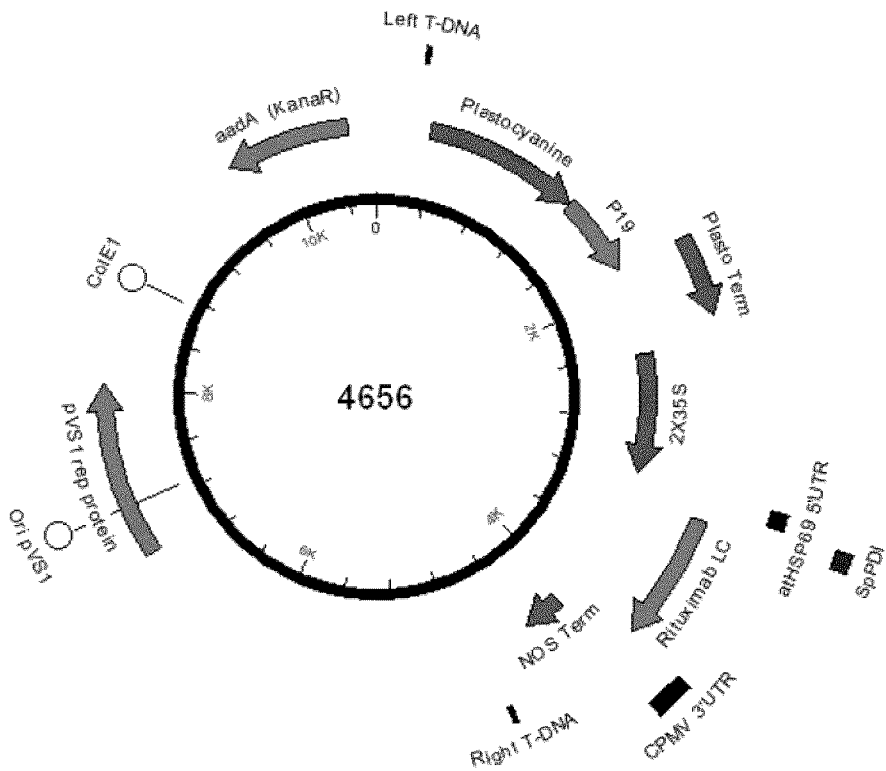

(2X35S-5'UTR nbMT78-SpPDI-HA0 H1 A-Cal-7-09-CPMV 3'UTR/NOS); FIG. 7I shows construct 4068 (2X35S-5'UTR nbPV55-SpPDI-HA0 H1 A-Cal-7-09-CPMV 3'UTR/NOS); FIG. 7J shows construct 4069 (2X35S-5'UTR nbPPI43-SpPDI-HA0 H1 A-Cal-7-09-CPMV 3'UTR/NOS); FIG. 7K shows construct 4070 (2X35S-5'UTR nbPM64-SpPDI-HA0 H1 A-Cal-7-09-CPMV 3'UTR/NOS); FIG. 7L shows construct 4071 (2X35S-5'UTR nbH2A86-SpPDI-HA0 H1 A-Cal-7-09-CPMV 3'UTR/NOS); FIG. 7M shows construct 4072 (2X35S-5'UTR atHSP69-SpPDI-HA0 H1 A-Cal-7-09-CPMV 3'UTR/NOS); FIG. 7N shows construct 4073 (2X35S-5'UTR atGRP62-SpPDI-HA0 H1 A-Cal-7-09-CPMV 3'UTR/NOS); FIG. 7O shows construct 4074 (2X35S-5'UTR atPK65-SpPDI-HA0 H1 A-Cal-7-09-CPMV 3'UTR/NOS); FIG. 7P shows construct 4075 (2X35S-5'UTR atRP46-SpPDI-HA0 H1 A-Cal-7-09-CPMV 3'UTR/NOS); Sp: signal peptide.

FIG. 8 shows constructs encoding H1-A/Michigan/45/2015; FIG. 8A shows construct 4013 (2X35S-5'UTR CPMV 160-SpPDI-H1 A-Mich-45-2015-CPMV 3'UTR/NOS); FIG. 8B shows construct 4701 (2X35S-5'UTR nbATL75-SpPDI-H1 A-Mich-45-2015-CPMV 3'UTR/NOS); FIG. 8C shows construct 4702 (2X35S-5'UTR nbCHP79-SpPDI-H1 A-Mich-45-2015-CPMV 3'UTR/NOS); FIG. 8D shows construct 4703 (2X35S-5'UTR nbMT78-SpPDI-H1 A-Mich-45-2015-CPMV 3'UTR/NOS); FIG. 8E shows construct 4704 (2X35S-5'UTR atHSP69-SpPDI-H1 A-Mich-45-2015-CPMV 3'UTR/NOS); Sp: signal peptide.

FIG. 9 shows constructs encoding H3-A/Hong Kong/4801/14; FIG. 9A shows construct 4014 (2X35S-5'UTR CPMV 160-SpPDI-H3 A-HK-4801-14-CPMV 3'UTR/NOS); FIG. 9B shows construct 4711 (2X35S-5'UTR nbATL75-SpPDI-H3 A-HK-4801-14-CPMV 3'UTR/NOS); FIG. 9C shows construct 4712 (2X35S-5'UTR nbCHP79-SpPDI-H3 A-HK-4801-14-CPMV 3'UTR/NOS); FIG. 9D shows construct 4713 (2X35S-5'UTR nbMT78-SpPDI-H3 A-HK-4801-14-CPMV 3'UTR/NOS); FIG. 9E shows construct 4714 (2X35S-5'UTR atHSP69-SpPDI-H3 A-HK-4801-14-CPMV 3'UTR/NOS); Sp: signal peptide.

FIG. 10 shows constructs encoding HA-B/Brisbane/60/08; FIG. 10A shows construct 4015 (2X35S-5'UTR CPMV 160-SpPDI-HA B/Bri/60/08—CPMV 3'UTR/NOS); FIG. 10B shows construct 4721 (2X35S-5'UTR nbATL75-SpPDI-HA B/Bri/60/08-CPMV 3'UTR/NOS); FIG. 10C shows construct 4722 (2X35S-5'UTR nbCHP79-SpPDI-HA B/Bri/60/08-CPMV 3'UTR/NOS); FIG. 10D shows construct 4723 (2X35S-5'UTR nbMT78-SpPDI-HA B/Bri/60/08-CPMV 3'UTR/NOS); FIG. 10E shows construct 4724 (2X35S-5'UTR atHSP69-SpPDI-HA B/Bri/60/08-CPMV 3'UTR/NOS); Sp: signal peptide.

FIG. 11 shows constructs encoding HAB/Phu/3073/13; FIG. 11A shows construct 4016 (2X35S-5'UTR CPMV 160-SpPDI-HA0 HA B/Phu/3073/13-CPMV 3'UTR/NOS); FIG. 11B shows construct 4731 (2X35S-5'UTR nbATL75-SpPDI-HA0 HA B/Phu/3073/13-CPMV 3'UTR/NOS); FIG. 11C shows construct 4732 (2X35S-5'UTR nbCHP79-SpPDI-HA0 HA B/Phu/3073/13-CPMV 3'UTR/NOS); FIG. 11D shows construct 4733 (2X35S-5'UTR nbMT78-SpPDI-HA0 HA B/Phu/3073/13-CPMV 3'UTR/NOS); FIG. 11E shows construct 4734 (2X35S-5'UTR atHSP69-SpPDI-HA0 HA B/Phu/3073/13-CPMV 3'UTR/NOS); Sp: signal peptide.

FIG. 12 shows constructs encoding VP1-GII.4 Sydney 12; FIG. 12A shows construct 4133 (2X35S-5'UTR CPMV 160-VP1 (GII.4 Syd12)-CPMV 3'UTR/NOS); FIG. 12B shows construct 4161 (2X35S-5'UTR nbATL75-VP1 (GII.4 Syd12)-CPMV 3'UTR/NOS); FIG. 12C shows construct 4162 (2X35S-5'UTR nbCHP79-VP1 (GII.4 Syd12)-CPMV 3'UTR/NOS); FIG. 12D shows construct 4163 (2X35S-5'UTR nbMT78-VP1 (GII.4 Syd12)-CPMV 3'UTR/NOS); FIG. 12E shows construct 4164 (2X35S-5'UTR atHSP69-VP1 (GII.4 Syd12)-CPMV 3'UTR/NOS);

FIG. 13 shows constructs encoding HC IgG1; FIG. 13A shows construct 3191 (2X35S-5'UTR CPMV 160-SpPDI-HC IgG1-CPMV 3'UTR/NOS); FIG. 13B shows construct 4643 (2X35S-5'UTR nbATL75-SpPDI-HC IgG1-CPMV 3'UTR/NOS); FIG. 13C shows construct 4644 (2X35S-5'UTR nbCHP79-SpPDI-HC IgG1-CPMV 3'UTR/NOS); FIG. 13D shows construct 4645 (2X35S-5'UTR nbMT78-SpPDI-HC IgG1-CPMV 3'UTR/NOS); FIG. 13E shows construct 4646 (2X35S-5'UTR atHSP69-SpPDI-HC IgG1-CPMV 3'UTR/NOS); Sp: signal peptide.

FIG. 14 shows constructs encoding LC IgG1; FIG. 14A shows construct 3192 (2X35S-5'UTR CPMV 160-SpPDI-LC IgG1-CPMV 3'UTR/NOS); FIG. 14B shows construct 4653 (2X35S-5'UTR nbATL75-SpPDI-LC IgG1-CPMV 3'UTR/NOS); FIG. 14C shows construct 4654 (2X35S-5'UTR nbCHP79-SpPDI-LC IgG1-CPMV 3'UTR/NOS); FIG. 14D shows construct 4655 (2X35S-5'UTR nbMT78-SpPDI-LC IgG1-CPMV 3'UTR/NOS); FIG. 14E shows construct 4656 (2X35S-5'UTR atHSP69-SpPDI-LC IgG1-CPMV 3'UTR/NOS); Sp: signal peptide.

FIG. 15A shows the nucleic acid sequence of nbMT78 (SEQ ID NO:1); FIG. 15B shows the nucleic acid sequence of nbATL75 (SEQ ID NO:2); FIG. 15C shows the nucleic acid sequence of nbDJ46 (SEQ ID NO:3); FIG. 15D shows the nucleic acid sequence of nbCHP79 (SEQ ID NO:4); FIG. 15E shows the nucleic acid sequence of nbEN42 (SEQ ID NO:5); FIG. 15F shows the nucleic acid sequence of atHSP69 (SEQ ID NO:6); FIG. 15G shows the nucleic acid sequence of atGRP62 (SEQ ID NO:7); FIG. 15H shows the nucleic acid sequence of atPK65 (SEQ ID NO:8); FIG. 15I shows the nucleic acid sequence of atRP46 (SEQ ID NO:9); FIG. 15J shows the nucleic acid sequence of nb30S72 (SEQ ID NO:10); FIG. 15K shows the nucleic acid sequence of nbGT61 (SEQ ID NO:11); FIG. 15L shows the nucleic acid sequence of nbPV55 (SEQ ID NO:12); FIG. 15M shows the nucleic acid sequence of nbPPI43 (SEQ ID NO:13); FIG. 15N shows the nucleic acid sequence of nbPM64 (SEQ ID NO:14); FIG. 15O shows the nucleic acid sequence of nbH2A86 (SEQ ID NO:15); FIG. 15P shows the nucleic acid sequence of CPMV 160 (SEQ ID NO:16) (prior art).

FIG. 16A shows the nucleic acid sequences of the primers used to prepare Dasher constructs. FIG. 16B shows the nucleic acid sequence of CPMV 160 5'UTR-Dasher (SEQ ID NO:20); FIG. 16C shows the nucleic acid sequence of Dasher (SEQ ID NO:78); FIG. 16D shows the amino acid sequence of Dasher (SEQ ID NO:21); FIG. 16E shows the nucleic acid sequence of construct 4467 (Dasher) from 2X35S promoter to NOS terminator (SEQ ID NO:75); FIG. 16F shows the nucleic acid sequence of the cloning vector for Dasher, construct 1666 from left to right of the T-DNA (SEQ ID NO:22).

FIG. 17A shows the nucleic acid sequences of the primers used to prepare H1 A Cal-7-09, H1 A-Mich-45-15, and H3 HK-4801-14, HA B-Bris-60-08, and HA B_Phu-3073-13 constructs; FIG. 17B shows the nucleic acid sequence of CPMV 160 5'UTR-PDI+H1 Cal (SEQ ID NO:79); FIG. 17C shows the nucleic acid sequence of CPMV 160 5'UTR-PDI+H1 Cal nucleic acid sequence (SEQ ID NO:80); FIG. 17D shows the amino acid sequence of PDI+H1 Cal (SEQ ID NO:81); FIG. 17E shows the nucleic acid sequence of construct 4160, the cloning vector used to prepare H3 and HA B constructs, from left to right T-DNA (SEQ ID NO:76).

FIG. 18A shows the nucleic acid sequence of CPMV 160 5'UTR-PDI+H1 Mich (SEQ ID NO:82); FIG. 18B shows the nucleic acid sequence of PDI+H1 Mich (SEQ ID NO:83); FIG. 18C shows the amino acid sequence of PDI+H1 Mich (SEQ ID NO:84); FIG. 18D shows the nucleic acid sequence of construct 4170, the cloning vector used to prepare VP1 GII.4 constructs, from left to right T-DNA (SEQ ID NO:77).

FIG. 19A shows the nucleic acid sequence of CPMV 160 5'UTR-PDI+H3 HK (SEQ ID NO:85); FIG. 19B shows the nucleic acid sequence of PDI+H3 HK (SEQ ID NO:86); FIG. 19C shows the amino acid sequence of PDI+H3 HK (SEQ ID NO:87).

FIG. 20A shows the nucleic acid sequence of CPMV 160 5'UTR-PDI+HA B Bri (SEQ ID NO:88); FIG. 20B shows the nucleic acid sequence of PDI+HA B Bri (SEQ ID NO:89); FIG. 20C shows the amino acid sequence of PDI+HA B Bri amino acid sequence (SEQ ID NO:90).

FIG. 21A shows the nucleic acid sequence of CPMV 160 5'UTR-PDI+HA B Phu SEQ ID NO:91); FIG. 21B shows the nucleic acid sequence of PDI+HA B Phu (SEQ ID NO:92); FIG. 21C shows the amino acid sequence of PDI+HA B Phu (SEQ ID NO:93).

FIG. 22A shows the nucleic acid sequence of primers used to prepare GII.4 VP1 constructs; FIG. 22B shows the nucleic acid sequence of CPMV 160 5'UTR-VP1 (GII.4), (SEQ ID NO:94); FIG. 22C shows the nucleic acid sequence of VP1 (GII.4), (SEQ ID NO:95); FIG. 22D shows the amino acid sequence of VP1 (GII.4) SEQ ID NO:96).

FIG. 23A shows the nucleic acid sequence of primers used to prepare Rituximab constructs; FIG. 23B shows the nucleic acid sequence of CPMV 160 5'UTR-PDI+Rituximab HC (SEQ ID NO:97); FIG. 23C shows the nucleic acid sequence of PDI+Rituximab HC (SEQ ID NO:98); FIG. 23D shows the amino acid sequence of PDI+Rituximab HC (SEQ ID NO:99); FIG. 23E shows the nucleic acid sequence of CPMV 160 5'UTR-PDI+Rituximab LC (SEQ ID NO:100); FIG. 23F shows the nucleic acid sequence of PDI+Rituximab LC (SEQ ID NO:101); FIG. 23G shows the amino acid sequence of PDI+Rituximab LC (SEQ ID NO:102).

DETAILED DESCRIPTION

The following description is of a preferred embodiment.

As used herein, the terms "comprising," "having," "including" and "containing," and grammatical variations thereof, are inclusive or open-ended and do not exclude additional, un-recited elements and/or method steps. The term "consisting essentially of" when used herein in connection with a use or method, denotes that additional elements and/or method steps may be present, but that these additions do not materially affect the manner in which the recited method or use functions. The term "consisting of" when used herein in connection with a use or method, excludes the presence of additional elements and/or method steps. A use or method described herein as comprising certain elements and/or steps may also, in certain embodiments, consist essentially of those elements and/or steps, and in other embodiments consist of those elements and/or steps, whether or not these embodiments are specifically referred to. In addition, the use of the singular includes the plural, and "or" means "and/or" unless otherwise stated. The term "plurality" as used herein means more than one, for example, two or more, three or more, four or more, and the like. Unless otherwise defined herein, all technical and scientific terms used herein have the same meaning as commonly understood by one of ordinary skill in the art. As used herein, the term "about" refers to an approximately +/−10% variation from a given value. It is to be understood that such a variation is always included in any given value provided herein, whether or not it is specifically referred to. The use of the word "a" or "an" when used herein in conjunction with the term "comprising" may mean "one," but it is also consistent with the meaning of "one or more," "at least one" and "one or more than one."

The term "plant", "portion of a plant", "plant portion", "plant matter", "plant biomass", "plant material", plant extract", or "plant leaves", as used herein, may comprise an entire plant, tissue, cells, or any fraction thereof, intracellular plant components, extracellular plant components, liquid or solid extracts of plants, or a combination thereof, that are capable of providing the transcriptional, translational, and post-translational machinery for expression of one or more than one nucleic acids described herein, and/or from which an expressed protein of interest or VLP may be extracted and purified. Plants may include, but are not limited to, agricultural crops including for example canola, *Brassica* spp., maize, *Nicotiana* spp., (tobacco) for example, *Nicotiana benthamiana*, *Nicotiana rustica*, *Nicotiana, tabacum*, *Nicotiana alata*, *Arabidopsis thaliana*, alfalfa, potato, sweet potato (*Ipomoea batatus*), ginseng, pea, oat, rice, soybean, wheat, barley, sunflower, cotton, corn, rye (*Secale cereale*), sorghum (*Sorghum bicolor, Sorghum vulgare*), safflower (*Carthamus tinctorius*).

The term "plant portion", as used herein, refers to any part of the plant including but not limited to leaves, stem, root, flowers, fruits, callus tissue or cell cultured plant tissue, a cluster of plant cells, a plant cell, for example a plant cell, cluster of plants cells callus or cultured plant tissue obtained from leaves, stem, root, flowers, fruits, a plant extract obtained from leaves, stem, root, flowers, fruits, or a combination thereof. The term plant cell refers to a cell of plant that is bounded by a plasma membrane and may or may not comprise a cell wall. A plant cell includes a protoplast (or spheroplast) that comprises an enzymatically digested cell and that may be obtained using techniques well known in the art (e.g. Davey M R et al., 2005, Biotechnology Advances 23:131-171; which is incorporated herein by reference). Callus plant tissue or cultured plant tissue may be produced using methods well known in the art (e.g. MK Razdan $2^{nd}$ Ed., Science Publishers, 2003; which is incorporated herein by reference) The term "plant extract", as used herein, refers to a plant-derived product that is obtained following treating a plant, a portion of a plant, a plant cell, or a combination thereof, physically (for example by freezing followed by extraction in a suitable buffer), mechanically (for example by grinding or homogenizing the plant or portion of the plant followed by extraction in a suitable buffer), enzymatically (for example using cell wall degrading enzymes), chemically (for example using one or more chelators or buffers), or a combination thereof. A plant extract may be further processed to remove undesired plant components for example cell wall debris. A plant extract may be obtained to assist in the recovery of one or more components from the plant, portion of the plant or plant cell, for example a protein (including protein complexes, protein surprastructures and/or VLPs), a nucleic acid, a lipid, a carbohydrate, or a combination thereof from the plant, portion of the plant, or plant cell. If the plant extract comprises proteins, then it may be referred to as a protein extract. A protein extract may be a crude plant extract, a partially purified plant or protein extract, or a purified product, that comprises one or more proteins, protein complexes, protein suprastructures, and/or VLPs, from the plant tissue. If desired a protein extract, or a plant extract, may be partially purified using techniques known to one of skill in the art, for example, the extract may be subjected to salt or pH precipitation, centrifugation, gradient density centrifugation, filtration, chromatography, for example, size exclusion chromatography, ion exchange chromatography, affinity chromatography, or a combination thereof. A protein extract may also be purified, using techniques that are known to one of skill in the art.

By "nucleotide (or nucleic acid) sequence of interest", or "coding region of interest", it is meant any nucleotide sequence, or coding region (these terms may be used interchangeably) that is to be expressed within a plant, portion of a plant, or a plant cell, to produce a protein of interest. Such a nucleotide sequence of interest may encode, but is not limited to, native or modified proteins, an industrial enzyme or a modified industrial enzyme, an agricultural protein or a modified agricultural protein, a helper protein, a protein supplement, a pharmaceutically active protein, a nutraceutical, a value-added product, or a fragment thereof for feed, food, or both feed and food use.

The protein of interest may comprise a native, or a non-native signal peptide; the non-native signal peptide may be of plant origin. For example, which is not to be considered limiting, the non-native signal peptide may be obtained from alfalfa protein disulfide isomerase (PDI SP; nucleotides 32-103 of Accession No. Z11499), potato patatin (PatA SP; located nucleotides 1738-1806 of GenBank Accession number A08215), Kiwi actinidin (Act), Tobacco cysteine proteinase 3 precursor (CP23), Corn ΔZein (ΔZein), *Papaya* proteinase I (Papain; Pap) and Thale cress cysteine proteinase RD21A (RD21). The native signal peptide may correspond to that of the protein of interest being expressed.

The nucleotide sequence of interest, or coding region of interest may also include a nucleotide sequence that encodes a pharmaceutically active protein, for example growth factors, growth regulators, antibodies, antigens, and fragments thereof, or their derivatives useful for immunization or vaccination and the like. Such proteins include, but are not limited to a protein that is a human pathogen, a viral protein, for example but not limited to virus like particle (VLP)-forming antigens, one or more proteins from Norovirus, Respiratory syncytial virus (RSV), Rotavirus, influenza virus, human immunodeficiency virus (HIV), Rabies virus, human papiloma virus (HPV), Enterovirus 71 (EV71), or interleukins, for example one or more than one of IL-1 to IL-24, IL-26 and IL-27, cytokines, Erythropoietin (EPO), insulin, G-CSF, GM-CSF, hPG-CSF, M-CSF or combinations thereof, interferons, for example, interferon-alpha, interferon-beta, interferon-gama, blood clotting factors, for example, Factor VIII, Factor IX, or tPA hGH, receptors, receptor agonists, antibodies for example but not limited to rituximab, neuropolypeptides, insulin, vaccines, growth factors for example but not limited to epidermal growth factor, keratinocyte growth factor, transformation growth factor, growth regulators, antigens, autoantigens, fragments thereof, or combinations thereof.

The protein of interest may include an influenza hemagglutinin (HA; see WO 2009/009876, WO 2009/076778, WO 2010/003225, which are incorporated herein by reference). HA is a homotrimeric membrane type I glycoprotein, generally comprising a signal peptide, an HA1 domain, and an HA2 domain comprising a membrane-spanning anchor site at the C-terminus and a small cytoplasmic tail. Nucleotide sequences encoding HA are well known and are available (see, for example, the BioDefense and Public Health Database (Influenza Research Database; Squires et al., 2008, Nucleic Acids Research 36: D497-D503) at URL: biohealthbase.org/GSearch/home.do?decorator=Influenza; or the databases maintained by the National Center for Biotechnology Information (see URL: ncbi.nlm.nih.gov), both of which are incorporated herein by reference).

An HA protein may be of a type A influenza, a type B influenza, or is a subtype of type A influenza HA selected from the group of H1, H2, H3, H4, H5, H6, H7, H8, H9, H10, H11, H12, H13, H14, H15, H16. H17 and H18. In some aspects of the invention, the HA may be from a type A influenza, selected from the group H1, H2, H3, H5, H6, H7 and H9. Fragments of the HAs listed above may also be considered a protein of interest. Furthermore, domains from an HA type or subtype listed above may be combined to produce chimeric HA's (see for example WO2009/076778 which is incorporated herein by reference).

Examples of subtypes comprising HA proteins include A/New Caledonia/20/99 (H1N1), A/Indonesia/5/2006 (H5N1), A/PuertoRico/8/34 (H1N1), A/Brisbane/59/2007 (H1N1), A/Solomon Islands 3/2006 (H1N1), A/California/04/2009 (H1N1), A/California/07/2009 (H1N1), A/chicken/New York/1995, A/Singapore/1/57 (H2N2), A/herring gull/DE/677/88 (H2N8), A/Texas/32/2003, A/mallard/MN/33/00, A/duck/Shanghai/1/2000, A/northern pintail/TX/828189/02, A/Brisbane 10/2007 (H3N2), A/Wisconsin/67/2005 (H3N2), A/Victoria/361/2011 (H3N2), A/Texas/50/2012 (H3N2), A/Hawaii/22/2012 (H3N2), A/New York/39/2012 (H3N2), A/Perth/16/2009 (H3N2), C/Johannesburg/66, A/Anhui/1/2005 (H5N1), A/Vietnam/1194/2004 (H5N1), A/Teal/HongKong/W312/97 (H6N1), A/Equine/Prague/56 (H7N7), A/Turkey/Ontario/6118/68(H8N4), H7 A/Hangzhou/1/2013, A/Anhui/1/2013 (H7N9), A/Shanghai/2/2013 (H7N9), A/shoveler/Iran/G54/03, A/HongKong/1073/99 (H9N2), A/chicken/Germany/N/1949(H10N7), A/duck/England/56(H11N6), A/duck/Alberta/60/76 (H12N5), A/Gull/Maryland/704/77(H13N6), A/Mallard/Gurjev/263/82, A/duck/Australia/341/83 (H15N8), A/black-headed gull/Sweden/5/99(H16N3), B/Malaysia/2506/2004, B/Florida/4/2006, B/Brisbane/60/08, B/Massachusetts/2/2012-like virus (Yamagata lineage), B/Wisconsin/1/2010 (Yamagata lineage), or B/Lee/40.

The HA may also be a modified or chimeric HA, for example, the native transmembrane domain of the HA may be replaced with a heterologous transmembrane domain (WO 2010/148511; which is incorporated herein by reference), the HA may comprise a chimeric ectodomain (WO2012/083445, which is incorporated herein by reference), or the HA may comprises a proteolytic loop deletion (WO 2014/153647, which is incorporated herein by reference).

The protein of interest may also include a norovirus protein or a modified norovirus protein as described in U.S. provisional applications 62/475,660 (filed Mar. 23, 2017; which is incorporated herein by reference), or 62/593,006 (filed Nov. 11, 2017; which is incorporated herein by reference). Norovirus is a non-enveloped viral strain of the genus norovirus of the family Caliciviridae that is characterized as having a single-stranded, positive-sense RNA. Norovirus strains may include any known norovirus strain, but also modifications to known norovirus strains that are known to develop on a regular basis over time. For example, norovirus strains may include, GI.1, GI.2, GI.3, GI.5, GI.7, GII. 1, GII.2, GII.3, GII.4, GII.5, GII.6, GII.7, GII. 12, GII. 13, GII. 14, GII. 17 and GII.21, for example but not limited to Hu/GI.1/United States/Norwalk/1968, Hu/GI.2/Leuven/2003/BEL, Hu/GI.3/S29/2008/Lilla Edet/Sweden, Hu/GI.5/

Siklos/Hun5407/2013/HUN, Hu/GII.1/Ascension208/2010/ USA, Hu/GII.2/CGMH47/2011/TW, Hu/GII.3/Jingzhou/ 2013402/CHN, Hu/GII.4/Sydney/NSW0514/2012/AU, US96/GII.4/Dresden174/1997/DE_AY741811, FH02/GII.4/ FarmingtonHills/2002/US_AY502023, Hnt04:GII.4/ Hunter-NSW504D/2004/AU DQ078814, 2006b: GII.4/ Shellharbour-NSW696T/2006/AU_EF684915, NO09: GII.4/Orange-NSW001P/2008/AU_GQ845367, Hu/GII.5/ AlbertaEI390/2013/CA, Hu/GII.6/Ohio/490/2012/USA, GII.7/Musa/2010/All73774, Hu/GII.12/HS206/2010/USA, GII.13/VA173/2010/H9AWU4, GII.14_Saga_2008_JPN_ADE28701 native VP1, Hu/GII.17/Kawasaki323/2014/JP, and Hu/GII.21/Salisbury150/2011/USA. Norovirus strains also include strains having from about 30-100% or any amount therebetween, amino acid sequence identity, to the VP1 protein, the VP2 protein, or both the VP1 and the VP2 proteins, with any of the above norovirus strains.

The terms "percent similarity", "sequence similarity", "percent identity", or "sequence identity", when referring to a particular sequence, are used for example as set forth in the University of Wisconsin GCG software program, or by manual alignment and visual inspection (see, e.g., Current Protocols in Molecular Biology, Ausubel et al., eds. 1995 supplement). Methods of alignment of sequences for comparison are well-known in the art. Optimal alignment of sequences for comparison can be conducted, using for example the algorithm of Smith & Waterman, (1981, Adv. Appl. Math. 2:482), by the alignment algorithm of Needleman & Wunsch, (1970, J. Mol. Biol. 48:443), by the search for similarity method of Pearson & Lipman, (1988, Proc. Natl. Acad. Sci. USA 85:2444), by computerized implementations of these algorithms (for example: GAP, BESTFIT, FASTA, and TFASTA in the Wisconsin Genetics Software Package, Genetics Computer Group (GCG), 575 Science Dr., Madison, Wis.).

An example of an algorithm suitable for determining percent sequence identity and sequence similarity are the BLAST and BLAST 2.0 algorithms, which are described in Altschul et al., (1977, Nuc. Acids Res. 25:3389-3402) and Altschul et al., (1990, J. Mol. Biol. 215:403-410), respectively. BLAST and BLAST 2.0 are used, with the parameters described herein, to determine percent sequence identity for the nucleic acids and proteins of the invention. For example the BLASTN program (for nucleotide sequences) may use as defaults a wordlength (W) of 11, an expectation (E) of 10, M=5, N=−4 and a comparison of both strands. For amino acid sequences, the BLASTP program may use as defaults a word length of 3, and expectation (E) of 10, and the BLOSUM62 scoring matrix (see Henikoff & Henikoff, 1989, Proc. Natl. Acad. Sci. USA 89:10915) alignments (B) of 50, expectation (E) of 10, M=5, N=−4, and a comparison of both strands. Software for performing BLAST analyses is publicly available through the National Center for Biotechnology Information (see URL: ncbi.nlm.nih.gov/).

The term "nucleic acid segment" as used herein refers to a sequence of nucleic acids that encodes a protein of interest. In addition to the sequence of nucleic acids, the nucleic acid segment comprise a regulatory region and a terminator that are operatively linked to the sequence of nucleic acids. The regulatory region may comprise a promoter, and an enhancer element (expression enhancer) operatively linked to the promoter.

The term "nucleic acid complex" as used herein refers to a combination of two or more than two nucleic acid segments. The two or more than two nucleic acid segments may be present in a single nucleic acid, so that the nucleic acid complex comprises two, or more than two nucleic acid segments, with each nucleic acid segment under the control of a regulatory region and a terminator. Alternatively, the nucleic acid complex may comprise two or more separate nucleic acids, each of the nucleic acids comprising one or more than one nucleic acid segment, where each nucleic acid segment is under the control of a regulatory region and a terminator. For example a nucleic acid complex may comprise one nucleic acid that comprises two nucleic acid segments, a nucleic acid complex may comprise two nucleic acids, each nucleic acid comprising one nucleic acid segment, or a nucleic acid complex may comprise two or more than two nucleic acids, with each nucleic acid comprising one or more than one nucleic acid segment.

The terms "vector" or "expression vector" as used herein, refer to a recombinant nucleic acid for transferring exogenous nucleic acid sequences into host cells (e.g. plant cells) and directing expression of the exogenous nucleic acid sequences in the host cells. The vector may be introduced to the plant, the portion of the plant, or a plant cell, directly, or the vectors may be introduced in the plant, the portion of the plant, or a plant cell as part of a plant expression system. The vector or expression vector comprise a construct or an expression construct. The construct or expression construct comprises a nucleotide sequence comprising a nucleic acid of interest under the control of, and operably (or operatively) linked to, an appropriate promoter, an expression enhancer, or other regulatory elements for transcription of the nucleic acid of interest in a host cell. As one of skill in the art would appreciate, the construct or expression cassette may comprise a termination (terminator) sequence that is any sequence that is active in the plant host. For example the termination sequence may be derived from the RNA-2 genome segment of a bipartite RNA virus, e.g. a comovirus, the termination sequence may be a NOS terminator, the terminator sequence may be obtained from the 3'UTR of the alfalfa plastocyanin gene, or a combination thereof.

The constructs of the present disclosure may further comprise a 3' untranslated region (UTR). A 3' untranslated region contains a polyadenylation signal and any other regulatory signals capable of effecting mRNA processing or gene expression. The polyadenylation signal is usually characterized by effecting the addition of polyadenylic acid tracks to the 3' end of the mRNA precursor. Polyadenylation signals are commonly recognized by the presence of homology to the canonical form 5' AATAAA-3' although variations are not uncommon. Non-limiting examples of suitable 3' regions are the 3' transcribed non-translated regions containing a polyadenylation signal of *Agrobacterium* tumor inducing (Ti) plasmid genes, such as the nopaline synthase (Nos gene) and plant genes such as the soybean storage protein genes, the small subunit of the ribulose-1, 5-bisphosphate carboxylase gene (ssRUBISCO; U.S. Pat. No. 4,962, 028; which is incorporated herein by reference), the promoter and/or terminator used in regulating plastocyanin expression.

For example, which is not to be considered limiting, a CPMV 3'UTR+NOS terminator may be used as a 3'UTR sequence that is operatively linked to the 3' end of the nucleic acid sequence encoding the protein of interest.

By "regulatory region" "regulatory element" or "promoter" it is meant a portion of nucleic acid typically, but not always, upstream of the protein coding region of a gene, which may be comprised of either DNA or RNA, or both DNA and RNA. When a regulatory region is active, and in operative association, or operatively linked, with a nucleotide sequence of interest, this may result in expression of the nucleotide sequence of interest. A regulatory element may be capable of mediating organ specificity, or controlling developmental or temporal gene activation. A "regulatory region" includes promoter elements, core promoter elements exhibiting a basal promoter activity, elements that are inducible in response to an external stimulus, elements that mediate promoter activity such as negative regulatory elements or transcriptional enhancers. "Regulatory region", as used herein, also includes elements that are active following transcription, for example, regulatory elements that modulate gene expression such as translational and transcriptional enhancers, translational and transcriptional repressors, upstream activating sequences, and mRNA instability determinants. Several of these latter elements may be located proximal to the coding region.

In the context of this disclosure, the term "regulatory element" or "regulatory region" typically refers to a sequence of DNA, usually, but not always, upstream (5') to the coding sequence of a structural gene, which controls the expression of the coding region by providing the recognition for RNA polymerase and/or other factors required for transcription to start at a particular site. However, it is to be understood that other nucleotide sequences, located within introns, or 3' of the sequence may also contribute to the regulation of expression of a coding region of interest. An example of a regulatory element that provides for the recognition for RNA polymerase or other transcriptional factors to ensure initiation at a particular site is a promoter element. Most, but not all, eukaryotic promoter elements contain a TATA box, a conserved nucleic acid sequence comprised of adenosine and thymidine nucleotide base pairs usually situated approximately 25 base pairs upstream of a transcriptional start site. A promoter element may comprise a basal promoter element, responsible for the initiation of transcription, as well as other regulatory elements that modify gene expression.

There are several types of regulatory regions, including those that are developmentally regulated, inducible or constitutive. A regulatory region that is developmentally regulated, or controls the differential expression of a gene under its control, is activated within certain organs or tissues of an organ at specific times during the development of that organ or tissue. However, some regulatory regions that are developmentally regulated may preferentially be active within certain organs or tissues at specific developmental stages, they may also be active in a developmentally regulated manner, or at a basal level in other organs or tissues within the plant as well. Examples of tissue-specific regulatory regions, for example seed-specific a regulatory region, include the napin promoter, and the cruciferin promoter (Rask et al., 1998, J. Plant Physiol. 152: 595-599; Bilodeau et al., 1994, Plant Cell 14: 125-130). An example of a leaf-specific promoter includes the plastocyanin promoter (see U.S. Pat. No. 7,125,978, which is incorporated herein by reference).

An inducible regulatory region is one that is capable of directly or indirectly activating transcription of one or more DNA sequences or genes in response to an inducer. In the absence of an inducer the DNA sequences or genes will not be transcribed. Typically the protein factor that binds specifically to an inducible regulatory region to activate transcription may be present in an inactive form, which is then directly or indirectly converted to the active form by the inducer. However, the protein factor may also be absent. The inducer can be a chemical agent such as a protein, metabolite, growth regulator, herbicide or phenolic compound or a physiological stress imposed directly by heat, cold, salt, or toxic elements or indirectly through the action of a pathogen or disease agent such as a virus. A plant cell containing an inducible regulatory region may be exposed to an inducer by externally applying the inducer to the cell or plant such as by spraying, watering, heating or similar methods. Inducible regulatory elements may be derived from either plant or non-plant genes (e.g. Gatz, C. and Lenk, I. R. P., 1998, Trends Plant Sci. 3, 352-358). Examples, of potential inducible promoters include, but not limited to, tetracycline-inducible promoter (Gatz, C., 1997, Ann. Rev. Plant Physiol. Plant Mol. Biol. 48, 89-108), steroid inducible promoter (Aoyama, T. and Chua, N. H., 1997, Plant J. 2, 397-404) and ethanol-inducible promoter (Salter, M. G., et al, 1998, Plant Journal 16, 127-132; Caddick, M. X., et al, 1998, Nature Biotech. 16, 177-180) cytokinin inducible IB6 and CKII genes (Brandstatter, I. and Kieber, J. J., 1998, Plant Cell 10, 1009-1019; Kakimoto, T., 1996, Science 274, 982-985) and the auxin inducible element, DR5 (Ulmasov, T., et al., 1997, Plant Cell 9, 1963-1971).

A constitutive regulatory region directs the expression of a gene throughout the various parts of a plant and continuously throughout plant development. Examples of known constitutive regulatory elements include promoters associated with the CaMV 35S transcript. (p35S; Odell et al., 1985, Nature, 313: 810-812; which is incorporated herein by reference), the rice actin 1 (Zhang et al, 1991, Plant Cell, 3: 1155-1165), actin 2 (An et al., 1996, *Plant J.,* 10: 107-121), or tms 2 (U.S. Pat. No. 5,428,147), and triosephosphate isomerase 1 (Xu et. al., 1994, Plant Physiol. 106: 459-467) genes, the maize ubiquitin 1 gene (Cornejo et al, 1993, Plant Mol. Biol. 29: 637-646), the *Arabidopsis* ubiquitin 1 and 6 genes (Holtorf et al, 1995, Plant Mol. Biol. 29: 637-646), the tobacco translational initiation factor 4A gene (Mandel et al, 1995 Plant Mol. Biol. 29: 995-1004); the Cassava Vein Mosaic Virus promoter, pCAS, (Verdaguer et al., 1996); the promoter of the small subunit of ribulose biphosphate carboxylase, pRbcS: (Outchkourov et al., 2003), the pUbi (for monocots and dicots).

The term "constitutive" as used herein does not necessarily indicate that a nucleotide sequence under control of the constitutive regulatory region is expressed at the same level in all cell types, but that the sequence is expressed in a wide range of cell types even though variation in abundance is often observed.

The constructs or expression constructs as described above may be present in a vector (or an expression vector). The vector may comprise border sequences which permit the transfer and integration of the expression cassette into the genome of the organism or host. The construct may be a plant binary vector, for example a binary transformation vector based on pPZP (Hajdukiewicz, et al. 1994). Other example constructs include pBin19 (see Frisch, D. A., L. W. Harris-Haller, et al. 1995, *Plant Molecular Biology* 27: 405-409).

A nucleotide sequence interest that encodes a protein requires the presence of a "translation initiation site" or "initiation site" or "translation start site" or "start site" or "start codon" located upstream of the gene to be expressed. Such initiation sites may be provided either as part of an enhancer sequence or as part of a nucleotide sequence encoding the protein of interest.

The term "native", "native protein" or "native domain", as used herein, refers to a protein or domain having a primary amino acid sequence identical to wildtype. Native proteins or domains may be encoded by nucleotide sequences having 100% sequence similarity to the wildtype sequence. A native amino acid sequence may also be encoded by a human codon (hCod) optimized nucleotide sequence or a nucleotide sequence comprising an increased GC content when compared to the wild type nucleotide sequence provided that the amino acid sequence encoded by the hCod-nucleotide sequence exhibits 100% sequence identity with the native amino acid sequence.

By a nucleotide sequence that is "human codon optimized" or an "hCod" nucleotide sequence, it is meant the selection of appropriate DNA nucleotides for the synthesis of an oligonucleotide sequence or fragment thereof that approaches the codon usage generally found within an oligonucleotide sequence of a human nucleotide sequence. By "increased GC content" it is meant the selection of appropriate DNA nucleotides for the synthesis of an oligonucleotide sequence or fragment thereof in order to approach codon usage that, when compared to the corresponding native oligonucleotide sequence, comprises an increase of GC content, for example, from about 1 to about 30%, or any amount therebetween, over the length of the coding portion of the oligonucleotide sequence. For example, from about 1, 2, 4, 6, 8, 10, 12, 14, 16, 18, 20, 22, 24, 26, 28, 30%, or any amount therebetween, over the length of the coding portion of the oligonucleotide sequence. As described below, a human codon optimized nucleotide sequence, or a nucleotide sequence comprising an increased GC content (when compared to the wild type nucleotide sequence) exhibits increased expression within a plant, portion of a plant, or a plant cell, when compared to expression of the non-human optimized (or lower GC content) nucleotide sequence.

The term "single construct" or "single constructs", as used herein, refers to a nucleic acid comprising a single nucleic acid sequence. The term "dual construct" or "dual constructs", as used herein, refers to a nucleic acid comprising two nucleic acid sequences.

By co-expression it is meant the introduction and expression of two or more nucleotide sequences, each of the two or more nucleotide sequences encoding a protein of interest, or a fragment of a protein of interest within a plant, portion of a plant or a plant cell. The two or more nucleotide sequences may be introduced into the plant, portion of the plant or the plant cell within one vector, so that each of the two or more nucleotide sequences is under the control of a separate regulatory region (e.g. comprising a dual construct). Alternatively, the two or more nucleotide sequences may be introduced into the plant, portion of the plant or the plant cell within separate vectors (e.g. comprising single constructs), and each vector comprising appropriate regulatory regions for the expression of the corresponding nucleic acid. For example, two nucleotide sequences, each on a separate vector and introduced into separate *Agrobacterium tumefaciens* hosts, may be co-expressed by mixing suspensions of each *A. tumefaciens* host in a desired volume (for example, an equal volume, or the ratios of each *A. tumefaciens* host may be altered) before vacuum infiltration. In this manner, co-infiltration of multiple *A. tumefaciens* suspensions permits co-expression of multiple transgenes.

The nucleic acid encoding a protein of interest as described herein may further comprise sequences that enhance expression of the protein of interest in the plant, portion of the plant, or plant cell. Sequences that enhance expression are described herein and for example, may include one or more of, an expression enhancer element obtained from a nucleic acid encoding a secretory protein (SPEE) or an expression enhancer element obtained from a nucleic acid encoding a cytosolic protein (CPEE), in operative association with the nucleic acid encoding the protein of interest. Non-limiting examples of using the expression enhancer as described herein for the expression of a secreted protein includes any protein of interest comprising a signal peptide or signal sequence that targets the protein of interest to the extracellular compartment, for example an antibody (see FIG. 5), or virus like particles (VLPs) that are known to bud from the plasma membrane, for example, influenza HA (see for example FIGS. 3A and 3B). Non-limiting examples of proteins that are produced cytosolically include any protein of interest that do not comprise a secretory peptide or signal sequence (see for example FIG. 2), or VLPs that are known to be produced and retained within the cytsol, for example norovirus (see FIG. 4).

The sequence encoding the protein of interest may also be optimized for human codon usage, increased GC content, or a combination thereof. Co-expression of a nucleic acid encoding a second protein of interest may lead to functional multimeric protein, for example an antibody comprising heavy and light chain components, or to an increased yield of protein. If the protein of interest results in the production of a VLP, then co-expression of two or more proteins may result in an increase yield, increased density, increased integrity, or combination thereof, of the VLPs that comprise the protein of interest. The increase in yield, density, integrity, or combination thereof, may be determined by comparing the yield, density, integrity, or combination thereof, obtained using the expression enhancer as described herein with the yield, density, integrity, or combination thereof, of the same nucleotide sequence encoding the heterologous open reading frame but not operatively linked to an expression enhancer, or for example, when operatively linked to the prior art expression enhancer CPMV 160 (SEQ ID NO:16).

A plant expression system comprising a nucleic acid comprising a regulatory region, operatively linked with one or more than one expression enhancer as described herein and a nucleotide sequence of interest is also provided. The plant expression system may comprise one or more than one vector, one or more than one construct or one or more than one nucleic acid, that comprises the regulatory region operatively linked with one or more than one expression enhancer as described herein and the nucleotide sequence or nucleic acid of interest, along with other components that may be introduced into the plant, the portion of the plant or a plant cell. For example, the plant expression system may also comprise additional vectors, constructs, or nucleic acids, additional Agrobacteria comprising vectors, constructs or nucleic acids for co-expression, one or more than one chemical compound to modify the efficiency of transformation, other components, or a combination thereof.

Furthermore, a nucleic acid comprising a promoter (regulatory region) sequence, operatively linked with an expression enhancer comprising an expression enhancer as described herein, and a nucleotide sequence of interest is described. The nucleic acid may further comprise a sequence encoding a 3'UTR, for example a comovirus 3' UTR, or a plastocyanin 3' UTR, and a terminator sequence, for example a NOS terminator, so that the nucleotide sequence of interest is inserted upstream from the 3'UTR.

"Expression enhancer(s)", "enhancer sequence(s)" or "enhancer element(s)", as referred to herein, when operatively linked to a nucleic acid of interest, for example a heterologous nucleic acid of interest, results in expression of the nucleic acid of interest. The expression enhancer may also enhance or increase expression of a downstream heterologous open reading frame (ORF) to which they are attached. The expression enhancer may be operatively linked at the 5'end of the enhancer sequence with a regulatory region that is active in a plant, and operatively linked to a nucleotide sequence of interest at the 3'end of the expression enhancer in order to drive expression of the nucleotide sequence of interest within a host, for example a plant, portion of a plant or a plant cell. Expression enhancers described herein include sequences derived from, or that share sequence similarity with, a nucleotide sequence selected from, nbMT78 (SEQ ID NO:1); nbATL75 (SEQ ID NO:2); nbDJ46 (SEQ ID NO:3); nbCHP79 (SEQ ID NO:4); nbEN42 (SEQ ID NO:5); atHSP69 (SEQ ID NO:6); atGRP62 (SEQ ID NO:7); atPK65 (SEQ ID NO:8); atRP46 (SEQ ID NO:9); nb30S72 (SEQ ID NO:10); nbGT61 (SEQ ID NO:11); nbPV55 (SEQ ID NO:12); nbPPI43 (SEQ ID NO:13); nbPM64 (SEQ ID NO:14); and nbH2A86 (SEQ ID NO:15).

By "operatively linked" it is meant that the particular sequences interact either directly or indirectly to carry out an intended function, such as mediation or modulation of expression of a nucleic acid sequence. The interaction of operatively linked sequences may, for example, be mediated by proteins that interact with the operatively linked sequences.

The term "5'UTR" or "5' untranslated region" or "5' leader sequence" refers to regions of an mRNA that are not translated. The 5'UTR typically begins at the transcription start site and ends just before the translation initiation site or start codon (usually AUG in an mRNA, ATG in a DNA sequence) of the coding region. The 5' UTR may modulate the stability and/or translation of an mRNA transcript. If desired, the length of the 5'UTR may be modified by mutation for example substitution, deletion or insertion of the 5'UTR.

The expression enhancer may further comprise one or more "restriction site(s)" or "restriction recognition site(s)", "multiple cloning site", "MCS", "cloning site(s)" "polylinker sequence" or "polylinker" to facilitate the insertion of the nucleotide of interest into the plant expression system. Restrictions sites are specific sequence motifs that are recognized by restriction enzymes and are well known in the art. The expression enhancer may comprise one or more restriction sites or cloning sites that are located downstream (3') of the 5'UTR. The polylinker sequence (multiple cloning site) may comprise any sequence of nucleic acids that are useful for adding and removing nucleic acid sequences, including a nucleotide sequence encoding a protein of interest, to the 3' end of the 5'UTR. A polylinker sequence may comprise from 4 to about 100 nucleic acids, or any amount therebetween. As would be evident to one of skill in the art, any multiple cloning site (MCS), or an MCS of different length (either shorter or longer) may be used.

Expression systems, or vectors, to produce one or more proteins of interest in a plant using one or more than one expression enhancers as described herein are also provided. The expression systems described herein comprise an expression cassette comprising one or more than one expression enhancer, or a sequence that comprises 80-100% sequence similarity, or any amount therebetween, with the one or more than one expression enhancer. The expression cassette comprising the expression enhancer may further comprise a regulatory region that is active in a plant that is operatively linked to the 5'end of the expression enhancer. A nucleotide sequence of interest may be operatively linked to the 3'end of the expression cassette so that when introduced within a plant, portion of the plant or a plant cell, expression of the nucleotide sequence of interest within a plant is achieved.

Plants, portions of plants, plant cells, plant tissues, whole plants, inoculum, nucleic acids, constructs comprising nucleotide sequences of interest encoding proteins of interest, expression cassettes or expression systems comprising the one or more than one expression enhancer as described herein, and methods of expressing a protein of interest in plants, portions of plants, or plant cells are also provided.

The constructs of the present invention can be introduced into plant cells in a stable or transient manner using Ti plasmids, Ri plasmids, plant virus vectors, direct DNA transformation, micro-injection, electroporation, infiltration, and the like. For reviews of such techniques see for example Weissbach and Weissbach, *Methods for Plant Molecular Biology*, Academy Press, New York VIII, pp. 421-463 (1988); Geierson and Corey, *Plant Molecular Biology*, 2d Ed. (1988); and Miki and Iyer, Fundamentals of Gene Transfer in Plants. In *Plant Metabolism*, 2d Ed. DT. Dennis, DH Turpin, DD Lefebrve, DB Layzell (eds), Addison-Wesley, Langmans Ltd. London, pp. 561-579 (1997). Other methods include direct DNA uptake, the use of liposomes, electroporation, for example using protoplasts, micro-injection, microprojectiles or whiskers, and vacuum infiltration. See, for example, Bilang, et al. (Gene 100: 247-250 (1991), Scheid et al. (Mol. Gen. Genet. 228: 104-112, 1991), Guerche et al. (Plant Science 52: 111-116, 1987), Neuhause et al. (Theor. Appl Genet. 75: 30-36, 1987), Klein et al., Nature 327: 70-73 (1987); Howell et al. (Science 208: 1265, 1980), Horsch et al. (Science 227: 1229-1231, 1985), DeBlock et al., Plant Physiology 91: 694-701, 1989), Methods for Plant Molecular Biology (Weissbach and Weissbach, eds., Academic Press Inc., 1988), Methods in Plant Molecular Biology (Schuler and Zielinski, eds., Academic Press Inc., 1989), Liu and Lomonossoff (J. Virol Meth, 105:343-348, 2002), U.S. Pat. Nos. 4,945,050; 5,036,006; 5,100,792; 6,403,865; 5,625,136, (all of which are hereby incorporated by reference).

Transient expression methods may be used to express the constructs of the present invention (see Liu and Lomonossoff, 2002, Journal of Virological Methods, 105:343-348; which is incorporated herein by reference). Alternatively, a vacuum-based transient expression method, as described by Kapila et al. 1997 (incorporated herein by reference) may be used. These methods may include, for example, but are not limited to, a method of Agro-inoculation or Agro-infiltration, however, other transient methods may also be used as noted above. With either Agro-inoculation or Agro-infiltration, a mixture of Agrobacteria comprising the desired nucleic acid enter the intercellular spaces of a tissue, for example the leaves, aerial portion of the plant (including stem, leaves and flower), other portion of the plant (stem, root, flower), or the whole plant. After crossing the epidermis the *Agrobacterium* infect and transfer t-DNA copies into the cells. The t-DNA is episomally transcribed and the mRNA translated, leading to the production of the protein of interest in infected cells, however, the passage of t-DNA inside the nucleus is transient.

If the nucleotide sequence of interest encodes a product that is directly or indirectly toxic to the plant, then by using the method of the present invention, such toxicity may be reduced throughout the plant by selectively expressing the nucleotide sequence of interest within a desired tissue or at a desired stage of plant development. In addition, the limited period of expression resulting from transient expression may reduce the effect when producing a toxic product in the plant. An inducible promoter, a tissue-specific promoter, or a cell specific promoter may be used to selectively direct expression of the sequence of interest.

The nucleotide sequence of interest may be fused (operatively linked) to the enhancer sequence comprising a plant regulatory region, using a variety of approaches. For example, which are not to be considered limiting, a nucleotide sequence of interest encoding a protein of interest may be fused to the 3' end of an expression enhancer immediately after the 5'UTR sequence.

Examples of expression enhancers as described herein include:

```
nbMT78 (SEQ ID NO: 1);
ACACAATTTGCTTTAGTGATTAAACTTTCTTTTACAACAAATTAAAGGT
CTATTATCTCCCAACAACATAAGAAAACA;

nbATL75 (SEQ ID NO: 2);
ATCTCCACCACCAAAAACCCTAATCGCCTCTCCGTTTCTTCATCAGATT
CTCGGTTCTCTTCTTCTACAGCAACA;

nbDJ46 (SEQ ID NO: 3);
ACTCACCAAGAAAATAAACAAATTAAAGAATTTTAAGAAAAACAAG;

nbCHP79 (SEQ ID NO: 4);
ATTCTGCCCTCAGTTAACTAAATTATCTCTCTGATTAACAGTACTTTCT
GATTTTCTGTGATTTCTACAAATCTGAGAC;

nbEN42 (SEQ ID NO:5);
ACTTTTGTATAGCTCCATTGAAATAGAGAAAAGAAAATAGCC;

atHSP69 (SEQ ID NO: 6);
AAAATTCAAAATTTAACACACAAACACAAACACACACACCAAAAAAACA
CAGACCTTAAAAAAATAAAA;

atGRP62 (SEQ ID NO: 7);
ATAACAAAACAAGATTTTGAAGTAAAACATAAAAGAAAATAAACCCTAA
GAATATATCGAAA;

atPK65 (SEQ ID NO: 8);
GCAAAAACAAAAATAAAAAAAACATCGCACAAGAAAATAAAAGATTTGT
AGAATCAACTAAGAAA;

atRP46 (SEQ ID NO: 9);
AGAAACAAAAAGAATTAAAAAAAAAAAAAAAAAAAGAATAAAGAA;

nb30S72 (SEQ ID NO: 10);
ATCTTTCCCTCAAAACCCTAGCCGCAGTCACTTCCGTAGGTGCTTACTT
CGCTGTTAGTGCAATTCCAAACC;

nbGT61 (SEQ ID NO: 11);
ATCCAGAAGTAGGAATTCTTCAGTATAATCTAGGGTTTTTTGAAAAGCA
AATTGATCGAAA;

nbPV55 (SEQ ID NO: 12);
AATTAAAGATCAATTCACTGTATCCCTCTTCTCCAAAAAAAACTCTGCT
GTAGTC;

nbPPI43 (SEQ ID NO: 13);
ACAAATCGTACACAGCGAAAACCTCACTGAAATATTTAGAGAG;

nbPM64 (SEQ ID NO: 14);
AGAAAGATTTGTTTCCTCTGAAATAGTTTTACAGAGCCAGAAGAAGAAA
AAGAAGAAGAGAGCA; and nbH2A86 (SEQ ID NO: 15);
ACTCAACACTCAAATCGCAATCCAAAAGCTTCAATTTTTCCTAATACTT
CTCTGTATTCAAGCTTCGTAAACTTTCATTCACATCA.
```

The enhancer sequence may be selected from any one of SEQ ID NO's: 1-15, or a nucleotide sequence that exhibits 100%, 99%, 98%, 97%, 96%, 95%, or 90%, or any amount therebetween, sequence identity to the sequence as set forth in any one of SEQ ID NO's: 1-15, wherein, the expression enhancer, when operatively linked to a nucleic acid of interest, results in the expression of the nucleic acid of interest, or increases the level of expression of the nucleic acid of interest when compared to the level of expression of the same nucleic acid of interest that is not operatively linked to the expression enhancer, or for example, when operatively linked to the prior art expression enhancer CPMV 160 (SEQ ID NO:16). Each of the enhancer sequences shown in SEQ ID NO's: 1-15 may be modified using methods known to one of skill in the art, including deletion, insertion, and/or substitution of one or more than one nucleotide of the enhancer sequence, to produce an expression enhancer that results in a similar or increased enhancer activity, or that results in another beneficial property of the expression enhancer (see for example Diamos et. al., Frontiers in Plant Science. 2016, vol7 pp. 1-15; Dvir S. et. al., 2013, PNAS published online Jul. 15, 2013; Leppek K et. al., 2018, Nature Reviews Mol. Cell Biol. 19:158-174; which are incorporated herein by reference). For example, a beneficial property may include improved transcriptional initiation, improved mRNA stability, improved mRNA translation, or a combination thereof.

Use of one or more than one of the above expression enhancer of SEQ ID NO's: 1-15, was observed to result in the expression of the nucleic acid of interest, or result in an increased expression of a nucleic acid of interest, or a protein of interest as shown with reference to FIGS. 2-5.

Figure 2:
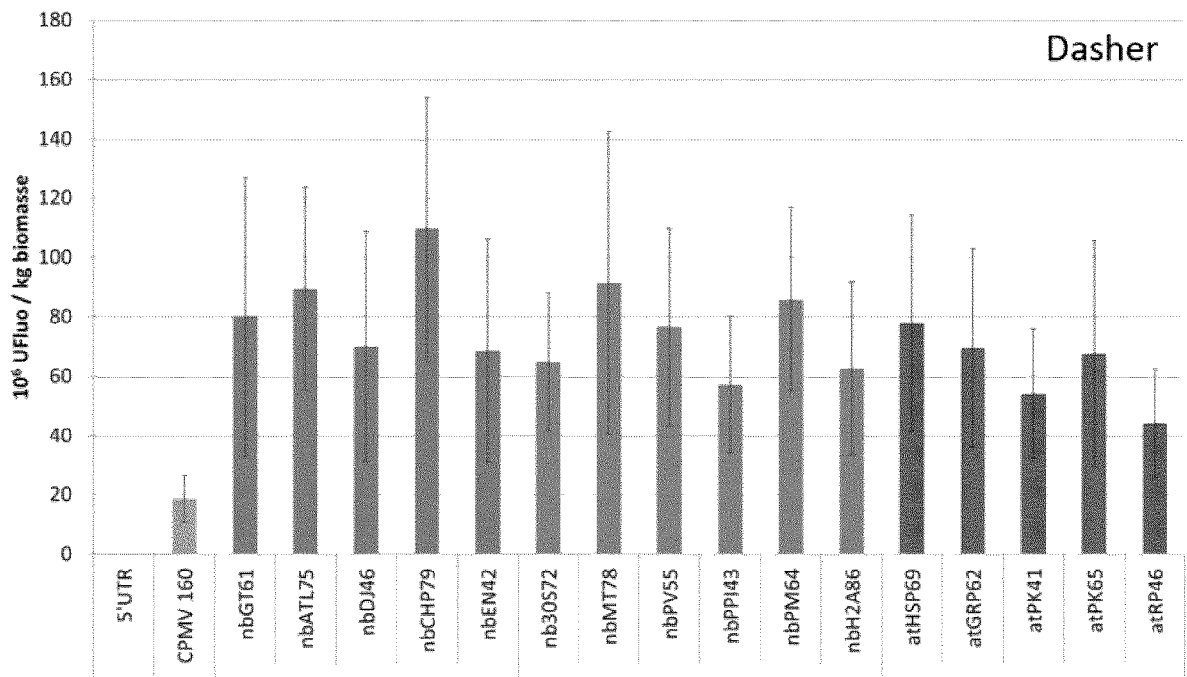
Figure 3B:
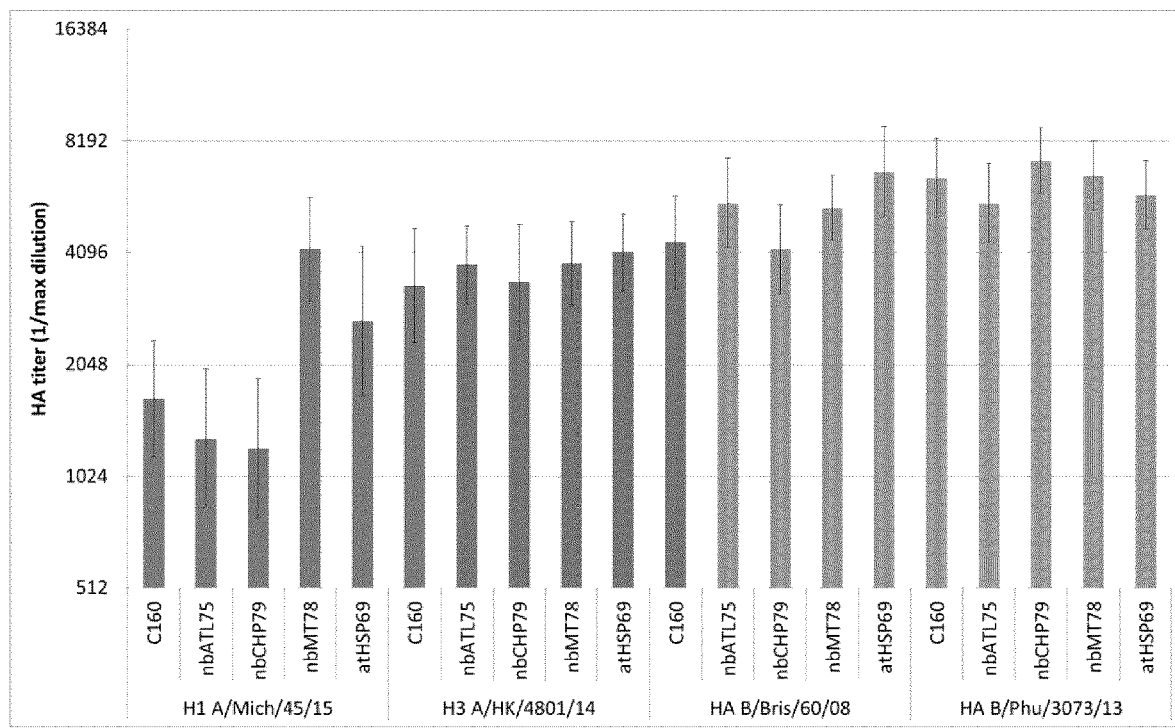
Figure 4:
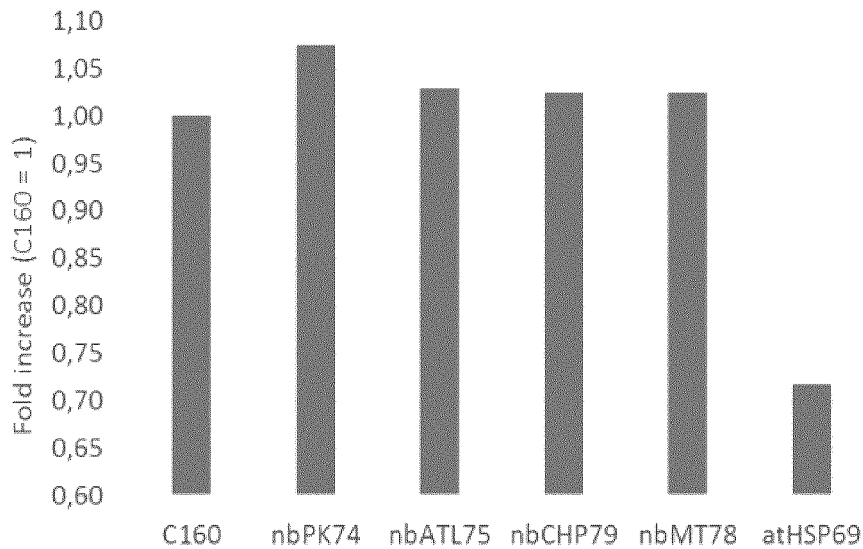

With reference to FIGS. 2, 3A and 3B, each of the expression enhancers, nbMT78 (SEQ ID NO:1); nbATL75 (SEQ ID NO:2); nbDJ46 (SEQ ID NO:3); nbCHP79 (SEQ ID NO:4); nbEN42 (SEQ ID NO:5); atHSP69 (SEQ ID NO:6); atGRP62 (SEQ ID NO:7); atPK65 (SEQ ID NO:8); atRP46 (SEQ ID NO:9); nb30S72 (SEQ ID NO:10); nbGT61 (SEQ ID NO:11); nbPV55 (SEQ ID NO:12); nbPPI43 (SEQ ID NO:13); nbPM64 (SEQ ID NO:14); and nbH2A86 (SEQ ID NO:15) when operatively linked to a nucleic acid sequence encoding a protein of interest, were observed to result in a similar, or an increased, expression of the protein, either Dasher (Dasher GFP; FPOB-27E-269; from ATUM.bio); FIG. 2), influenza hemagglutinin H1 A (FIG. 3A), H1 Mich/45/15, H3 HK/4801/14+CysTm, HA B Bris/60/08, or HA B Phu/3073/13 (FIG. 3B), when compared to the activity of the prior art expression enhancer sequence CMPV 160 (SEQ ID NO:16; WO 2015/103704) operatively linked to the same nucleic acid sequence encoding the same proteins of interest, and expressed under similar conditions, or where indicated, when compared to the activity of the prior art expression enhancer sequence atPK41 (termed AtPsaK 3' in Diamos et. al., Frontiers in Plant Science. 2016, vol7 pp. 1-15) operatively linked to the same nucleic acid sequence encoding the same proteins of interest, and expressed under similar conditions.

Figure 1A:
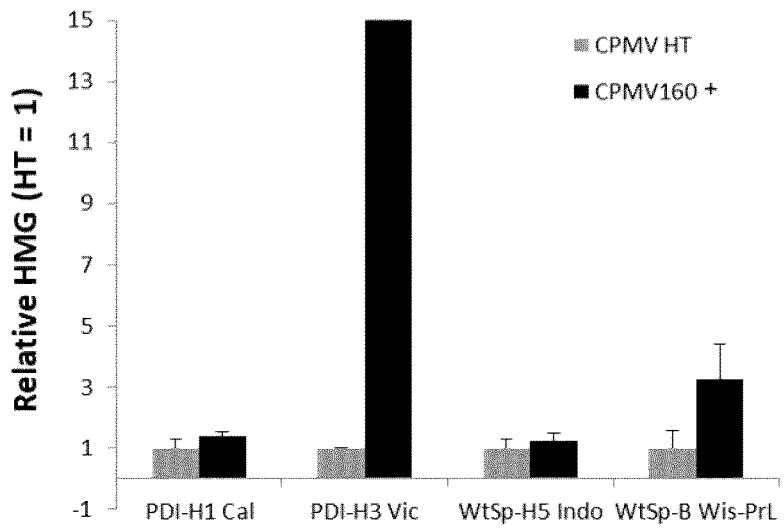
FIG. 1A is prior art and shows the relative titer of influenza H1 California, H3 Victoria, H5 Indonesia and B Wisconsin produced in plants by expressing a nucleic acid encoding each of these proteins wherein the nucleic acid is operatively linked to CPMV HT expression enhancer (described in WO 2009/087 mos et. al., Frontiers in Plant Science. 2016, vol7 pp. 1-15), or expression enhancers of the present invention: nbMT78 (SEQ ID NO:1); nbATL75 (SEQ ID NO:2), nbDJ46 (SEQ ID NO:3), nbCHP79 (SEQ ID NO:4), nbEN42 (SEQ ID NO:5), atHSP69 (SEQ ID NO:6), atGRP62 (SEQ ID NO:7); atPK65 (SEQ ID NO:8); atRP46 (SEQ ID NO:9), nb30S72 (SEQ ID NO:10); nbGT61 (SEQ ID NO:11), nbPV55 (SEQ ID NO:12); nbPPI43 (SEQ ID NO:13); nbPM64 (SEQ ID NO:14); and nbH2A86 (SEQ ID NO:15).
Figure 1B:
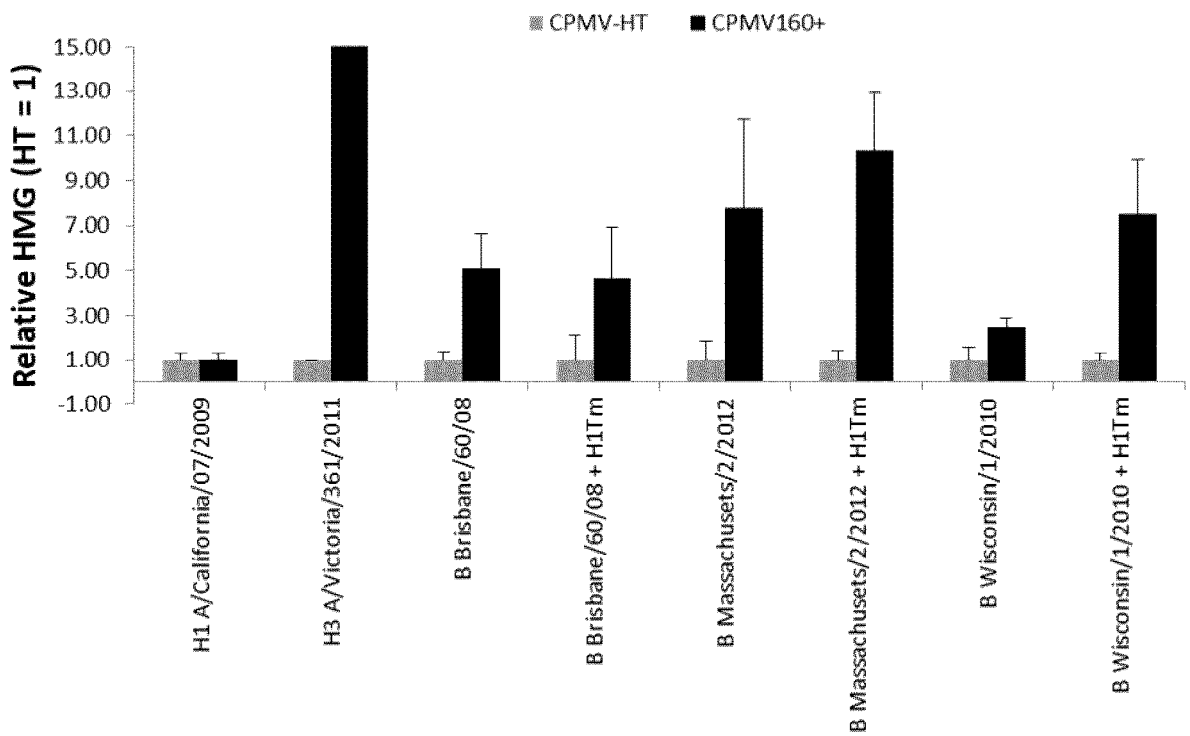
Figure 1C:
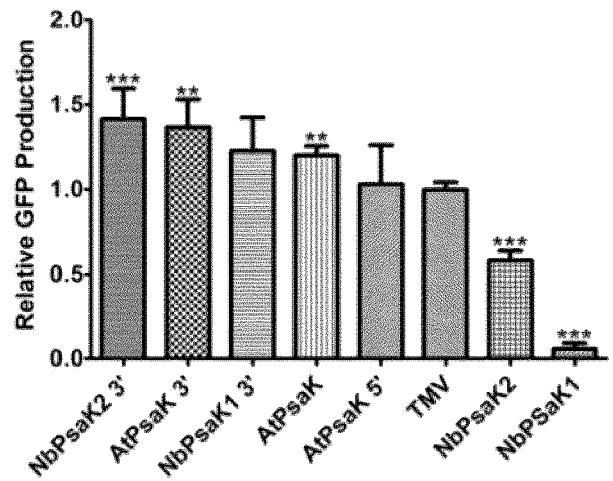

The activity of the prior art expression enhancer CPMV 160 (SEQ ID NO:16), operatively linked to a nucleic acid sequence encoding a protein of interest, is shown relative to the prior art expression enhancer, CPMV-HT, in FIGS. 1A and 1B. The CPMV HT enhancer element refers to a nucleotide sequence encoding the 5'UTR regulating the Cowpea Mosaic Virus (CPMV) RNA2 polypeptide or a modified CPMV sequence as described in WO2009/087391; Sainsbury F., and Lomonossoff G. P., (2008, Plant Physiol. 148: pp. 1212-1218). The CPMV 160 expression enhancer refers to a nucleotide sequence comprising a truncated 5'UTR from CPMV RNA2 as describe in WO 2015/103704. The CPMV 160 and CPMV 160+expression enhancers both comprise the first 160 nucleic acids of the 5'UTR of CMPV RNA 2, however, the CPMV 160+expression enhancer further comprises a multiple cloning site and a plant kozak sequence at the 3' end of the expression enhancer).

Therefore, the expression enhancers described herein may be used within a plant expression system comprising a regulatory region that is operatively linked with the expression enhancer sequence and a nucleotide sequence of interest.

For example, the present invention provides a method of producing a protein of interest, or increasing production of a protein of interest, for example but not limited to an influenza HA protein, modified influenza HA protein, norovirus protein, or modified norovirus protein, in plants. The method involves introducing a nucleic acid comprising an expression enhancer as described herein operatively linked to nucleotide sequence encoding the protein of interest, for example the influenza HA protein, a modified influenza HA protein, a norovirus protein, or a modified norovirus protein, into the plant, portion of the plant, or plant cell, and expressing the protein in the plant, portion of the plant, or plant cell in a transient or stable manner. Where, the increase in expression may be determined by comparing the level of expression of the nucleotide sequence operatively linked to an expression enhancer, with the level of expression of the same nucleotide sequence that is not operatively linked to the expression enhancer, or for example, when operatively linked to the prior art expression enhancer CPMV 160 (SEQ ID NO:6). Alternatively, the method may comprise providing a plant, portion of the plant, or plant cell that comprises an expression enhancer as described herein operatively linked to nucleotide sequence encoding the protein of interest, for example the influenza HA protein, modified influenza HA protein, norovirus protein, modified norovirus protein, or multimeric protein, and expressing the nucleic acid encoding the protein in the plant, portion of the plant or plant cell in a transient or stable manner.

Furthermore, the present invention provides plant matter, a plant extract, or a protein extract comprising a protein of interest, for example an influenza HA protein, modified influenza HA protein, norovirus protein, or modified norovirus protein. The plant matter, plant extract, or protein extract may be used to induce immunity, for example, to influenza or norovirus infection in a subject. Alternatively, the protein of interest, for example influenza HA protein, modified influenza HA protein, norovirus protein, or modified norovirus protein may be purified or partially purified, and the purified or partially purified preparation may be used to induce immunity, for example, to influenza or norovirus infection in a subject, or the protein of interest, for example the influenza HA protein, modified influenza HA protein, norovirus protein, or modified norovirus protein may be used within a composition for inducing an immune response, and a pharmaceutically acceptable carrier, adjuvant, vehicle, or excipient.

The expression enhancers described herein may be used for the production of any protein of interest or for the production of virus like particles (VLPs). For example, with reference to FIG. 4, several expression enhancers described herein are shown to be effective for the production of Norovirus VLPs.

Therefore, the present invention also provides a method of producing, or increasing production of VLPs comprising an influenza HA protein, modified influenza HA protein, norovirus protein, or modified norovirus protein, in plants. For example, the method may involve introducing a nucleic acid comprising an expression enhancer as described herein operatively linked to nucleotide sequence encoding an influenza HA protein, a modified influenza HA protein, a norovirus protein, or a modified norovirus protein, into the plant, portion of the plant, or plant cell in a transient or stable manner, and expressing the protein in the plant, portion of the plant, or plant cell, in order to produce a VLP comprising the influenza HA protein, modified influenza HA protein, norovirus protein, or modified norovirus protein. The increase in expression may be determined by comparing the level of expression of the nucleotide sequence operatively linked to an expression enhancer, with the level of expression of the same nucleotide sequence that is not operatively linked to the expression enhancer, or for example, when operatively linked to the prior art expression enhancer CPMV 160 (SEQ ID NO:16). Alternatively, the method may comprise providing a plant, portion of the plant, or plant cell that comprises an expression enhancer as described herein operatively linked to nucleotide sequence encoding the influenza HA protein, modified influenza HA protein, norovirus protein, or modified norovirus protein, and expressing the nucleic acid encoding the protein in order to produce a VLP comprising the influenza HA protein, modified influenza HA protein, norovirus protein, or modified norovirus protein.

Furthermore, the present invention provides plant matter, a plant extract, or a protein extract comprising VLPs comprising an influenza HA protein, modified influenza HA protein, norovirus protein, or modified norovirus protein. The plant matter, plant extract, or protein extract may be used to induce immunity to norovirus infection in a subject. Alternatively, VLPs comprising the influenza HA protein, modified influenza HA protein, norovirus protein, or modified norovirus protein may be purified or partially purified, and the purified or partially purified preparation may be used to induce immunity to a norovirus infection in a subject, or the VLPs comprising influenza HA protein, modified influenza HA protein, norovirus protein, or modified norovirus protein may be used within a composition for inducing an immune response, and a pharmaceutically acceptable carrier, adjuvant, vehicle, or excipient.

Figure 5:
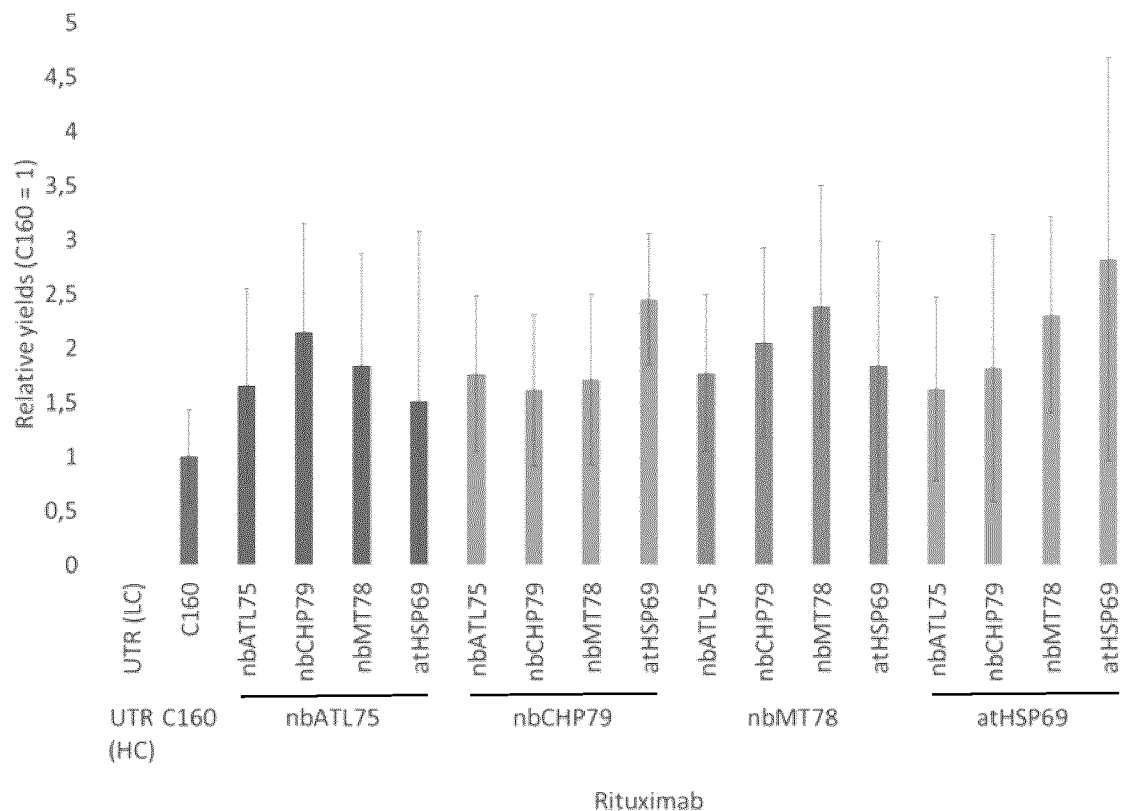

The expression enhancers described herein may also be used for the production of a multimeric protein of interest, for example an antibody. As shown with reference to FIG. 5, co-expression of two nucleic acids encoding the light chain (LC) and the heavy chain (HC) of an antibody, for example Rituximab, may be expressed in a plant, when each of the nucleic acid sequences are operatively linked to the same or different expression enhancers described herein. For example, co-expression of a first nucleic acid, encoding the HC of rituximab, and operatively linked to the expression enhancer nbATLK75, along with a second nucleic acid, encoding the LC of rituximab, and operatively linked to either the same expression enhancer, nbATLK75, or to a different expression enhancer, either nbCHP79, nbMT78, or atHSP69, resulted in expression of the multimeric protein, or an increase in expression of the multimeric protein, when compared to co-expression of first and second nucleic acids encoding the same HC and LC sequences, but each of the first and second nucleic acids operatively linked to the prior art expression enhancer CPMV 160 (SEQ ID NO:16). Similar results were observed when the first and second nucleic acids were co-expressed using other combination of the expression enhancers described herein, as shown in FIG. 5.

Therefore, the present invention also provides a method of producing or increasing production of a multimeric protein in plants. For example, the method may involve introducing, in a transient or stable manner, a first nucleic acid comprising an expression enhancer as described herein operatively linked to nucleotide sequence encoding a first protein component, and a second nucleic acid comprising an expression enhancer as described herein operatively linked to nucleotide sequence encoding a second protein component, into the plant, portion of the plant, or plant cell, and co-expressing the first and second nucleic acids in the plant, portion of the plant, or plant cell, in order to produce the multimeric protein. The increase in expression may be determined by comparing the level of expression of the first and second nucleic acid, each operatively linked to an expression enhancer(s), with the level of expression of the same first and second nucleic acids, each of which are not operatively linked to the expression enhancer(s), or for example, when operatively linked to the prior art expression enhancer CPMV 160 (SEQ ID NO:16). Alternatively, the method may comprise providing a plant, portion of the plant, or plant cell that comprises the first nucleic acid comprising an expression enhancer as described herein operatively linked to nucleotide sequence encoding a first protein component, and a second nucleic acid comprising an expression enhancer as described herein operatively linked to nucleotide sequence encoding a second protein component and co-expressing the first and second nucleic acid sequences to produce the multimeric protein.

Furthermore, the present invention provides plant matter, a plant extract, or a protein extract comprising the multimeric protein, or the multimeric protein may be purified or partially purified.

As described herein, there is provided a nucleic acid construct comprising an expression enhancer sequence operatively linked to a nucleotide sequence of interest encoding a protein of interest. Also provided are plant expression systems and vectors, comprising the construct or one or more than one nucleic acid comprising an enhancer sequence as described herein. Also provided is a plant expression system, a vector, a construct, or a nucleic acid, comprising a plant regulatory region, in operative association with an enhancer sequence that is operatively linked to a nucleotide sequence of interest, the nucleotide sequence of interest encoding a protein of interest. The enhancer sequence may be selected from any one of SEQ ID NO's: 1, 15, or a nucleotide sequence that exhibits 100%, 99%, 98%, 97%, 96%, 95%, or 90%, or any amount therebetween, sequence identity to the sequence as set forth in any one of SEQ ID NO's: 1-15, wherein, the expression enhancer, when operatively linked to a nucleic acid of interest, results in the expression of the nucleic acid of interest, or increases the level of expression of the nucleic acid of interest when compared to the level of expression of the same nucleic acid of interest that is not operatively linked to the expression enhancer, or for example, when operatively linked to the prior art expression enhancer CPMV 160 (SEQ ID NO:16).

The enhancer sequence of any one of SEQ ID NO's: 1-15 may be modified using methods known to one of skill in the art, including deletion, insertion, and/or substitution of one or more than one nucleotide of the enhancer sequence, to produce an expression enhancer that results in a similar or increased enhancer activity, or that results in another beneficial property of the expression enhancer. For example, a beneficial property may include improved transcriptional initiation, improved mRNA stability, improved mRNA translation, or a combination thereof.

The enhancer sequence of the present invention may be used to express a protein of interest in a host organism for example a plant. In this case, the protein of interest may also be heterologous to the host organism in question and introduced into the plant cells using transformation techniques know in the art. A heterologous gene in an organism may replace an endogenous equivalent gene, i.e. one which normally performs the same or a similar function, or the inserted sequence may be additional to the endogenous gene or other sequence.

The invention further provides an expression cassette comprising in series, a promoter or plant regulatory region, operatively linked to an expression enhancer sequence as described herein which is fused with a nucleotide sequence of interest, a 3'UTR sequence, and a terminator sequence. The enhancer sequence may be defined by, any one of SEQ ID NO's:1-15, or a nucleotide sequence that exhibits 100%, 99%, 98%, 97%, 96%, 95%, or 90%, sequence identity, or any amount therebetween, to the sequence as set forth in any one of SEQ ID NO's: 1-15. The enhancer sequence may also be modified using techniques known to one of skill in the art, provided that the enhancer sequence results in the expression of the nucleic acid of interest, or increases the level of expression of the nucleotide sequence of interest, for example, determined by comparing the level of expression of the nucleotide sequence operatively linked to an expression enhancer, with the level of expression of the same nucleotide sequence that is not operatively linked to the expression enhancer, or for example, when operatively linked to the prior art expression enhancer CPMV 160 (SEQ ID NO:16).

The sequences described in the present application are listed in Table 1.

TABLE 1

List of nucleic acid and amino acid sequences:

| | SEQ ID NO: | FIG. # |
|---|---|---|
| nbMT78 | 1 | 15A |
| nbATL75 | 2 | 15B |
| nbDJ46 | 3 | 15C |
| nbCHP79 | 4 | 15D |
| nbEN42 | 5 | 15E |
| atHSP69 | 6 | 15F |
| atGRP62 | 7 | 15G |
| atPK65 | 8 | 15H |
| atRP46 | 9 | 15I |
| nb30S72 | 10 | 15J |
| nbGT61 | 11 | 15K |
| nbPV55 | 12 | 15L |
| nbPPI43 | 13 | 15M |
| nbPM64 | 14 | 15N |
| nbH2A86 | 15 | 15O |
| CPMV 160 | 16 | 15P |
| nbMT78_Dasher.c | 17 | 16A |
| IF-Dasher (27-609).r | 18 | 16A |
| IF-nbMT78.c | 19 | 16A |
| CPMV 160 5'UTR-Dasher nucleic acid | 20 | 16B |
| Dasher amino acid | 21 | 16D |
| Cloning vector 1666 L to R boarder pCAMBIA | 22 | 16F |
| IF-(2X35S + C)_CPMV160.c | 23 | 16A |
| nbGT61_Dasher.c | 24 | 16A |
| IF-nbGT61.c | 25 | 16A |
| nbATL75_Dasher.c | 26 | 16A |
| IF-nbATL75.c | 27 | 16A |
| nbDJ46_Dasher.c | 28 | 16A |
| IF-nbDJ46.c | 29 | 16A |
| nbCHP79_Dasher.c | 30 | 16A |
| IF-nbCHP79.c | 31 | 16A |
| nbEN42_Dasher.c | 32 | 16A |
| IF-nbEN42.c | 33 | 16A |
| nb30S72_Dasher.c | 34 | 16A |
| IF-nb30S72.c | 35 | 16A |
| nbPV55_Dasher.c | 36 | 16A |
| IF-nbPV55.c | 37 | 16A |
| nbPPI43_Dasher.c | 38 | 16A |
| IF-nbPPI43.c | 39 | 16A |

TABLE 1-continued

List of nucleic acid and amino acid sequences:

| | SEQ ID NO: | FIG. # |
|---|---|---|
| nbPM64_Dasher.c | 40 | 16A |
| IF-nbPM64.c | 41 | 16A |
| nbH2A86_Dasher.c | 42 | 16A |
| IF-nbH2A86.c | 43 | 16A |
| atHSP69_Dasher.c | 44 | 16A |
| IF-atHSP69.c | 45 | 16A |
| atGRP62_Dasher.c | 46 | 16A |
| IF-atGRP62.c | 47 | 16A |
| atPK65_Dasher.c | 48 | 16A |
| IF-atPK65.c | 49 | 16A |
| IF-atRP46_Dasher.c | 50 | 16A |
| IF-H1cTMCT.s1-4r | 51 | 17A |
| nbGT61_SpPDI.c | 52 | 17A |
| nbATL75_SpPDI.c | 53 | 17A |
| nbDJ46_SpPDI.c | 54 | 17A |
| nbCHP79_SpPDI.c | 55 | 17A |
| nbEN42_SpPDI.c | 56 | 17A |
| nb30S72_SpPDI.c | 57 | 17A |
| nbMT78_SpPDI.c | 58 | 17A |
| nbPV55_SpPDI.c | 59 | 17A |
| nbPPI43_SpPDI.c | 60 | 17A |
| nbPM64_SpPDI.c | 61 | 17A |
| nbH2A86_SpPDI.c | 62 | 17A |
| atHSP69_SpPDI.c | 63 | 17A |
| atGRP62_SpPDI.c | 64 | 17A |
| atPK65_SpPDI.c | 65 | 17A |
| IF-atRP46_SpPDI.c | 66 | 17A |
| IF-H3_Swi_13.r | 67 | 17A |
| IF-GII4Syd12VP1.r | 68 | 22A |
| nbATL75 + GII4Syd12.c | 69 | 22A |
| nbCHP79 + GII4Syd12.c | 70 | 22A |
| nbMT78 + GII4Syd12.c | 71 | 22A |
| atHSP69 + GII4Syd12.c | 72 | 22A |
| IF**-HC(Ritux).s1-6r | 73 | 23A |
| IF**-LC(Ritux).s1-6r | 74 | 23A |
| Construct 4467 | 75 | 16E |
| Plasmid 4160 | 76 | 17E |
| Plasmid 4170 | 77 | 18D |
| Dasher nucleic acid | 78 | 16C |
| CPMV 160 5'UTR-PDI + H1 Cal nucleic acid | 79 | 17B |
| PDI + H1 Cal nucleic acid sequence | 80 | 17C |
| PDI + H1 Cal amino acid | 81 | 17D |
| CPMV 160 5'UTR-PDI + H1 Mich nucleic acid | 82 | 18A |
| PDI + H1 Mich nucleic acid | 83 | 18B |
| PDI + H1 Mich amino acid | 84 | 18C |
| CPMV 160 5'UTR-PDI + H3 HK nucleic acid | 85 | 19A |
| PDI + H3 HK nucleic acid | 86 | 19B |
| PDI + H3 HK amino acid | 87 | 19C |
| CPMV 160 5'UTR-PDI + HA B Bri nucleic acid | 88 | 20A |
| PDI + HA B Bri nucleic acid | 89 | 20B |
| PDI + HA B Bri amino acid | 90 | 20C |
| CPMV 160 5'UTR-PDI + HA B Phu nucleic acid | 91 | 21A |
| PDI + HA B Phu nucleic acid | 92 | 21B |
| PDI + HA B Phu amino acid | 93 | 21C |
| CPMV 160 5'UTR-VP1 (GII.4) nucleic acid | 94 | 22B |
| VP1 (GII.4) nucleic acid | 95 | 22C |
| VP1 (GII.4) amino acid | 96 | 22D |
| CPMV 160 5'UTR-PDI + Rituximab HC nucleic acid | 97 | 23B |
| PDII + Rituximab HC nucleic acid | 98 | 23C |
| PDII + Rituximab HC amino acid | 99 | 23D |
| CPMV 160 5'UTR-PDI + Rituximab LC nucleic acid | 100 | 23E |
| PDII + Rituximab LC nucleic acid | 101 | 23F |
| PDII + Rituximab LC amino acid | 102 | 23G |

The present invention will be further illustrated in the following examples.

Example 1: Selection of Plant 5' UTR Sequences Using Polysome/CAGE Analysis mRNA was extracted from non-infiltrated and infiltrated biomass or cell culture under different stresses using standard phenol-chloroform protocols and mRNA in low and high translational state was separated using standard centrifugation through sucrose gradient. mRNA in each non-polysomal and polysomal fractions was extracted using standard phenol-chloroform extraction protocols. Sequencing of the beginning of the 5'UTR of each mRNA present in each polysomal and non-polysomal fraction was performed using the cap analysis of gene expression (CAGE) method. After removal of unwanted sequences tags (ribosomal RNAs, chloroplastic RNAs and uncapped tags), sequenced tags were compared to a reference genome database, for example TAIR for *Arabidopsis thaliana* (see URL: arabidopsis.org/) or the Sol Genomic network for *Nicotiana benthamiana* (see URL: solgenomics.net/), for gene identification. Number of sequenced tags for each given gene was analyzed and normalized. The translational state was evaluated by establishing the polysomal ratio (PR ratio) by dividing the number of normalized tags found in the polysomal fraction by the total number of tags for each given gene. Gene mRNA with high translational states under infiltration conditions was used to identify potential 5'UTR candidates.

As a result of this analysis, 15 candidate 5'UTRs were identified and further characterized:
1. nbMT78 (SEQ ID NO:1): the 78 bp 5'UTR is part of the gene located in locus Niben 101Scf38767g00006.1 that codes for a Metallothionein-like protein 1.
2. nbATL75 (SEQ ID NO:2): the 75 bp 5' UTR is part of a gene located in locus Niben 101Scf08015g04003.1 that codes for a At4g36060-like protein (a basic helix-loop-helix (bHLH) DNA-binding superfamily protein; TAIR:AT3G19860.1).

3. nbDJ46 (SEQ ID NO:3): the 46 bp 5' UTR is part of the gene located in locus Niben101Scf16258g02004.1 that code for the defensin J1-2 protein.
4. nbCHP79 (SEQ ID NO:4): the 79 bp 5' UTR is part of the gene located in locus Niben101Scf02509g07005.1 that codes for a conserved hypothetical protein (*Ricinus communis*, GenBank no EEF49157.1, 68 AA protein) of unknown function.
5. nbEN42 (SEQ ID NO:5): the 42 bp 5'UTR is part of the gene located in locus Niben101Scf06633g02009.1 that codes for an early modulin-like protein 2. In *A. thaliana* (AT3G20570.1), the protein may be an electron carrier activity and a copper ion binding membrane protein.
6. atHSP69 (SEQ ID NO:6): the 69 bp 5'UTR is obtained from the nucleotide sequence (AT2G40000.1_00069) encoding a nematode resistance protein-like HSPRO2, which functions as a positive regulator of basal resistance from pathogens in plant defense, in response to oxidative stress and salicylic acid.
7. atGRP62 (SEQ ID NO:7): the 62 bp 5'UTR is obtained from the nucleotide sequence (AT5G61660.1_00062) encoding a glycine-rich protein of unknown function.
8. atPK65 (SEQ ID NO:8): the 65 bp 5'UTR is obtained from the nucleotide sequence (AT1G30380.1_00065) encoding a chloroplastic multi-pass membrane protein member of the plant photosystem I super-complex (psi) family. This protein is involved in chlorophyll-binding and photosynthesis.
9. atRP46 (SEQ ID NO:9); the 46 bp 5'UTR is obtained from the nucleotide sequence (AT4G21210.1_00046) encoding a chloroplastic ATRP1, PPDK regulatory protein, RP1.
10. nb30S72 (SEQ ID NO:10): the 72 bp 5'UTR is part of the gene located in locus Niben101Scf04081g02005.1 that codes for the 30S ribosomal protein S19. The small chloroplast-located S19 protein (92 AA) forms a complex with S13 that binds strongly to the 16S ribosomal RNA.
11. nbGT61 (SEQ ID NO:11): the 61 bp 5' UTR is a part of a gene located in locus Niben101Scf17164g00027.1 that codes for a glutaredoxins (GRX), a family of small redox enzymes that use glutathione as cofactor.
12. nbPV55 (SEQ ID NO:12): the 55 bp 5'UTR is part of the gene located in locus Niben101Scf03733g03018.1 that codes for a photosystem I reaction center subunit V chloroplastic protein of unknown function.
13. nbPPI43 (SEQ ID NO:13): the 143 bp 5'UTR is part of the gene located in locus Niben101Scf01847g03004.1 that codes for peptidyl-prolyl cis-trans isomerase A (PPi).
14. nbPM64 (SEQ ID NO:14): the 64 bp 5'UTR is part of the gene located in locus Niben 101Scf05678g02004.1 that codes for a proteasome maturation protein homolog.
15. nbH2A86 (SEQ ID NO:15): the 86 bp 5'UTR is part of the gene located in locus Niben 101Scf00369g03018.1 that codes for a histone 2A protein.

The following constructs comprising the enhancers identified above were prepared as follows:
2X35S/nbMT78 5'UTR/Dasher/CPMV 3'UTR/NOS Term (Construct Number 4467; SEQ ID NO:75)

Figure 6A:
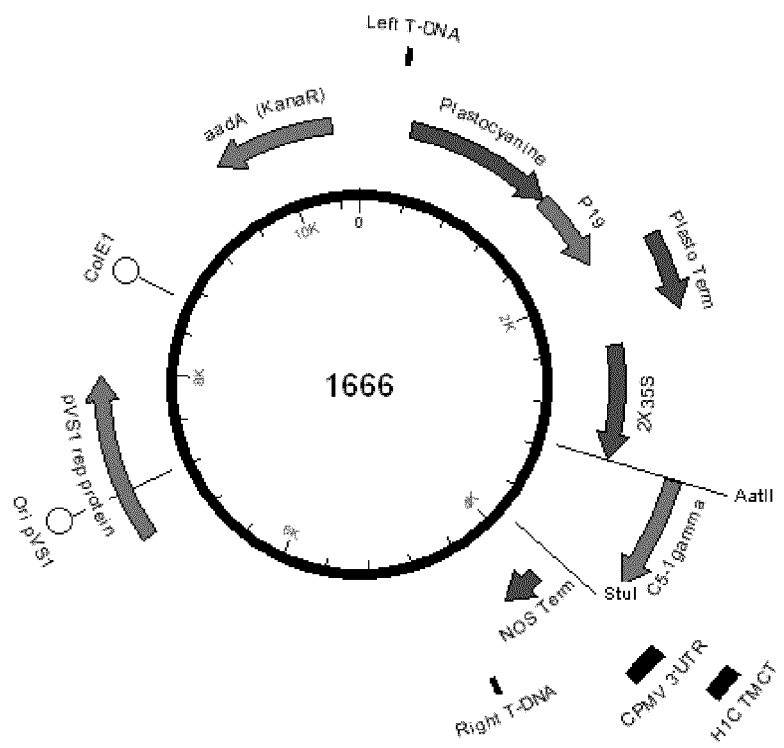
Figure 6B:
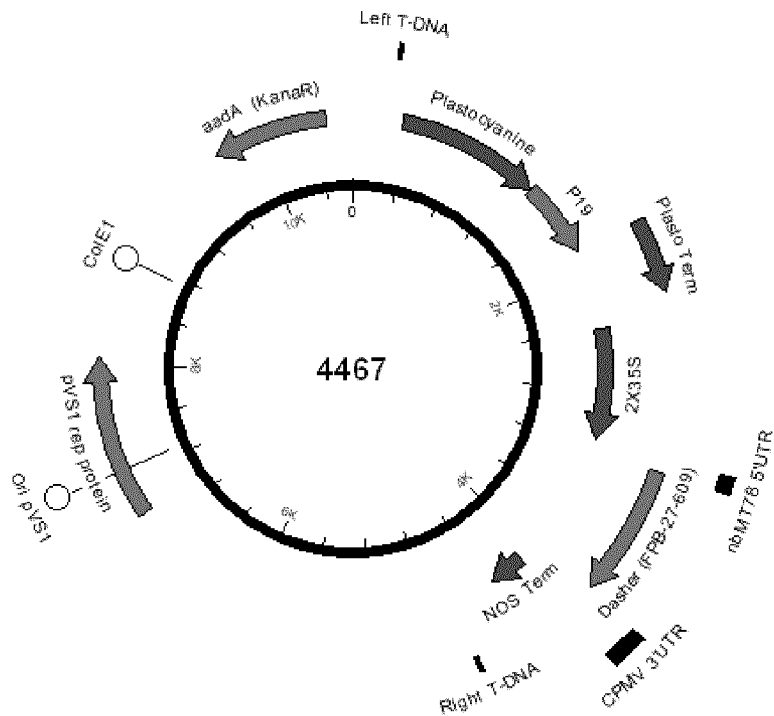

A sequence encoding Dasher fluorescent protein (Atum, Cat #FPB-27-609) fused to the nbMT78 5'UTR was cloned into 2X35S promoter+CPMV 3'UTR/NOS expression system using the following PCR-based method. In a first round of PCR, a fragment containing the Dasher fluorescent protein was amplified using primers nbMT78_Dasher.c (SEQ ID NO:17) and IF-Dasher (27-609).r (SEQ ID NO: 18) using Dasher gene sequence (SEQ ID NO: 20; FIG. 16B) as template. The PCR product from the first round of amplification (F1 in Table 2) was as used as template to add the atMT78 5'UTR sequence using IF-nbMT78.c (SEQ ID NO:19) and IF-Dasher (27-609).r (SEQ ID NO:18) as primers. The final PCR product (F2 in Table 2) was cloned in 2X35S promoter+CPMV 3'UTR/NOS expression system using In-Fusion cloning system (Clontech, Mountain View, CA). Construct number 1666 (FIG. 6A) was digested with AatII and StuI restriction enzymes and the linearized plasmid was used for the In-Fusion assembly reaction. Construct number 1666 is an acceptor plasmid intended for "In Fusion" cloning of genes of interest in a 2X35S promoter+CPMV 3'UTR/NOS-based expression cassette. It also incorporates a gene construct for the co-expression of the TBSV P19 suppressor of silencing under the alfalfa Plastocyanin gene promoter and terminator. The backbone is a pCAMBIA binary plasmid and the sequence from left to right t-DNA borders is as presented in SEQ ID NO:22. The resulting construct was given number 4467 (SEQ ID NO:75; SEQ ID NO: FIG. 16E). The amino acid sequence of Dasher fluorescent protein is presented in SEQ ID NO:21. A representation of construct 4467 is presented in FIG. 6B.

Primers, templates as well as nucleic acid and protein sequences for all constructs described herein, are presented in Table 2.

Figure 6C:
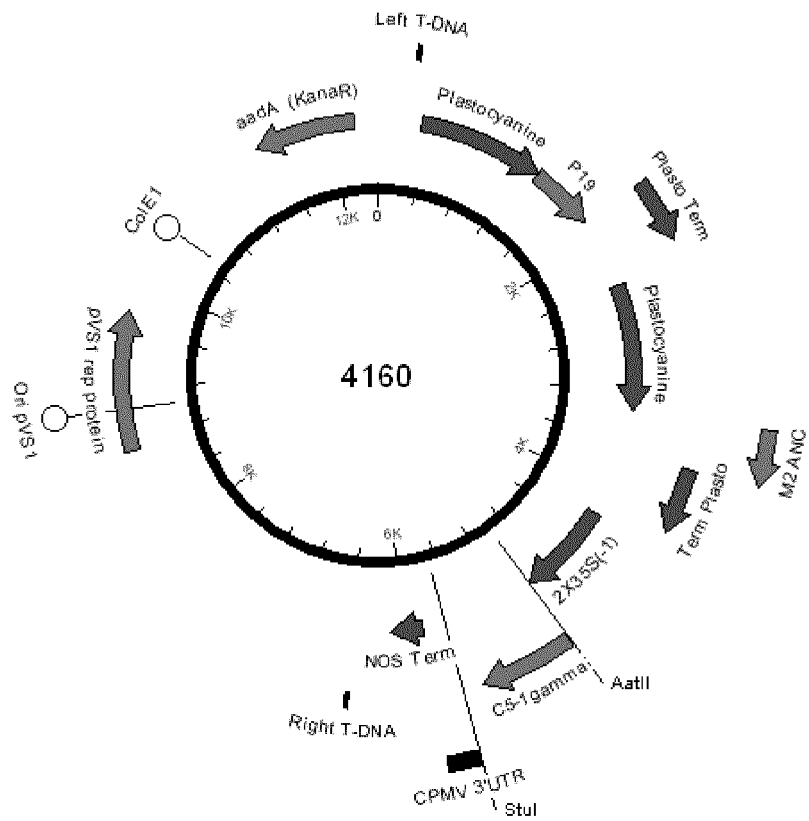

For Influenza H3 and HA B constructs, the cloning vector used integrates an influenza M2 ion channel gene under the control of Alfalfa Plastocyanin promoter and terminator in addition to the 2X35S promoter+CPMV 3'UTR/NOS-based expression cassette. Plasmid number 4160 (SEQ ID NO: 76; FIGS. 6C; 17E) was digested with AatII and StuI restriction enzymes and used for the In-Fusion reaction.

Figure 6D:
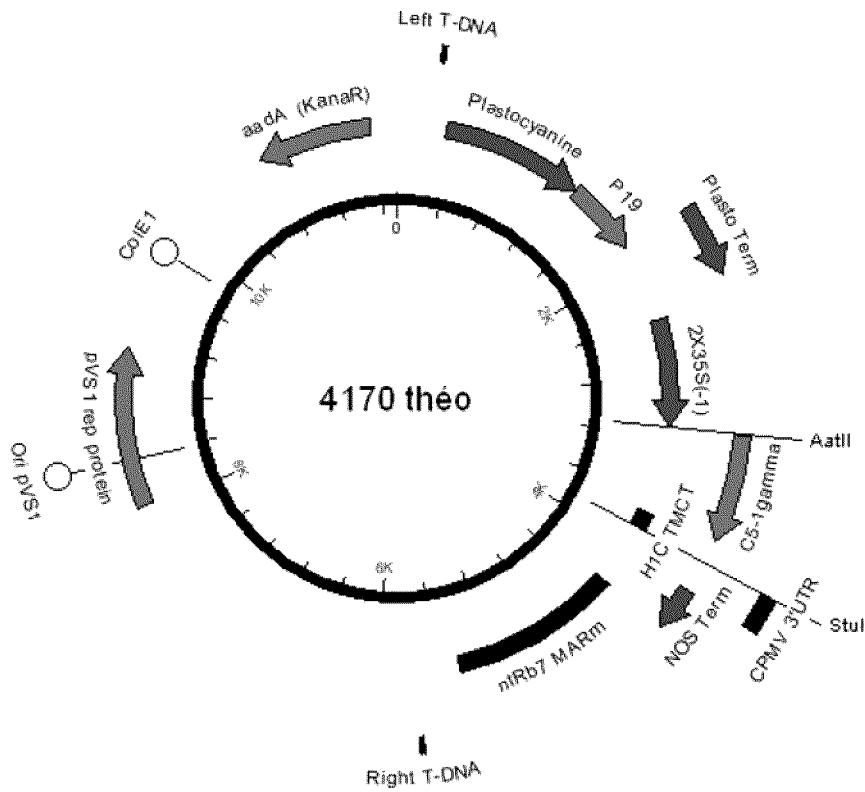
Figure 6E:
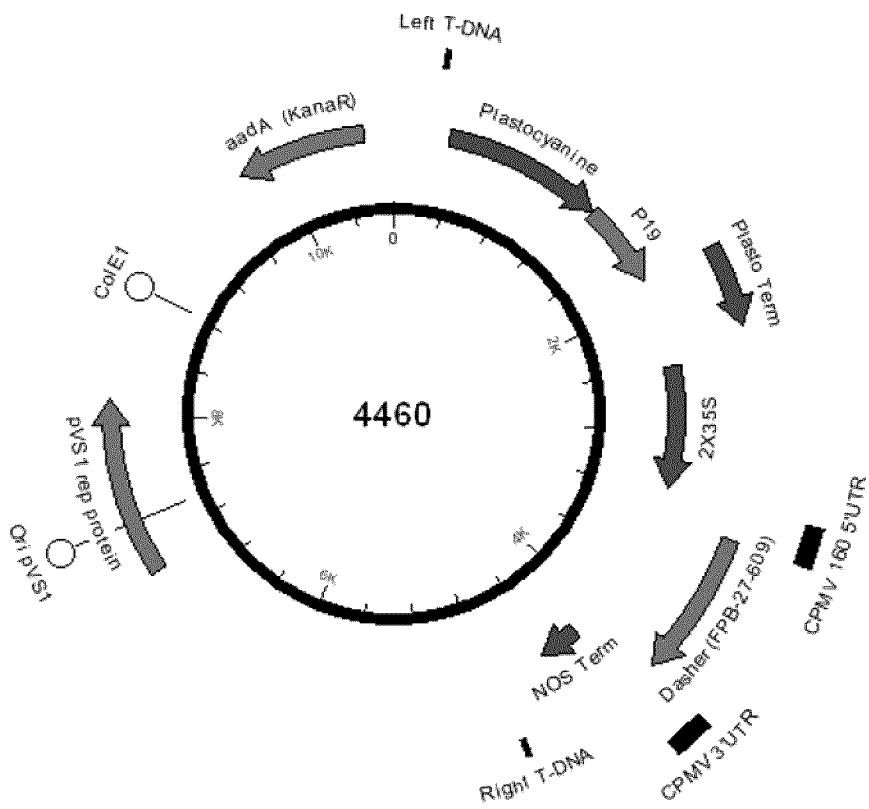
Figure 6F:
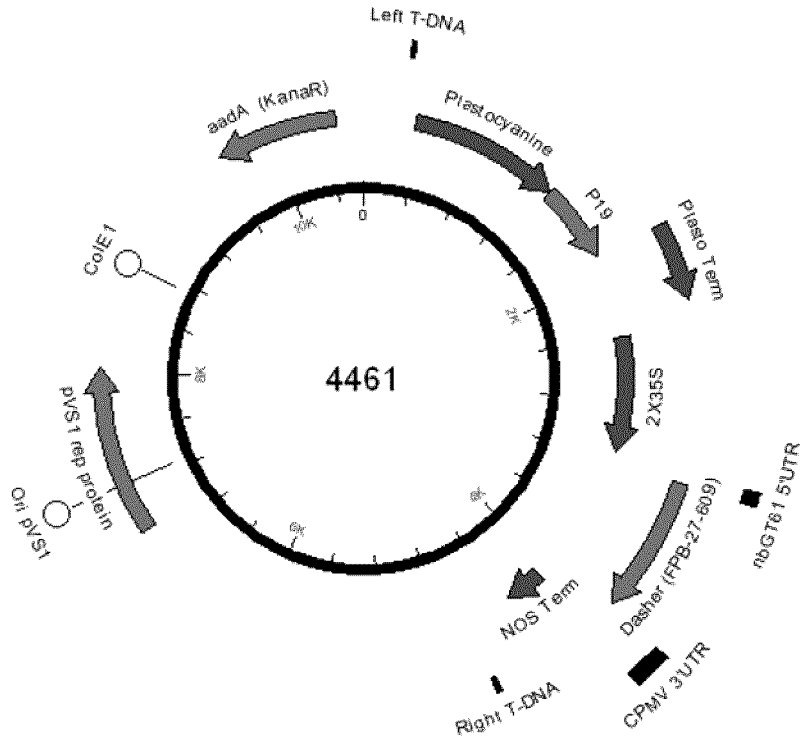
Figure 6G:
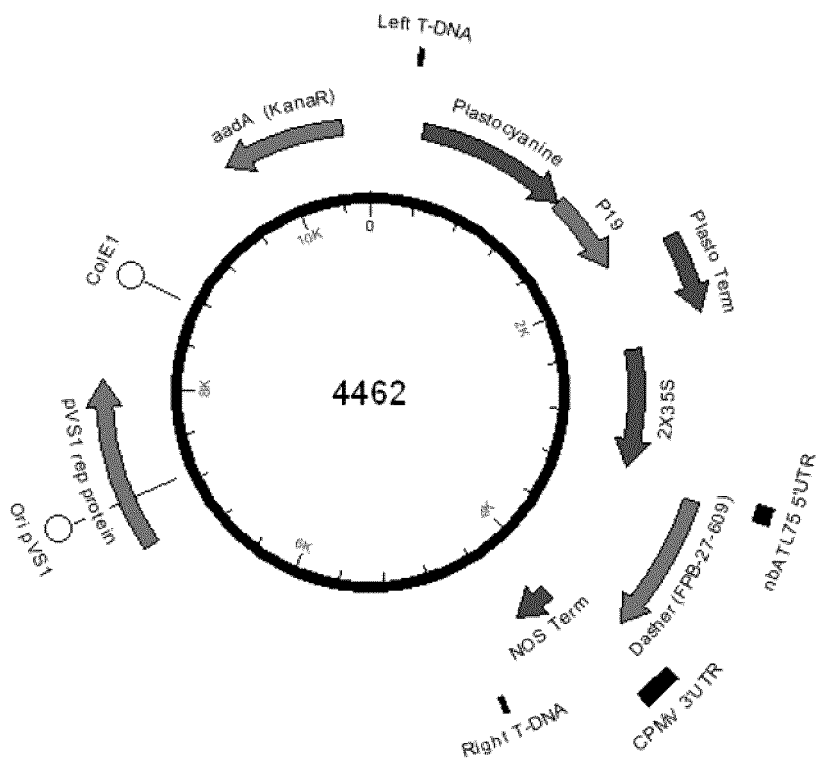
Figure 6H:
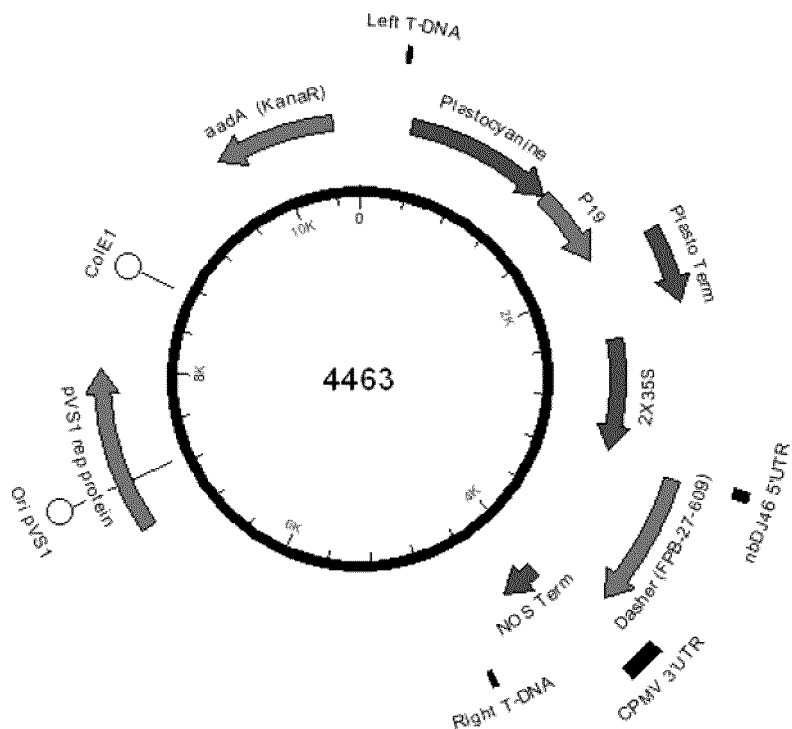
Figure 6I:
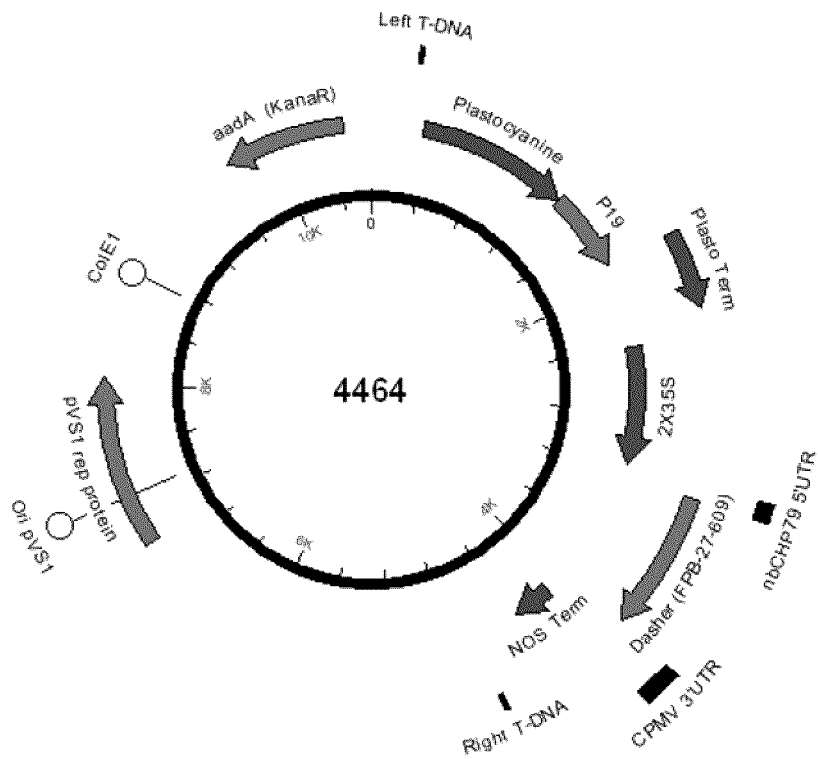
Figure 6J:
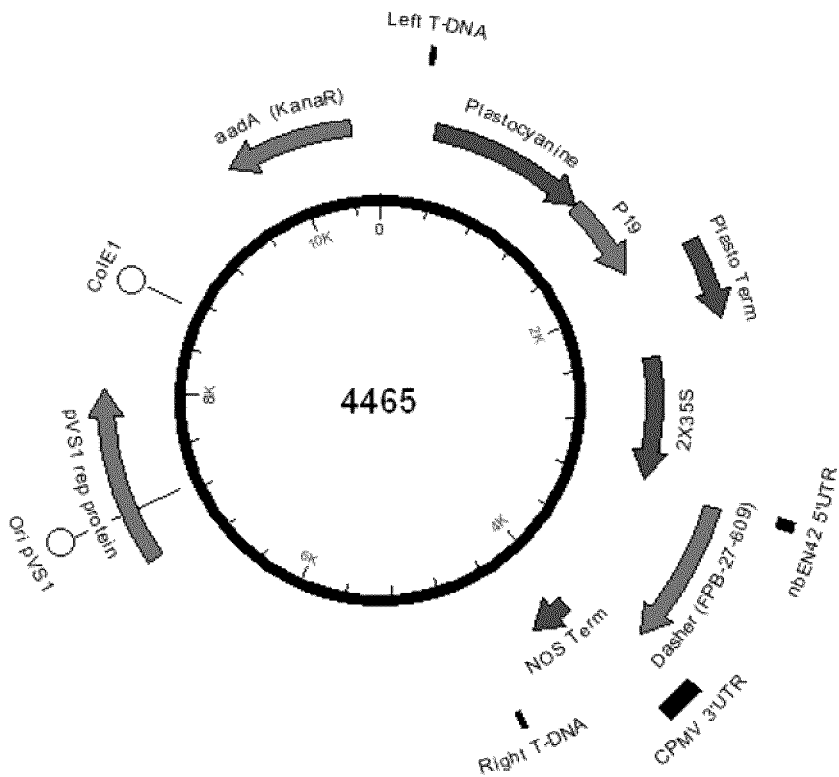
Figure 6K:
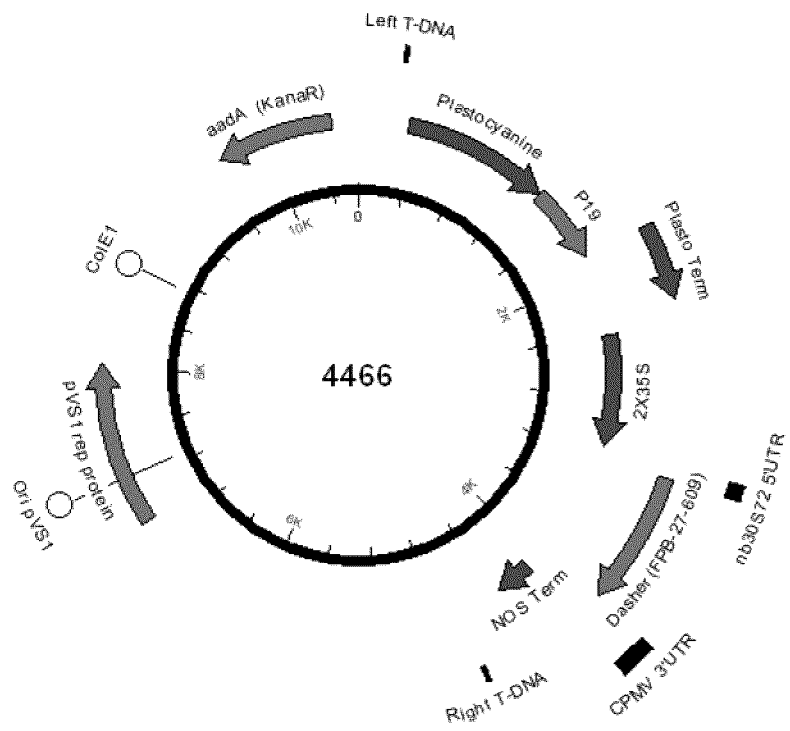
Figure 6L:
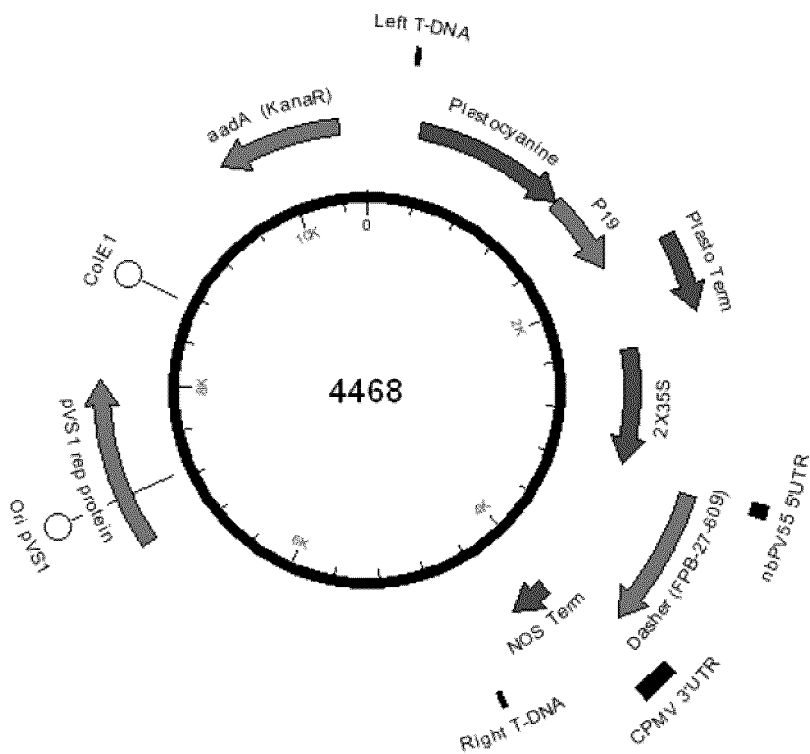
Figure 6M:
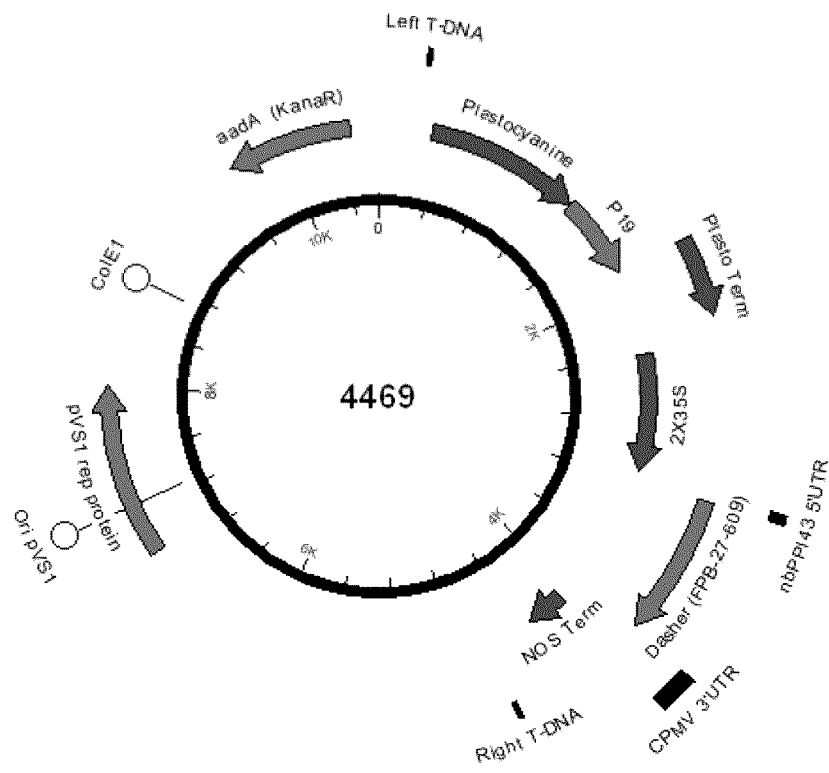
Figure 6N:
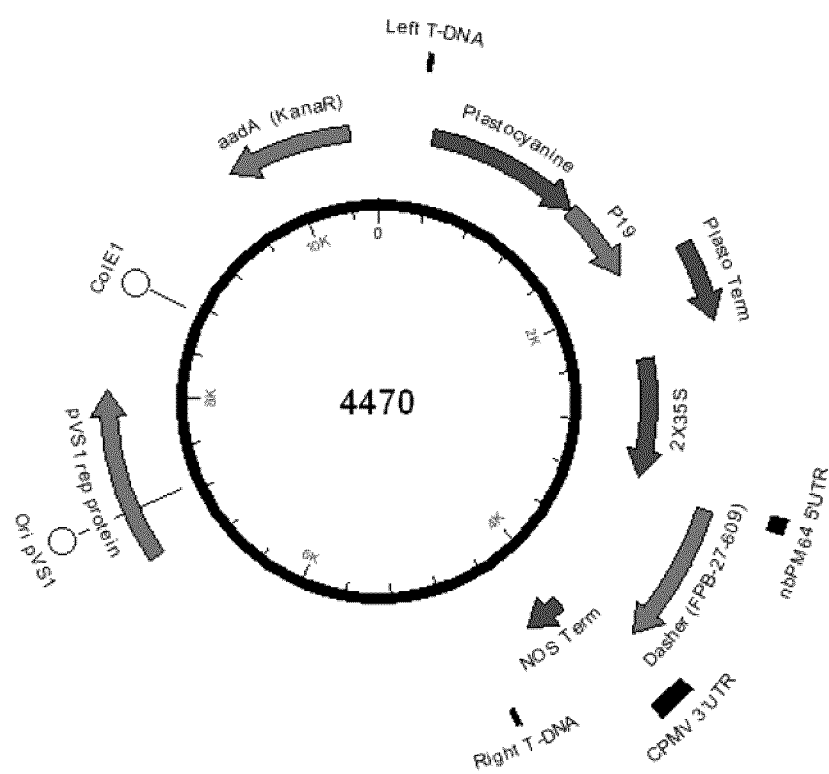
Figure 6O:
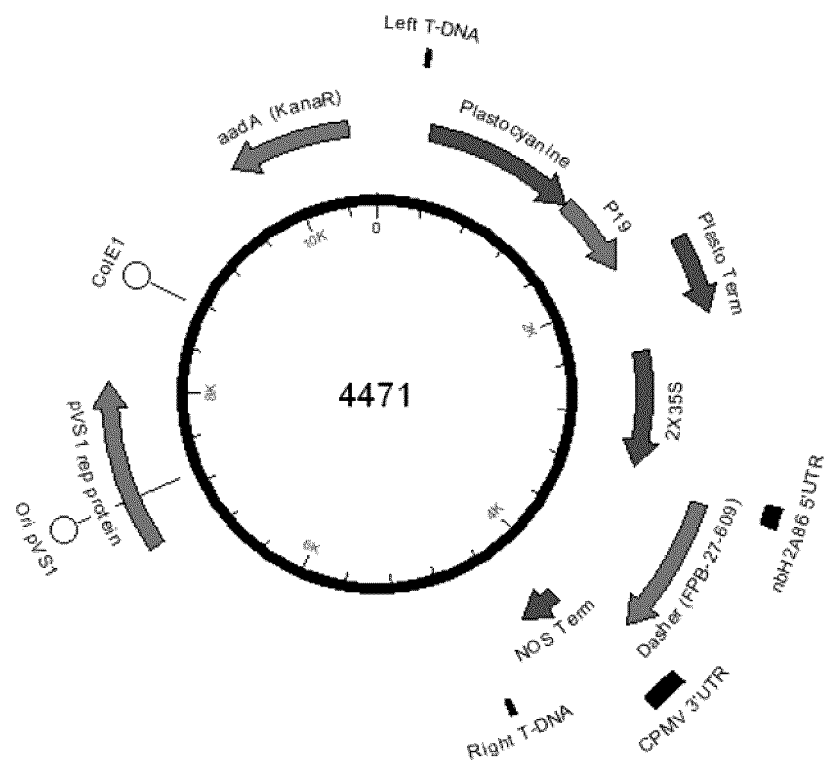
Figure 6P:
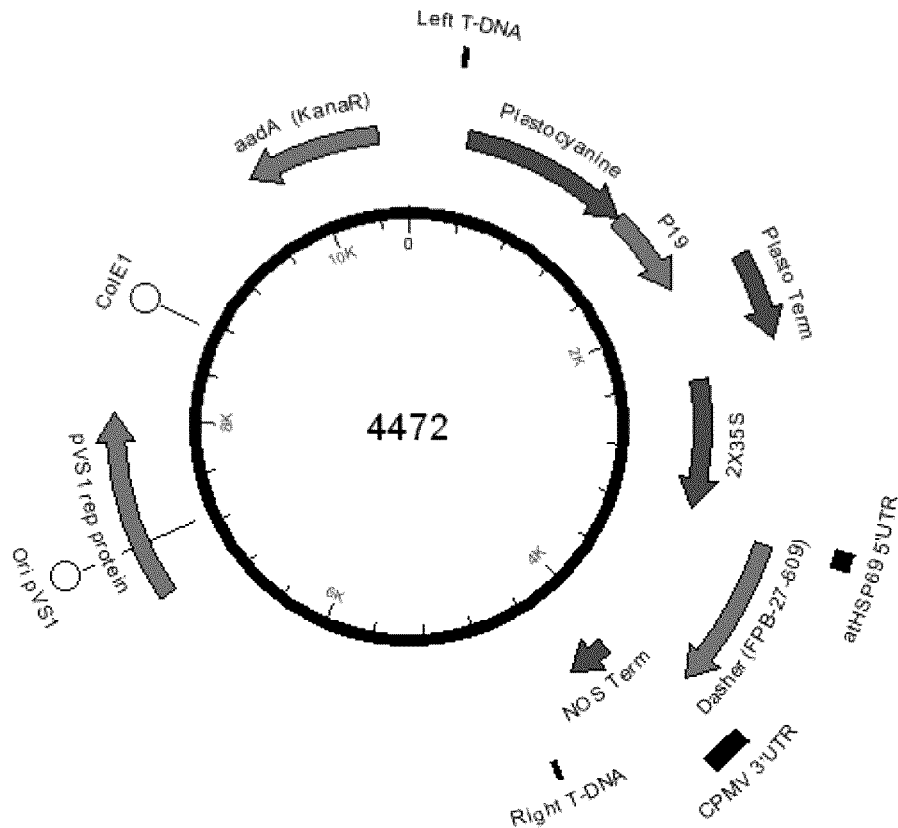
Figure 6Q:
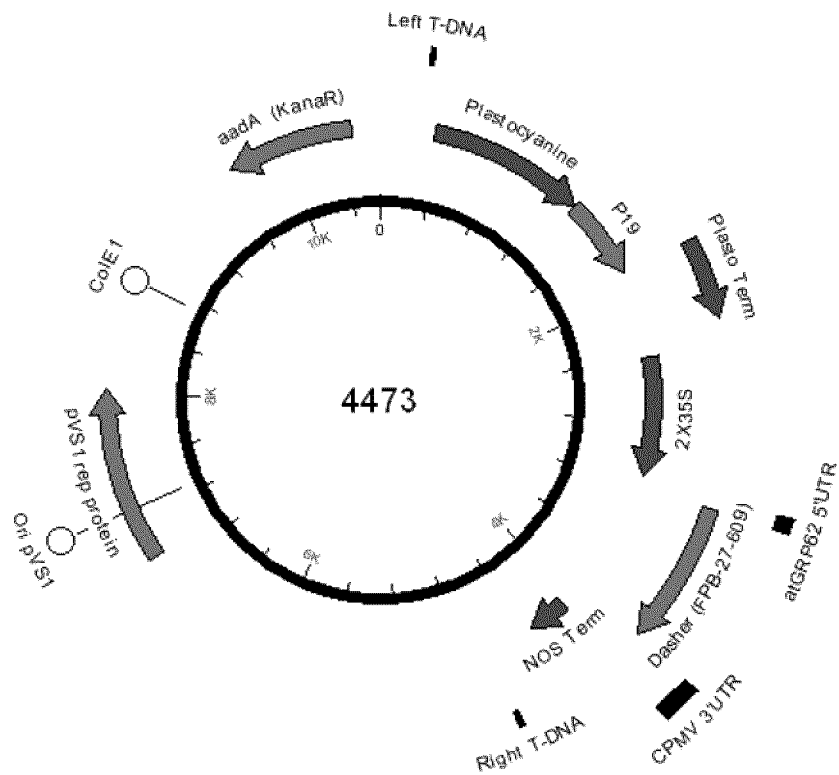
Figure 6R:
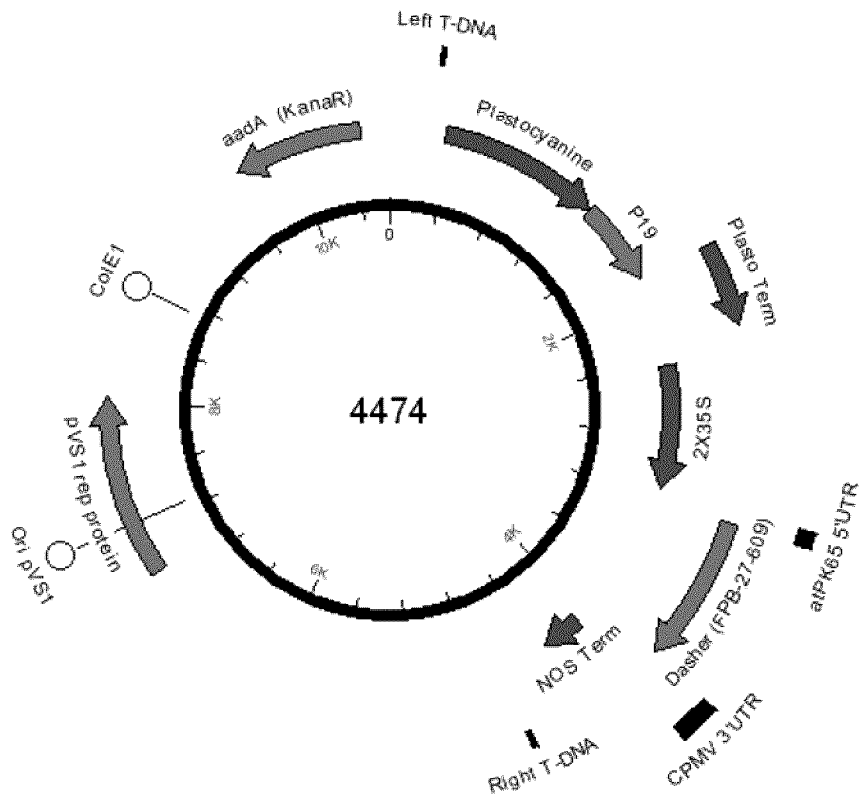
Figure 6S:
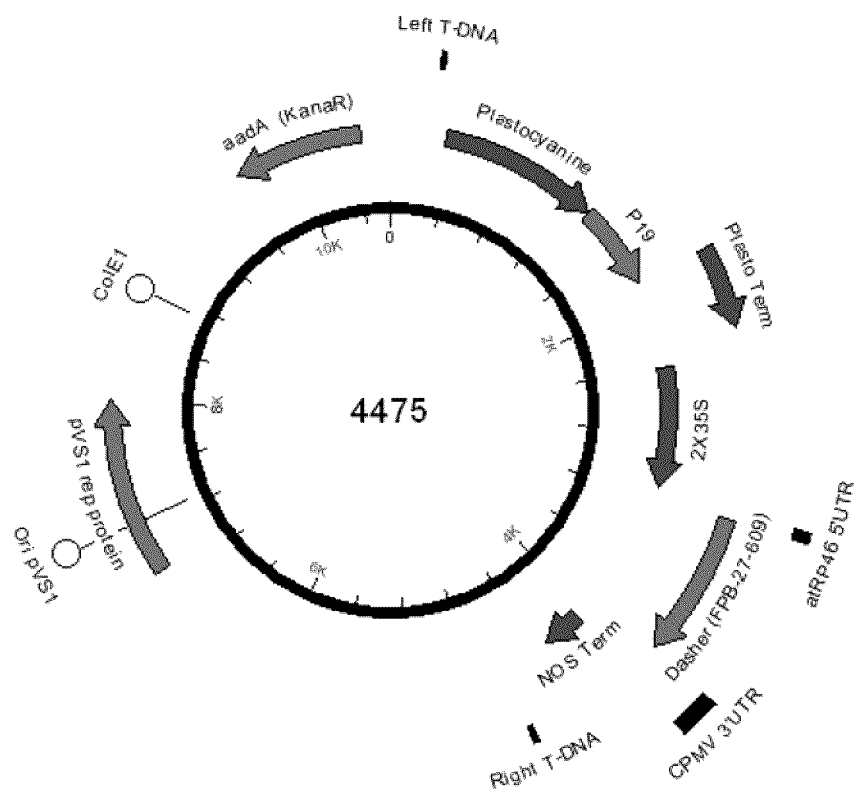

For Norovirus VP1 constructs, the cloning vector used integrates a Matrix attachment region (MAR) regulatory element from the tobacco RB7 gene after the NOS terminator in addition to the 2X35S promoter+CPMV 3'UTR/NOS-based expression cassette. Plasmid number 4170 (SEQ ID NO: 77; FIGS. 6D; 18D) was digested with AatII and StuI restriction enzymes and used for the In-Fusion reaction.

TABLE 2

Primers, templates and sequences of interest for construct preparation

| Constructs | | | SEQ ID NO: | | | | | | | |
|---|---|---|---|---|---|---|---|---|---|---|
| 5'UTR | Sp | SOI* | Const # | Primer 1* | Primer 2* | Primer 3* | F1 Template | F2 Template | SOI NA: | SOI AA |
| CPMV 160 | — | Dasher | 4460 | 23 | | 18 | — | 20 | 78 | 21 |
| nbGT61 | — | Dasher | 4461 | 25 | 24 | 18 | 20 | F1 | 78 | 21 |
| nbATL75 | — | Dasher | 4462 | 27 | 26 | 18 | 20 | F1 | 78 | 21 |

TABLE 2-continued

Primers, templates and sequences of interest for construct preparation

| Constructs | | | | SEQ ID NO: | | | | | | |
|---|---|---|---|---|---|---|---|---|---|---|
| 5'UT R | Sp | SOI* | Const # | Primer 1* | Primer 2* | Primer 3* | F1 Template | F2 Template | SOI NA: | SOI AA |
| nbDJ46 | — | Dasher | 4463 | 29 | 28 | 18 | 20 | F1 | 78 | 21 |
| nbCHP79 | — | Dasher | 4464 | 31 | 30 | 18 | 20 | F1 | 78 | 21 |
| nbEN42 | — | Dasher | 4465 | 33 | 32 | 18 | 20 | F1 | 78 | 21 |
| nb30S72 | — | Dasher | 4466 | 35 | 34 | 18 | 20 | F1 | 78 | 21 |
| nbMT78 | | Dasher | 4467 | 19 | 17 | 18 | 20 | F1 | 78 | 21 |
| nbPV55 | — | Dasher | 4468 | 37 | 36 | 18 | 20 | F1 | 78 | 21 |
| nbPPI43 | — | Dasher | 4469 | 39 | 38 | 18 | 20 | F1 | 78 | 21 |
| nbPM64 | — | Dasher | 4470 | 41 | 40 | 18 | 20 | F1 | 78 | 21 |
| nbH2A86 | — | Dasher | 4471 | 43 | 42 | 18 | 20 | F1 | 78 | 21 |
| atHSP69 | — | Dasher | 4472 | 45 | 44 | 18 | 20 | F1 | 78 | 21 |
| atGRP62 | — | Dasher | 4473 | 47 | 46 | 18 | 20 | F1 | 78 | 21 |
| atPK65 | — | Dasher | 4474 | 49 | 48 | 18 | 20 | F1 | 78 | 21 |
| atRP46 | — | Dasher | 4475 | 50 | — | 18 | — | 20 | 78 | 21 |
| CPMV 160 | SpPDI | HA0 H1 A-Cal-7-09 | 4021 | 23 | — | 51 | — | 79 | 80 | 81 |
| nbGT61 | SpPDI | HA0 H1 A-Cal-7-09 | 4061 | 25 | 52 | 51 | 79 | F1 | 80 | 81 |
| nbATL75 | SpPDI | HA0 H1 A-Cal-7-09 | 4062 | 27 | 53 | 51 | 79 | F1 | 80 | 81 |
| nbDJ46 | SpPDI | HA0 H1 A-Cal-7-09 | 4063 | 29 | 54 | 51 | 79 | F1 | 80 | 81 |
| nbCHP79 | SpPDI | HA0 H1 A-Cal-7-09 | 4064 | 31 | 55 | 51 | 79 | F1 | 80 | 81 |
| nbEN42 | SpPDI | HA0 H1 A-Cal-7-09 | 4065 | 33 | 56 | 51 | 79 | F1 | 80 | 81 |
| nb30S72 | SpPDI | HA0 H1 A-Cal-7-09 | 4066 | 35 | 57 | 51 | 79 | F1 | 80 | 81 |
| nbMT78 | SpPDI | HA0 H1 A-Cal-7-09 | 4067 | 19 | 58 | 51 | 79 | F1 | 80 | 81 |
| nbPV55 | SpPDI | HA0 H1 A-Cal-7-09 | 4068 | 37 | 59 | 51 | 79 | F1 | 80 | 81 |
| nbPPI43 | SpPDI | HA0 H1 A-Cal-7-09 | 4069 | 39 | 60 | 51 | 79 | F1 | 80 | 81 |
| nbPM64 | SpPDI | HA0 H1 A-Cal-7-09 | 4070 | 41 | 61 | 51 | 79 | F1 | 80 | 81 |
| nbH2A86 | SpPDI | HA0 H1 A-Cal-7-09 | 4071 | 43 | 62 | 51 | 79 | F1 | 80 | 81 |
| atHSP69 | SpPDI | HA0 H1 A-Cal-7-09 | 4072 | 45 | 63 | 51 | 79 | F1 | 80 | 81 |
| atGRP62 | SpPDI | HA0 H1 A-Cal-7-09 | 4073 | 47 | 64 | 51 | 79 | F1 | 80 | 81 |
| atPK65 | SpPDI | HA0 H1 A-Cal-7-09 | 4074 | 49 | 65 | 51 | 79 | F1 | 80 | 81 |
| atRP46 | SpPDI | HA0 H1 A-Cal-7-09 | 4075 | 66 | — | 51 | 79 | F1 | 80 | 81 |
| CPMV 160 | SpPDI | H1 A-Mich-45-2015 | 4013 | 23 | — | 51 | — | 82 | 83 | 84 |
| nbATL75 | SpPDI | H1 A-Mich-45-2015 | 4701 | 27 | 53 | 51 | 82 | F1 | 83 | 84 |
| nbCHP79 | SpPDI | H1 A-Mich-45-2015 | 4702 | 31 | 55 | 51 | 82 | F1 | 83 | 84 |
| nbMT78 | SpPDI | H1 A-Mich-45-2015 | 4703 | 19 | 58 | 51 | 82 | F1 | 83 | 84 |
| atHSP69 | SpPDI | H1 A-Mich-45-2015 | 4704 | 45 | 63 | 51 | 82 | F1 | 83 | 84 |
| CPMV 160 | SpPDI | H3 A-HK-4801-14 | 4014 | 23 | — | 67 | — | 85 | 86 | 87 |
| nbATL75 | SpPDI | H3 A-HK-4801-14 | 4711 | 27 | 53 | 67 | 85 | F1 | 86 | 87 |
| nbCHP79 | SpPDI | H3 A-HK-4801-14 | 4712 | 31 | 55 | 67 | 85 | F1 | 86 | 87 |
| nbMT78 | SpPDI | H3 A-HK-4801-14 | 4713 | 19 | 58 | 67 | 85 | F1 | 86 | 87 |
| atHSP69 | SpPDI | H3 A-HK-4801-14 | 4714 | 45 | 63 | 67 | 85 | F1 | 86 | 87 |
| CPMV 160 | SpPDI | HA B/Bri/60/08 | 4015 | 23 | — | 51 | — | 88 | 89 | 90 |
| nbATL75 | SpPDI | HA B/Bri/60/08 | 4721 | 27 | 53 | 51 | 88 | F1 | 89 | 90 |
| nbCHP79 | SpPDI | HA B/Bri/60/08 | 4722 | 31 | 55 | 51 | 88 | F1 | 89 | 90 |
| nbMT78 | SpPDI | HA B/Bri/60/08 | 4723 | 19 | 58 | 51 | 88 | F1 | 89 | 90 |
| atHSP69 | SpPDI | HA B/Bri/60/08 | 4724 | 45 | 63 | 51 | 88 | F1 | 89 | 90 |
| CPMV 160 | SpPDI | HA0 HA B/Phu/3073/13 | 4016 | 23 | — | 51 | — | 91 | 92 | 93 |

TABLE 2-continued

Primers, templates and sequences of interest for construct preparation

| Constructs | | | | SEQ ID NO: | | | | | | |
|---|---|---|---|---|---|---|---|---|---|---|
| 5'UTR | Sp | SOI* | Const # | Primer 1* | Primer 2* | Primer 3* | F1 Template | F2 Template | SOI NA: | SOI AA |
| nbATL75 | SpPDI | HA0 HA B/Phu/3073/13 | 4731 | 27 | 53 | 51 | 91 | F1 | 92 | 93 |
| nbCHP79 | SpPDI | HA0 HA B/Phu/3073/13 | 4732 | 31 | 55 | 51 | 91 | F1 | 92 | 93 |
| nbMT78 | SpPDI | HA0 HA B/Phu/3073/13 | 4733 | 19 | 58 | 51 | 91 | F1 | 92 | 93 |
| atHSP69 | SpPDI | HA0 HA B/Phu/3073/13 | 4734 | 45 | 63 | 51 | 91 | F1 | 92 | 93 |
| CPMV 160 | — | VP1 (GII.4 Syd12) | 4133 | 23 | — | 68 | — | 94 | 95 | 96 |
| nbATL75 | — | VP1 (GII.4 Syd12) | 4161 | 27 | 69 | 68 | 94 | F1 | 95 | 96 |
| nbCHP79 | — | VP1 (GII.4 Syd12) | 4162 | 31 | 70 | 68 | 94 | F1 | 95 | 96 |
| nbMT78 | — | VP1 (GII.4 Syd12) | 4163 | 19 | 71 | 68 | 94 | F1 | 95 | 96 |
| atHSP69 | — | VP1 (GII.4 Syd12) | 4164 | 45 | 72 | 68 | 94 | F1 | 95 | 96 |
| CPMV 160 | SpPDI | HC IgG1 | 3191 | 23 | — | 73 | — | 97 | 98 | 99 |
| nbATL75 | SpPDI | HC IgG1 | 4643 | 27 | 53 | 73 | 97 | F1 | 98 | 99 |
| nbCHP79 | SpPDI | HC IgG1 | 4644 | 31 | 55 | 73 | 97 | F1 | 98 | 99 |
| nbMT78 | SpPDI | HC IgG1 | 4645 | 19 | 58 | 73 | 97 | F1 | 98 | 99 |
| atHSP69 | SpPDI | HC IgG1 | 4646 | 45 | 63 | 73 | 97 | F1 | 98 | 99 |
| CPMV 160 | SpPDI | LC IgG1 | 3192 | 23 | — | 74 | — | 100 | 101 | 102 |
| nbATL75 | SpPDI | LC IgG1 | 4653 | 27 | 53 | 74 | 100 | F1 | 101 | 102 |
| nbCHP79 | SpPDI | LC IgG1 | 4654 | 31 | 55 | 74 | 100 | F1 | 101 | 102 |
| nbMT78 | SpPDI | LC IgG1 | 4655 | 19 | 58 | 74 | 100 | F1 | 101 | 102 |
| atHSP69 | SpPDI | LC IgG1 | 4656 | 45 | 63 | 74 | 100 | F1 | 101 | 102 |

*SOA: sequence of interest; Primer 1: Primer 1 (For In-fusion cloning); Primer 2: Primer 2 (to create fragment no 1 to amplify GOI with primer 3): Primer 3: Primer 3 (For In-fusion cloning) Example 2: Methods

*Agrobacterium tumefaciens* Transfection

*Agrobacterium tumefaciens* strain AGL1 was transfected (transformed) by electroporation with the different expression vectors using the methods described by D'Aoust et al., 2008 (*Plant Biotech. J.* 6:930-40). Transfected *Agrobacterium* were grown in LB medium supplemented with 10 mM 2-(N-morpholino)ethanesulfonic acid (MES) and 50 µg/ml kanamycin pH5.6 to an OD600 between 0.6 and 1.6 and frozen in 100 µl aliquots.

Preparation of Plant Biomass, Inoculum and Agroinfiltration

*N. benthamiana* plants were grown from seeds in flats filled with a commercial peat moss substrate. The plants were allowed to grow in the greenhouse under a 16/8 photoperiod and a temperature regime of 25° C. day/20° C. night. Three weeks after seeding, individual plantlets were picked out, transplanted in pots and left to grow in the greenhouse for three additional weeks under the same environmental conditions Agrobacteria transfected (transformed) with each expression vector were grown in a LB medium supplemented with 10 mM 2-(N-morpholino)ethanesulfonic acid (MES) and 50 µg/ml kanamycin pH5.6 until they reached an OD600 between 0.6 and 1.6. *Agrobacterium* suspensions were centrifuged before use and resuspended in infiltration medium (10 mM MgCl$_2$ and 10 mM MES pH 5.6) and stored overnight at 4° C. On the day of infiltration, culture batches were diluted in 2.5 culture volumes and allowed to warm before use. Whole plants of *N. benthamiana* were placed upside down in the bacterial suspension in an air-tight stainless steel tank under a vacuum of 20-40 Torr for 2-min. Plants were returned to the greenhouse for a 6 or 9 day incubation period until harvest.

Leaf Harvest and Total Protein Extraction

Following incubation, the aerial part of plants was harvested, frozen at −80° C. and crushed into pieces. Total soluble proteins were extracted by homogenizing (Polytron) each sample of frozen-crushed plant material in 2 volumes of cold 50 mM Tris buffer pH 8.0+500 mM NaCl, 0.4 µg/ml Metabisulfite and 1 mM phenylmethanesulfonyl fluoride. After homogenization, the slurries were centrifuged at 10,000 g for 10 min at 4° C. and these clarified crude extracts (supernatant) kept for analyses.

The total protein content of clarified crude extracts was determined by the Bradford assay (Bio-Rad, Hercules, California) using bovine serum albumin as the reference standard. Proteins were separated by SDS-PAGE under reducing conditions using Criterion™ TGX Stain-Free™ precast gels (Bio-Rad Laboratories, Hercules, CA). Proteins were visualized by staining the gels with Coomassie Brilliant Blue. Alternatively, proteins were visualized with Gel Doc™ EZ imaging system (Bio-Rad Laboratories, Hercules, CA) and electrotransferred onto polyvinylene difluoride (PVDF) membranes (Roche Diagnostics Corporation, Indianapolis, Indiana) for immunodetection. Prior to immunoblotting, the membranes were blocked with 5% skim milk and 0.1% Tween-20 in Tris-buffered saline (TBS-T) for 16-18 h at 4° C.

Dasher Expression as Determined by Direct Fluorescence in Crude Extract

Dasher expression was quantified by direct measure of fluorescence in crude extracts. Frozen biomass was extracted using 50 mM Tris+150 mM NaCl pH 7.4 extraction buffer by mechanical extraction and centrifuged 10 minutes at 10000g at 4° C. to remove insoluble debris. Clarified crude extracts were diluted 1/16, 1/48 and 1/144 in PBS and fluorescence was measured using a Fluoroskan (Ascent) instrument using 485 nm as excitation filter and 518 nm as emission filter.

HA Expression as Determined Using Hemagglutination Assay (HA Titer)

Hemagglutination assay was based on a method described by Nayak and Reichl (2004, J. Virol. Methods 122:9-15). Serial double dilutions of the test samples (100 µL) were made in V-bottomed 96-well microtiter plates containing 100 µL PBS, leaving 100 µL of diluted sample per well. One hundred microliters of a 0.25% turkey red blood cells suspension (Bio Link Inc., Syracuse, NY; for all B strains, H1, H5 and H7) or 0.5% guinea pig red blood cells suspension (for H3) were added to each well, and plates were incubated for 2 h at room temperature. The reciprocal of the highest dilution showing complete hemagglutination was recorded as HA activity.

Rituximab Expression as Determined by In-Gel Densitometry

For Rituximab expression analysis, crude protein extracts (2g biomass/EU) were produced from leaves by mechanical extraction in 150 mM Tris, pH 7.4 buffer with 150 mM NaCl and the extracts were electrophoresed on SDS-PAGE under non-reducing conditions for in-gel densitometry quantification of the band corresponding to the fully assembled $H_2L_2$ form of the antibody. Protein electrophoresis was performed in Stain-Free gels from Bio-Rad and gel imaging system was carried-out using Gel Doc XR+ system, including the Image Lab software for image analyses and in-gel quantification.

Analysis of VLP Formation/Iodixanol Gradients

Proteins were extracted from frozen biomass by mechanical extraction in a blender with 2 volumes of extraction buffer (100 mM phosphate buffer pH 7.2+150 mM NaCl). The slurry was filtered through a large pore nylon filter to remove large debris and centrifuged 5000 g for 5 min at 4° ° C. The supernatant was collected and centrifuged again at 5000 g for 30 min (4° C.) to remove additional debris. The supernatant is then loaded on a discontinuous iodixanol density gradient. Analytical density gradient centrifugation was performed as follows: 38 ml tubes containing discontinuous iodixanol density gradient in acetate buffer (1 ml at 45%, 2 ml at 35%, 2 ml at 33%, 2 ml at 31%, 2 ml at 29% and 5 ml at 25% of iodixanol) were prepared and overlaid with 25 ml of the extracts containing the virus-like particles. The gradients were centrifuged at 175 000 g for 4 hours (4° C.). After centrifugation, 1 ml fractions were collected from the bottom to the top and fractions were analyzed by SDS-PAGE combined with protein staining or Western blot.

Example 3: Protein Production in Plants

N. benthamiana leaves were, vacuum infiltrated, as described in Example 2, with Agrobacterium tumefaciens comprising expression vectors encoding the protein of interest operatively linked to the defined expression enhancer, to permit expression of the protein of interest, and the leaves examined for the protein of interest production. After 9 days post infiltration (DPI), total crude protein extracts were prepared from leaf homogenates, and hemagglutinin titer was determined as described above.

With reference to FIG. 2, each of the expression enhancers, nbMT78 (SEQ ID NO:1); nbATL75 (SEQ ID NO:2); nbDJ46 (SEQ ID NO:3); nbCHP79 (SEQ ID NO:4); nbEN42 (SEQ ID NO:5); atHSP69 (SEQ ID NO:6); atGRP62 (SEQ ID NO:7); atPK65 (SEQ ID NO:8); atRP46 (SEQ ID NO:9); nb30S72 (SEQ ID NO:10); nbGT61 (SEQ ID NO:11); nbPV55 (SEQ ID NO:12); nbPPI43 (SEQ ID NO:13); nbPM64 (SEQ ID NO:14); and nbH2A86 (SEQ ID NO:15) operatively linked to a nucleic acid sequence encoding Dasher was observed to result in increased expression of the protein, when compared to the activity of the prior art expression enhancer sequence CMPV 160 (WO 2015/103704) or the prior art expression enhancer sequence atPK41 (termed AtPsaK 3' in Diamos et. al., Frontiers in Plant Science. 2016, vol7 pp. 1-15) operatively linked to the same nucleic acid sequence encoding the same proteins of interest, and expressed under similar conditions.

As shown in FIG. 3A each of the expression enhancers, nbMT78 (SEQ ID NO:1); nbATL75 (SEQ ID NO:2); nbDJ46 (SEQ ID NO:3); nbCHP79 (SEQ ID NO:4); nbEN42 (SEQ ID NO:5); atHSP69 (SEQ ID NO:6); atGRP62 (SEQ ID NO:7); atPK65 (SEQ ID NO:8); atRP46 (SEQ ID NO:9); nb30S72 (SEQ ID NO:10); nbGT61 (SEQ ID NO:11); nbPV55 (SEQ ID NO:12); nbPPI43 (SEQ ID NO:13); nbPM64 (SEQ ID NO:14); and nbH2A86 (SEQ ID NO:15), operatively linked to a nucleic acid sequence encoding influenza hemagglutinin H1 A/California/7/09 (FIG. 3A), was observed to result in a similar, or slightly increased, expression of the protein when compared to the activity of the prior art expression enhancer sequence CMPV 160 (WO 2015/103704) or the prior art expression enhancer sequence atPK41 (termed AtPsaK 3' in Diamos et. al., Frontiers in Plant Science. 2016, vol7 pp. 1-15) operatively linked to the same nucleic acid sequence encoding the same proteins of interest, and expressed under similar conditions.

With reference to FIG. 3B, each of the expression enhancers, nbMT78 (SEQ ID NO:1); nbATL75 (SEQ ID NO:2), nbCHP79 (SEQ ID NO:4), atHSP69 (SEQ ID NO:6), operatively linked to a nucleic acid sequence encoding a modified H1 Michigan/45/15, a modified H3 Hong Kong/4801/14, and modified HA B/Phuket Bris/60/08, or a modified HA B/Phuket/3073/13, was observed to result in a similar, or slightly increased, expression of the protein when compared to the activity of the prior art expression enhancer sequence CMPV 160 (WO 2015/103704) operatively linked to the same nucleic acid sequence encoding the same proteins of interest, and expressed under similar conditions.

These results demonstrate the expression enhancer sequences described herein may be used for the expression of a protein of interest that is operatively linked to the expression enhancer, in a plant, portion of plant, or a plant cell.

Example 4: Norovirus VP1 Protein and VLP Production in Plants

N. benthamiana leaves were vacuum infiltrated, as described in Example 2, with Agrobacterium tumefaciens comprising expression vectors encoding norovirus VP1 from GII.4 genotype, and the leaves examined for VLP production. After 9 days post infiltration (DPI), total crude protein extracts were separated by SDS-PAGE, and stained with Coomassie (VP1 production), or separated using discontinuous iodixanol density gradients as described in Example 2, above (VLP production). Fractions from the density gradients were examined using Coomassie-stained SDS-PAGE. Norovirus VP1 proteins appear at an approximate 55-60 kDa band. The occurrence of the VP1 protein within a fraction of the density gradients is indicative of the fraction(s) to which the VLPs equilibrate during density gradient centrifugation. The yield of VLPs obtained from peak fractions after density gradient centrifugation was also determined.

Each of the expression enhancers, nbMT78 (SEQ ID NO:1); nbATL75 (SEQ ID NO:2), nbCHP79 (SEQ ID NO:4), and atHSP69 (SEQ ID NO:6), operatively linked to a nucleic acid sequence encoding a modified norovirus GII.4/Sydney/2012 VP1 was observed to result in expression of the norovirus protein. Furthermore, yields of the norovirus GII.4 VP1 VLPs using the above expression enhancer were similar to those obtained using the prior art CPMV 160 expression enhancer (WO2015/103704), or the prior art expression enhancer nbPK74 (termed NbPsaK2 3' in Diamos et. al., Frontiers in Plant Science. 2016, vol7 pp. 1-15). These results demonstrate that the expression enhancers described herein may be used for the production of virus like particles (VLPs).

Example 5: Multimeric Protein Production in Plants

The expression enhancers described herein may also be used for the production of a multimeric protein of interest, for example an antibody. *N. benthamiana* leaves were, vacuum infiltrated, as described in Example 2, with *Agrobacterium tumefaciens* comprising expression vectors encoding the protein of interest operatively linked to the defined expression enhancer, to permit expression of the protein of interest, and the leaves examined for the protein of interest production. After 9 days post infiltration (DPI), total crude protein extracts were prepared from leaf homogenates were separated by SDS-PAGE and expression levels were determined by in-gel densitometry of complete IgG, as described above.

As shown with reference to FIG. 5, co-expression of two nucleic acids, the first nucleic acid encoding the light chain (LC) of Rituximab operatively linked to one of the following expression enhancers nbMT78 (SEQ ID NO:1); nbATL75 (SEQ ID NO:2), nbCHP79 (SEQ ID NO:4), and atHSP69 (SEQ ID NO:6), and the second nucleic acid encoding the heavy chain (HC) of rituximab operatively linked to one of the following expression enhancers nbMT78 (SEQ ID NO:1); nbATL75 (SEQ ID NO:2), nbCHP79 (SEQ ID NO:4), and atHSP69 (SEQ ID NO:6), resulted in the same, or slightly increased, yield of the multimeric protein in a plant, when compared to co-expression of first and second nucleic acids encoding the same HC and LC rituximab sequences, with each of the first and second nucleic acids operatively linked to the prior art expression enhancer CPMV 160.

These results demonstrate that the expression enhancers described herein may be used to produce multimeric proteins, such as an antibody, and that the same or different the expression enhancers as described herein may be operatively linked to each of the nucleic acid sequences used to encode the components of the multimeric protein.

All citations are hereby incorporated by reference.

The present invention has been described with regard to one or more embodiments. However, it will be apparent to persons skilled in the art that a number of variations and modifications can be made without departing from the scope of the invention as defined in the claims.

SEQUENCE LISTING

```
<160> NUMBER OF SEQ ID NOS: 102

<210> SEQ ID NO 1
<211> LENGTH: 78
<212> TYPE: DNA
<213> ORGANISM: Unknown
<220> FEATURE:
<223> OTHER INFORMATION: Expression enhancer nbMT78

<400> SEQUENCE: 1
acacaatttg ctttagtgat taaactttct tttacaacaa attaaaggtc tattatctcc     60
caacaacata agaaaaca                                                   78

<210> SEQ ID NO 2
<211> LENGTH: 75
<212> TYPE: DNA
<213> ORGANISM: Unknown
<220> FEATURE:
<223> OTHER INFORMATION: Expression enhancer nbATL75

<400> SEQUENCE: 2
atctccacca ccaaaaaccc taatcgcctc tccgtttctt catcagattc tcggttctct     60
tcttctacag caaca                                                      75

<210> SEQ ID NO 3
<211> LENGTH: 46
<212> TYPE: DNA
<213> ORGANISM: Unknown
<220> FEATURE:
<223> OTHER INFORMATION: Expression enhancer

<400> SEQUENCE: 3
```

```
actcaccaag aaaataaaca aattaaagaa ttttaagaaa aacaag              46

<210> SEQ ID NO 4
<211> LENGTH: 79
<212> TYPE: DNA
<213> ORGANISM: Unknown
<220> FEATURE:
<223> OTHER INFORMATION: Expression enhancer

<400> SEQUENCE: 4
attctgccct cagttaacta aattatctct ctgattaaca gtactttctg attttctgtg  60
atttctacaa atctgagac                                              79

<210> SEQ ID NO 5
<211> LENGTH: 42
<212> TYPE: DNA
<213> ORGANISM: Unknown
<220> FEATURE:
<223> OTHER INFORMATION: Expression enhancer nbEN42

<400> SEQUENCE: 5
acttttgtat agctccattg aaatagagaa agaaaatag cc                    42

<210> SEQ ID NO 6
<211> LENGTH: 69
<212> TYPE: DNA
<213> ORGANISM: Unknown
<220> FEATURE:
<223> OTHER INFORMATION: Expression enhancer atHSP69

<400> SEQUENCE: 6
aaattcaaaa tttaacacac aaacacaaac acacacacca aaaaaaacac agaccttaaa  60
aaaataaaa                                                         69

<210> SEQ ID NO 7
<211> LENGTH: 62
<212> TYPE: DNA
<213> ORGANISM: Unknown
<220> FEATURE:
<223> OTHER INFORMATION: Expression enhancer atGRP62

<400> SEQUENCE: 7
ataacaaaac aagattttga agtaaaacat aaaagaaaat aaaccctaag aatatatcga  60
aa                                                                62

<210> SEQ ID NO 8
<211> LENGTH: 65
<212> TYPE: DNA
<213> ORGANISM: Unknown
<220> FEATURE:
<223> OTHER INFORMATION: Expression enhancer atPK65

<400> SEQUENCE: 8
gcaaaaacaa aaataaaaaa aacatcgcac aagaaaataa aagatttgta gaatcaacta  60
agaaa                                                             65

<210> SEQ ID NO 9
<211> LENGTH: 46
<212> TYPE: DNA
<213> ORGANISM: Unknown
<220> FEATURE:
<223> OTHER INFORMATION: Expression enhancer atRP46
```

```
<400> SEQUENCE: 9
agaaacaaaa agaattaaaa aaaaaaaaaa aaaaagaat aaagaa            46

<210> SEQ ID NO 10
<211> LENGTH: 72
<212> TYPE: DNA
<213> ORGANISM: Unknown
<220> FEATURE:
<223> OTHER INFORMATION: Expression enhancer nb30S72

<400> SEQUENCE: 10
atctttccct caaaaccta gccgcagtca cttccgtagg tgcttacttc gctgttagtg   60
caattccaaa cc                                                     72

<210> SEQ ID NO 11
<211> LENGTH: 61
<212> TYPE: DNA
<213> ORGANISM: Unknown
<220> FEATURE:
<223> OTHER INFORMATION: Expression enhancer nbGT61

<400> SEQUENCE: 11
atccagaagt aggaattctt cagtataatc tagggttttt tgaaaagcaa attgatcgaa   60
a                                                                  61

<210> SEQ ID NO 12
<211> LENGTH: 55
<212> TYPE: DNA
<213> ORGANISM: Unknown
<220> FEATURE:
<223> OTHER INFORMATION: Expression enhancer nbPV55

<400> SEQUENCE: 12
aattaaagat caattcactg tatccctctt ctccaaaaaa aactctgctg tagtc        55

<210> SEQ ID NO 13
<211> LENGTH: 43
<212> TYPE: DNA
<213> ORGANISM: Unknown
<220> FEATURE:
<223> OTHER INFORMATION: Expression enhancer nbPPI43

<400> SEQUENCE: 13
acaaatcgta cacagcgaaa acctcactga aatatttaga gag                   43

<210> SEQ ID NO 14
<211> LENGTH: 64
<212> TYPE: DNA
<213> ORGANISM: Unknown
<220> FEATURE:
<223> OTHER INFORMATION: Expression enhancer nbPM64

<400> SEQUENCE: 14
agaaagattt gtttcctctg aaatagtttt acagagccag aagaagaaaa agaagaagag   60
agca                                                               64

<210> SEQ ID NO 15
<211> LENGTH: 86
<212> TYPE: DNA
<213> ORGANISM: Unknown
<220> FEATURE:
<223> OTHER INFORMATION: Expression enhancer nbH2A86

<400> SEQUENCE: 15
```

```
actcaacact caaatcgcaa tccaaaagct tcaattttc  ctaatacttc tctgtattca    60
agcttcgtaa actttcattc acatca                                         86

<210> SEQ ID NO 16
<211> LENGTH: 160
<212> TYPE: DNA
<213> ORGANISM: Artificial Sequence
<220> FEATURE:
<223> OTHER INFORMATION: CPMV 160

<400> SEQUENCE: 16
tattaaaatc ttaataggtt ttgataaaag cgaacgtggg gaaacccgaa ccaaaccttc    60
ttctaaactc tctctcatct ctcttaaagc aaacttctct cttgtctttc ttgcgtgagc   120
gatcttcaac gttgtcagat cgtgcttcgg caccagtaca                         160

<210> SEQ ID NO 17
<211> LENGTH: 59
<212> TYPE: DNA
<213> ORGANISM: Artificial Sequence
<220> FEATURE:
<223> OTHER INFORMATION: Primer nbMT78_Dasher.c

<400> SEQUENCE: 17
ttaaaggtct attatctccc aacaacataa gaaaacaatg actgccctga ccgaaggtg     59

<210> SEQ ID NO 18
<211> LENGTH: 56
<212> TYPE: DNA
<213> ORGANISM: Artificial Sequence
<220> FEATURE:
<223> OTHER INFORMATION: Primer IF-Dasher(27-609).r

<400> SEQUENCE: 18
actaaagaaa ataggccttt actgataggt atcgagatcg acggccttga ccactt         56

<210> SEQ ID NO 19
<211> LENGTH: 89
<212> TYPE: DNA
<213> ORGANISM: Artificial Sequence
<220> FEATURE:
<223> OTHER INFORMATION: Primer IF-nbMT78.c

<400> SEQUENCE: 19
tttcatttgg agaggcacac aatttgcttt agtgattaaa ctttctttta caacaaatta    60
aaggtctatt atctcccaac aacataaga                                      89

<210> SEQ ID NO 20
<211> LENGTH: 871
<212> TYPE: DNA
<213> ORGANISM: Artificial Sequence
<220> FEATURE:
<223> OTHER INFORMATION: Primer CPMV 160 5'UTR-Dasher nucleic acid
      sequence

<400> SEQUENCE: 20
tattaaaatc ttaataggtt ttgataaaag cgaacgtggg gaaacccgaa ccaaaccttc    60
ttctaaactc tctctcatct ctcttaaagc aaacttctct cttgtctttc ttgcgtgagc   120
gatcttcaac gttgtcagat cgtgcttcgg caccagtaca atgactgccc tgaccgaagg   180
tgctaagctg tttgagaagg agattccgta catcaccgag ctggaagggg acgtcgaagg   240
aatgaagttc atcatcaagg gagaaggaac cggggacgct acgactggaa ccattaaggc   300
```

```
caagtatatc tgtaccactg gagatctgcc agtgccttgg gccacccttg tgtcaaccct      360
ctcgtatgga gtgcagtgtt ttgctaagta ccctagccac attaaggact tcttcaaatc      420
cgccatgccg gaaggttata cccaagagcg caccatttct tttgagggag atggagtgta      480
caagacccgc gcgatggtca cctatgagag gggatctatc tacaaccggg tgactctgac      540
tggagaaaac tttaagaagg acgggcatat tcttcggaag aatgtcgcct ccagtgccc       600 tcccagcatc ctttacattc tccccgacac tgtgaacaac ggaatccgcg tggagttcaa      660
tcaagcctac gacatcgagg gggtgacgga agctggtg accaagtgta gccagatgaa        720
tcggccactg gccggttcag cggctgtcca cattccgcgc taccatcata tcacttatca      780
cactaagctc tccaaagacc gcgatgagag gagagatcac atgtgcctgg tggaagtggt      840
caaggccgtc gatctcgata cctatcagta a                                      871
```

<210> SEQ ID NO 21
<211> LENGTH: 236
<212> TYPE: PRT
<213> ORGANISM: Artificial Sequence
<220> FEATURE:
<223> OTHER INFORMATION: Dasher Primer amino acid sequence

<400> SEQUENCE: 21

```
Met Thr Ala Leu Thr Glu Gly Ala Lys Leu Phe Glu Lys Glu Ile Pro
1               5                   10                  15

Tyr Ile Thr Glu Leu Glu Gly Asp Val Glu Gly Met Lys Phe Ile Ile
            20                  25                  30

Lys Gly Glu Gly Thr Gly Asp Ala Thr Thr Gly Thr Ile Lys Ala Lys
        35                  40                  45

Tyr Ile Cys Thr Thr Gly Asp Leu Pro Val Pro Trp Ala Thr Leu Val
    50                  55                  60

Ser Thr Leu Ser Tyr Gly Val Gln Cys Phe Ala Lys Tyr Pro Ser His
65                  70                  75                  80

Ile Lys Asp Phe Phe Lys Ser Ala Met Pro Glu Gly Tyr Thr Gln Glu
                85                  90                  95

Arg Thr Ile Ser Phe Glu Gly Asp Gly Val Tyr Lys Thr Arg Ala Met
            100                 105                 110

Val Thr Tyr Glu Arg Gly Ser Ile Tyr Asn Arg Val Thr Leu Thr Gly
        115                 120                 125

Glu Asn Phe Lys Lys Asp Gly His Ile Leu Arg Lys Asn Val Ala Phe
    130                 135                 140

Gln Cys Pro Pro Ser Ile Leu Tyr Ile Leu Pro Asp Thr Val Asn Asn
145                 150                 155                 160

Gly Ile Arg Val Glu Phe Asn Gln Ala Tyr Asp Ile Glu Gly Val Thr
                165                 170                 175

Glu Lys Leu Val Thr Lys Cys Ser Gln Met Asn Arg Pro Leu Ala Gly
            180                 185                 190

Ser Ala Ala Val His Ile Pro Arg Tyr His His Ile Thr Tyr His Thr
        195                 200                 205

Lys Leu Ser Lys Asp Arg Asp Glu Arg Arg Asp His Met Cys Leu Val
    210                 215                 220

Glu Val Val Lys Ala Val Asp Leu Asp Thr Tyr Gln
225                 230                 235
```

<210> SEQ ID NO 22
<211> LENGTH: 4337

```
<212> TYPE: DNA
<213> ORGANISM: Artificial Sequence
<220> FEATURE:
<223> OTHER INFORMATION: Cloning vector (for Dasher) 1666 from left to
      right T-DNA

<400> SEQUENCE: 22
tggcaggata tattgtggtg taaacaaatt gacgcttaga caacttaata acacattgcg      60
gacgttttta atgtactgaa ttaacgccga atcccgggct ggtatattta tatgttgtca     120
aataactcaa aaaccataaa agtttaagtt agcaagtgtg tacatttta cttgaacaaa      180 aatattcacc tactactgtt ataaatcatt attaaacatt agagtaaaga aatatggatg     240
ataagaacaa gagtagtgat attttgacaa caattttgtt gcaacatttg agaaaatttt     300
gttgttctct cttttcattg gtcaaaaaca atagagagag aaaaaggaag agggagaata     360
aaaacataat gtgagtatga gagagaaagt tgtacaaaag ttgtaccaaa atagttgtac     420
aaatatcatt gaggaatttg acaaaagcta cacaaataag ggttaattgc tgtaaataaa     480
taaggatgac gcattagaga gatgtaccat tagagaattt ttggcaagtc attaaaaaga     540
aagaataaat tattttttaaa attaaaagtt gagtcatttg attaaacatg tgattattta     600
atgaattgat gaaagagttg gattaaagtt gtattagtaa ttagaatttg gtgtcaaatt     660
taatttgaca tttgatcttt tcctatatat tgccccatag agtcagttaa ctcattttta     720
tatttcatag atcaaataag agaaataacg gtatattaat ccctccaaaa aaaaaaaacg     780
gtatatttac taaaaaatct aagccacgta ggaggataac aggatccccg taggaggata     840
acatccaatc caaccaatca caacaatcct gatgagataa cccactttaa gcccacgcat     900
ctgtggcaca tctacattat ctaaatcaca cattcttcca cacatctgag ccacacaaaa     960
accaatccac atcttatca cccattctat aaaaaatcac actttgtgag tctacacttt    1020
gattcccttc aaacacatac aaagagaaga gactaattaa ttaattaatc atcttgagag    1080
aaaatggaac gagctataca aggaaacgac gctagggaac aagctaacag tgaacgttgg    1140
gatggaggat caggaggtac cacttctccc ttcaaacttc ctgacgaaag tccgagttgg    1200
actgagtggc ggctacataa cgatgagacg aattcgaatc aagataatcc ccttggtttc    1260
aaggaaagct ggggtttcgg gaaagttgta tttaagagat atctcagata cgacaggacg    1320
gaagcttcac tgcacagagt ccttggatct tggacgggag attcggttaa ctatgcagca    1380
tctcgatttt tcggtttcga ccagatcgga tgtacctata gtattcggtt tcgaggagtt    1440
agtatcaccg tttctggagg gtcgcgaact cttcagcatc tctgtgagat ggcaattcgg    1500
tctaagcaag aactgctaca gcttgcccca atcgaagtgg aaagtaatgt atcaagagga    1560
tgccctgaag gtactcaaac cttcgaaaaa gaaagcgagt aagttaaaat gcttcttcgt    1620 ctcctatttta taatatggtt tgttattgtt aattttgttc ttgtagaaga gcttaattaa    1680
tcgttgttgt tatgaaatac tatttgtatg agatgaactg gtgtaatgta attcattac    1740 ataagtggag tcagaatcag aatgtttcct ccataactaa ctagacatga agacctgccg    1800
cgtacaattg tcttatattt gaacaactaa aattgaacat cttttgccac aactttataa    1860
gtggttaata tagctcaaat atatggtcaa gttcaataga ttaataatgg aaatatcagt    1920
tatcgaaatt cattaacaat caacttaacg ttattaacta ctaattttat atcatcccct    1980
ttgataaatg atagtacacc aattaggaag gagcatgctc gcctaggaga ttgtcgtttc    2040
ccgccttcag tttgcaagct gctctagccg tgtagccaat acgcaaaccg cctctccccg    2100
cgcgttggga attactagcg cgtgtcgaca agcttgcatg ccggtcaaca tggtggagca    2160
```

-continued

```
cgacacactt gtctactcca aaaatatcaa agatacagtc tcagaagacc aaagggcaat    2220
tgagactttt caacaaaggg taatatccgg aaacctcctc ggattccatt gcccagctat    2280
ctgtcacttt attgtgaaga tagtggaaaa ggaaggtggc tcctacaaat gccatcattg    2340
cgataaagga aaggccatcg ttgaagatgc ctctgccgac agtggtccca agatggacc     2400 cccacccacg aggagcatcg tggaaaaaga agacgttcca accacgtctt caaagcaagt    2460
ggattgatgt gataacatgg tggagcacga cacacttgtc tactccaaaa atatcaaaga    2520
tacagtctca gaagaccaaa gggcaattga acttttcaa caaagggtaa tatccggaaa     2580
cctcctcgga ttccattgcc cagctatctg tcactttatt gtgaagatag tggaaaagga    2640
aggtggctcc tacaaatgcc atcattgcga taaaggaaag gccatcgttg aagatgcctc    2700
tgccgacagt ggtcccaaag atggacccc acccacgagg agcatcgtgg aaaaagaaga    2760
cgttccaacc acgtcttcaa agcaagtgga ttgatgtgat atctccactg acgtaaggga    2820
tgacgcacaa tcccactatc cttcgcaaga cccttcctct atataaggaa gttcatttca    2880
tttggagagg acgtcactcc tcagccaaaa cgacaccccc atctgtctat ccactggccc    2940
ctggatctgc tgcccaaact aactccatgg tgaccctggg atgcctggtc aagggctatt    3000
tccctgagcc agtgacagtg acctggaact ctggatccct gtccagcggt gtgcacacct    3060
tcccagctgt cctgcagtct gacctctaca ctctgagcag ctcagtgact gtcccctcca    3120
gcacctggcc cagcgagacc gtcacctgca acgttgccca cccggccagc agcaccaagg    3180
tggacaagaa aattgtgccc agggattgtg gttgtaagcc ttgcatatgt acagtcccag    3240
aagtatcatc tgtcttcatc ttccccccaa agcccaagga tgtgctcacc attactctga    3300
ctcctaaggt cacgtgtgtt gtggtagaca tcagcaagga tgatcccgag gtccagttca    3360
gctggtttgt agatgatgtg gaggtgcaca cagctcagac gcaaccccgg gaggagcagt    3420
tcaacagcac tttccgctca gtcagtgaac ttcccatcat gcaccaggac tggctcaatg    3480
gcaaggagac gtccagattt tggcgatcta ttcaactgtc gccagttcat tggtactggt    3540
agtctccctg ggggcaatca gtttctggat gtgctctaat gggtctctac agtgtagaat    3600
atgtatttaa aggcctattt tctttagttt gaatttactg ttattcggtg tgcatttcta    3660
tgtttggtga gcggttttct gtgctcagag tgtgtttatt ttatgtaatt taatttcttt    3720
gtgagctcct gtttagcagg tcgtcccttc agcaaggaca caaaaagatt ttaattttat    3780
tatcgttcaa acatttggca ataaagtttc ttaagattga atcctgttgc cggtcttgcg    3840
atgattatca tataatttct gttgaattac gttaagcatg taataattaa catgtaatgc    3900
atgacgttat ttatgagatg ggttttatg attagagtcc cgcaattata catttaatac    3960
gcgatagaaa acaaaatata gcgcgcaaac taggataaat tatcgcgcgc ggtgtcatct    4020
atgttactag atctctagag tctcaagctt ggcgcgccca cgtgactagt ggcactggcc    4080
gtcgttttac aacgtcgtga ctgggaaaac cctggcgtta cccaacttaa tcgccttgca    4140
gcacatcccc ctttcgccag ctggcgtaat agcgaagagg cccgcaccga tcgcccttcc    4200
caacagttgc gcagcctgaa tggcgaatgc tagagcagct tgagcttgga tcagattgtc    4260
gtttcccgcc ttcagtttaa actatcagtg tttgacagga tatattggcg ggtaaaccta    4320
agagaaaaga gcgttta                                                   4337
```

<210> SEQ ID NO 23
<211> LENGTH: 48
<212> TYPE: DNA

<213> ORGANISM: Artificial Sequence
<220> FEATURE:
<223> OTHER INFORMATION: Primer IF-(2X35S+C)_CPMV160.c

<400> SEQUENCE: 23
tttcatttgg agaggctatt aaaatcttaa taggttttga taaaagcg　　　　　　　　48

<210> SEQ ID NO 24
<211> LENGTH: 59
<212> TYPE: DNA
<213> ORGANISM: Artificial Sequence
<220> FEATURE:
<223> OTHER INFORMATION: Primer nbGT61_Dasher.c

<400> SEQUENCE: 24 agggttttt gaaaagcaaa ttgatcgaaa atgactgccc tgaccgaagg tgctaagct　　59

<210> SEQ ID NO 25
<211> LENGTH: 74
<212> TYPE: DNA
<213> ORGANISM: Artificial Sequence
<220> FEATURE:
<223> OTHER INFORMATION: Primer IF-nbGT61.c

<400> SEQUENCE: 25
tttcatttgg agaggcatcc agaagtagga attcttcagt ataatctagg gttttttgaa　　60 aagcaaattg atcg　　　　　　　　　　　　　　　　　　　　　　　　　　　　74

<210> SEQ ID NO 26
<211> LENGTH: 59
<212> TYPE: DNA
<213> ORGANISM: Artificial Sequence
<220> FEATURE:
<223> OTHER INFORMATION: Primer nbATL75_Dasher.c

<400> SEQUENCE: 26
gattctcggt tctcttcttc tacagcaaca atgactgccc tgaccgaagg tgctaagct　　59

<210> SEQ ID NO 27
<211> LENGTH: 87
<212> TYPE: DNA
<213> ORGANISM: Artificial Sequence
<220> FEATURE:
<223> OTHER INFORMATION: Primer IF-nbATL75.c

<400> SEQUENCE: 27
tttcatttgg agaggcatct ccaccaccaa aaaccctaat cgcctctccg tttcttcatc　　60 agattctcgg ttctcttctt ctacagc　　　　　　　　　　　　　　　　　　　87

<210> SEQ ID NO 28
<211> LENGTH: 59
<212> TYPE: DNA
<213> ORGANISM: Artificial Sequence
<220> FEATURE:
<223> OTHER INFORMATION: Primer nbDJ46_Dasher.c

<400> SEQUENCE: 28
taaacaaatt aaagaatttt aagaaaaaca agatgactgc cctgaccgaa ggtgctaag　　59

<210> SEQ ID NO 29
<211> LENGTH: 59
<212> TYPE: DNA
<213> ORGANISM: Artificial Sequence
<220> FEATURE:
<223> OTHER INFORMATION: Primer IF-nbDJ46.c

```
<400> SEQUENCE: 29
tttcatttgg agaggcactc accaagaaaa taaacaaatt aaagaattt  aagaaaaac      59

<210> SEQ ID NO 30
<211> LENGTH: 59
<212> TYPE: DNA
<213> ORGANISM: Artificial Sequence
<220> FEATURE:
<223> OTHER INFORMATION: Primer nbCHP79_Dasher.c

<400> SEQUENCE: 30
ttctgatttt ctgtgatttc tacaaatctg agacatgact gccctgaccg aaggtgcta      59

<210> SEQ ID NO 31
<211> LENGTH: 86
<212> TYPE: DNA
<213> ORGANISM: Artificial Sequence
<220> FEATURE:
<223> OTHER INFORMATION: Primer IF-nbCHP79.c

<400> SEQUENCE: 31
tttcatttgg agaggcattc tgccctcagt taactaaatt atctctctga ttaacagtac      60
tttctgattt tctgtgattt ctacaa                                          86

<210> SEQ ID NO 32
<211> LENGTH: 59
<212> TYPE: DNA
<213> ORGANISM: Artificial Sequence
<220> FEATURE:
<223> OTHER INFORMATION: Primer nbEN42_Dasher.c

<400> SEQUENCE: 32
ctccattgaa atagagaaaa gaaatagcc atgactgccc tgaccgaagg tgctaagct       59

<210> SEQ ID NO 33
<211> LENGTH: 52
<212> TYPE: DNA
<213> ORGANISM: Artificial Sequence
<220> FEATURE:
<223> OTHER INFORMATION: Primer IF-nbEN42.c

<400> SEQUENCE: 33
tttcatttgg agaggcactt ttgtatagct ccattgaaat agagaaaga aa              52

<210> SEQ ID NO 34
<211> LENGTH: 59
<212> TYPE: DNA
<213> ORGANISM: Artificial Sequence
<220> FEATURE:
<223> OTHER INFORMATION: Primer nb30S72_Dasher.c

<400> SEQUENCE: 34
tgcttacttc gctgttagtg caattccaaa ccatgactgc cctgaccgaa ggtgctaag      59

<210> SEQ ID NO 35
<211> LENGTH: 85
<212> TYPE: DNA
<213> ORGANISM: Artificial Sequence
<220> FEATURE:
<223> OTHER INFORMATION: Primer IF-nb30S72.c

<400> SEQUENCE: 35
tttcatttgg agaggcatct ttccctcaaa accctagccg cagtcacttc cgtaggtgct     60
```
tacttcgctg ttagtgcaat tccaa        85

<210> SEQ ID NO 36
<211> LENGTH: 59
<212> TYPE: DNA
<213> ORGANISM: Artificial Sequence
<220> FEATURE:
<223> OTHER INFORMATION: Primer nbPV55_Dasher.c

<400> SEQUENCE: 36
ccctcttctc caaaaaaaac tctgctgtag tcatgactgc cctgaccgaa ggtgctaag        59

<210> SEQ ID NO 37
<211> LENGTH: 70
<212> TYPE: DNA
<213> ORGANISM: Artificial Sequence
<220> FEATURE:
<223> OTHER INFORMATION: Primer IF-nbPV55.c

<400> SEQUENCE: 37
tttcatttgg agaggcaatt aaagatcaat tcactgtatc cctcttctcc aaaaaaaact        60
ctgctgtagt        70

<210> SEQ ID NO 38
<211> LENGTH: 59
<212> TYPE: DNA
<213> ORGANISM: Artificial Sequence
<220> FEATURE:
<223> OTHER INFORMATION: Primer nbPPI43_Dasher.c

<400> SEQUENCE: 38
cagcgaaaac ctcactgaaa tatttagaga gatgactgcc ctgaccgaag gtgctaagc        59

<210> SEQ ID NO 39
<211> LENGTH: 57
<212> TYPE: DNA
<213> ORGANISM: Artificial Sequence
<220> FEATURE:
<223> OTHER INFORMATION: Primer IF-nbPPI43.c

<400> SEQUENCE: 39
tttcatttgg agaggcacaa atcgtacaca gcgaaaacct cactgaaata tttagag        57

<210> SEQ ID NO 40
<211> LENGTH: 59
<212> TYPE: DNA
<213> ORGANISM: Artificial Sequence
<220> FEATURE:
<223> OTHER INFORMATION: Primer nbPM64_Dasher.c

<400> SEQUENCE: 40
agagccagaa gaagaaaaag aagaagagag caatgactgc cctgaccgaa ggtgctaag        59

<210> SEQ ID NO 41
<211> LENGTH: 79
<212> TYPE: DNA
<213> ORGANISM: Artificial Sequence
<220> FEATURE:
<223> OTHER INFORMATION: Primer IF-nbPM64.c

<400> SEQUENCE: 41
tttcatttgg agaggcagaa agatttgttt cctctgaaat agttttacag agccagaaga        60
agaaaaagaa gaagagagc        79

```
<210> SEQ ID NO 42
<211> LENGTH: 59
<212> TYPE: DNA
<213> ORGANISM: Artificial Sequence
<220> FEATURE:
<223> OTHER INFORMATION: Primer nbH2A86_Dasher.c

<400> SEQUENCE: 42
gtattcaagc ttcgtaaact ttcattcaca tcaatgactg ccctgaccga aggtgctaa    59

<210> SEQ ID NO 43
<211> LENGTH: 100
<212> TYPE: DNA
<213> ORGANISM: Artificial Sequence
<220> FEATURE:
<223> OTHER INFORMATION: Primer IF-nbH2A86.c

<400> SEQUENCE: 43
tttcatttgg agaggcactc aacactcaaa tcgcaatcca aaagcttcaa ttttcctaa     60 tacttctctg tattcaagct tcgtaaactt tcattcacat                         100

<210> SEQ ID NO 44
<211> LENGTH: 59
<212> TYPE: DNA
<213> ORGANISM: Artificial Sequence
<220> FEATURE:
<223> OTHER INFORMATION: Primer atHSP69_Dasher.c

<400> SEQUENCE: 44
ccaaaaaaaa cacagacctt aaaaaaataa aaatgactgc cctgaccgaa ggtgctaag    59

<210> SEQ ID NO 45
<211> LENGTH: 84
<212> TYPE: DNA
<213> ORGANISM: Artificial Sequence
<220> FEATURE:
<223> OTHER INFORMATION: Primer IF-atHSP69.c

<400> SEQUENCE: 45
tttcatttgg agaggcaaat tcaaaattta acacacaaac acaaacacac acccaaaaa    60 aaacacagac cttaaaaaaa taaa                                          84

<210> SEQ ID NO 46
<211> LENGTH: 59
<212> TYPE: DNA
<213> ORGANISM: Artificial Sequence
<220> FEATURE:
<223> OTHER INFORMATION: Primer atGRP62_Dasher.c

<400> SEQUENCE: 46
aagaaaataa accctaagaa tatatcgaaa atgactgccc tgaccgaagg tgctaagct    59

<210> SEQ ID NO 47
<211> LENGTH: 77
<212> TYPE: DNA
<213> ORGANISM: Artificial Sequence
<220> FEATURE:
<223> OTHER INFORMATION: Primer IF-atGRP62.c

<400> SEQUENCE: 47
tttcatttgg agaggcataa caaaacaaga ttttgaagta aaacataaaa gaaaataaac    60
cctaagaata tatcgaa                                                  77

<210> SEQ ID NO 48
```

```
<211> LENGTH: 59
<212> TYPE: DNA
<213> ORGANISM: Artificial Sequence
<220> FEATURE:
<223> OTHER INFORMATION: Primer atPK65_Dasher.c

<400> SEQUENCE: 48
aataaaagat tgtagaatc aactaagaaa atgactgccc tgaccgaagg tgctaagct      59

<210> SEQ ID NO 49
<211> LENGTH: 80
<212> TYPE: DNA
<213> ORGANISM: Artificial Sequence
<220> FEATURE:
<223> OTHER INFORMATION: Primer IF-atPK65.c

<400> SEQUENCE: 49
tttcatttgg agaggcgcaa aaacaaaaat aaaaaaaaca tcgcacaaga aaataaaaga    60
tttgtagaat caactaagaa                                                80

<210> SEQ ID NO 50
<211> LENGTH: 89
<212> TYPE: DNA
<213> ORGANISM: Artificial Sequence
<220> FEATURE:
<223> OTHER INFORMATION: Primer IF-atRP46_Dasher.c

<400> SEQUENCE: 50
tttcatttgg agaggcagaa acaaaagaa ttaaaaaaaa aaaaaaaaa aagaataaag      60 aaatgactgc cctgaccgaa ggtgctaag                                      89

<210> SEQ ID NO 51
<211> LENGTH: 46
<212> TYPE: DNA
<213> ORGANISM: Artificial Sequence
<220> FEATURE:
<223> OTHER INFORMATION: Primer IF-H1cTMCT.s1-4r

<400> SEQUENCE: 51
actaaagaaa ataggccttt aaatacatat tctacactgt agagac                   46

<210> SEQ ID NO 52
<211> LENGTH: 59
<212> TYPE: DNA
<213> ORGANISM: Artificial Sequence
<220> FEATURE:
<223> OTHER INFORMATION: Primer nbGT61_SpPDI.c

<400> SEQUENCE: 52
tagggttttt tgaaaagcaa attgatcgaa aatggcgaaa aacgttgcga ttttcggct     59

<210> SEQ ID NO 53
<211> LENGTH: 59
<212> TYPE: DNA
<213> ORGANISM: Artificial Sequence
<220> FEATURE:
<223> OTHER INFORMATION: Primer nbATL75_SpPDI.c

<400> SEQUENCE: 53
ttctcggttc tcttcttcta cagcaacaat ggcgaaaaac gttgcgattt tcggcttat     59

<210> SEQ ID NO 54
<211> LENGTH: 59
<212> TYPE: DNA
<213> ORGANISM: Artificial Sequence
```

```
<220> FEATURE:
<223> OTHER INFORMATION: Primer nbDJ46_SpPDI.c

<400> SEQUENCE: 54
aaacaaatta agaattta agaaaaacaa gatggcgaaa acgttgcga ttttcggct      59

<210> SEQ ID NO 55
<211> LENGTH: 59
<212> TYPE: DNA
<213> ORGANISM: Artificial Sequence
<220> FEATURE:
<223> OTHER INFORMATION: Primer nbCHP79_SpPDI.c

<400> SEQUENCE: 55
ctttctgatt ttctgtgatt tctacaaatc tgagacatgg cgaaaaacgt tgcgatttt   59

<210> SEQ ID NO 56
<211> LENGTH: 59
<212> TYPE: DNA
<213> ORGANISM: Artificial Sequence
<220> FEATURE:
<223> OTHER INFORMATION: Primer nbEN42_SpPDI.c

<400> SEQUENCE: 56
gctccattga aatagagaaa agaaaatagc catggcgaaa acgttgcga ttttcggct    59

<210> SEQ ID NO 57
<211> LENGTH: 59
<212> TYPE: DNA
<213> ORGANISM: Artificial Sequence
<220> FEATURE:
<223> OTHER INFORMATION: Primer nb30S72_SpPDI.c

<400> SEQUENCE: 57
aggtgcttac ttcgctgtta gtgcaattcc aaaccatggc gaaaaacgtt gcgattttc   59

<210> SEQ ID NO 58
<211> LENGTH: 59
<212> TYPE: DNA
<213> ORGANISM: Artificial Sequence
<220> FEATURE:
<223> OTHER INFORMATION: Primer nbMT78_SpPDI.c

<400> SEQUENCE: 58
tattatctcc caacaacata agaaaacaat ggcgaaaaac gttgcgattt tcggcttat   59

<210> SEQ ID NO 59
<211> LENGTH: 59
<212> TYPE: DNA
<213> ORGANISM: Artificial Sequence
<220> FEATURE:
<223> OTHER INFORMATION: Primer nbPV55_SpPDI.c

<400> SEQUENCE: 59
cctcttctcc aaaaaaaact ctgctgtagt catggcgaaa acgttgcga ttttcggct    59

<210> SEQ ID NO 60
<211> LENGTH: 59
<212> TYPE: DNA
<213> ORGANISM: Artificial Sequence
<220> FEATURE:
<223> OTHER INFORMATION: Primer nbPPI43_SpPDI.c

<400> SEQUENCE: 60
cagcgaaaac ctcactgaaa tatttagaga gatggcgaaa acgttgcga ttttcggct    59
```

```
<210> SEQ ID NO 61
<211> LENGTH: 59
<212> TYPE: DNA
<213> ORGANISM: Artificial Sequence
<220> FEATURE:
<223> OTHER INFORMATION: Primer nbPM64_SpPDI.c

<400> SEQUENCE: 61
cagaagaaga aaagaagaa gagagcaatg gcgaaaaacg ttgcgatttt cggcttatt        59

<210> SEQ ID NO 62
<211> LENGTH: 59
<212> TYPE: DNA
<213> ORGANISM: Artificial Sequence
<220> FEATURE:
<223> OTHER INFORMATION: Primer nbH2A86_SpPDI.c

<400> SEQUENCE: 62
caagcttcgt aaactttcat tcacatcaat ggcgaaaaac gttgcgattt tcggcttat        59

<210> SEQ ID NO 63
<211> LENGTH: 59
<212> TYPE: DNA
<213> ORGANISM: Artificial Sequence
<220> FEATURE:
<223> OTHER INFORMATION: Primer atHSP69_SpPDI.c

<400> SEQUENCE: 63
caaaaaaaac acagacctta aaaaaataaa aatggcgaaa aacgttgcga ttttcggct        59

<210> SEQ ID NO 64
<211> LENGTH: 59
<212> TYPE: DNA
<213> ORGANISM: Artificial Sequence
<220> FEATURE:
<223> OTHER INFORMATION: Primer atGRP62_SpPDI.c

<400> SEQUENCE: 64
aaagaaaata aaccctaaga atatatcgaa aatggcgaaa aacgttgcga ttttcggct        59

<210> SEQ ID NO 65
<211> LENGTH: 59
<212> TYPE: DNA
<213> ORGANISM: Artificial Sequence
<220> FEATURE:
<223> OTHER INFORMATION: atPK65_SpPDI.c

<400> SEQUENCE: 65
aaataaaaga tttgtagaat caactaagaa aatggcgaaa aacgttgcga ttttcggct        59

<210> SEQ ID NO 66
<211> LENGTH: 89
<212> TYPE: DNA
<213> ORGANISM: Artificial Sequence
<220> FEATURE:
<223> OTHER INFORMATION: Primer IF-atRP46_SpPDI.c

<400> SEQUENCE: 66
tttcatttgg agaggcagaa acaaaaagaa ttaaaaaaaa aaaaaaaaaa aagaataaag        60
aaatggcgaa aaacgttgcg attttcggc                                        89

<210> SEQ ID NO 67
<211> LENGTH: 51
<212> TYPE: DNA
<213> ORGANISM: Artificial Sequence
```

<220> FEATURE:
<223> OTHER INFORMATION: Primer IF-H3_Swi_13.r

<400> SEQUENCE: 67
actaaagaaa ataggccttc aaatgcaaat gttgcaccta atgttgccct t         51

<210> SEQ ID NO 68
<211> LENGTH: 48
<212> TYPE: DNA
<213> ORGANISM: Artificial Sequence
<220> FEATURE:
<223> OTHER INFORMATION: Primer IF-GII4Syd12VP1.r

<400> SEQUENCE: 68
actaaagaaa ataggccttc agacagccct gcgtctgcca gtcccatt              48

<210> SEQ ID NO 69
<211> LENGTH: 59
<212> TYPE: DNA
<213> ORGANISM: Artificial Sequence
<220> FEATURE:
<223> OTHER INFORMATION: Primer nbATL75+GII4Syd12.c

<400> SEQUENCE: 69
ttctcggttc tcttcttcta cagcaacaat gaaaatggcc tcgagtgacg ctaaccta   59

<210> SEQ ID NO 70
<211> LENGTH: 59
<212> TYPE: DNA
<213> ORGANISM: Artificial Sequence
<220> FEATURE:
<223> OTHER INFORMATION: Primer nbCHP79+GII4Syd12.c

<400> SEQUENCE: 70
ttctgatttt ctgtgatttc tacaaatctg agacatgaaa atggcctcga gtgacgcta   59

<210> SEQ ID NO 71
<211> LENGTH: 59
<212> TYPE: DNA
<213> ORGANISM: Artificial Sequence
<220> FEATURE:
<223> OTHER INFORMATION: Primer nbMT78+GII4Syd12.c

<400> SEQUENCE: 71
tctattatct cccaacaaca taagaaaaca atgaaaatgg cctcgagtga cgctaaccc   59

<210> SEQ ID NO 72
<211> LENGTH: 59
<212> TYPE: DNA
<213> ORGANISM: Artificial Sequence
<220> FEATURE:
<223> OTHER INFORMATION: Primer atHSP69+GII4Syd12.c

<400> SEQUENCE: 72
aaacacagac cttaaaaaaa taaaaatgaa aatggcctcg agtgacgcta accctagtg   59

<210> SEQ ID NO 73
<211> LENGTH: 51
<212> TYPE: DNA
<213> ORGANISM: Artificial Sequence
<220> FEATURE:
<223> OTHER INFORMATION: Primer IF -HC(Ritux).s1-6r

<400> SEQUENCE: 73
actaaagaaa ataggccttc actttccagg agaaagagaa agggactttt g          51

<210> SEQ ID NO 74
<211> LENGTH: 51
<212> TYPE: DNA
<213> ORGANISM: Artificial Sequence
<220> FEATURE:
<223> OTHER INFORMATION: IF -LC(Ritux).s1-6r

<400> SEQUENCE: 74
actaaagaaa ataggccttc aacactctcc cctgttgaag ctctttgtga c        51

<210> SEQ ID NO 75
<211> LENGTH: 1959
<212> TYPE: DNA
<213> ORGANISM: Artificial Sequencw
<220> FEATURE:
<223> OTHER INFORMATION: Construct 4467 (Dasher) from 2X35S promoter to
      NOS terminator

<400> SEQUENCE: 75
gtcaacatgg tggagcacga cacacttgtc tactccaaaa atatcaaaga tacagtctca    60
gaagaccaaa gggcaattga acttttcaa caaagggtaa tatccggaaa cctcctcgga   120
ttccattgcc cagctatctg tcactttatt gtgaagatag tggaaaagga aggtggctcc   180
tacaaatgcc atcattgcga taaggaaag gccatcgttg aagatgcctc tgccgacagt    240
ggtcccaaag atggacccc acccacgagg agcatcgtgg aaaagaaga cgttccaacc    300 acgtcttcaa gcaagtgga ttgatgtgat aacatggtgg agcacgacac acttgtctac   360
tccaaaaata tcaaagatac agtctcagaa gaccaaaggg caattgagac ttttcaacaa   420
agggtaatat ccggaaacct cctcggattc cattgcccag ctatctgtca ctttattgtg   480
aagatagtgg aaaaggaagg tggctcctac aaatgccatc attgcgataa ggaaaggcc   540 atcgttgaag atgcctctgc cgacagtggt cccaaagatg gacccccacc cacgaggagc   600
atcgtggaaa aagaagacgt tccaaccacg tcttcaaagc aagtggattg atgtgatatc   660
tccactgacg taagggatga cgcacaatcc cactatcctt cgcaagaccc ttcctctata   720
taaggaagtt catttcattt ggagaggcac acaatttgct ttagtgatta aacttctttt   780
tacaacaaat taaggtctta ttatctccca acaacataag aaaacaatga ctgccctgac   840
cgaaggtgct aagctgtttg agaaggagat tccgtacatc accgagctgg aaggggacgt   900
cgaaggaatg aagttcatca tcaagggaga aggaaccggg gacgctacga ctggaaccat   960
taaggccaag tatatctgta ccactggaga tctgccagtg ccttgggcca cccttgtgtc  1020
aaccctctcg tatggagtgc agtgttttgc taagtaccct agccacatta aggacttctt  1080
caaatccgcc atgccggaag ttatacccca agagcgcacc atttcttttg agggagatgg  1140
agtgtacaag acccgcgcga tggtcaccta tgagagggga tctatctaca accgggtgac  1200
tctgactgga gaaaacttta agaaggacgg gcatattctt cggaagaatg tcgccttcca  1260
gtgccctccc agcatccttt acattctccc cgacactgtg aacaacgaa tccgcgtgga   1320 gttcaatcaa gcctacgaca tcgagggggt gacggagaag ctggtgacca agtgtagcca  1380
gatgaatcgg ccactggccg gttcagcggc tgtccacatt ccgcgctacc atcatatcac  1440
ttatcacact aagctctcca agaccgcga tgagaggaga gatcacatgt gcctggtgga  1500
agtggtcaag gccgtcgatc tcgatacccta tcagtaaagg cctatttttct ttagtttgaa  1560 tttactgtta ttcggtgtgc atttctatgt ttggtgagcg gttttctgtg ctcagagtgt  1620 gtttattttta tgtaatttaa tttctttgtg agctcctgtt tagcaggtcg tcccttcagc  1680

| | |
|---|---|
| aaggacacaa aaagatttta attttattat cgttcaaaca tttggcaata aagtttctta | 1740 |
| agattgaatc ctgttgccgg tcttgcgatg attatcatat aatttctgtt gaattacgtt | 1800 |
| aagcatgtaa taattaacat gtaatgcatg acgttattta tgagatgggt ttttatgatt | 1860 |
| agagtcccgc aattatacat ttaatacgcg atagaaaaca aaatatagcg cgcaaactag | 1920 |
| gataaattat cgcgcgcggt gtcatctatg ttactagat | 1959 |

<210> SEQ ID NO 76
<211> LENGTH: 6156
<212> TYPE: DNA
<213> ORGANISM: Artificial Sequence
<220> FEATURE:
<223> OTHER INFORMATION: Cloning vector (for H3 and HA B) 4160 from left
to right T-DNA

<400> SEQUENCE: 76

| | |
|---|---|
| tggcaggata tattgtggtg taaacaaatt gacgcttaga caacttaata acacattgcg | 60 |
| gacgtttta atgtactgaa ttaacgccga atcccgggct ggtatattta tatgttgtca | 120 |
| aataactcaa aaccataaa agtttaagtt agcaagtgtg tacatttta cttgaacaaa | 180 |
| aatattcacc tactactgtt ataaatcatt attaaacatt agagtaaaga aatatggatg | 240 |
| ataagaacaa gagtagtgat attttgacaa caattttgtt gcaacatttg agaaaatttt | 300 |
| gttgttctct cttttcattg gtcaaaaaca atagagagag aaaaggaag agggagaata | 360 |
| aaaacataat gtgagtatga gagagaaagt tgtacaaaag ttgtaccaaa atagttgtac | 420 |
| aaatatcatt gaggaatttg acaaaagcta cacaaataag ggttaattgc tgtaaataaa | 480 |
| taaggatgac gcattagaga gatgtaccat tagagaattt ttggcaagtc attaaaaaga | 540 |
| aagaataaat tatttttaaa attaaaagtt gagtcatttg attaaacatg tgattatta | 600 |
| atgaattgat gaaagagttg gattaaagtt gtattagtaa ttagaatttg gtgtcaaatt | 660 |
| taatttgaca tttgatcttt tcctatatat tgccccatag agtcagttaa ctcatttta | 720 |
| tatttcatag atcaaataag agaaataacg gtatattaat ccctccaaaa aaaaaaaacg | 780 |
| gtatatttac taaaaaatct aagccacgta ggaggataac aggatccccg taggaggata | 840 |
| acatccaatc caaccaatca caacaatcct gatgagataa cccactttaa gcccacgcat | 900 |
| ctgtggcaca tctacattat ctaaatcaca cattcttcca cacatctgag ccacacaaaa | 960 |
| accaatccac atcttatca cccattctat aaaaaatcac actttgtgag tctacacttt | 1020 |
| gattcccttc aaacacatac aaagagaaga gactaattaa ttaattaatc atcttgagag | 1080 |
| aaaatggaac gagctataca aggaaacgac gctagggaac aagctaacag tgaacgttgg | 1140 |
| gatggaggat caggaggtac cacttctccc ttcaaacttc ctgacgaaag tccgagttgg | 1200 |
| actgagtggc ggctacataa cgatgagacg aattcgaatc aagataatcc ccttggtttc | 1260 |
| aaggaaagct ggggtttcgg gaagttgta tttaagagat atctcagata cgacaggacg | 1320 |
| gaagcttcac tgcacagagt ccttggatct tggacgggag attcggttaa ctatgcagca | 1380 |
| tctcgatttt tcggtttcga ccagatcgga tgtacctata gtattcggtt tcgaggagtt | 1440 |
| agtatcaccg tttctggagg gtcgcgaact cttcagcatc tctgtgagat ggcaattcgg | 1500 |
| tctaagcaag aactgctaca gcttgccca atcgaagtgg aaagtaatgt atcaagagga | 1560 |
| tgccctgaag gtactcaaac cttcgaaaaa gaaagcgagt aagttaaaat gcttcttcgt | 1620 |
| ctcctatta taatatggtt tgttattgtt aattttgttc ttgtagaaga gcttaattaa | 1680 |
| tcgttgttgt tatgaaatac tatttgtatg agatgaactg gtgtaatgta attcatttac | 1740 |

```
ataagtggag tcagaatcag aatgtttcct ccataactaa ctagacatga agacctgccg    1800
cgtacaattg tcttatattt gaacaactaa aattgaacat cttttgccac aactttataa    1860
gtggttaata tagctcaaat atatggtcaa gttcaataga ttaataatgg aaatatcagt    1920
tatcgaaatt cattaacaat caacttaacg ttattaacta ctaattttat atcatcccct    1980
ttgataaatg atagtacacc aattaggaag gagcatgctc gcctaggaga ttgtcgtttc    2040
ccgccttcag tttgcaagct gctctagccg tgtagccaat acgcaaaccg cctctccccg    2100
cgcgttggga attactagcg cgtgtcgaca cgcgtggcgc gccctggtat atttatatgt    2160
tgtcaaataa ctcaaaaacc ataaaagttt aagttagcaa gtgtgtacat ttttacttga    2220
acaaaaatat tcacctacta ctgttataaa tcattattaa acattagagt aaagaaatat    2280
ggatgataag aacaagagta gtgatatttt gacaacaatt ttgttgcaac atttgagaaa    2340
attttgttgt tctctctttt cattggtcaa aaacaataga gagagaaaaa ggaagaggga    2400
gaataaaaac ataatgtgag tatgagagag aaagttgtac aaaagttgta ccaaaatagt    2460
tgtacaaata tcattgagga atttgacaaa agctacacaa ataaggggtta attgctgtaa    2520
ataaataagg atgacgcatt agagagatgt accattagag aattttttggc aagtcattaa    2580
aaagaaagaa taaattattt ttaaaattaa aagttgagtc atttgattaa acatgtgatt    2640
atttaatgaa ttgatgaaag agttggatta aagttgtatt agtaattaga atttggtgtc    2700
aaatttaatt tgacatttga tcttttccta tatattgccc catagagtca gttaactcat    2760
ttttatattt catagatcaa ataagagaaa taacggtata ttaatccctc caaaaaaaaa    2820
aaacggtata tttactaaaa aatctaagcc acgtaggagg ataacaggat ccccgtagga    2880
ggataacatc caatccaacc aatcacaaca atcctgatga gataacccac tttaagccca    2940
cgcatctgtg gcatctctac attatctaaa tcacacattc ttccacacat ctgagccaca    3000
caaaaaccaa tccacatctt tatcacccat tctataaaaa atcacacttt gtgagtctac    3060
actttgattc ccttcaaaca catacaaaga gaagagacta attaattaat taatcatctt    3120
gagagaaaat gagtcttcta accgaggtcg aaacgcctat cagaaacgaa tggggggtgca    3180
gatgcaacga ttcaagtgat cctcttgttg ttgccgcaag tataattggg attgtgcacc    3240
tgatattgtg gattattgat cgcccttttt tccaaaagcat ttatcgtatc tttaaacacg    3300
gtttaaaaag agggccttct acggaaggag taccagagtc tatgagggaa gaatatcgag    3360
aggaacagca gaatgctgtg gatgctgacg atggtcattt tgtcagcata gagctggagt    3420
aagagctcta agttaaaatg cttcttcgtc tcctatttat aatatggttt gttattgtta    3480
attttgttct tgtagaagag cttaattaat cgttgttgtt atgaaatact atttgtatga    3540
gatgaactgg tgtaatgtaa ttcatttaca taagtggagt cagaatcaga atgtttcctc    3600
cataactaac tagacatgaa gacctgccgc gtacaattgt cttatatttg aacaactaaa    3660
attgaacatc ttttgccaca actttataag tggttaatat agctcaaata tatggtcaag    3720
ttcaatagat taataatgga aatatcagtt atcgaaattc attaacaatc aacttaacgt    3780
tattaactac taattttata tcatcccctt tgataaatga tagtacacca attaggaagg    3840
aactaggaga ttgtcgtttc ccgccttcag tttgcaagct gctctagccg tgtagccaat    3900
acgcaaaccg cctctccccg cgcgttggga attactagcg cgtgtcgaca agcttgcatg    3960
ccggtcaaca tggtggagca cgacacactt gtctactcca aaaatatcaa agatacagtc    4020
tcagaagacc aaagggcaat tgagactttt caacaagggg taatatccgg aaacctcctc    4080
ggattccatt gcccagctat ctgtcacttt attgtgaaga tagtggaaaa ggaaggtggc    4140
```

```
tcctacaaat gccatcattg cgataaagga aaggccatcg ttgaagatgc ctctgccgac   4200
agtggtccca agatggacc cccacccacg aggagcatcg tggaaaaaga agacgttcca   4260
accacgtctt caaagcaagt ggattgatgt gataacatgg tggagcacga cacacttgtc   4320
tactccaaaa atatcaaaga tacagtctca gaagaccaaa gggcaattga acttttcaa   4380 caaagggtaa tatccggaaa cctcctcgga ttccattgcc cagctatctg tcactttatt   4440
gtgaagatag tggaaaagga aggtggctcc tacaaatgcc atcattgcga taaggaaag   4500 gccatcgttg aagatgcctc tgccgacagt ggtcccaaag atggaccccc acccacgagg   4560
agcatcgtgg aaaagaaga cgttccaacc acgtcttcaa agcaagtgga ttgatgtgat   4620
atctccactg acgtaaggga tgacgcacaa tcccactatc cttcgcaaga cccttcctct   4680
atataaggaa gttcatttca tttggagaga cgtcactcct cagccaaaac gacacccca   4740 tctgtctatc cactggcccc tggatctgct gcccaaacta actccatggt gaccctggga   4800
tgcctggtca agggctattt ccctgagcca gtgacagtga cctggaactc tggatccctg   4860
tccagcggtg tgcacacctt cccagctgtc ctgcagtctg acctctacac tctgagcagc   4920
tcagtgactg tccctccag cacctggccc agcgagaccg tcacctgcaa cgttgcccac   4980
ccggccagca gcaccaaggt ggacaagaaa attgtgccca gggattgtgg ttgtaagcct   5040
tgcatatgta cagtcccaga agtatcatct gtcttcatct tcccccaaa gcccaaggat   5100 gtgctcacca ttactctgac tcctaaggtc acgtgtgttg tggtagacat cagcaaggat   5160
gatcccgagg tccagttcag ctggtttgta gatgatgtgg aggtgcacac agctcagacg   5220
caaccccggg aggagcagtt caacagcact ttccgctcag tcagtgaact tcccatcatg   5280
caccaggact ggctcaatgg caaggagacg tccagatttt ggcgatctat tcaactgtcg   5340
ccagttcatt ggtactggta gtctccctgg gggcaatcag tttctggatg tgctctaatg   5400
ggtctctaca gtgtagaata tgtatttaaa ggcctatttt ctttagtttg aatttactgt   5460
tattcggtgt gcatttctat gtttggtgag cggttttctg tgctcagagt gtgtttattt   5520
tatgtaattt aatttctttg tgagctcctg tttagcaggt cgtcccttca gcaaggacac   5580
aaaaagattt taatttatt atcgttcaaa catttggcaa taaagtttct taagattgaa   5640
tcctgttgcc ggtcttgcga tgattatcat ataatttctg ttgaattacg ttaagcatgt   5700
aataattaac atgtaatgca tgacgttatt tatgagatgg ttttttatga ttagagtccc   5760
gcaattatac atttaatacg cgatagaaaa caaatatag cgcgcaaact aggataaatt   5820
atcgcgcgcg gtgtcatcta tgttactaga tctctagagt ctcaagcttg gcgcgcccac   5880
gtgactagtg gcactggccg tcgttttaca acgtcgtgac tgggaaaacc ctggcgttac   5940
ccaacttaat cgccttgcag cacatccccc tttcgccagc tggcgtaata gcgaagaggc   6000
ccgcaccgat cgcccttccc aacagttgcg cagcctgaat ggcgaatgct agagcagctt   6060
gagcttggat cagattgtcg tttccccgcct tcagtttaaa ctatcagtgt ttgacaggat   6120
atattggcgg gtaaacctaa gagaaaagag cgttta                             6156
```

<210> SEQ ID NO 77
<211> LENGTH: 5502
<212> TYPE: DNA
<213> ORGANISM: Artificial Sequence
<220> FEATURE:
<223> OTHER INFORMATION: Cloning vector (for Norovirus VP1) 4170 from
      left to right T-DNA

<400> SEQUENCE: 77

-continued

```
tggcaggata tattgtggtg taaacaaatt gacgcttaga caacttaata acacattgcg      60
gacgttttta atgtactgaa ttaacgccga atcccgggct ggtatattta tatgttgtca     120
aataactcaa aaaccataaa agtttaagtt agcaagtgtg tacattttta cttgaacaaa     180
aatattcacc tactactgtt ataaatcatt attaaacatt agagtaaaga aatatggatg     240
ataagaacaa gagtagtgat attttgacaa caattttgtt gcaacatttg agaaaatttt     300
gttgttctct cttttcattg gtcaaaaaca atagagagag aaaaaggaag agggagaata     360
aaaacataat gtgagtatga gagagaaagt tgtacaaaag ttgtaccaaa atagttgtac     420
aaatatcatt gaggaatttg acaaaagcta cacaaataag ggttaattgc tgtaaataaa     480
taaggatgac gcattagaga gatgtaccat tagagaattt ttggcaagtc attaaaaaga     540
aagaataaat tattttttaaa attaaaagtt gagtcatttg attaaacatg tgattattta     600
atgaattgat gaaagagttg gattaaagtt gtattagtaa ttagaatttg gtgtcaaatt     660
taatttgaca tttgatcttt tcctatatat tgccccatag agtcagttaa ctcatttttta    720 tatttcatag atcaaataag agaaataacg gtatattaat ccctccaaaa aaaaaaaacg     780
gtatatttac taaaaaatct aagccacgta ggaggataac aggatccccg taggaggata     840
acatccaatc caaccaatca caacaatcct gatgagataa cccactttaa gcccacgcat     900
ctgtggcaca tctacattat ctaaatcaca cattcttcca cacatctgag ccacacaaaa     960
accaatccac atctttatca cccattctat aaaaaatcac actttgtgag tctacacttt    1020
gattcccttc aaacacatac aaagagaaga gactaattaa ttaattaatc atcttgagag    1080
aaaatggaac gagctataca aggaaacgac gctagggaac aagctaacag tgaacgttgg    1140
gatggaggat caggaggtac cacttctccc ttcaaacttc ctgacgaaag tccgagttgg    1200
actgagtggc ggctacataa cgatgagacg aattcgaatc aagataatcc ccttggtttc    1260
aaggaaagct gggggtttcgg gaaagttgta tttaagagat atctcagata cgacaggacg    1320
gaagcttcac tgcacagagt ccttggatct tggacgggag attcggttaa ctatgcagca    1380
tctcgatttt tcggtttcga ccagatcgga tgtacctata gtattcggtt tcgaggagtt    1440
agtatcaccg tttctggagg gtcgcgaact cttcagcatc tctgtgagat ggcaattcgg    1500
tctaagcaag aactgctaca gcttgcccca atcgaagtgg aaagtaatgt atcaagagga    1560
tgccctgaag gtactcaaac cttcgaaaaa gaaagcgagt aagttaaaat gcttcttcgt    1620 ctcctatttta taatatggtt tgttattgtt aattttgttc ttgtagaaga gcttaattaa    1680
tcgttgttgt tatgaaatac tatttgtatg agatgaactg gtgtaatgta attcatttac    1740
ataagtggag tcagaatcag aatgtttcct ccataactaa ctagacatga agacctgccg    1800
cgtacaattg tcttatattt gaacaactaa aattgaacat cttttgccac aactttataa    1860
gtggttaata tagctcaaat atatggtcaa gttcaataga ttaataatgg aaatatcagt    1920
tatcgaaatt cattaacaat caacttaacg ttattaacta ctaattttat atcatccccct   1980 ttgataaatg atagtacacc aattaggaag gagcatgctc gcctaggaga ttgtcgtttc    2040
ccgccttcag tttgcaagct gctctagccg tgtagccaat acgcaaaccg cctctccccg    2100
cgcgttggga attactagcg cgtgtcgaca agcttgcatg ccggtcaaca tggtggagca    2160
cgacacactt gtctactcca aaaatatcaa agatacagtc tcagaagacc aaagggcaat    2220
tgagactttt caacaaaggg taatatccgg aaacctcctc ggattccatt gcccagctat    2280
ctgtcacttt attgtgaaga tagtggaaaa ggaaggtggc tcctacaaat gccatcattg    2340
```

```
cgataaagga aaggccatcg ttgaagatgc ctctgccgac agtggtccca aagatggacc   2400
cccacccacg aggagcatcg tggaaaaaga agacgttcca accacgtctt caaagcaagt   2460
ggattgatgt gataacatgg tggagcacga cacacttgtc tactccaaaa atatcaaaga   2520
tacagtctca gaagaccaaa gggcaattga acttttcaa caaagggtaa tatccggaaa   2580
cctcctcgga ttccattgcc cagctatctg tcactttatt gtgaagatag tggaaaagga   2640
aggtggctcc tacaaatgcc atcattgcga taaaggaaag gccatcgttg aagatgcctc   2700
tgccgacagt ggtcccaaag atggaccccc acccacgagg agcatcgtgg aaaaagaaga   2760
cgttccaacc acgtcttcaa agcaagtgga ttgatgtgat atctccactg acgtaaggga   2820
tgacgcacaa tcccactatc cttcgcaaga cccttcctct ataaaggaa gttcatttca   2880
tttggagaga cgtcactcct cagccaaaac gacacccca tctgtctatc cactggcccc   2940
tggatctgct gcccaaacta actccatggt gaccctggga tgcctggtca agggctattt   3000
ccctgagcca gtgacagtga cctggaactc tggatccctg tccagcggtg tgcacacctt   3060
cccagctgtc ctgcagtctg acctctacac tctgagcagc tcagtgactg tcccctccag   3120
cacctggccc agcgagaccg tcacctgcaa cgttgcccac ccggccagca gcaccaaggt   3180
ggacaagaaa attgtgccca gggattgtgg ttgtaagcct tgcatatgta cagtcccaga   3240
agtatcatct gtcttcatct tccccccaaa gcccaaggat gtgctcacca ttactctgac   3300
tcctaaggtc acgtgtgttg tggtagacat cagcaaggat gatcccgagg tccagttcag   3360
ctggtttgta gatgatgtgg aggtgcacac agctcagacg caaccccggg aggagcagtt   3420
caacagcact ttccgctcag tcagtgaact tcccatcatg caccaggact ggctcaatgg   3480
caaggagacg tccagatttt ggcgatctat tcaactgtcg ccagttcatt ggtactggta   3540
gtctccctgg gggcaatcag tttctggatg tgctctaatg ggtctctaca gtgtagaata   3600
tgtatttaaa ggcctatttt ctttagtttg aatttactgt tattcggtgt gcatttctat   3660
gtttggtgag cggttttctg tgctcagagt gtgtttattt tatgtaattt aatttctttg   3720
tgagctcctg tttagcaggt cgtcccttca gcaaggacac aaaaagattt taatttat   3780
atcgttcaaa catttggcaa taaagtttct taagattgaa tcctgttgcc ggtcttgcga   3840
tgattatcat ataatttctg ttgaattacg ttaagcatgt aataattaac atgtaatgca   3900
tgacgttatt tatgagatgg gttttttatga ttagagtccc gcaattatac atttaatacg   3960
cgatagaaaa caaaatatag cgcgcaaact aggataaatt atcgcgcgcg gtgtcatcta   4020
tgttactaga tctctaggta aaatcccaa ttatatttgg tctaatttag tttggtattg   4080
agtaaaacaa attcgaacca aaccaaaata taaatatata gtttttatat atatgccttt   4140
aagactttt atagaatttt ctttaaaaaa tatcaagaaa tatttgcgac tcttctggca   4200
tgtaatatt cgttaaatat gaagtgctcc atttttatta actttaaata attggttgta   4260
cgatcacttt cttatcaagt gttactaaaa tgcgtcaatc tctttgttct tccatattca   4320
tatgtcaaaa tctatcaaaa ttcttatata tcttttttcga atttgaagtg aaatttcgat   4380
aatttaaaat taaatagaac atatcattat ttaggtatca tattgatttt tatacttaat   4440
tactaaatt ggttaacttt gaaagtgtac atcaacgaaa aattagtcaa acgactaaaa   4500
taaataaata tcatgtgtta ttaagaaaat tctcctataa gaatatttta atagatcata   4560
tgtttgtaaa aaaaattaat ttttactaac acatatattt acttatcaaa aatttgacaa   4620
agtaagatta aaataaatatt catctaacaa aaaaaaaacc agaaaatgct gaaaacccgg   4680
caaaaccgaa ccaatccaaa ccgatatagt tggtttggtt tgattttgat ataaaccgaa   4740
```

| | |
|---|---|
| ccaactcggt ccatttgcac ccctaatcat aatagcttta atatttcaag atattattaa | 4800 |
| gttaacgttg tcaatatcct ggaaattttg caaaatgaat caagcctata tggctgtaat | 4860 |
| atgaatttaa aagcagctcg atgtggtggt aatatgtaat ttacttgatt ctaaaaaaat | 4920 |
| atcccaagta ttaataattt ctgctaggaa aaggttagc tacgatttac agcaaagcca | 4980 |
| gaatacaaag aaccataaag tgattgaagc tcgaaatata cgaaggaaca aatattttta | 5040 |
| aaaaaatacg caatgacttg gaacaaaaga agtgatata ttttttgttc ttaaacaagc | 5100 |
| atcccctcta aagaatggca gttttccttt gcatgtaact attatgctcc cttcgttaca | 5160 |
| aaaatttttgg actactattg gaacttctt ctgaaaattc tagagtctca agcttggcgc | 5220 |
| gcccacgtga ctagtggcac tggccgtcgt tttacaacgt cgtgactggg aaaaccctgg | 5280 |
| cgttacccaa cttaatcgcc ttgcagcaca tccccctttc gccagctggc gtaatagcga | 5340 |
| agaggcccgc accgatcgcc cttcccaaca gttgcgcagc ctgaatggcg aatgctagag | 5400 |
| cagcttgagc ttggatcaga ttgtcgtttc ccgccttcag tttaaactat cagtgtttga | 5460 |
| caggatatat tggcgggtaa acctaagaga aaagagcgtt ta | 5502 |

<210> SEQ ID NO 78
<211> LENGTH: 711
<212> TYPE: DNA
<213> ORGANISM: Artificial Sequence
<220> FEATURE:
<223> OTHER INFORMATION: Dasher primer nucleic acid sequence

<400> SEQUENCE: 78

| | |
|---|---|
| atgactgccc tgaccgaagg tgctaagctg tttgagaagg agattccgta catcaccgag | 60 |
| ctggaagggg acgtcgaagg aatgaagttc atcatcaagg gagaaggaac cggggacgct | 120 |
| acgactggaa ccattaaggc caagtatatc tgtaccactg gagatctgcc agtgccttgg | 180 |
| gccacccttg tgtcaacct ctcgtatgga gtgcagtgtt ttgctaagta ccctagccac | 240 |
| attaaggact tcttcaaatc cgccatgccg gaaggttata cccaagagcg caccatttct | 300 |
| tttgagggag atggagtgta caagacccgc gcgatggtca cctatgagag ggatctatc | 360 |
| tacaaccggg tgactctgac tggagaaaac tttaagaagg acgggcatat tcttcggaag | 420 |
| aatgtcgcct ccagtgcccc tcccagcatc ctttacattc tccccgacac tgtgaacaac | 480 |
| ggaatccgcg tggagttcaa tcaagcctac gacatcgagg gggtgacgga aagctggtg | 540 |
| accaagtgta gccagatgaa tcggccactg gccggttcag cggctgtcca cattccgcgc | 600 |
| taccatcata tcacttatca cactaagctc tccaaagacc gcgatgagag gagagatcac | 660 |
| atgtgcctgg tggaagtggt caaggccgtc gatctcgata cctatcagta a | 711 |

<210> SEQ ID NO 79
<211> LENGTH: 1882
<212> TYPE: DNA
<213> ORGANISM: Artificial Sequence
<220> FEATURE:
<223> OTHER INFORMATION: Primer CPMV 160 5'UTR-PDI+H1 Cal nucleic acid
     sequence

<400> SEQUENCE: 79

| | |
|---|---|
| tattaaaatc ttaataggtt tgataaaag cgaacgtggg gaaacccgaa ccaaaccttc | 60 |
| ttctaaactc tctctcatct ctcttaaagc aaacttctct cttgtctttc ttgcgtgagc | 120 |
| gatcttcaac gttgtcagat cgtgcttcgg caccagtaca atggcgaaaa acgttgcgat | 180 |
| tttcggctta ttgttttctc ttcttgtgtt ggttccttct cagatcttcg cggacacatt | 240 |

-continued

```
atgtataggt tatcatgcga acaattcaac agacactgta gacacagtac tagaaaagaa    300
tgtaacagta acacactctg ttaaccttct agaagacaag cataacggga aactatgcaa    360
actaagaggg gtagccccat tgcatttggg taaatgtaac attgctggct ggatcctggg    420
aaatccagag tgtgaatcac tctccacagc aagctcatgg tcctacattg tggaaacacc    480
tagttcagac aatggaacgt gttacccagg agatttcatc gattatgagg agctaagaga    540
gcaattgagc tcagtgtcat catttgaaag gtttgagata tcccccaaga caagttcatg    600
gcccaatcat gactcgaaca aaggtgtaac ggcagcatgt cctcatgctg gagcaaaaag    660
cttctacaaa aatttaatat ggctagttaa aaaaggaaat tcatacccaa agctcagcaa    720
atcctacatt aatgataaag ggaaagaagt cctcgtgcta tggggcattc accatccatc    780
tactagtgct gaccaacaaa gtctctatca gaatgcagat gcatatgttt ttgtgggggtc    840 atcaagatac agcaagaagt tcaagccgga aatagcaata agacccaaag tgagggatca    900
agaagggaga tgaactatt actggacact agtagagccg ggagacaaaa taacattcga    960
agcaactgga aatctagtgg taccgagata tgcattcgca atggaaagaa atgctggatc   1020
tggtattatc atttcagata caccagtcca cgattgcaat acaacttgtc aaacacccaa   1080
gggtgctata aacaccagcc tcccatttca gaatatacat ccgatcacaa ttggaaaatg   1140
tccaaaatat gtaaaagca caaaattgag actggccaca ggattgagga atatcccgtc   1200
tattcaatct agaggactat ttgggggccat tgccggtttc attgaagggg ggtggacagg   1260
gatggtagat ggatggtacg gttatcacca tcaaaatgag cagggggtcag gatatgcagc   1320 cgacctgaag agcacacaga atgccattga cgagattact aacaaagtaa attctgttat   1380
tgaaaagatg aatacacagg acacagcagt aggtaaagag ttcaaccacc tggaaaaaag   1440
aatagagaat ttaaataaaa aagttgatga tggtttcctg gacatttgga cttacaatgc   1500
cgaactgttg gttctattgg aaaatgaaag aactttggac taccacgatt caaatgtgaa   1560
gaacttatat gaaaaggtaa gaagccagct aaaaaacaat gccaaggaaa ttggaaacgg   1620
ctgctttgaa ttttaccaca aatgcgataa cacgtgcatg gaaagtgtca aaaatgggac   1680
ttatgactac ccaaaatact cagaggaagc aaaattaaac agagaagaaa tagatggggt   1740
aaagctggaa tcaacaagga tttaccagat tttggcgatc tattcaactg tcgccagttc   1800
attggtactg gtagtctccc tgggggcaat cagtttctgg atgtgctcta atgggtctct   1860
acagtgtaga atatgtattt aa                                            1882
```

<210> SEQ ID NO 80
<211> LENGTH: 1722
<212> TYPE: DNA
<213> ORGANISM: Artificial Sequence
<220> FEATURE:
<223> OTHER INFORMATION: PDI+H1 Cal nucleic acid sequence

<400> SEQUENCE: 80

```
atggcgaaaa acgttgcgat tttcggctta ttgtttctc ttcttgtgtt ggttccttct     60
cagatcttcg cggacacatt atgtataggt tatcatgcga acaattcaac agacactgta    120
gacacagtac tagaaaagaa tgtaacagta acacactctg ttaaccttct agaagacaag    180
cataacggga aactatgcaa actaagaggg gtagccccat tgcatttggg taaatgtaac    240
attgctggct ggatcctggg aaatccagag tgtgaatcac tctccacagc aagctcatgg    300
tcctacattg tggaaacacc tagttcagac aatggaacgt gttacccagg agatttcatc    360
```

```
gattatgagg agctaagaga gcaattgagc tcagtgtcat catttgaaag gtttgagata      420
ttccccaaga caagttcatg gcccaatcat gactcgaaca aaggtgtaac ggcagcatgt      480
cctcatgctg gagcaaaaag cttctacaaa aatttaatat ggctagttaa aaaggaaat      540 tcatacccaa agctcagcaa atcctacatt aatgataaag ggaaagaagt cctcgtgcta      600
tggggcattc accatccatc tactagtgct gaccaacaaa gtctctatca gaatgcagat      660
gcatatgttt ttgtgggtc atcaagatac agcaagaagt tcaagccgga atagcaata       720 agacccaaag tgagggatca agaagggaga atgaactatt actggacact agtagagccg      780
ggagacaaaa taacattcga agcaactgga atctagtgg taccgagata tgcattcgca      840
atggaaagaa atgctggatc tggtattatc atttcagata caccagtcca cgattgcaat      900
acaacttgtc aaacacccaa gggtgctata acaccagcc tcccatttca gaatatacat      960
ccgatcacaa ttggaaaatg tccaaaatat gtaaaaagca caaaattgag actggccaca     1020
ggattgagga atatcccgtc tattcaatct agaggactat ttggggccat tgccggtttc     1080
attgaagggg ggtggacagg gatggtagat ggatggtacg ttatcacca tcaaaatgag      1140 caggggtcag gatatgcagc cgacctgaag agcacacaga atgccattga cgagattact     1200
aacaaagtaa attctgttat tgaaaagatg aatacacagg acacagcagt aggtaaagag     1260
ttcaaccacc tggaaaaaag aatagagaat ttaaataaaa aagttgatga tggtttcctg     1320
gacatttgga cttacaatgc cgaactgttg gttctattgg aaaatgaaag aactttggac     1380
taccacgatt caaatgtgaa gaacttatat gaaaaggtaa aagccagct aaaaaacaat     1440 gccaaggaaa ttgaaaacgg ctgctttgaa ttttaccaca aatgcgataa cacgtgcatg     1500
gaaagtgtca aaaatgggac ttatgactac ccaaaatact cagaggaagc aaaattaaac     1560
agagaagaaa tagatggggt aaagctggaa tcaacaagga tttaccagat tttggcgatc     1620
tattcaactg tcgccagttc attggtactg gtagtctccc tgggggcaat cagtttctgg     1680
atgtgctcta atgggtctct acagtgtaga atatgtattt aa                       1722
```

<210> SEQ ID NO 81
<211> LENGTH: 573
<212> TYPE: PRT
<213> ORGANISM: Artificial Sequence
<220> FEATURE:
<223> OTHER INFORMATION: PDI+H1 Cal amino acid sequence

<400> SEQUENCE: 81

```
Met Ala Lys Asn Val Ala Ile Phe Gly Leu Leu Phe Ser Leu Leu Val
1               5                   10                  15

Leu Val Pro Ser Gln Ile Phe Ala Asp Thr Leu Cys Ile Gly Tyr His
                20                  25                  30

Ala Asn Asn Ser Thr Asp Thr Val Asp Thr Val Leu Glu Lys Asn Val
            35                  40                  45

Thr Val Thr His Ser Val Asn Leu Leu Glu Asp Lys His Asn Gly Lys
        50                  55                  60

Leu Cys Lys Leu Arg Gly Val Ala Pro Leu His Leu Gly Lys Cys Asn
65                  70                  75                  80

Ile Ala Gly Trp Ile Leu Gly Asn Pro Glu Cys Glu Ser Leu Ser Thr
                85                  90                  95

Ala Ser Ser Trp Ser Tyr Ile Val Glu Thr Pro Ser Ser Asp Asn Gly
            100                 105                 110

Thr Cys Tyr Pro Gly Asp Phe Ile Asp Tyr Glu Glu Leu Arg Glu Gln
        115                 120                 125
```

```
Leu Ser Ser Val Ser Ser Phe Glu Arg Phe Glu Ile Phe Pro Lys Thr
    130                 135                 140
Ser Ser Trp Pro Asn His Asp Ser Asn Lys Gly Val Thr Ala Ala Cys
145                 150                 155                 160
Pro His Ala Gly Ala Lys Ser Phe Tyr Lys Asn Leu Ile Trp Leu Val
                165                 170                 175
Lys Lys Gly Asn Ser Tyr Pro Lys Leu Ser Lys Ser Tyr Ile Asn Asp
            180                 185                 190
Lys Gly Lys Glu Val Leu Val Leu Trp Gly Ile His His Pro Ser Thr
        195                 200                 205
Ser Ala Asp Gln Gln Ser Leu Tyr Gln Asn Ala Asp Ala Tyr Val Phe
    210                 215                 220
Val Gly Ser Ser Arg Tyr Ser Lys Lys Phe Lys Pro Glu Ile Ala Ile
225                 230                 235                 240
Arg Pro Lys Val Arg Asp Gln Glu Gly Arg Met Asn Tyr Tyr Trp Thr
                245                 250                 255
Leu Val Glu Pro Gly Asp Lys Ile Thr Phe Glu Ala Thr Gly Asn Leu
            260                 265                 270
Val Val Pro Arg Tyr Ala Phe Ala Met Glu Arg Asn Ala Gly Ser Gly
        275                 280                 285
Ile Ile Ile Ser Asp Thr Pro Val His Asp Cys Asn Thr Thr Cys Gln
    290                 295                 300
Thr Pro Lys Gly Ala Ile Asn Thr Ser Leu Pro Phe Gln Asn Ile His
305                 310                 315                 320
Pro Ile Thr Ile Gly Lys Cys Pro Lys Tyr Val Lys Ser Thr Lys Leu
                325                 330                 335
Arg Leu Ala Thr Gly Leu Arg Asn Ile Pro Ser Ile Gln Ser Arg Gly
            340                 345                 350
Leu Phe Gly Ala Ile Ala Gly Phe Ile Glu Gly Gly Trp Thr Gly Met
        355                 360                 365
Val Asp Gly Trp Tyr Gly Tyr His His Gln Asn Glu Gln Gly Ser Gly
        370                 375                 380
Tyr Ala Ala Asp Leu Lys Ser Thr Gln Asn Ala Ile Asp Glu Ile Thr
385                 390                 395                 400
Asn Lys Val Asn Ser Val Ile Glu Lys Met Asn Thr Gln Asp Thr Ala
                405                 410                 415
Val Gly Lys Glu Phe Asn His Leu Glu Lys Arg Ile Glu Asn Leu Asn
            420                 425                 430
Lys Lys Val Asp Asp Gly Phe Leu Asp Ile Trp Thr Tyr Asn Ala Glu
        435                 440                 445
Leu Leu Val Leu Leu Glu Asn Glu Arg Thr Leu Asp Tyr His Asp Ser
    450                 455                 460
Asn Val Lys Asn Leu Tyr Glu Lys Val Arg Ser Gln Leu Lys Asn Asn
465                 470                 475                 480
Ala Lys Glu Ile Gly Asn Gly Cys Phe Glu Phe Tyr His Lys Cys Asp
                485                 490                 495
Asn Thr Cys Met Glu Ser Val Lys Asn Gly Thr Tyr Asp Tyr Pro Lys
            500                 505                 510
Tyr Ser Glu Glu Ala Lys Leu Asn Arg Glu Glu Ile Asp Gly Val Lys
        515                 520                 525
Leu Glu Ser Thr Arg Ile Tyr Gln Ile Leu Ala Ile Tyr Ser Thr Val
    530                 535                 540
```

```
Ala Ser Ser Leu Val Leu Val Val Ser Leu Gly Ala Ile Ser Phe Trp
545                 550                 555                 560

Met Cys Ser Asn Gly Ser Leu Gln Cys Arg Ile Cys Ile
                565                 570
```

<210> SEQ ID NO 82
<211> LENGTH: 1882
<212> TYPE: DNA
<213> ORGANISM: Artificial Sequence
<220> FEATURE:
<223> OTHER INFORMATION: CPMV 160 5'UTR-PDI+H1 Mich nucleic acid
      sequence

<400> SEQUENCE: 82

```
tattaaaatc ttaataggtt tgataaaag cgaacgtggg gaaacccgaa ccaaaccttc      60
ttctaaactc tctctcatct ctcttaaagc aaacttctct cttgtctttc ttgcgtgagc    120
gatcttcaac gttgtcagat cgtgcttcgg caccagtaca atggcgaaaa acgttgcgat    180
tttcggctta ttgttttctc ttcttgtgtt ggttccttct cagatcttcg cggacacatt    240
atgtataggt tatcatgcga acaattcaac agacactgta gacacagtac tagaaaagaa    300
tgtaacagta acacactctg ttaaccttct ggaagacaag cataacggaa aactatgcaa    360
actaagaggg gtagccccat tgcatttggg taaatgtaac attgctggct ggatcctggg    420
aaatccagag tgtgaatcac tctccacagc aagttcatgg tcctacattg tggaaacatc    480
taattcagac aatggaacgt gttacccagg agatttcatc aattatgagg agctaagaga    540
gcaattgagc tcagtgtcat catttgaaag gtttgagata ttccccaaga caagttcatg    600
gcccaatcat gactcgaaca aggtgtaac ggcagcatgt cctcacgctg agcaaaaag     660 cttctacaaa aacttgatat ggctagttaa aaaaggaaat tcatacccaa agcttaacca    720
atcctacatt aatgataaag ggaagaagt cctcgtgctg tggggcattc accatccatc    780
tactactgct gaccaacaaa gtctctatca gaatgcagat gcatatgttt ttgtggggac    840
atcaagatac agcaagaagt tcaagccgga aatagcaaca agacccaaag tgagggatca    900
agaagggaga atgaactatt actggacact agtagagccg ggagacaaaa taacattcga    960
agcaactgga aatctagtgg taccgagata tgcattcaca atggaaagaa atgctggatc   1020
tggtattatc atttcagata caccagtcca cgattgcaat acaacttgtc agacacccga   1080
gggtgctata aacaccagcc tcccatttca gaatatacat ccgatacaa ttggaaaatg    1140 tccaaagtat gtaaaaagca caaaattgag actggccaca ggattgagga atgttccgtc   1200
tattcaatct agaggcctat tcggggccat tgccggcttc attgaagggg ggtggacagg   1260
gatggtagat ggatggtacg gttatcacca tcaaaatgag cagggggtcag gatatgcagc   1320 cgacctgaag agcacacaaa atgccattga caagattact aacaaagtaa attctgttat   1380
tgaaaagatg aatacacagg acacagcagt gggtaaagag ttcaaccacc tggaaaaaag   1440
aatagagaat ctaaataaaa aagttgatga tggtttcctg gacatttgga cttacaatgc   1500
cgaactgttg gttctaatgg aaaatgaaag aactttggac tatcacgatt caaatgtgaa   1560
gaacttgtat gaaaaagtaa gaaaccagtt aaaaaacaat gccaaggaaa ttggaaacgg   1620
ctgctttgaa ttttaccaca aatgcgataa cacgtgcatg gaaagtgtca aaaatgggac   1680
ttatgactac ccaaaatact cagaggaagc aaaattaaac agagaaaaaa tagatggggt   1740
aaagctggaa tcaacaagga tttaccagat tttggcgatc tattcaactg tcgccagttc   1800
attggtactg gtagtctccc tgggggcaat cagcttctgg atgtgctcta atgggtctct   1860
```

```
acagtgtaga atatgtattt aa                                             1882
```

<210> SEQ ID NO 83
<211> LENGTH: 1722
<212> TYPE: DNA
<213> ORGANISM: Artificial Sequence
<220> FEATURE:
<223> OTHER INFORMATION: PDI+H1 Mich nucleic acid sequence

<400> SEQUENCE: 83

```
atggcgaaaa acgttgcgat tttcggctta ttgttttctc ttcttgtgtt ggttccttct     60
cagatcttcg cggacacatt atgtataggt tatcatgcga acaattcaac agacactgta    120
gacacagtac tagaaaagaa tgtaacagta acacactctg ttaaccttct ggaagacaag    180
cataacggaa aactatgcaa actaagaggg gtagccccat tgcatttggg taaatgtaac    240
attgctggct ggatcctggg aaatccagag tgtgaatcac tctccacagc aagttcatgg    300
tcctacattg tggaaacatc taattcgac aatggaacgt gttacccagg agatttcatc    360
aattatgagg agctaagaga gcaattgagc tcagtgtcat catttgaaag gtttgagata    420
ttccccaaga caagttcatg gcccaatcat gactcgaaca aggtgtaac ggcagcatgt     480
cctcacgctg agcaaaaag cttctacaaa aacttgatat ggctagttaa aaaggaaat     540
tcatacccaa agcttaacca atcctacatt aatgataaag ggaagaagt cctcgtgctg    600
tgggcattc accatccatc tactactgct gaccaacaaa gtctctatca gaatgcagat    660
gcatatgttt tgtggggac atcaagatac agcaagaagt tcaagccgga aatagcaaca    720
agacccaaag tgagggatca agaagggaga atgaactatt actggacact agtagagccg    780
ggagacaaaa taacattcga agcaactgga aatctagtgg taccgagata tgcattcaca    840
atggaaagaa atgctggatc tggtattatc atttcagata caccagtcca cgattgcaat    900
acaacttgtc agacaccga gggtgctata acaccagcc tcccatttca gaatatacat    960
ccgatcacaa ttggaaaatg tccaaagtat gtaaaaagca caaaattgag actggccaca   1020
ggattgagga atgttccgtc tattcaatct agaggcctat cggggccat tgccggcttc   1080
attgaagggg gtggacagg gatggtagat ggatggtacg ttatcacca tcaaaatgag    1140
caggggtcag gatatgcagc cgacctgaag agcacacaaa atgccattga caagattact    1200
aacaaagtaa attctgttat tgaaaagatg aatacacagg acacagcagt gggtaaagag    1260
ttcaaccacc tggaaaaaag aatagagaat ctaaataaaa aagttgatga tggtttcctg    1320
gacatttgga cttacaatgc cgaactgttg gttctaatgg aaaatgaaag aactttggac    1380
tatcacgatt caaatgtgaa gaacttgtat gaaaaagtaa gaaaccagtt aaaaaacaat    1440
gccaaggaaa ttggaaacgg ctgctttgaa ttttaccaca aatgcgataa cacgtgcatg    1500
gaaagtgtca aaaatgggac ttatgactac ccaaatacc cagaggaagc aaaattaaac    1560
agagaaaaaa tagatggggt aaagctgaa tcaacaagga tttaccagat tttggcgatc    1620
tattcaactg tcgccagttc attggtactg gtagtctccc tgggggcaat cagcttctgg   1680
atgtgctcta atgggtctct acagtgtaga atatgtattt aa                       1722
```

<210> SEQ ID NO 84
<211> LENGTH: 573
<212> TYPE: PRT
<213> ORGANISM: Artificial Sequence
<220> FEATURE:
<223> OTHER INFORMATION: PDI+H1 Mich amino acid sequence

<400> SEQUENCE: 84

```
Met Ala Lys Asn Val Ala Ile Phe Gly Leu Leu Phe Ser Leu Leu Val
1               5                   10                  15

Leu Val Pro Ser Gln Ile Phe Ala Asp Thr Leu Cys Ile Gly Tyr His
            20                  25                  30

Ala Asn Asn Ser Thr Asp Thr Val Asp Thr Val Leu Glu Lys Asn Val
            35                  40                  45

Thr Val Thr His Ser Val Asn Leu Leu Glu Asp Lys His Asn Gly Lys
        50                  55                  60

Leu Cys Lys Leu Arg Gly Val Ala Pro Leu His Leu Gly Lys Cys Asn
65                  70                  75                  80

Ile Ala Gly Trp Ile Leu Gly Asn Pro Glu Cys Glu Ser Leu Ser Thr
                85                  90                  95

Ala Ser Ser Trp Ser Tyr Ile Val Glu Thr Ser Asn Ser Asp Asn Gly
                100                 105                 110

Thr Cys Tyr Pro Gly Asp Phe Ile Asn Tyr Glu Glu Leu Arg Glu Gln
            115                 120                 125

Leu Ser Ser Val Ser Ser Phe Glu Arg Phe Glu Ile Phe Pro Lys Thr
        130                 135                 140

Ser Ser Trp Pro Asn His Asp Ser Asn Lys Gly Val Thr Ala Ala Cys
145                 150                 155                 160

Pro His Ala Gly Ala Lys Ser Phe Tyr Lys Asn Leu Ile Trp Leu Val
                165                 170                 175

Lys Lys Gly Asn Ser Tyr Pro Lys Leu Asn Gln Ser Tyr Ile Asn Asp
                180                 185                 190

Lys Gly Lys Glu Val Leu Val Leu Trp Gly Ile His His Pro Ser Thr
            195                 200                 205

Thr Ala Asp Gln Gln Ser Leu Tyr Gln Asn Ala Asp Ala Tyr Val Phe
        210                 215                 220

Val Gly Thr Ser Arg Tyr Ser Lys Lys Phe Lys Pro Glu Ile Ala Thr
225                 230                 235                 240

Arg Pro Lys Val Arg Asp Gln Glu Gly Arg Met Asn Tyr Tyr Trp Thr
                245                 250                 255

Leu Val Glu Pro Gly Asp Lys Ile Thr Phe Glu Ala Thr Gly Asn Leu
                260                 265                 270

Val Val Pro Arg Tyr Ala Phe Thr Met Glu Arg Asn Ala Gly Ser Gly
            275                 280                 285

Ile Ile Ile Ser Asp Thr Pro Val His Asp Cys Asn Thr Thr Cys Gln
        290                 295                 300

Thr Pro Glu Gly Ala Ile Asn Thr Ser Leu Pro Phe Gln Asn Ile His
305                 310                 315                 320

Pro Ile Thr Ile Gly Lys Cys Pro Lys Tyr Val Lys Ser Thr Lys Leu
                325                 330                 335

Arg Leu Ala Thr Gly Leu Arg Asn Val Pro Ser Ile Gln Ser Arg Gly
                340                 345                 350

Leu Phe Gly Ala Ile Ala Gly Phe Ile Glu Gly Gly Trp Thr Gly Met
            355                 360                 365

Val Asp Gly Trp Tyr Gly Tyr His His Gln Asn Glu Gln Gly Ser Gly
        370                 375                 380

Tyr Ala Ala Asp Leu Lys Ser Thr Gln Asn Ala Ile Asp Lys Ile Thr
385                 390                 395                 400

Asn Lys Val Asn Ser Val Ile Glu Lys Met Asn Thr Gln Asp Thr Ala
                405                 410                 415
```

```
Val Gly Lys Glu Phe Asn His Leu Glu Lys Arg Ile Glu Asn Leu Asn
            420                 425                 430

Lys Lys Val Asp Asp Gly Phe Leu Asp Ile Trp Thr Tyr Asn Ala Glu
        435                 440                 445

Leu Leu Val Leu Met Glu Asn Glu Arg Thr Leu Asp Tyr His Asp Ser
    450                 455                 460

Asn Val Lys Asn Leu Tyr Glu Lys Val Arg Asn Gln Leu Lys Asn Asn
465                 470                 475                 480

Ala Lys Glu Ile Gly Asn Gly Cys Phe Glu Phe Tyr His Lys Cys Asp
                485                 490                 495

Asn Thr Cys Met Glu Ser Val Lys Asn Gly Thr Tyr Asp Tyr Pro Lys
            500                 505                 510

Tyr Ser Glu Glu Ala Lys Leu Asn Arg Glu Lys Ile Asp Gly Val Lys
        515                 520                 525

Leu Glu Ser Thr Arg Ile Tyr Gln Ile Leu Ala Ile Tyr Ser Thr Val
    530                 535                 540

Ala Ser Ser Leu Val Leu Val Val Ser Leu Gly Ala Ile Ser Phe Trp
545                 550                 555                 560

Met Cys Ser Asn Gly Ser Leu Gln Cys Arg Ile Cys Ile
                565                 570
```

<210> SEQ ID NO 85
<211> LENGTH: 1885
<212> TYPE: DNA
<213> ORGANISM: Artificial Sequence
<220> FEATURE:
<223> OTHER INFORMATION: CPMV 160 5'UTR-PDI+H3 HK nucleic acid sequence

<400> SEQUENCE: 85

```
tattaaaatc ttaataggtt ttgataaaag cgaacgtggg gaaacccgaa ccaaaccttc      60
ttctaaactc tctctcatct ctcttaaagc aaacttctct cttgtctttc ttgcgtgagc     120
gatcttcaac gttgtcagat cgtgcttcgg caccagtaca atggcgaaaa acgttgcgat     180
tttcggctta ttgttttctc ttcttgtgtt ggttccttct cagatcttcg cgcaaaaaat     240
tcctggaaat gacaatagca cggcaacgct gtgccttggg catcatgcag taccaaacgg     300
aacgatagtg aaaacaatca cgaatgaccg aattgaagtt actaatgcta ctgagctggt     360
tcagaattcc tcaataggtg aaatatgcga cagtcctcat cagatccttg atggagaaaa     420
ctgcacacta atagatgctc tattgggaga ccctcagtgt gatggctttc aaaataagaa     480
atgggacctt tttgttgaac gaagcaaagc ctacagcaac tgttacccct atgatgtgcc     540
ggattatgcc tcccttaggt cactagttgc ctcatccggc acactggagt ttaacaatga     600
aagcttcaat tggactggag tcactcaaaa cggaacaagt tctgcttgca taaggagatc     660
tagtagtagt ttctttagta gattaaattg gttgacccac ttaaactaca catacccagc     720
attgaacgtg actatgccaa acaatgaaca atttgacaaa ttgtacattt gggggttca     780
ccacccgggt acggacaagg accaaatctt cctgtatgct caatcatcag gaagaatcac     840
agtatctacc aaaagaagcc aacaagctgt aatcccaaat atcggatcta gacccagaat     900
aagggatatc cctagcagaa taagcatcta ttggacaata gtaaaaccgg agacatact     960
tttgattaac agcacaggga atctaattgc tcctaggggt tacttcaaaa tacgaagtgg    1020
gaaaagctca ataatgagat cagatgcacc cattggcaaa tgcaagtctg aatgcatcac    1080
tccaaatgga agcattccca tgacaaaacc attccaaaat gtaaacagga tcacatacgg    1140
ggcctgtccc agatatgtta agcatagcac tctgaaattg gcaacaggaa tgcgaaatgt    1200
```

```
accagagaaa caaactagag gcatatttgg tgcaatagcg ggtttcatag aaaatggttg    1260
ggagggaatg gtggatggtt ggtacggttt caggcatcaa aattctgagg gaagaggaca    1320
agcagcagat ctcaaaagca ctcaagcagc aatcgatcaa atcaatggga agctggctcg    1380
agtgatcggg aaaaccaacg agaaattcca tcagattgaa aaagaattct cagaagtaga    1440
aggaagaatt caggaccttg agaaatatgt tgaggacact aaaatagatc tctggtcata    1500
caacgcggag cttcttgttg ccctggagaa ccaacataca attgatctaa ctgactcaga    1560
aatgaacaaa ctgtttgaaa aacaaagaa gcaactgagg gaaaatgctg aggatatggg    1620
caatggttgt ttcaaaatat accacaaatg tgacaatgcc tgcataggat caataagaaa    1680
tggaacttat gaccacaatg tgtacaggga tgaagcatta acaaccggt tccagatcaa    1740 gggagttgag ctgaagtcag ggtacaaaga ttggatccta tggatttcct ttgccatatc    1800
atcccttgta ctgttagttg ctttgttggg gttcatcatg tgggcctgcc aaaagggcaa    1860
cattaggtgc aacatttgca tttga                                          1885
```

<210> SEQ ID NO 86
<211> LENGTH: 1725
<212> TYPE: DNA
<213> ORGANISM: Artificial Sequence
<220> FEATURE:
<223> OTHER INFORMATION: PDI+H3 HK nucleic acid sequence

<400> SEQUENCE: 86

```
atggcgaaaa acgttgcgat tttcggctta ttgttttctc ttcttgtgtt ggttccttct      60
cagatcttcg cgcaaaaaat tcctggaaat gacaatagca cggcaacgct gtgccttggg    120
catcatgcag taccaaacgg aacgatagtg aaaacaatca cgaatgaccg aattgaagtt    180
actaatgcta ctgagctggt tcagaattcc tcaataggtg aaatatgcga cagtcctcat    240
cagatccttg atggagaaaa ctgcacacta atagatgctc tattgggaga ccctcagtgt    300
gatggctttc aaaataagaa atgggacctt tttgttgaac gaagcaaagc ctacagcaac    360
tgttacccct tatgatgtgcc ggattatgcc tcccttaggt cactagttgc ctcatccggc    420
acactggagt ttaacaatga agcttcaat tggactggag tcactcaaaa cggaacaagt    480
tctgcttgca taaggagatc tagtagtagt ttctttagta gattaaattg gttgacccac    540
ttaaactaca catacccagc attgaacgtg actatgccaa acaatgaaca atttgacaaa    600
ttgtacattt gggggggttca ccacccgggt acggacaagg accaaatctt cctgtatgct    660
caatcatcag gaagaatcac agtatctacc aaaagaagcc aacaagctgt aatcccaaat    720
atcggatcta gacccagaat aagggatatc cctagcagaa taagcatcta ttggacaata    780
gtaaaaccgg agacatact tttgattaac agcacaggga atctaattgc tcctagggg    840 tacttcaaaa tacgaagtgg gaaaagctca ataatgagat cagatgcacc cattggcaaa    900
tgcaagtctg aatgcatcac tccaaatgga agcattccca atgacaaacc attccaaaat    960
gtaaacagga tcacatacgg ggcctgtccc agatatgtta agcatagcac tctgaaattg   1020
gcaacaggaa tgcgaaatgt accagagaaa caaactagag gcatatttgg tgcaatagcg   1080
ggtttcatag aaaatggttg ggagggaatg gtggatggtt ggtacggttt caggcatcaa   1140
aattctgagg gaagaggaca agcagcagat ctcaaaagca ctcaagcagc aatcgatcaa   1200
atcaatggga agctggctcg agtgatcggg aaaaccaacg agaaattcca tcagattgaa   1260
aaagaattct cagaagtaga aggaagaatt caggaccttg agaaatatgt tgaggacact   1320
```

```
aaaatagatc tctggtcata caacgcggag cttcttgttg ccctggagaa ccaacataca    1380
attgatctaa ctgactcaga aatgaacaaa ctgtttgaaa aaacaaagaa gcaactgagg    1440
gaaaatgctg aggatatggg caatggttgt ttcaaaatat accacaaatg tgacaatgcc    1500
tgcataggat caataagaaa tggaacttat gaccacaatg tgtacaggga tgaagcatta    1560
aacaaccggt tccagatcaa gggagttgag ctgaagtcag ggtacaaaga ttggatccta    1620
tggatttcct ttgccatatc atcccttgta ctgttagttg ctttgttggg gttcatcatg    1680
tgggcctgcc aaaagggcaa cattaggtgc aacatttgca tttga                    1725
```

<210> SEQ ID NO 87
<211> LENGTH: 574
<212> TYPE: PRT
<213> ORGANISM: Artificial Sequence
<220> FEATURE:
<223> OTHER INFORMATION: PDI+H3 HK amino acid sequence

<400> SEQUENCE: 87

```
Met Ala Lys Asn Val Ala Ile Phe Gly Leu Leu Phe Ser Leu Leu Val
1               5                   10                  15

Leu Val Pro Ser Gln Ile Phe Ala Gln Lys Ile Pro Gly Asn Asp Asn
                20                  25                  30

Ser Thr Ala Thr Leu Cys Leu Gly His His Ala Val Pro Asn Gly Thr
            35                  40                  45

Ile Val Lys Thr Ile Thr Asn Asp Arg Ile Glu Val Thr Asn Ala Thr
        50                  55                  60

Glu Leu Val Gln Asn Ser Ser Ile Gly Glu Ile Cys Asp Ser Pro His
65                  70                  75                  80

Gln Ile Leu Asp Gly Glu Asn Cys Thr Leu Ile Asp Ala Leu Leu Gly
                85                  90                  95

Asp Pro Gln Cys Asp Gly Phe Gln Asn Lys Lys Trp Asp Leu Phe Val
            100                 105                 110

Glu Arg Ser Lys Ala Tyr Ser Asn Cys Tyr Pro Tyr Asp Val Pro Asp
        115                 120                 125

Tyr Ala Ser Leu Arg Ser Leu Val Ala Ser Ser Gly Thr Leu Glu Phe
    130                 135                 140

Asn Asn Glu Ser Phe Asn Trp Thr Gly Val Thr Gln Asn Gly Thr Ser
145                 150                 155                 160

Ser Ala Cys Ile Arg Arg Ser Ser Ser Phe Ser Arg Leu Asn
                165                 170                 175

Trp Leu Thr His Leu Asn Tyr Thr Tyr Pro Ala Leu Asn Val Thr Met
                180                 185                 190

Pro Asn Asn Glu Gln Phe Asp Lys Leu Tyr Ile Trp Gly Val His His
            195                 200                 205

Pro Gly Thr Asp Lys Asp Gln Ile Phe Leu Tyr Ala Gln Ser Ser Gly
        210                 215                 220

Arg Ile Thr Val Ser Thr Lys Arg Ser Gln Gln Ala Val Ile Pro Asn
225                 230                 235                 240

Ile Gly Ser Arg Pro Arg Ile Arg Asp Ile Pro Ser Arg Ile Ser Ile
                245                 250                 255

Tyr Trp Thr Ile Val Lys Pro Gly Asp Ile Leu Leu Ile Asn Ser Thr
            260                 265                 270

Gly Asn Leu Ile Ala Pro Arg Gly Tyr Phe Lys Ile Arg Ser Gly Lys
        275                 280                 285

Ser Ser Ile Met Arg Ser Asp Ala Pro Ile Gly Lys Cys Lys Ser Glu
```

```
    290                 295                 300

Cys Ile Thr Pro Asn Gly Ser Ile Pro Asn Asp Lys Pro Phe Gln Asn
305                 310                 315                 320

Val Asn Arg Ile Thr Tyr Gly Ala Cys Pro Arg Tyr Val Lys His Ser
                325                 330                 335

Thr Leu Lys Leu Ala Thr Gly Met Arg Asn Val Pro Glu Lys Gln Thr
            340                 345                 350

Arg Gly Ile Phe Gly Ala Ile Ala Gly Phe Ile Glu Asn Gly Trp Glu
        355                 360                 365

Gly Met Val Asp Gly Trp Tyr Gly Phe Arg His Gln Asn Ser Glu Gly
    370                 375                 380

Arg Gly Gln Ala Ala Asp Leu Lys Ser Thr Gln Ala Ala Ile Asp Gln
385                 390                 395                 400

Ile Asn Gly Lys Leu Ala Arg Val Ile Gly Lys Thr Asn Glu Lys Phe
                405                 410                 415

His Gln Ile Glu Lys Glu Phe Ser Glu Val Glu Gly Arg Ile Gln Asp
            420                 425                 430

Leu Glu Lys Tyr Val Glu Asp Thr Lys Ile Asp Leu Trp Ser Tyr Asn
        435                 440                 445

Ala Glu Leu Leu Val Ala Leu Glu Asn Gln His Thr Ile Asp Leu Thr
    450                 455                 460

Asp Ser Glu Met Asn Lys Leu Phe Glu Lys Thr Lys Lys Gln Leu Arg
465                 470                 475                 480

Glu Asn Ala Glu Asp Met Gly Asn Gly Cys Phe Lys Ile Tyr His Lys
                485                 490                 495

Cys Asp Asn Ala Cys Ile Gly Ser Ile Arg Asn Gly Thr Tyr Asp His
            500                 505                 510

Asn Val Tyr Arg Asp Glu Ala Leu Asn Asn Arg Phe Gln Ile Lys Gly
        515                 520                 525

Val Glu Leu Lys Ser Gly Tyr Lys Asp Trp Ile Leu Trp Ile Ser Phe
    530                 535                 540

Ala Ile Ser Ser Leu Val Leu Leu Val Ala Leu Leu Gly Phe Ile Met
545                 550                 555                 560

Trp Ala Cys Gln Lys Gly Asn Ile Arg Cys Asn Ile Cys Ile
                565                 570
```

<210> SEQ ID NO 88
<211> LENGTH: 1894
<212> TYPE: DNA
<213> ORGANISM: Artificial Sequence
<220> FEATURE:
<223> OTHER INFORMATION: CPMV 160 5'UTR-PDI+HA B Bri nucleic acid sequence

<400> SEQUENCE: 88

```
tattaaaatc ttaataggtt ttgataaaag cgaacgtggg gaaacccgaa ccaaaccttc      60
ttctaaactc tctctcatct ctcttaaagc aaacttctct cttgtctttc ttgcgtgagc     120
gatcttcaac gttgtcagat cgtgcttcgg caccagtaca atggcgaaaa acgttgcgat     180
tttcggctta ttgttttctc ttcttgtgtt ggttccttct cagatcttcg cggatcgaat     240
ctgcactgga ataacatcgt caaactcacc acatgtcgtc aaaactgcta ctcaagggga     300
ggtcaatgtg actggtgtaa taccactgac aacaacaccc accaaatctc attttgcaaa     360
tctcaaagga acagaaacca gggggaaact atgcccaaaa tgcctcaact gcacagatct     420
ggacgtagcc ttgggcagac caaaatgcac ggggaaaata ccctcggcaa gagtttcaat     480
```

```
actccatgaa gtcagacctg ttacatctgg gtgctttcct ataatgcacg acagaacaaa    540
aattagacag ctgcctaacc ttctccgagg atacgaacat atcaggttat caacccataa    600
cgttatcaat gcagaaaatg caccaggagg accctacaaa attggaacct cagggtcttg    660
ccctaacatt accaatggaa acggattttt cgcaacaatg gcttgggccg tcccaaaaaa    720
cgacaaaaac aaaacagcaa caaatccatt aacaatagaa gtaccataca tttgtacaga    780
aggagaagac caaattaccg tttgggggtt ccactctgac aacgagaccc aaatggcaaa    840
gctctatggg gactcaaagc cccagaagtt cacctcatct gccaacggag tgaccacaca    900
ttacgtttca cagattggtg gcttcccaaa tcaaacagaa gacggaggac taccacaaag    960
tggtagaatt gttgttgatt acatggtgca aaaatctggg aaaacaggaa caattaccta   1020
tcaaaggggt attttattgc ctcaaaaggt gtggtgcgca agtggcagga gcaaggtaat   1080
aaaaggatcc ttgcctttaa ttggagaagc agattgcctc cacgaaaaat acggtggatt   1140
aaacaaaagc aagccttact acacagggga acatgcaaag gccataggaa attgcccaat   1200
atgggtgaaa acacccttga agctggccaa tggaaccaaa tatagacctc ctggtggagg   1260
atgggaagga atgattgcag gttggcacgg atacacatcc catggggcac atggagtagc   1320
ggtggcagca gaccttaaga gcactcaaga ggccataaac aagataacaa aaaatctcaa   1380
ctctttgagt gagctggaag taaagaatct tcaaagacta agcggtgcca tggatgaact   1440
ccacaacgaa atactagaac tagatgagaa agtggatgat ctcagagctg atacaataag   1500
ctcacaaata gaactcgcag tcctgctttc caatgaagga ataataaaca gtgaagatga   1560
acatctcttg gcgcttgaaa gaaagctgaa gaaaatgctg ggcccctctg ctgtagagat   1620
agggaatgga tgctttgaaa ccaaacacaa gtgcaaccag acctgtctcg acagaatagc   1680
tgctggtacc tttgatgcag gagaattttc tctccccacc tttgattcac tgaatattac   1740
tgctgcatct ttaaatgacg atggattgga taattaccag attttggcga tctattcaac   1800
tgtcgccagt tcattggtac tggtagtctc cctgggggca atcagtttct ggatgtgctc   1860
taatgggtct ctacagtgta gaatatgtat ttaa                                1894
```

<210> SEQ ID NO 89
<211> LENGTH: 1734
<212> TYPE: DNA
<213> ORGANISM: Artificial Sequence
<220> FEATURE:
<223> OTHER INFORMATION: PDI+HA B Bri nucleic acid sequence

<400> SEQUENCE: 89

```
atggcgaaaa acgttgcgat tttcggctta ttgttttctc ttcttgtgtt ggttccttct     60
cagatcttcg cggatcgaat ctgcactgga ataacatcgt caaactcacc acatgtcgtc    120
aaaactgcta ctcaagggga ggtcaatgtg actggtgtaa taccactgac aacaacaccc    180
accaaatctc attttgcaaa tctcaaagga acagaaacca gggggaaact atgcccaaaa    240
tgcctcaact gcacagatct ggacgtagcc ttgggcagac caaaatgcac ggggaaaata    300
ccctcggcaa gagtttcaat actccatgaa gtcagacctg ttacatctgg gtgctttcct    360
ataatgcacg acagaacaaa aattagacag ctgcctaacc ttctccgagg atacgaacat    420
atcaggttat caacccataa cgttatcaat gcagaaaatg caccaggagg accctacaaa    480
attggaacct cagggtcttg ccctaacatt accaatggaa acggattttt cgcaacaatg    540
gcttgggccg tcccaaaaaa cgacaaaaac aaaacagcaa caaatccatt aacaatagaa    600
```

```
gtaccataca tttgtacaga aggagaagac caaattaccg tttgggggtt ccactctgac      660
aacgagaccc aaatggcaaa gctctatggg gactcaaagc cccagaagtt cacctcatct      720
gccaacggag tgaccacaca ttacgtttca cagattggtg gcttcccaaa tcaaacagaa      780
gacggaggac taccaaaagt ggtagaattg ttgttgatt acatggtgca aaaatctggg       840
aaaacaggaa caattaccta tcaaagggt attttattgc ctcaaaaggt gtggtgcgca       900
agtggcagga gcaaggtaat aaaaggatcc ttgcctttaa ttggagaagc agattgcctc      960
cacgaaaaat acggtggatt aaacaaaagc aagccttact acacagggga acatgcaaag     1020
gccataggaa attgcccaat atgggtgaaa cacccttga agctggccaa tggaaccaaa      1080
tatagacctc ctggtggagg atgggaagga atgattgcag gttggcacgg atacacatcc    1140
catggggcac atgagtagc ggtggcagca gaccttaaga gcactcaaga ggccataaac       1200
aagataacaa aaaatctcaa ctctttgagt gagctggaag taagaatct tcaaagacta     1260 agcggtgcca tggatgaact ccacaacgaa atactagaac tagatgagaa agtggatgat     1320
ctcagagctg atacaataag ctcacaaata gaactcgcag tcctgctttc caatgaagga    1380
ataataaaca gtgaagatga acatctcttg gcgcttgaaa gaaagctgaa gaaaatgctg    1440
ggcccctctg ctgtagagat agggaatgga tgctttgaaa ccaaacacaa gtgcaaccag    1500
acctgtctcg acagaatagc tgctggtacc tttgatgcag agaattttc tctccccacc    1560 tttgattcac tgaatattac tgctgcatct ttaaatgacg atggattgga taattaccag    1620
attttggcga tctattcaac tgtcgccagt tcattggtac tggtagtctc cctgggggca    1680
atcagtttct ggatgtgctc taatgggtct ctacagtgta aatatgtat ttaa             1734
```

<210> SEQ ID NO 90
<211> LENGTH: 577
<212> TYPE: PRT
<213> ORGANISM: Artificial Sequence
<220> FEATURE:
<223> OTHER INFORMATION: PDI+HA B Bri amino acid sequence

<400> SEQUENCE: 90

```
Met Ala Lys Asn Val Ala Ile Phe Gly Leu Leu Phe Ser Leu Leu Val
1               5                   10                  15

Leu Val Pro Ser Gln Ile Phe Ala Asp Arg Ile Cys Thr Gly Ile Thr
                20                  25                  30

Ser Ser Asn Ser Pro His Val Val Lys Thr Ala Thr Gln Gly Glu Val
            35                  40                  45

Asn Val Thr Gly Val Ile Pro Leu Thr Thr Thr Pro Thr Lys Ser His
        50                  55                  60

Phe Ala Asn Leu Lys Gly Thr Glu Thr Arg Gly Lys Leu Cys Pro Lys
65                  70                  75                  80

Cys Leu Asn Cys Thr Asp Leu Asp Val Ala Leu Gly Arg Pro Lys Cys
                85                  90                  95

Thr Gly Lys Ile Pro Ser Ala Arg Val Ser Ile Leu His Glu Val Arg
            100                 105                 110

Pro Val Thr Ser Gly Cys Phe Pro Ile Met His Asp Arg Thr Lys Ile
        115                 120                 125

Arg Gln Leu Pro Asn Leu Leu Arg Gly Tyr Glu His Ile Arg Leu Ser
    130                 135                 140

Thr His Asn Val Ile Asn Ala Glu Asn Ala Pro Gly Gly Pro Tyr Lys
145                 150                 155                 160

Ile Gly Thr Ser Gly Ser Cys Pro Asn Ile Thr Asn Gly Asn Gly Phe
```

```
            165                 170                 175
Phe Ala Thr Met Ala Trp Ala Val Pro Lys Asn Asp Lys Asn Lys Thr
            180                 185                 190

Ala Thr Asn Pro Leu Thr Ile Glu Val Pro Tyr Ile Cys Thr Glu Gly
            195                 200                 205

Glu Asp Gln Ile Thr Val Trp Gly Phe His Ser Asp Asn Glu Thr Gln
        210                 215                 220

Met Ala Lys Leu Tyr Gly Asp Ser Lys Pro Gln Lys Phe Thr Ser Ser
225                 230                 235                 240

Ala Asn Gly Val Thr Thr His Tyr Val Ser Gln Ile Gly Gly Phe Pro
                245                 250                 255

Asn Gln Thr Glu Asp Gly Gly Leu Pro Gln Ser Gly Arg Ile Val Val
            260                 265                 270

Asp Tyr Met Val Gln Lys Ser Gly Lys Thr Gly Thr Ile Thr Tyr Gln
            275                 280                 285

Arg Gly Ile Leu Leu Pro Gln Lys Val Trp Cys Ala Ser Gly Arg Ser
        290                 295                 300

Lys Val Ile Lys Gly Ser Leu Pro Leu Ile Gly Glu Ala Asp Cys Leu
305                 310                 315                 320

His Glu Lys Tyr Gly Gly Leu Asn Lys Ser Lys Pro Tyr Tyr Thr Gly
                325                 330                 335

Glu His Ala Lys Ala Ile Gly Asn Cys Pro Ile Trp Val Lys Thr Pro
            340                 345                 350

Leu Lys Leu Ala Asn Gly Thr Lys Tyr Arg Pro Pro Gly Gly Gly Trp
            355                 360                 365

Glu Gly Met Ile Ala Gly Trp His Gly Tyr Thr Ser His Gly Ala His
        370                 375                 380

Gly Val Ala Val Ala Ala Asp Leu Lys Ser Thr Gln Glu Ala Ile Asn
385                 390                 395                 400

Lys Ile Thr Lys Asn Leu Asn Ser Leu Ser Glu Leu Glu Val Lys Asn
                405                 410                 415

Leu Gln Arg Leu Ser Gly Ala Met Asp Glu Leu His Asn Glu Ile Leu
            420                 425                 430

Glu Leu Asp Glu Lys Val Asp Asp Leu Arg Ala Asp Thr Ile Ser Ser
            435                 440                 445

Gln Ile Glu Leu Ala Val Leu Leu Ser Asn Glu Gly Ile Ile Asn Ser
        450                 455                 460

Glu Asp Glu His Leu Leu Ala Leu Glu Arg Lys Leu Lys Lys Met Leu
465                 470                 475                 480

Gly Pro Ser Ala Val Glu Ile Gly Asn Gly Cys Phe Glu Thr Lys His
                485                 490                 495

Lys Cys Asn Gln Thr Cys Leu Asp Arg Ile Ala Ala Gly Thr Phe Asp
            500                 505                 510

Ala Gly Glu Phe Ser Leu Pro Thr Phe Asp Ser Leu Asn Ile Thr Ala
            515                 520                 525

Ala Ser Leu Asn Asp Asp Gly Leu Asp Asn Tyr Gln Ile Leu Ala Ile
        530                 535                 540

Tyr Ser Thr Val Ala Ser Ser Leu Val Leu Val Val Ser Leu Gly Ala
545                 550                 555                 560

Ile Ser Phe Trp Met Cys Ser Asn Gly Ser Leu Gln Cys Arg Ile Cys
                565                 570                 575

Ile
```

<210> SEQ ID NO 91
<211> LENGTH: 1891
<212> TYPE: DNA
<213> ORGANISM: Artificial Sequence
<220> FEATURE:
<223> OTHER INFORMATION: CPMV 160 5'UTR-PDI+HA B Phu nucleic acid sequence

<400> SEQUENCE: 91
tattaaaatc ttaataggtt ttgataaaag cgaacgtggg gaaacccgaa ccaaaccttc 60
ttctaaactc tctctcatct ctcttaaagc aaacttctct cttgtctttc ttgcgtgagc 120
gatcttcaac gttgtcagat cgtgcttcgg caccagtaca atggcgaaaa acgttgcgat 180
tttcggctta ttgttttctc ttcttgtgtt ggttccttct cagatcttcg cggatcgaat 240
ctgcactggg ataacatctt caaactcacc tcatgtggtc aaaacagcta ctcaagggga 300
ggtcaatgtg actggcgtga taccactgac aacaacacca acaaaatctt attttgcaaa 360
tctcaaagga acaaggacca gagggaaact atgcccggac tgtctcaact gtacagatct 420
ggatgtggcc ttgggcaggc caatgtgtgt ggggaccaca ccttctgcta aagcttcaat 480
actccatgag gtcagacctg ttacatccgg gtgctttcct ataatgcacg acagaacaaa 540
aatcaggcaa ctacccaatc ttctcagagg atatgaaaag atcaggttat caacccaaaa 600
cgttatcgat gcagaaaaag caccaggagg accctacaga cttggaacct caggatcttg 660
ccctaacgct accagtaaaa tcggattttt tgcaacaatg gcttgggctg tcccaaagga 720
caactacaaa aatgcaacga acccactaac agtggaagta ccatacattt gtacagaagg 780
ggaagaccaa attactgttt gggggttcca ttcggataac aaaacccaaa tgaagagcct 840
ctatggagac tcaaatcctc aaaagttcac ctcatctgct aatggagtaa ccacgcatta 900
tgtttctcag attggcgact tcccagatca aacagaagac ggaggactac cacaaagcgg 960
cagaattgtt gttgattaca tgatgcaaaa acctgggaaa acaggaacaa ttgtctatca 1020
aaggggtgtt ttgttgcctc aaaaggtgtg gtgcgcgagt ggcaggagca aagtaataaa 1080
agggtcattg cctttaattg gtgaagcaga ttgccttcat gaagaatacg gtggattaaa 1140
caaaagcaag ccttactaca caggaaaaca tgcaaaagcc ataggaaatt gcccaatatg 1200
ggtaaaaaca cctttgaagc ttgccaatgg aaccaaatat agacctcctg gtggaggatg 1260
ggaaggaatg attgcaggtt ggcacggata cacatctcac ggagcacatg gagtggcagt 1320
ggcggcagac cttaagagta cacaagaagc tataaataag ataacaaaaa atctcaattc 1380
tttgagtgaa ctagaagtaa agaaccttca aagactaagt ggtgccatgg atgaactcca 1440
caacgaaata ctcgagctgg atgaaaaagt ggatgatctc agagctgaca ctataagctc 1500
acaaatagaa cttgcagtct tgctttccaa cgaaggaata ataaacagtg aagacgagca 1560
tctattggca cttgagagaa aactaaagaa aatgctgggt ccctctgctg tagacatagg 1620
aaacggatgc ttcgaaacca aacacaaatg caaccagacc tgcttagaca ggatagctgc 1680
tggcaccttt aatgcaggag aattttctct ccccactttt gattcattga acattactgc 1740
tgcatcttta aatgatgatg gattggataa ctaccagatt ttggcgatct attcaactgt 1800
cgccagttca ttggtactgg tagtctccct gggggcaatc agtttctgga tgtgctctaa 1860
tgggtctcta cagtgtagaa tatgtattta a 1891

<210> SEQ ID NO 92
<211> LENGTH: 1731
<212> TYPE: DNA

<213> ORGANISM: Artificial Sequence
<220> FEATURE:
<223> OTHER INFORMATION: PDI+HA B Phu nucleic acid sequence

<400> SEQUENCE: 92

```
atggcgaaaa acgttgcgat tttcggctta ttgttttctc ttcttgtgtt ggttccttct      60
cagatcttcg cggatcgaat ctgcactggg ataacatctt caaactcacc tcatgtggtc     120
aaaacagcta ctcaagggga ggtcaatgtg actggcgtga taccact

```
Ser Ser Asn Ser Pro His Val Lys Thr Ala Thr Gln Gly Glu Val
        35                  40                  45
Asn Val Thr Gly Val Ile Pro Leu Thr Thr Pro Thr Lys Ser Tyr
 50                  55                  60
Phe Ala Asn Leu Lys Gly Thr Arg Thr Gly Lys Leu Cys Pro Asp
 65                  70                  75                  80
Cys Leu Asn Cys Thr Asp Leu Asp Val Ala Leu Gly Arg Pro Met Cys
                 85                  90                  95
Val Gly Thr Thr Pro Ser Ala Lys Ala Ser Ile Leu His Glu Val Arg
             100                 105                 110
Pro Val Thr Ser Gly Cys Phe Pro Ile Met His Asp Arg Thr Lys Ile
             115                 120                 125
Arg Gln Leu Pro Asn Leu Leu Arg Gly Tyr Glu Lys Ile Arg Leu Ser
         130                 135                 140
Thr Gln Asn Val Ile Asp Ala Glu Lys Ala Pro Gly Gly Pro Tyr Arg
145                 150                 155                 160
Leu Gly Thr Ser Gly Ser Cys Pro Asn Ala Thr Ser Lys Ile Gly Phe
                 165                 170                 175
Phe Ala Thr Met Ala Trp Ala Val Pro Lys Asp Asn Tyr Lys Asn Ala
             180                 185                 190
Thr Asn Pro Leu Thr Val Glu Val Pro Tyr Ile Cys Thr Glu Gly Glu
         195                 200                 205
Asp Gln Ile Thr Val Trp Gly Phe His Ser Asp Asn Lys Thr Gln Met
     210                 215                 220
Lys Ser Leu Tyr Gly Asp Ser Asn Pro Gln Lys Phe Thr Ser Ser Ala
225                 230                 235                 240
Asn Gly Val Thr Thr His Tyr Val Ser Gln Ile Gly Asp Phe Pro Asp
                 245                 250                 255
Gln Thr Glu Asp Gly Gly Leu Pro Gln Ser Gly Arg Ile Val Val Asp
             260                 265                 270
Tyr Met Met Gln Lys Pro Gly Lys Thr Gly Thr Ile Val Tyr Gln Arg
         275                 280                 285
Gly Val Leu Leu Pro Gln Lys Val Trp Cys Ala Ser Gly Arg Ser Lys
     290                 295                 300
Val Ile Lys Gly Ser Leu Pro Leu Ile Gly Glu Ala Asp Cys Leu His
305                 310                 315                 320
Glu Glu Tyr Gly Gly Leu Asn Lys Ser Lys Pro Tyr Tyr Thr Gly Lys
                 325                 330                 335
His Ala Lys Ala Ile Gly Asn Cys Pro Ile Trp Val Lys Thr Pro Leu
             340                 345                 350
Lys Leu Ala Asn Gly Thr Lys Tyr Arg Pro Pro Gly Gly Gly Trp Glu
         355                 360                 365
Gly Met Ile Ala Gly Trp His Gly Tyr Thr Ser His Gly Ala His Gly
     370                 375                 380
Val Ala Val Ala Ala Asp Leu Lys Ser Thr Gln Glu Ala Ile Asn Lys
385                 390                 395                 400
Ile Thr Lys Asn Leu Asn Ser Leu Ser Glu Leu Glu Val Lys Asn Leu
                 405                 410                 415
Gln Arg Leu Ser Gly Ala Met Asp Glu Leu His Asn Glu Ile Leu Glu
             420                 425                 430
Leu Asp Glu Lys Val Asp Asp Leu Arg Ala Asp Thr Ile Ser Ser Gln
         435                 440                 445
```

```
Ile Glu Leu Ala Val Leu Leu Ser Asn Glu Gly Ile Ile Asn Ser Glu
    450                 455                 460

Asp Glu His Leu Leu Ala Leu Glu Arg Lys Leu Lys Lys Met Leu Gly
465                 470                 475                 480

Pro Ser Ala Val Asp Ile Gly Asn Gly Cys Phe Glu Thr Lys His Lys
                485                 490                 495

Cys Asn Gln Thr Cys Leu Asp Arg Ile Ala Ala Gly Thr Phe Asn Ala
                500                 505                 510

Gly Glu Phe Ser Leu Pro Thr Phe Asp Ser Leu Asn Ile Thr Ala Ala
                515                 520                 525

Ser Leu Asn Asp Asp Gly Leu Asp Asn Tyr Gln Ile Leu Ala Ile Tyr
    530                 535                 540

Ser Thr Val Ala Ser Ser Leu Val Leu Val Val Ser Leu Gly Ala Ile
545                 550                 555                 560

Ser Phe Trp Met Cys Ser Asn Gly Ser Leu Gln Cys Arg Ile Cys Ile
                565                 570                 575

<210> SEQ ID NO 94
<211> LENGTH: 1783
<212> TYPE: DNA
<213> ORGANISM: Artificial Sequence
<220> FEATURE:
<223> OTHER INFORMATION: Primer CPMV 160 5'UTR-VP1 (GII.4) nucleic acid
      sequence

<400> SEQUENCE: 94
tattaaaatc ttaataggtt ttgataaaag cgaacgtggg gaaacccgaa ccaaaccttc      60
ttctaaactc tctctcatct ctcttaaagc aaacttctct cttgtctttc ttgcgtgagc    120
gatcttcaac gttgtcagat cgtgcttcgg caccagtaca atgaaaatgg cctcgagtga    180
cgctaaccct agtgacggca cgccgccaa tcttgtgcct gaggttaata atgaggtgat     240
ggccctggag cctgtggtgg gcgcagccat agcagcgccc gtggccggtc agcagaatgt    300
gattgacccg tggatacgca caatttttgt ccaagcccct ggtggggagt tcaccgttag    360
cccgagaaat gcgccaggag aaatcctgtg gtcggccagc ttgggacccg atctgaaccc    420
ctatttgtca catctcgctc ggatgtacaa cgggtatgcc ggcggatttg aagtgcaggt    480
gattctggct gggaacgcgt tcactgctgg caaagtgatc tttgcagcgg tgcctcccaa    540 cttcccact gaaggactgt ctccaagcca ggtcacaatg tttccacaca tcgtggtgga    600
cgtacggcag ctagagcctg tcctgattcc cctccctgat gtacgcaata atttctacca    660
ctacaatcaa tccaatgatc cgaccattaa actcatcgcg atgttgtaca cccctctgcg    720
cgctaacaat gctggagacg acgtattcac cgtgtcatgc agagtgctca ccagaccttc    780
accagacttt gactttatct tcttagtgcc cccactgtt gagagccgaa ccaagccctt    840
tagtgtcccc gtactcacag tcgaggagat gacaaatagc cgctttccaa tccccttga    900 gaaactgttc acaggacctt cctcggcatt cgtggttcag ccacagaacg gacgctgcac    960
aactgacggc gtgctgctcg gaaccaccca gcttagccct gttaatatct gtacgtttag   1020
aggcgacgta actcacataa ctggctcacg gaactatacc atgaatctgg catcacagaa   1080
ttggaatgac tacgacccaa ccgaagagat tcccgcacct cttggaaccc ccgactttgt   1140
gggaaaaata cagggcgtcc tgacacaaac caccagaacc gatggctcca cgggggaca   1200 caaggcaacc gtctacactg gctctgccga ttttgccccg aaactgggta gagtgcagtt   1260
tgagaccgac actgaccggg actttgaagc caatcagaat actaagttca cacctgtagg   1320
```

| | |
|---|---|
| agtgattcag gacgggggca ccactcaccg gaacgagccg caacaatggg tcctgccctc | 1380 |
| ttatagcggg aggaatactc ataatgtgca tttggctcct gcagtggctc ccacgtttcc | 1440 |
| cggggaacaa ctgctctttt ttcgttcaac catgcctgga tgctccggat atcccaatat | 1500 |
| ggatctcgat tgcctgctcc cacaggaatg ggtgcagtat ttttatcaag aggccgcacc | 1560 |
| agcccaatcc gacgtcgcac ttctgcggtt cgtgaatcca gacacaggcc gcgtgttgtt | 1620 |
| tgagtgcaaa ttgcacaaat caggatacgt tacagtggct catactggac agcatgacct | 1680 |
| ggtgatccca cccaacggat attttaggtt cgactcctgg gtgaatcagt tttatacatt | 1740 |
| agccccccatg gggaatggga ctggcagacg cagggctgtc tga | 1783 |

<210> SEQ ID NO 95
<211> LENGTH: 1623
<212> TYPE: DNA
<213> ORGANISM: Artificial Sequence
<220> FEATURE:
<223> OTHER INFORMATION: VP1 (GII.4) nucleic acid sequence

<400> SEQUENCE: 95

| | |
|---|---|
| atgaaaatgg cctcgagtga cgctaaccct agtgacggca gcgccgccaa tcttgtgcct | 60 |
| gaggttaata atgaggtgat ggccctggag cctgtggtgg gcgcagccat agcagcgccc | 120 |
| gtggccggtc agcagaatgt gattgacccg tggatacgca acaattttgt ccaagcccct | 180 |
| ggtgggagt tcaccgttag cccgagaaat gcgccaggaa aatcctgtg gtcggccagc | 240 |
| ttgggacccg atctgaaccc ctatttgtca catctcgctc ggatgtacaa cgggtatgcc | 300 |
| ggcggatttg aagtgcaggt gattctggct gggaacgcgt tcactgctgg caaagtgatc | 360 |
| tttgcagcgg tgcctcccaa cttccccact gaaggactgt ctccaagcca ggtcacaatg | 420 |
| tttccacaca cgtggtgga cgtacggcag ctagagcctg tcctgattcc cctccctgat | 480 |
| gtacgcaata atttctacca ctacaatcaa tccaatgatc cgaccattaa actcatcgcg | 540 |
| atgttgtaca cccctctgcg cgctaacaat gctggagacg acgtattcac cgtgtcatgc | 600 |
| agagtgctca ccagaccttc accagacttt gactttatct tcttagtgcc cccactgttt | 660 |
| gagagccgaa ccaagccctt tagtgtcccc gtactcacag tcgaggagat gacaaatagc | 720 |
| cgcttccaa tccccttga gaaactgttc acaggacctt cctcggcatt cgtggttcag | 780 |
| ccacagaacg gacgctgcac aactgacggc gtgctgctcg gaaccaccca gcttagccct | 840 |
| gttaatatct gtacgtttag aggcgacgta actcacataa ctggctcacg gaactatacc | 900 |
| atgaatctgg catcacagaa ttggaatgac tacgacccaa ccgaagagat tcccgcacct | 960 |
| cttggaaccc ccgactttgt gggaaaaata cagggcgtcc tgacacaaac caccagaacc | 1020 |
| gatggctcca cacggggaca caaggcaacc gtctacactg gctctgccga ttttgccccg | 1080 |
| aaactgggta gagtgcagtt tgagaccgac actgaccggg actttgaagc caatcagaat | 1140 |
| actaagttca cacctgtagg agtgattcag gacgggggca ccactcaccg gaacgagccg | 1200 |
| caacaatggg tcctgccctc ttatagcggg aggaatactc ataatgtgca tttggctcct | 1260 |
| gcagtggctc ccacgtttcc cggggaacaa ctgctctttt ttcgttcaac catgcctgga | 1320 |
| tgctccggat atcccaatat ggatctcgat tgcctgctcc cacaggaatg ggtgcagtat | 1380 |
| ttttatcaag aggccgcacc agcccaatcc gacgtcgcac ttctgcggtt cgtgaatcca | 1440 |
| gacacaggcc gcgtgttgtt tgagtgcaaa ttgcacaaat caggatacgt tacagtggct | 1500 |
| catactggac agcatgacct ggtgatccca cccaacggat attttaggtt cgactcctgg | 1560 |
| gtgaatcagt tttatacatt agccccccatg gggaatggga ctggcagacg cagggctgtc | 1620 |

-continued tga                                                                1623

<210> SEQ ID NO 96
<211> LENGTH: 540
<212> TYPE: PRT
<213> ORGANISM: Artificial Sequence
<220> FEATURE:
<223> OTHER INFORMATION: VP1 (GII.4) amino acid sequence

<400> SEQUENCE: 96

Met Lys Met Ala Ser Ser Asp Ala Asn Pro Ser Asp Gly Ser Ala Ala
1               5                   10                  15

Asn Leu Val Pro Glu Val Asn Asn Glu Val Met Ala Leu Glu Pro Val
            20                  25                  30

Val Gly Ala Ala Ile Ala Ala Pro Val Ala Gly Gln Gln Asn Val Ile
        35                  40                  45

Asp Pro Trp Ile Arg Asn Asn Phe Val Gln Ala Pro Gly Gly Glu Phe
    50                  55                  60

Thr Val Ser Pro Arg Asn Ala Pro Gly Glu Ile Leu Trp Ser Ala Ser
65                  70                  75                  80

Leu Gly Pro Asp Leu Asn Pro Tyr Leu Ser His Leu Ala Arg Met Tyr
                85                  90                  95

Asn Gly Tyr Ala Gly Gly Phe Glu Val Gln Val Ile Leu Ala Gly Asn
            100                 105                 110

Ala Phe Thr Ala Gly Lys Val Ile Phe Ala Ala Val Pro Pro Asn Phe
        115                 120                 125

Pro Thr Glu Gly Leu Ser Pro Ser Gln Val Thr Met Phe Pro His Ile
    130                 135                 140

Val Val Asp Val Arg Gln Leu Glu Pro Val Leu Ile Pro Leu Pro Asp
145                 150                 155                 160

Val Arg Asn Asn Phe Tyr His Tyr Asn Gln Ser Asn Asp Pro Thr Ile
                165                 170                 175

Lys Leu Ile Ala Met Leu Tyr Thr Pro Leu Arg Ala Asn Asn Ala Gly
            180                 185                 190

Asp Asp Val Phe Thr Val Ser Cys Arg Val Leu Thr Arg Pro Ser Pro
        195                 200                 205

Asp Phe Asp Phe Ile Phe Leu Val Pro Pro Thr Val Glu Ser Arg Thr
    210                 215                 220

Lys Pro Phe Ser Val Pro Val Leu Thr Val Glu Glu Met Thr Asn Ser
225                 230                 235                 240

Arg Phe Pro Ile Pro Leu Glu Lys Leu Phe Thr Gly Pro Ser Ser Ala
                245                 250                 255

Phe Val Val Gln Pro Gln Asn Gly Arg Cys Thr Thr Asp Gly Val Leu
            260                 265                 270

Leu Gly Thr Thr Gln Leu Ser Pro Val Asn Ile Cys Thr Phe Arg Gly
        275                 280                 285

Asp Val Thr His Ile Thr Gly Ser Arg Asn Tyr Thr Met Asn Leu Ala
    290                 295                 300

Ser Gln Asn Trp Asn Asp Tyr Asp Pro Thr Glu Glu Ile Pro Ala Pro
305                 310                 315                 320

Leu Gly Thr Pro Asp Phe Val Gly Lys Ile Gln Gly Val Leu Thr Gln
                325                 330                 335

Thr Thr Arg Thr Asp Gly Ser Thr Arg Gly His Lys Ala Thr Val Tyr
            340                 345                 350

-continued

```
Thr Gly Ser Ala Asp Phe Ala Pro Lys Leu Gly Arg Val Gln Phe Glu
            355                 360                 365
Thr Asp Thr Asp Arg Asp Phe Glu Ala Asn Gln Asn Thr Lys Phe Thr
    370                 375                 380
Pro Val Gly Val Ile Gln Asp Gly Gly Thr Thr His Arg Asn Glu Pro
385                 390                 395                 400
Gln Gln Trp Val Leu Pro Ser Tyr Ser Gly Arg Asn Thr His Asn Val
                405                 410                 415
His Leu Ala Pro Ala Val Ala Pro Thr Phe Pro Gly Glu Gln Leu Leu
            420                 425                 430
Phe Phe Arg Ser Thr Met Pro Gly Cys Ser Gly Tyr Pro Asn Met Asp
        435                 440                 445
Leu Asp Cys Leu Leu Pro Gln Glu Trp Val Gln Tyr Phe Tyr Gln Glu
    450                 455                 460
Ala Ala Pro Ala Gln Ser Asp Val Ala Leu Leu Arg Phe Val Asn Pro
465                 470                 475                 480
Asp Thr Gly Arg Val Leu Phe Glu Cys Lys Leu His Lys Ser Gly Tyr
                485                 490                 495
Val Thr Val Ala His Thr Gly Gln His Asp Leu Val Ile Pro Pro Asn
            500                 505                 510
Gly Tyr Phe Arg Phe Asp Ser Trp Val Asn Gln Phe Tyr Thr Leu Ala
        515                 520                 525
Pro Met Gly Asn Gly Thr Gly Arg Arg Arg Ala Val
    530                 535                 540
```

<210> SEQ ID NO 97
<211> LENGTH: 1588
<212> TYPE: DNA
<213> ORGANISM: Artificial Sequence
<220> FEATURE:
<223> OTHER INFORMATION: CPMV 160 5'UTR-PDI+Rituximab HC nucleic acid
      sequence

<400> SEQUENCE: 97

```
tattaaaatc ttaataggtt ttgataaaag cgaacgtggg gaaacccgaa ccaaaccttc      60
ttctaaactc tctctcatct ctcttaaagc aaacttctct cttgtctttc ttgcgtgagc     120
gatcttcaac gttgtcagat cgtgcttcgg caccagtaca atggcgaaaa acgttgcgat     180
tttcggctta ttgttttctc ttcttgtgtt ggttccttct cagatcttcg cgcaggtaca     240
actgcagcag cctggggctg agctggtgaa gcctggggcc tcagtgaaga tgtcctgcaa     300
ggcttctggc tacacattta ccagttacaa tatgcactgg gtaaaacaga cacctggtcg     360
gggcctggaa tggattggag ctatttatcc cggaaatggt gatacttcct acaatcagaa     420
gttcaaaggc aaggccacat tgactgcaga caaatcctcc agcacagcct acatgcagct     480
cagcagcctg acatctgagg actctgcggt ctattactgt gcaagatcga cttactacgg     540
cggtgactgg tacttcaatg tctggggcgc agggaccacg gtcaccgtct ctgcagctag     600
caccaagggc ccatcggtct tccccctggc accctcctcc aagagcacct ctgggggcac     660
agcggccctg ggctgcctgg tcaaggacta cttccccgaa ccggtgacgg tgtcgtggaa     720
ctcaggcgcc ctgaccagcg gcgtgcacac cttcccggct gtcctacagt cctcaggact     780
ctactccctc agcagcgtgg tgaccgtgcc ctccagcagc ttgggcaccc agacctacat     840
ctgcaacgtg aatcacaagc ccagcaacac caaggtggac aagaaagttg agcccaaatc     900
ttgtgacaaa actcacacat gcccaccgtg cccagcacct gaactcctgg ggggaccgtc     960
```

```
agtcttcctc ttcccccaa aacccaagga caccctcatg atctcccgga cccctgaggt    1020
cacatgcgtg gtggtggacg tgagccacga agaccctgag gtcaagttca actggtacgt    1080
ggacggcgtg gaggtgcata atgccaagac aaagccgcgg gaggagcagt acaacagcac    1140
gtaccgtgtg gtcagcgtcc tcaccgtcct gcaccaggac tggctgaatg gcaaggagta    1200
caagtgcaag gtctccaaca aagccctccc agcccccatc gagaaaacca tctccaaagc    1260
caaagggcag cctagggaac cacaagtgta cactcttcca ccatctaggg atgagcttac    1320
taagaaccaa gtttctctta cttgtcttgt gaagggattt tatccatctg acatcgccgt    1380
ggaatgggaa tccaacggac aaccagagaa caattacaag actactccac cagttcttga    1440
ttctgatgga tccttctttc tttattccaa gcttactgtt gataagtcca gatggcagca    1500
aggaaatgtg ttctcttgtt ctgttatgca cgaagctctt cataatcatt atactcaaaa    1560 gtcccttttct ctttctcctg gaaagtga                                      1588
```

<210> SEQ ID NO 98
<211> LENGTH: 1428
<212> TYPE: DNA
<213> ORGANISM: Artificial Sequence
<220> FEATURE:
<223> OTHER INFORMATION: PDI+Rituximab HC nucleic acid sequence

<400> SEQUENCE: 98

```
atggcgaaaa acgttgcgat ttcggctta ttgttttctc ttcttgtgtt ggttccttct      60
cagatcttcg cgcaggtaca actgcagcag cctggggctg agctggtgaa gcctggggcc    120
tcagtgaaga tgtcctgcaa ggcttctggc tacacattta ccagttacaa tatgcactgg    180
gtaaaacaga cacctggtcg gggcctggaa tggattggag ctatttatcc cggaaatggt    240
gatacttcct acaatcagaa gttcaaaggc aaggccacat tgactgcaga caaatcctcc    300
agcacagcct acatgcagct cagcagcctg acatctgagg actctgcggt ctattactgt    360
gcaagatcga cttactacgg cggtgactgg tacttcaatg tctggggcgc agggaccacg    420
gtcaccgtct ctgcagctag caccaagggc ccatcggtct tcccctggc acctcctcc     480 aagagcacct ctggggcac agcggccctg ggctgcctgg tcaaggacta cttccccgaa    540
ccggtgacgg tgtcgtggaa ctcaggcgcc ctgaccagcg gcgtgcacac cttcccggct    600
gtcctacagt cctcaggact ctactccctc agcagcgtgg tgaccgtgcc ctccagcagc    660
ttgggcaccc agacctacat ctgcaacgtg aatcacaagc ccagcaacac caaggtggac    720
aagaaagttg agcccaaatc ttgtgacaaa actcacacat gcccaccgtg cccagcacct    780
gaactcctgg ggggaccgtc agtcttcctc ttcccccaa aacccaagga caccctcatg    840
atctcccgga cccctgaggt cacatgcgtg gtggtggacg tgagccacga agaccctgag    900
gtcaagttca actggtacgt ggacggcgtg gaggtgcata atgccaagac aaagccgcgg    960
gaggagcagt acaacagcac gtaccgtgtg gtcagcgtcc tcaccgtcct gcaccaggac   1020
tggctgaatg gcaaggagta caagtgcaag gtctccaaca aagccctccc agcccccatc   1080
gagaaaacca tctccaaagc caaagggcag cctagggaac cacaagtgta cactcttcca   1140
ccatctaggg atgagcttac taagaaccaa gtttctctta cttgtcttgt gaagggattt   1200
tatccatctg acatcgccgt ggaatgggaa tccaacggac aaccagagaa caattacaag   1260
actactccac cagttcttga ttctgatgga tccttctttc tttattccaa gcttactgtt   1320
gataagtcca gatggcagca aggaaatgtg ttctcttgtt ctgttatgca cgaagctctt   1380
cataatcatt atactcaaaa gtcccttttct ctttctcctg gaaagtga                1428
```

<210> SEQ ID NO 99
<211> LENGTH: 475
<212> TYPE: PRT
<213> ORGANISM: Artificial Sequence
<220> FEATURE:
<223> OTHER INFORMATION: Primer PDI+Rituximab HC amino acid sequence

<400> SEQUENCE: 99

```
Met Ala Lys Asn Val Ala Ile Phe Gly Leu Leu Phe Ser Leu Leu Val
1               5                   10                  15

Leu Val Pro Ser Gln Ile Phe Ala Gln Val Gln Leu Gln Gln Pro Gly
            20                  25                  30

Ala Glu Leu Val Lys Pro Gly Ala Ser Val Lys Met Ser Cys Lys Ala
        35                  40                  45

Ser Gly Tyr Thr Phe Thr Ser Tyr Asn Met His Trp Val Lys Gln Thr
    50                  55                  60

Pro Gly Arg Gly Leu Glu Trp Ile Gly Ala Ile Tyr Pro Gly Asn Gly
65                  70                  75                  80

Asp Thr Ser Tyr Asn Gln Lys Phe Lys Gly Lys Ala Thr Leu Thr Ala
                85                  90                  95

Asp Lys Ser Ser Ser Thr Ala Tyr Met Gln Leu Ser Ser Leu Thr Ser
            100                 105                 110

Glu Asp Ser Ala Val Tyr Tyr Cys Ala Arg Ser Thr Tyr Tyr Gly Gly
        115                 120                 125

Asp Trp Tyr Phe Asn Val Trp Gly Ala Gly Thr Thr Val Thr Val Ser
    130                 135                 140

Ala Ala Ser Thr Lys Gly Pro Ser Val Phe Pro Leu Ala Pro Ser Ser
145                 150                 155                 160

Lys Ser Thr Ser Gly Gly Thr Ala Ala Leu Gly Cys Leu Val Lys Asp
                165                 170                 175

Tyr Phe Pro Glu Pro Val Thr Val Ser Trp Asn Ser Gly Ala Leu Thr
            180                 185                 190

Ser Gly Val His Thr Phe Pro Ala Val Leu Gln Ser Ser Gly Leu Tyr
        195                 200                 205

Ser Leu Ser Ser Val Val Thr Val Pro Ser Ser Ser Leu Gly Thr Gln
    210                 215                 220

Thr Tyr Ile Cys Asn Val Asn His Lys Pro Ser Asn Thr Lys Val Asp
225                 230                 235                 240

Lys Lys Val Glu Pro Lys Ser Cys Asp Lys Thr His Thr Cys Pro Pro
                245                 250                 255

Cys Pro Ala Pro Glu Leu Leu Gly Gly Pro Ser Val Phe Leu Phe Pro
            260                 265                 270

Pro Lys Pro Lys Asp Thr Leu Met Ile Ser Arg Thr Pro Glu Val Thr
        275                 280                 285

Cys Val Val Val Asp Val Ser His Glu Asp Pro Glu Val Lys Phe Asn
    290                 295                 300

Trp Tyr Val Asp Gly Val Glu Val His Asn Ala Lys Thr Lys Pro Arg
305                 310                 315                 320

Glu Glu Gln Tyr Asn Ser Thr Tyr Arg Val Val Ser Val Leu Thr Val
                325                 330                 335

Leu His Gln Asp Trp Leu Asn Gly Lys Glu Tyr Lys Cys Lys Val Ser
            340                 345                 350

Asn Lys Ala Leu Pro Ala Pro Ile Glu Lys Thr Ile Ser Lys Ala Lys
        355                 360                 365
```

```
Gly Gln Pro Arg Glu Pro Gln Val Tyr Thr Leu Pro Pro Ser Arg Asp
        370                 375                 380

Glu Leu Thr Lys Asn Gln Val Ser Leu Thr Cys Leu Val Lys Gly Phe
385                 390                 395                 400

Tyr Pro Ser Asp Ile Ala Val Glu Trp Glu Ser Asn Gly Gln Pro Glu
                405                 410                 415

Asn Asn Tyr Lys Thr Thr Pro Pro Val Leu Asp Ser Asp Gly Ser Phe
            420                 425                 430

Phe Leu Tyr Ser Lys Leu Thr Val Asp Lys Ser Arg Trp Gln Gln Gly
        435                 440                 445

Asn Val Phe Ser Cys Ser Val Met His Glu Ala Leu His Asn His Tyr
    450                 455                 460

Thr Gln Lys Ser Leu Ser Leu Ser Pro Gly Lys
465                 470                 475

<210> SEQ ID NO 100
<211> LENGTH: 874
<212> TYPE: DNA
<213> ORGANISM: Artificial Sequence
<220> FEATURE:
<223> OTHER INFORMATION: CPMV 160 5'UTR-PDI+Rituximab LC nucleic acid
      sequence

<400> SEQUENCE: 100
tattaaaatc ttaataggtt ttgataaaag cgaacgtggg gaaacccgaa ccaaaccttc     60
ttctaaactc tctctcatct ctcttaaagc aaacttctct cttgtctttc ttgcgtgagc    120
gatcttcaac gttgtcagat cgtgcttcgg caccagtaca atggcgaaaa acgttgcgat    180
tttcggctta ttgttttctc ttcttgtgtt ggttccttct cagatcttcg cgcaaattgt    240
tctctcccag tctccagcaa tcctgtctgc atctccaggg gagaaggtca caatgacttg    300
cagggccagc tcaagtgtaa gttacatcca ctggttccag cagaagccag gatcctcccc    360
caaaccctgg atttatgcca catccaacct ggcttctgga gtccctgttc gcttcagtgg    420
cagtgggtct gggacttctt actctctcac aatcagcaga gtggaggctg aagatgctgc    480
cacttattac tgccagcagt ggactagtaa cccacccacg ttcggagggg ggaccaagct    540
ggaaatcaaa cgtacggtgg ctgcaccatc tgtcttcatc ttcccgccat ctgatgagca    600
gttgaaatct ggaactgcct ctgttgtgtg cctgctgaat aacttctatc ccagagaggc    660
caaagtacag tggaaggtgg ataacgccct ccaatcgggt aactcccagg agagtgtcac    720
agagcaggac agcaaggaca gcacctacag cctcagcagc accctgacgc tgagcaaagc    780
agactacgag aaacacaaag tctacgcctg cgaagtcacc catcagggcc tgagctcgcc    840
cgtcacaaag agcttcaaca ggggagagtg ttga                                874

<210> SEQ ID NO 101
<211> LENGTH: 714
<212> TYPE: DNA
<213> ORGANISM: Artificial Sequence
<220> FEATURE:
<223> OTHER INFORMATION: PDI+Rituximab LC nucleic acid sequence

<400> SEQUENCE: 101
atggcgaaaa acgttgcgat tttcggctta ttgttttctc ttcttgtgtt ggttccttct     60
cagatcttcg cgcaaattgt tctctcccag tctccagcaa tcctgtctgc atctccaggg    120
gagaaggtca caatgacttg cagggccagc tcaagtgtaa gttacatcca ctggttccag    180
```

| | |
|---|---|
| cagaagccag gatcctcccc caaaccctgg atttatgcca catccaacct ggcttctgga | 240 |
| gtccctgttc gcttcagtgg cagtgggtct gggacttctt actctctcac aatcagcaga | 300 |
| gtggaggctg aagatgctgc cacttattac tgccagcagt ggactagtaa cccacccacg | 360 |
| ttcggagggg ggaccaagct ggaaatcaaa cgtacggtgg ctgcaccatc tgtcttcatc | 420 |
| ttcccgccat ctgatgagca gttgaaatct ggaactgcct ctgttgtgtg cctgctgaat | 480 |
| aacttctatc ccagagaggc caaagtacag tggaaggtgg ataacgccct ccaatcgggt | 540 |
| aactcccagg agagtgtcac agagcaggac agcaaggaca gcacctacag cctcagcagc | 600 |
| accctgacgc tgagcaaagc agactacgag aaacacaaag tctacgcctg cgaagtcacc | 660 |
| catcagggcc tgagctcgcc cgtcacaaag agcttcaaca ggggagagtg ttga | 714 |

<210> SEQ ID NO 102
<211> LENGTH: 237
<212> TYPE: PRT
<213> ORGANISM: Artificial Sequenc3
<220> FEATURE:
<223> OTHER INFORMATION: PDI+Rituximab LC amino acid sequence

<400> SEQUENCE: 102

```
Met Ala Lys Asn Val Ala Ile Phe Gly Leu Leu Phe Ser Leu Leu Val
1               5                   10                  15

Leu Val Pro Ser Gln Ile Phe Ala Gln Ile Val Leu Ser Gln Ser Pro
            20                  25                  30

Ala Ile Leu Ser Ala Ser Pro Gly Glu Lys Val Thr Met Thr Cys Arg
        35                  40                  45

Ala Ser Ser Ser Val Ser Tyr Ile His Trp Phe Gln Gln Lys Pro Gly
    50                  55                  60

Ser Ser Pro Lys Pro Trp Ile Tyr Ala Thr Ser Asn Leu Ala Ser Gly
65                  70                  75                  80

Val Pro Val Arg Phe Ser Gly Ser Gly Ser Gly Thr Ser Tyr Ser Leu
                85                  90                  95

Thr Ile Ser Arg Val Glu Ala Glu Asp Ala Ala Thr Tyr Tyr Cys Gln
            100                 105                 110

Gln Trp Thr Ser Asn Pro Pro Thr Phe Gly Gly Gly Thr Lys Leu Glu
        115                 120                 125

Ile Lys Arg Thr Val Ala Ala Pro Ser Val Phe Ile Phe Pro Pro Ser
    130                 135                 140

Asp Glu Gln Leu Lys Ser Gly Thr Ala Ser Val Val Cys Leu Leu Asn
145                 150                 155                 160

Asn Phe Tyr Pro Arg Glu Ala Lys Val Gln Trp Lys Val Asp Asn Ala
                165                 170                 175

Leu Gln Ser Gly Asn Ser Gln Glu Ser Val Thr Glu Gln Asp Ser Lys
            180                 185                 190

Asp Ser Thr Tyr Ser Leu Ser Ser Thr Leu Thr Leu Ser Lys Ala Asp
        195                 200                 205

Tyr Glu Lys His Lys Val Tyr Ala Cys Glu Val Thr His Gln Gly Leu
    210                 215                 220

Ser Ser Pro Val Thr Lys Ser Phe Asn Arg Gly Glu Cys
225                 230                 235
```

What is claimed is:

1. A nucleic acid comprising an expression enhancer operatively linked with a heterologous nucleotide sequence encoding a protein of interest, the expression enhancer consisting of:

nbMT78 (SEQ ID NO:1).

2. The nucleic acid of claim 1, where the heterologous nucleotide sequence encodes a viral protein or an antibody.

3. The nucleic acid of claim 2, wherein the viral protein is an influenza protein or a norovirus protein.

4. The nucleic acid of claim 3, wherein the influenza protein is a hemagglutinin protein selected from the group of H1, H2, H3, H4, H5, H6, H7, H8, H9, H10, H11, H12, H13, H14, H15, H16, and an influenza type B hemagglutinin.

5. The nucleic acid of claim 3, wherein the norovirus protein is a VP1, a VP2, or a combination thereof selected from the group of GI.1, GI.2, GI.3, GI.5, GI.7, GII.1, GII.2, GII.3, GII.4, GII.5, GII.6, GII.7, GII. 12, GII. 13, GII. 14, GII. 17 and GII.21.

6. A plant expression system comprising one or more than one of the nucleic acid of claim 1.

7. A plant expression system comprising one or more than one of nucleic acid of claim 2.

8. A plant expression system comprising one or more than one of the nucleic acid of claim 3.

9. A plant expression system comprising one or more than one of the nucleic acid of claim 4.

10. A plant expression system comprising one or more than one of the nucleic acid of claim 5.

11. The plant expression system of claim 6 further comprising a comovirus 3' UTR.

12. A method of producing a protein of interest in a plant, a portion of a plant, or a plant cell, comprising, introducing into the plant, the portion of a plant, or the plant cell, in a stable or transient manner, the plant expression system of claim 7 comprising the one or more than one nucleic acid, and incubating the plant or the portion of a plant under conditions that permit expression of each of the heterologous nucleotide sequence encoding the protein of interest.

13. The method of claim 12, wherein the protein of interest is a viral protein.

14. The method of claim 13, wherein the viral protein is an influenza protein or a norovirus protein.

15. The method of claim 14, wherein the influenza protein is a hemagglutinin protein selected from the group of H1, H2, H3, H4, H5, H6, H7, H8, H9, H10, H11, H12, H13, H14, H15, H16, and an influenza type B hemagglutinin.

16. The method of claim 14, wherein the norovirus protein is a VP1, a VP2, or a combination thereof selected from the group of GI.1, GI.2, GI,3, GI.5, GI.7, GII. 1, GII.2, GII.3, GII.4, GII.5, GII.6, GII.7, GII. 12, GII. 13, GII. 14, GII. 17 and GII.21.

17. The method of claim 12, wherein the protein of interest is a multimeric protein, and the step of introducing involves co-expressing two or more than two of the nucleotide sequence, each of the two or more than two of the nucleotide sequence encoding a component of the multimeric protein.

18. A plant, portion of a plant, or a plant cell, transiently transformed or stably transformed with the plant expression system of claim 7.

19. The nucleic acid of claim 1, wherein the expression enhancer increases expression of the heterologous nucleotide sequence encoding the protein of interest in a *Nicotiana benthamiana* plant when compared to the level of expression of the same heterologous nucleotide sequence that is not operatively linked to the expression enhancer.

* * * * *